(12) United States Patent
Guan et al.

(10) Patent No.: US 7,361,747 B2
(45) Date of Patent: Apr. 22, 2008

(54) ISOLATION AND CHARACTERIZATION OF THE PRECURSOR VIRUS OF HUMAN SARS VIRUS: SARS-ASSOCIATED CORONA VIRUS-LIKE VIRUS

(75) Inventors: Yi Guan, Hong Kong (CN); Bo-Jiang Zheng, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 506 days.

(21) Appl. No.: 10/852,357

(22) Filed: May 24, 2004

(65) Prior Publication Data

US 2008/0069839 A1    Mar. 20, 2008

Related U.S. Application Data

(60) Provisional application No. 60/473,255, filed on May 22, 2003.

(51) Int. Cl.
*C07H 21/02*    (2006.01)
*C07H 19/00*    (2006.01)
(52) U.S. Cl. .................................. 536/23.1; 536/23.72
(58) Field of Classification Search ...................... None
See application file for complete search history.

(56) References Cited

U.S. PATENT DOCUMENTS

2005/0100885 A1* 5/2005 Crooke et al. ................. 435/5

FOREIGN PATENT DOCUMENTS

WO    WO 200166689 A2 *    9/2001

* cited by examiner

*Primary Examiner*—Bruce R. Campell
*Assistant Examiner*—Louise Humphrey
(74) *Attorney, Agent, or Firm*—Saliwanchik, Lloyd & Saliwanchik

(57) ABSTRACT

The present invention relates to isolation and characterization of a class of isolated novel viruses which is the precursor of the virus causing Severe Acute Respiratory Syndrome (SARS) in humans ("hSARS virus"). The precursor virus which is a SARS coronavirus-like virus ("SCoV-like virus") is identified to be morphologically and phylogenetically similar to hSARS virus. The present invention relates to a nucleotide sequence comprising the genomic sequence of the SCoV-like virus. The invention further relates to nucleotide sequences comprising a portion of the genomic sequence of the SCoV-like virus. The invention also relates to the deduced amino acid sequences of the SCoV-like virus. The invention further relates to the nucleic acids and peptides encoded by and/or derived from these sequences and their use in diagnostic methods and therapeutic methods. The invention further encompasses chimeric or recombinant viruses encoded by said nucleotide sequences and antibodies directed against polypeptides encoded by the nucleotide sequences. Furthermore, the invention relates to vaccine preparations comprising the SCoV-like virus, including recombinant and chimeric forms of said virus.

5 Claims, 82 Drawing Sheets

5'-CCTACTGGTTACCAACCTGAATGGAATAT-3'

FIG. 2

```
   1 ctacccagga aaagccaacc aacctcgatc tcttgtagat ctgttctcta aacgaacttt
  61 aaaatctgtg tagctgtcgc tcggctgcat gcctagtgca cctacgcagt ataaacaata
 121 ataaatttta ctgtcgttga caagaaacga gtaactcgtc cctcttctgc agactgctta
 181 cggtttcgtc cgtgttgcag tcgatcatca gcatacctag gtttcgtccg ggtgtgaccg
 241 aaaggtaaga tggagagcct tgttcttggt gtcaacgaga aaacacacgt ccaactcagt
 301 ttgcctgtcc ttcaggttag agacgtgcta gtgcgtggct tcggggactc tgtggaagag
 361 gccctatcgg aggcacgtga acacctcaaa aatggcactt gtggtctagt agagctggaa
 421 aaaggcgtac tgccccagct tgaacagccc tatgtgttca ttaaacgttc tgatgcctta
 481 agcaccaatc acggccacaa ggtcgttgag ctggttgcag aaatggacgg cattcagtac
 541 ggtcgtagcg gtataacact gggagtactc gtgccacatg tgggcgaaac cccaattgca
 601 taccgcaatg ttcttcttcg taagaacggt aataagggag ccggtggtca tagctatggc
 661 atcgatctaa agtcttatga cttaggtgac gagcttggca ctgatcccat tgaagattat
 721 gaacaaaact ggaacactaa gcatggcagt ggtgcactcc gtgaactcac tcgtgagctc
 781 aatggaggtg cagtcactcg ctatgtcgac aacaatttct gtggcccaga tgggtaccct
 841 cttgattgca tcaaagattt tctcgcacgc gcgggcaagt caatgtgcac tctttccgaa
 901 caacttgatt acatcgagtc gaagagaggt gtctactgct gccgtgacca tgagcatgaa
 961 attgcctggt tcactgagcg ctctgataag agctacgagc accagacacc cttcgaaatt
1021 aagagtgcca agaaatttga cactttcaaa ggggaatgcc caaagttgt gtttcctctt
1081 aactcaaaag tcaaagtcat tcaaccacgt gttgaaaaga aaaagactga gggtttcatg
1141 gggcgtatac gctctgtgta ccctgttgca tctccacagg agtgtaacaa tatgcacttg
1201 tctaccttga tgaaatgtaa tcattgcgat gaagtttcat ggcagacgtg cgactttctg
1261 aaagccactt gtgaacattg tggcactgaa aatttagtta ttgaaggacc tactacatgt
1321 gggtacctac ctactaatgc tgtagtgaaa atgccatgtc ctgcctgtca agacccagag
1381 attggacctg agcatagtgt tgcagattat cacaaccact caaacattga aactcgactc
1441 cgcaagggag gtaggactag atgttttgga ggctgtgtgt ttgcctatgt tggctgctat
1501 aataagcgtg cctactgggt tcctcgtgct agtgctgata ttggctcagg ccatactggc
1561 attactggtg acaatgtgga gaccttgaat gaggatctcc ttgagatact gagtcgtgaa
1621 cgtgttaaca ttaacattgt tggcgatttt catttgaatg aagaggttgc catcattttg
1681 gcatctttct ctgcttctac aagtgccttt attgacacta taaagagtct tgattacaag
1741 tcttttcaaaa ccattgttga gtcctgcggt aactataaag ttaccaaggg aaagcccgta
1801 aaaggtgctt ggaacattgg acaacagaga tcagttttaa caccactgtg tggttttccc
1861 tcacaggctg ctggtgttat cagatcaatt tttgcgcgca cacttgatgc agcaaaccac
1921 tcaattcctg atttgcaaag agcagctgtc accatacttg atggtatttc tgaacagtca
1981 ttacgtcttg tcgacgccat ggtttatact tcagacctgc tcaccaacag tgtcattatt
2041 atggcatatg taactggtgg tcttgtacaa cagacttctc agtggttgtc taatctttg
2101 ggcactactg ttgaaaaact caggcctatc tttgaatgga ttgaggcgaa acttagtgca
2161 ggagttgaat tctcaagga tgcttgggag attctcaaat ttctcattac aggtgttttt
2221 gacatcgtca agggtcaaat acaggttgct tcagataaca tcaaggattg tgtaaaatgc
2281 ttcattgatg ttgttaacaa ggcactcgaa atgtgcattg atcaagtcac tatcgctggc
2341 gcaaagttgc gatcactcaa cttaggtgaa gtcttcatcg ctcaaagcaa gggactttac
2401 cgtcagtgta tacgtggcaa ggagcagctg caactactca tgcctcttaa ggaccaaaaa
2461 gaagtaacct ttcttgaagg tgattcacat gacacagtac ttacctctga ggaggttgtt
2521 ctcaagaacg gtgaactcga agcactcgag acgcccgttg atagcttcac aaatggagct
2581 atcgttggca caccagtctg tgtaaatggc ctcatgctct tagagattaa ggacaaagaa
2641 caatactgcg cattgtctcc tggttactg gctacaaaca atgtctttcg cttaaaaggg
2701 ggtgcaccaa ttaaaggtgt aaccttggga gaagatactg tttgggaagt tcaaggttac
2761 aagaatgtga gaatcacatt tgagcttgat gaacgtgttg acaaagtgct taatgaaaag
2821 tgctctgtct acactgttga atccggtacc gaagttactg agtttgcatg tgttgtagca
2881 gaggctgttg tgaagacttt acaaccagtt tctgatctcc ttaccaacat gggtattgat
2941 cttgatgagt ggagtgtagc tacattctac ttatttgatg atgctggtga agaaaacttt
3001 tcatcacgta tgtattgttc ctttttaccct ccagatgagg aagaagagga cgatgcagag
3061 tgtgaggaag aagaaattga tgaaacctgt gaacatgagt acggtacaga ggatgattat
3121 caaggtctcc ctctggaatt tggtgcctca gctgaaacag ttcgagttga ggaagaagaa
3181 gaggaagact ggctggatga tactactgag caatcagaga ttgagccaga accagaacct
3241 acacctgaag aaccagttaa tcagtttact ggttatttaa aacttactga caatgttgcc
```

FIG. 3

```
3301 attaaatgtg ttgacatcgt taaggaggca caaagtgcta atcctatggt gattgtaaat
3361 gctgctaaca tacacctgaa acatggtggt ggtgtagcag gtgcactcaa caaggcaacc
3421 aatggtgcca tgcaaaagga gagtgatgat tacattaagc taaatggccc tcttacagta
3481 ggagggtctt gtttgctttc tggacataat cttgctaaga agtgtctgca tgttgttgga
3541 cctaacctaa atgcaggtga ggacatccag cttcttaagg cagcatatga aaatttcaat
3601 tcacaggaca tcttacttgc accattgttg tcagcaggca tatttggtgc taaaccactt
3661 cagtctttac aagtgtgcgt gcagacggtt cgtacacagg tttatattgc agtcaatgac
3721 aaagctcttt atgagcaggt tgtcatggat tatcttgata acctgaagcc tagagtggaa
3781 gcacctaaac aagaggagcc accaaacaca gaagattcca aaactgagga gaaatctgtc
3841 gtacagaagc ctgtcgatgt gaagccaaaa attaaggcct gcattgatga ggttaccaca
3901 acactggaag aaactaagtt tcttaccaat aagttactct tgtttgctga tatcaatggt
3961 aagctttacc atgattctca gaacatgctt agaggtgaag atatgtcttt ccttgagaag
4021 gatgcacctt acatggtagg tgatgttatc actagtggtg atatcacttg tgttgtaata
4081 ccctccaaaa aggctggtgg cactactgag atgctctcaa gagctttgaa gaaagtgcca
4141 gttgatgagt atataaccac gtaccctgga caaggatgtg ctggttatac acttgaggaa
4201 gctaagactg ctcttaagaa atgcaaatct gcattttatg tactaccttc agaagcacct
4261 aatgctaagg aagagattct aggaactgta tcctggaatt tgagagaaat gcttgctcat
4321 gctgaagaga caagaaaatt aatgcctata tgcatggatg ttagagccat aatggcaacc
4381 atccaacgta agtataaagg aattaaaatt caagagggca tcgttgacta tggtgtccga
4441 ttcttctttt atactagtaa agagcctgta gcttctatta ttacgaagct gaactctcta
4501 aatgagccgc ttgtcacaat gccaattggt tatgtgacac atggttttaa tcttgaagag
4561 gctgcgcgct gtatgcgttc tcttaaagct cctgccgtag tgtcagtatc atcaccagat
4621 gctgttacta catataatgg ataccatcact tcgtcatcaa agacatctga ggagcacttt
4681 gtagaaacag tttcttttggc tggctcttac agagattggt cctattcagg acagcgtaca
4741 gagttaggtg ttgaatttct taagcgtggt gacaaaattg tgtaccacac tctggagagc
4801 cccgtcgagt ttcatcttga cggtgaggtt ctttcacttg acaaactaaa gagtctctta
4861 tccctgcggg aggttaagac tataaaagtg ttcacaactg tggacaacac taatctccac
4921 acacagcttg tggatatgtc tatgacatat ggacagcagt ttggtccaac atacttggat
4981 ggtgctgatg ttacaaaaat taaacctcat gtaaatcatg agggtaagac tttcttttgta
5041 ctacctagtg atgacacact acgtagtgaa gctttcgagt actaccatac tcttgatgag
5101 agttttcttg gtaggtacat gtctgcttta aaccacacaa agaaatggaa atttcctcaa
5161 gttggtggtt aacttcaat taaatgggct gataacaatt gttatttgtc tagtgttta
5221 ttagcacttc aacagcttga agtcaaattc aatgcaccag cacttcaaga ggcttattat
5281 agagcccgtg ctggtgatgc tgctaacttt tgtgcactca tactcgctta cagtaataaa
5341 actgttggcg agcttggtga tgtcagagaa actatgaccc atcttctaca gcatgctaat
5401 ttggaatctg caaagcgagt tcttaatgtg gtgtgtaaac attgtggtca gaaaactact
5461 accttaacgg tgtagaagc tgtgatgtat atgggtactc tatcttatga taatcttaag
5521 acaggtgttt ccattccatg tgtgtgtggt cgtgatgcta cacaatatct agtacaacaa
5581 gagtcttctt ttgttatgat gtctgcacca cctgctgagt ataaattaca gcaaggtaca
5641 ttcttatgtg cgaatgagta cactggtaac tatcagtgtg gtcattacac tcatataact
5701 gctaaggaga ccctctatcg tattgacgga gctcacctta caaagatgtc agagtacaaa
5761 ggaccagtga ctgatgtttt ctacaaggaa acatcttaca ctacaaccat caagcctgtg
5821 tcgtataaac tcgatggagt tacttacaca gagattgaac caaattgga tgggtattat
5881 aaaaaggata atgcttacta tacagagcag cctatagacc ttgtaccaac tcaaccatta
5941 ccaaatgcga gttttgataa tttcaaactc acatgttcta acacaaaatt tgctgatgat
6001 ttaaatcaaa tgacaggctt cacaaagcca gcttcacgag ctatctgt cacattcttc
6061 ccagacttga atggcgatgt agtggctatt gactatagac actattcagc gagtttcaag
6121 aaaggtgcta aattactgca taagccaatt gtttggcaca ttaaccaggc tacaaccaag
6181 acaacgttca aaccaaacac ttggtgttta cgttgtcttt ggagtacaaa gccagtagat
6241 acttcaaatt catttgaagt tctggcagta gaagacacac aaggaatgga caatcttgct
6301 tgtgaaagtc aacaacccac ctctgaagaa gtagtggaaa tcctaccat acagaaggaa
6361 gtcatagagt gtgacgtgaa aactaccgaa gttgtaggca atgtcatact taaaccatca
6421 gatgaaggtg ttaaagtaac acaagagtta ggtcatgagg atcttatggc tgcttatgtg
6481 gaaaacacaa gcattaccat taagaaacct aatgagcttt cactagcctt aggtttaaaa
6541 acaattgcca ctcatggtat tgctgcaatt aatagtgttc cttggagtaa aattttggct
```

FIG. 3 CONT'D

```
6601 tatgtcaaac cattcttagg acaagcagca attacaacat caaattgcgc taagagatta
6661 gcacaacgtg tgtttaacaa ttatatgcct tatgtgttta cattattgtt ccaattgtgt
6721 acttttacta aaagtaccaa ttctagaatt agagcttcac tacctacaac tattgctaaa
6781 aatagtgtta agagtgttgc taaattatgt ttggatgccg gcattaatta tgtgaagtca
6841 cccaaatttt ctaaattgtt cacaatcgct atgtggctat tgttgttaag tatttgctta
6901 ggttctctaa tctgtgtaac tgctgctttt ggtgtactct tatctaattt tggtgctcct
6961 tcttattgta atggcgttag agaattgtat cttaattcgt ctaacgttac tactatggat
7021 ttctgtgaag gttcttttcc ttgcagcatt tgtttaagtg gattagactc ccttgattct
7081 tatccagctc ttgaaaccat tcaggtgacg atttcatcgt acaagctaga cttgacaatt
7141 ttaggtctgg ccgctgagtg ggttttggca tatatgttgt tcacaaaatt ctttattta
7201 ttaggtcttt cagctataat gcaggtgttc tttggctatt tgctagtca tttcatcagc
7261 aattcttggc tcatgtggtt tatcattagt attgtacaaa tggcacccgt ttctgcaatg
7321 gttaggatgt acatcttctt tgcttctttc tactacatat ggaagagcta tgttcatatc
7381 atggatggtt gcacctcttc gacttgcatg atgtgctata agcgcaatcg tgccacacgc
7441 gttgagtgta aactattgt taatggcatg aagagatctt tctatgtcta tgcaaatgga
7501 ggccgtggct ctgcaagac tcacaattgg aattgtctca attgtgacac attttgcact
7561 ggtagtacat tcattagtga tgaagttgct cgtgatttgt cactccagtt taaaagacca
7621 atcaacccta ctgaccagtc atcgtatatt gttgatagtg ttgctgtgaa aaatggcgcg
7681 cttcacctct actttgacaa ggctggtcaa aagacctatg agagacatcc tctctcccat
7741 tttgtcaatt tagacaattt gagagctaac aacactaaag gttcactgcc tattaatgtc
7801 atagttttg atggcaagtc caaatgcgac gagtctgctt ctaagtctgc ttctgtgtac
7861 tacagtcagc tgatgtgcca acctattctg ttgcttgacc aagctcttgt atcagacgtt
7921 ggagatagta ctgaagtttc cgttaagatg tttgatgctt atgtcgacac cttttcagca
7981 acttttagtg ttcctatgga aaacttaag gcacttgttg ctacagctca cagcgagtta
8041 gcaaagggtg tagctttaga tggtgtcctt tctacattcg tgtcagctgc ccgacaaggt
8101 gttgttgata ccgatgttga cacaaaggat gttattgaat gtctcaaact ttcacatcac
8161 tctgacttag aagtgacagg tgacagttgt aacaatttca tgctcaccta ataaggtt
8221 gaaaacatga cgcccagaga tcttggcgca tgtattgact gtaatgcaag gcatatcaat
8281 gcccaagtag caaaaagtca caatgtttca ctcatctgga atgtaaaga ctacatgtct
8341 ttatctgaac agctgcgtaa acaaattcgt agtgctgcca agaagaacaa catacctttt
8401 agactaactt gtgctacaac tagacaggtt gtcaatgtca taactactaa aatctcactc
8461 aagggtggta agattgttag tacttgttt aaacttatgc ttaaggccac attattgtgc
8521 gttcttctg cattggtttg ttatatcgtt atgccagtac atacattgtc aatccatgat
8581 ggttacacaa atgaaatcat tggttacaaa gccattcagg atggtgtcac tcgtgacatc
8641 atttctactg atgattgttt tgcaaataaa catgctggtt ttgacgcatg gtttagccag
8701 cgtggtggtt catacaaaaa tgacaaaagc tgccctgtag tagctgctat cattacaaga
8761 gagattggtt tcatagtgcc tggcttaccg ggtactgtgc tgagagcaat caatggtgac
8821 ttcttgcatt ttctacctcg tgtttttagt gctgttggca acatttgcta cacaccttcc
8881 aaactcattg agtatagtga ttttgctacc tctgcttgcg ttcttgctgc tgagtgtaca
8941 atttttaagg atgctatggg caaacctgtg ccatattgtt atgacactaa tttgctagag
9001 ggttctattt cttatagtga gcttcgtcca gacactcgtt atgtgcttat ggatggttcc
9061 atcatacagt ttcctaacac ttacctggag ggttctgtta gagtagtaac aactttgat
9121 gctgagtact gtagacatgg tacatgcgaa aggtcagaag taggtatttg cctatctacc
9181 agtggtagat gggttcttaa taatgagcat acagagctc tatcaggagt tttctgtggt
9241 gttgatgcga tgaatctcat agctaacatc tttactcctc ttgtgcaacc tgtgggtgct
9301 ttagatgtgt ctgcttcagt agtggctggt ggtattattg ccatattggt gacttgtgct
9361 gcctactact ttatgaaatt cagacgtgct tttggtgagt acaaccatgt tgttgctgct
9421 aatgcacttt tgtttttgat gtctttcact atactctgtc tggcaccagc ttacagcttt
9481 ctgccgggag tctactcagt cttttacttg tacttgacat ctatttcac caatgatgtt
9541 tcattcttgg ctcaccttca atggtttgcc atgtttctc ctattgtgcc ttttggata
9601 acagcaatct atgtattctg tatttctctg aagcactgcc attggttctt taacaactat
9661 cttaggaaaa gagtcatgtt taatggagtt acatttagta ccttcgagga ggctgctttg
9721 tgtaccttt tgctcaacaa ggaaatgtac ctaaaattgc gtagcgagac actgttgcca
9781 cttacacagt ataacaggta tcttgctcta tataacaagt acaagtattt cagtggagcc
9841 ttagatacta ccagctatcg tgaagcagct tgctgccact tagcaaaggc tctaaatgac
```

FIG. 3 CONT'D

```
 9901 tttagcaact caggtgctga tgttctctac caaccaccac agacatcaat cacttctgct
 9961 gttctgcaga gtggttttag gaaaatggca ttcccgtcag gcaaagttga agggtgcatg
10021 gtacaagtaa cctgtggaac tacaactctt aatggattgt ggttggatga cacagtatac
10081 tgtccaagac atgtcatttg cacagcagaa gacatgctta atcctaacta tgaagatctg
10141 ctcattcgca aatccaacca tagctttctt gttcaggctg gcaatgttca acttcgtgtt
10201 attggccatt ctatgcaaaa ttgtctgctt aggcttaaag ttgatacttc taaccctaag
10261 acacccaagt ataaatttgt ccgtatccaa cctggtcaaa cattttcagt tctagcatgc
10321 tacaatggtt caccatctgg tgtttatcag tgtgccatga gacctaatca taccattaaa
10381 ggttctttcc ttaatggatc atgtggtagt gttggtttta acattgatta tgattgcgtg
10441 tctttctgct atatgcatca tatggagctt ccaacaggag tacacgctgg tactgactta
10501 gaaggtaaat tctatggtcc atttgttgac agacaaactg cacaggctgc aggtacagac
10561 acaaccataa cattaaatgt tttggcatgg ctgtatgctg ctgttatcaa tggtgatagg
10621 tggtttctta atagattcac cactactttg aatgacttta accttgtggc aatgaagtac
10681 aactatgaac ctttgacaca agatcatgtt gacatattgg gacctctttc tgctcaaaca
10741 ggaattgccg tcttagatat gtgtgctgct ttgaaagagc tgctgcagaa tggtatgaat
10801 ggtcgtacta tccttggtag cactatttta gaagatgagt ttacaccatt tgatgttgtt
10861 agacaatgct ctggtgttac cttccaaggt aagttcaaga aaattgttaa gggcactcat
10921 cattggatgc ttttaacttt cttgacatca ctattgattc ttgttcaaag tacacagtgg
10981 tcactgtttt tctttgttta cgagaatgct ttcttgccat ttactcttgg tattatggca
11041 attgctgcat gtgctatgct gcttgttaag cataagcacg cattcttgtg cttgtttctg
11101 ttaccttctc ttgcaacagt tgcttacttt aatatggtct acatgcctgc tagctgggtg
11161 atgcgtatca tgacatggct tgaattggct gacactagct tgtctggtta taggcttaag
11221 gattgtgtta tgtatgcttc agctttagtt ttgcttattc tcatgacagc tcgcactgtt
11281 tatgatgatg ctgctagacg tgtttggaca ctgatgaatg tcattacact tgtttacaaa
11341 gtctactatg gtaatgcttt agatcaagct atttccatgt gggccttagt tatttctgta
11401 acctctaact attctggtgt cgttacgact atcatgtttt tagctagagc tatagtgttt
11461 gtgtgtgttg agtattaccc attgttattt attactggca acaccttaca gtgtatcatg
11521 cttgtttatt gtttcttagg ctattgttgc tgctgctact ttggcctttt ctgtttactc
11581 aaccgttact tcaggcttac tcttggtgtt tatgactact tggtctctac acaagaattt
11641 aggtatatga actcccaggg gcttttgcct cctaagagta gtattgatgc tttcaagctt
11701 aacattaagt tgtgggtat tggaggtaaa ccatgtatca aggttgctac tgtacagtct
11761 aaaatgtctg acgtaaagtg cacatctgtg gtactgctct cggttcttca acaacttaga
11821 gtagagtcat cttctaaatt gtgggcacaa tgtgtacaac tccacaatga tattcttctt
11881 gcaaaagaca caactgaagc tttcgagaag atggttctc ttttgtctgt tttgctatcc
11941 atgcagggtg ctgtagacat taataggttg tgcgaggaaa tgctcgataa ccgtgctact
12001 cttcaggcta ttgcttcaga atttagttct ttaccatcat atgccgctta tgccactgcc
12061 caggaggcct atgagcaggc tgtagctaat ggtgattctg aagtcgttct caaaaagtta
12121 aagaaatctt tgaatgtggc taaatctgag tttgaccgtg atgctgccat gcaacgcaag
12181 ttggaaaaga tggcagatca ggctatgacc caaatgtaca aacaggcaag atctgaggac
12241 aagagggcaa agtaactag tgctatgcaa acaatgctct tcactatgct taggaagctt
12301 gataatgatg cacttaacaa cattatcaac aatgcgcgtg atggttgtgt tccactcaac
12361 atcataccat tgactacagc agccaaactc atggttgttg ccctgatta tgtacctac
12421 aagaacactt gtgatggtaa cacctttaca tatgcatctg cactctggga atccagcaa
12481 gttgttgatg cggatagcaa gattgttcaa cttagtgaaa ttaacatgga caattcacca
12541 aatttggctt ggcctcttat tgttacagct ctaagagcca actcagctgt taaactacag
12601 aataatgaac tgagtccagt agcactacga cagatgtcct gtgcggctgg taccacacaa
12661 acagcttgta ctgatgacaa tgcacttgcc tactataaca ttcgaagggg aggtaggttt
12721 gtgctggcat tactatcaga ccaccaagat ctcaaatggg ctagattccc taagagtgat
12781 ggtacaggta caatttacac agaactggaa ccaccttgta ggtttgttac agacacacca
12841 aaagggccta agtgaaata cttgtacttc atcaaaggct taaacaacct aaatagaggt
12901 atggtgctgg gcagtttagc tgctacagta cgtcttcagg ctggaaatgc tacagaagta
12961 cctgccaatt caactgtgct ttccttctgt gcttttgcag tagaccctgc taaagcatat
13021 aaggattacc tagcaagtgg aggacaacca atcaccaact gtgtgaagat gttgtgtaca
13081 cacactggta caggacaggc aattactgta acaccagaag ctaacatgga ccaagagtcc
13141 tttggtggtg cttcatgttg tctgtattgt agatgccaca ttgaccatcc aaatcctaaa
```

```
13201 ggattctgtg acttgaaagg taagtacgtc caaataccta ccacttgtgc taatgaccca
13261 gtgggtttta cacttagaaa cacagtctgt accgtctgcg gaatgtggaa aggttatggc
13321 tgtagttgtg accaactccg cgaacccttg atgcagtctg cggatgcatc aacgttttta
13381 aacgggtttg cggtgtaagt gcagcccgtc ttacaccgtg cggcacaggc actagtactg
13441 atgtcgtcta cagggctttt gatatttaca acgaaaaagt tgctggtttt gcaaagttcc
13501 taaaaactaa ttgctgtcgc ttccaggaga aggatgagga aggcaattta ttagactctt
13561 actttgtagt taagaggcat actatgtcta actaccaaca tgaagagact atttataact
13621 tggttaaaga ttgtccagcg gttgctgtcc atgactttt caagtttaga gtagatggtg
13681 acatggtacc acatatatca cgtcagcgtc taactaaata cacaatggct gatttagtct
13741 atgctctacg tcatttgat gagggtaatt gtgatacatt aaaagaaata ctcgtcacat
13801 acaattgctg tgatgatgat tatttcaata agaaggattg gtatgacttc gtagagaatc
13861 ctgacatctt acgcgtatat gctaacttag gtgagcgtgt acgccaatca ttattaaaga
13921 ctgtacaatt ctgcgatgct atgcgtgatg caggcattgt aggcgtactg acattagata
13981 atcaggatct taatgggaac tggtacgatt tcggtgattt cgtacaagta gcaccaggct
14041 gcggagttcc tattgtggat tcatattact cattgctgat gcccatcctc actttgacta
14101 gggcattggc tgctgagtcc catatggatg ctgatctcgc aaaaccactt attaagtggg
14161 atttgctgaa atatgatttt acggaagaga ctttgtct cttcgaccgt tatttaaat
14221 atttgggacca gacataccat cccaattgta ttaactgttt ggatgatagg tgtatccttc
14281 attgtgcaaa ctttaatgtg ttatttcta ctgtgtttcc acctacaagt tttggaccac
14341 tagtaagaaa aatatttgta gatggtgttc cttttgttgt ttcaactgga taccattttc
14401 gtgagttagg agtcgtacat aatcaggatg taaacttaca tagctcgcgt ctcagtttca
14461 aggaactttt agtgtatgct gctgatccag ctatgcatgc agcttctggc aatttattgc
14521 tagataaacg cactacatgc ttttcagtag ctgcactaac aaacaatgtt gcttttcaaa
14581 ctgtcaaacc cggtaatttt aataaagact tttatgactt gctgtgtct aaaggttct
14641 ttaaggaagg aagttctgtt gaactaaaac acttcttctt tgctcaggat ggcaacgctg
14701 ctatcagtga ttatgactat tatcgttata atctgccaac aatgtgtgat atcagacaac
14761 tcctattcgt agttgaagtt gttgataaat actttgattg ttacgatggt ggctgtatta
14821 atgccaacca agtaatcgtt aacaatctgg ataaatcagc tggtttccca tttaataaat
14881 ggggtaaggc tagactttat tatgactcaa tgagttatga ggatcaagat gcacttttcg
14941 cgtatactaa gcgtaatgtc atccctacta taactcaaat gaatcttaag tatgccatta
15001 gtgcaaagaa tagagctcgc accgtagctg gtgtctctat ctgtagtact atgacaaata
15061 gacagtttca tcagaaatta ttgaagtcaa tagccgccac tagaggagct actgtggtaa
15121 ttggaacaag caagttttac ggtggctggc ataatatgtt aaaaactgtt tacagtgatg
15181 tagaaactcc acaccttatg ggttgggatt atccaaaatg tgacagagcc atgcctaaca
15241 tgcttaggat aatggcctct cttgttcttg ctcgcaaaca taacacttgc tgtaacttat
15301 cacaccgttt ctacaggtta gctaacgagt gtgcgcaagt attaagtgag atggtcatgt
15361 gtggcggctc actatatgtt aaaccaggtg gaacatcatc cggtgatgct acaactgctt
15421 atgctaatag tgtctttaac atttgtcaag ctgttacagc caatgtaaat gcacttcttt
15481 caactgatgg taataagata gctgacaagt atgtccgcaa tctacaacac aggctctatg
15541 agtgtctcta tagaaatagg gatgttgatc atgaattcgt ggatgagttt acgcttacc
15601 tgcgtaaaca tttctccatg atgattcttt ctgatgatgc cgttgtgtgc tataacagta
15661 actatgcggc tcaaggttta gtagctagca ttaagaactt taaggcagtt ctttattatc
15721 aaaataatgt gttcatgtct gaggcaaaat gttggactga gactgacctt actaaaggac
15781 ctcacgaatt ttgctcacag catacaatgc tagttaaaca aggagatgat tacgtgtacc
15841 tgccttaccc agatccatca agaatattag gcgcaggctg ttttgtcgat gatattgtca
15901 aaacagatgg tacacttatg attgaaaggt tcgtgtcact ggctattgat gcttacccac
15961 ttacaaaaca tcctaatcag gagtatgctg atgtctttca cttgtattta caatacatta
16021 gaaagttaca tgatgagctt actggccaca tgttggacat gtattccgta atgctaacta
16081 atgataacac ctcacggtac tgggaacctg agttttatga ggctatgtac acaccacata
16141 cagtcttgca ggctgtaggt gcttgtgtat tgtgcaattc acagacttca cttcgttgcg
16201 gtgcctgtat taggagacca ttcctatgtt gcaagtgctg ctatgaccat gtcatttcaa
16261 catcacacaa attagtgttg tctgttaatc cctatgtttg caatgcccca ggttgtgatg
16321 tcactgatgt gacacaactg tatctaggag gtatgagcta ttattcaag tcacataagc
16381 ctcccattag tttttccatta tgtgctaatg gtcaggtttt tggtttatac aaaaacacat
16441 gtgtaggcag tgacaatgtc actgacttca atgcgatagc aacatgtgat tggactaatg
```

FIG. 3 CONT'D

```
16501 ctggcgatta catacttgcc aacacttgta ctgagagact caagcttttc gcagcagaaa
16561 cgctcaaagc cactgaggaa acatttaagc tgtcatatgg tattgccact gtacgcgaag
16621 tactctctga cagagaattg catctttcat gggaggttgg aaaacctaga ccaccattga
16681 acagaaacta tgtctttact ggttaccgtg taactaaaaa tagtaaagta cagattggag
16741 agtcacactt tgaaaaaggt gactatggtg atgctgttgt gtacagaggt actacgacat
16801 acaagttgaa tgttggtgat tactttgtgt tgacatctca cactgtaatg ccacttagtg
16861 cacctactct agtgccacaa gagcactatg tgagaattac tggcttgtac ccaacactca
16921 acatctcaga tgagttttct agcaatgttg caaattatca aaaggtcggc atgcaaaagt
16981 actctacact ccaaggacca cctggtactg gtaagagtca ttttgccatc ggacttgctc
17041 tctattaccc atctgctcgc atagtgtata cggcatgctc tcatgcagct gttgatgccc
17101 tatgtgaaaa ggcattaaaa tatttgccca tagataaatg tagtagaatc atacctgcgc
17161 gtgcgcgcgt agagtgtttt gataaattca aagtgaattc aacactagaa cagtatgttt
17221 tctgcactgt aaatgcattg ccagaaacaa ctgctgacat tgtagtcttt gatgaaatct
17281 ctatggctac taattatgac ttgagtgttg tcaatgctag acttcgtgca aaacactacg
17341 tctatattgg cgatcctgct caattaccag ccccccgcac attgctgact aaaggcacac
17401 tagaaccaga atattttaat tcagtgtgca gacttatgaa aacaataggt ccagacatgt
17461 tccttggaac ttgtcgccgt tgtcctgctg aaattgttga cactgtgagt gctttagttt
17521 atgacaataa gctaaaagca cacaaggaga agtcagctca atgcttcaaa atgttctaca
17581 aaggtgttat tacacatgat gtttcatctg caatcaacag acctcaaata ggcgttgtaa
17641 gagaatttct tacacgcaat cctgcttgga gaaaagctgt ttttatctca ccttataatt
17701 cacagaacgc tgtagcttca aaaatcttag gattgcctac gcagactgtt gattcatcac
17761 agggttctga atatgactat gtcatattca cacaaactac tgaaacagca cactcttgta
17821 atgtcaaccg tttcaatgtg gctatcacaa gggcaaaaat tggcattttg tgcataatgt
17881 ctgatagaga tctttatgac aaactgcaat ttacaagtct agaaatacca cgtcgcaatg
17941 tggctacatt acaagcagaa aatgtaactg gacttttaa ggactgtagt aagatcatta
18001 ctggtcttca tcctacacag gcacctacac acctcagcgt tgatataaag ttcaagactg
18061 aaggattatg tgttgacata ccaggcatac caaaggacat gacctaccgt agactcatct
18121 ctatgatggg tttcaaaatg aattaccaag tcaatggtta ccctaatatg tttatcaccc
18181 gcgaagaagc tattcgtcac gttcgtgcgt ggattggctt tgatgtagag ggctgtcatg
18241 caactagaga tgctgtgggt actaacctac ctctccagct aggattttct acaggtgtta
18301 acttagtagc tgtaccgact ggttatgttg acactgaaaa taacacagaa ttcaccagag
18361 ttaatgcaaa acctccacca ggtgaccagt ttaaacatct tataccactc atgtataaag
18421 gcttgccctg gaatgtagtg cgtattaaga gtacaaaat gctcagtgat acactgaaag
18481 gattgtcaga cagagtcgtg ttcgtccttt gggcgcatgg ctttgagctt acatcaatga
18541 agtactttgt caagattgga cctgaaagaa cgtgttgtct gtgtgacaaa cgtgcaactt
18601 gcttttctac ttcatcagat acttatgcct gctggaatca ttctgtgggt tttgactatg
18661 tctataaccc atttatgatt gatgttcagc agtggggctt tacgggtaac cttcagagta
18721 accatgacca acattgccag gtacatggaa atgcacatgt ggctagttgt gatgctatca
18781 tgactagatg tttagcagtc catgagtgct tgttaagcg cgttgattgg tctgttgaat
18841 accctattat aggagatgaa ctgagggtta ttctgcttg cagaaagta caacacatgg
18901 ttgtgaagtc tgcattgctt gctgataagt ttccagttct tcatgacatt ggaaatccaa
18961 aggctatcaa gtgtgtgcct caggctgaag tagaatggaa gttctacgat gctcagccat
19021 gtagtgacaa agcttacaaa atagaggagc tcttctatc ttatgctaca catcacgata
19081 aattcactga tggtgtttgt ttgttttgga attgtaacgt tgatcgttac ccagccaatg
19141 caattgtgtg taggtttgac acaagagtct tgtcaaactt gaacttacca ggctgtgatg
19201 gtggtagttt gtatgtgaat aagcatgcat tccacactcc agcttttgat aaaagtgcat
19261 ttactaattt aaagcaattg cctttctttt actattctga tagtccttgt gagtctcatg
19321 gcaaacaagt agtgtcggat attgattatg ttccactcaa atctgctacg tgtattacac
19381 gatgcaattt aggtggtgct gtttgcagac accatgcaaa tgagtaccga cagtacttgg
19441 atgcatataa tatgatgatt tctgctggat ttagcctatg gatttacaaa caatttgata
19501 cttataacct gtggaataca tttaccaggt tacagagttt agaaaatgtg gcttataatg
19561 ttgttaataa aggacacttt gatggacacg ccggcgaagc acctgtttcc atcattaata
19621 atgctgttta cacaaaggta gatggtattg atgtggagat ctttgaaaat aagacaacac
19681 ttcctgttaa tgttgcattt gagctttggg ctaagcgtaa cattaaacca gtgccagaga
19741 ttaagatact caataatttg ggtgttgata tcgctgctaa tactgtaatc tgggactaca
```

```
19801 aaagagaagc cccagcacat gtatctacaa taggtgtctg cacaatgact gacattgcca
19861 agaaacctac tgagagtgct tgttcttcac ttactgtctt gtttgatggt agagtggaag
19921 gacaggtaga ccttttaga aacgccgta atggtgtttt aataacagaa ggttcagtca
19981 aaggtctaac accttcaaag ggaccagcac aagctagcgt caatggagtc acattaattg
20041 gagaatcagt aaaaacacag tttaactact ttaagaaagt agacggcatt attcaacagt
20101 tgcctgaaac ctactttact cagagcagag acttagagga ttttaagccc agatcacaaa
20161 tggaaactga ctttctcgag ctcgctatgg atgaattcat acagcgatat aagctcgagg
20221 gctatgcctt cgaacacatc gtttatggag atttcagtca tggacaactt ggcggtcttc
20281 atttaatgat aggcttagcc aagcgctcac aagattcacc acttaaatta gaggattta
20341 tccctatgga cagcacagtg aaaaattact tcataacaga tgcgcaaaca ggttcatcaa
20401 aatgtgtgtg ttctgtgatt gatcttttac ttgatgactt tgtcgagata ataaagtcac
20461 aagatttgtc agtgatttca aagtggtca aggttacaat tgactatgct gaaatttcat
20521 tcatgctttg gtgtaaggat ggacatgttg aaaccttcta cccaaaacta caagcaagtc
20581 aagcgtggca accaggtgtt gcgatgccta acttgtacaa gatgcaaaga atgcttcttg
20641 aaaagtgtga ccttcagaat tatggtgaaa atgctgttat accaaaagga ataatgatga
20701 atgtcgcaaa gtatactcaa ctgtgtcaat acttaaatac acttacttta gctgtaccct
20761 acaacatgag agttattcac tttggtgctg gctctgataa aggagttgca ccaggtacag
20821 ctgtgctcag acaatggttg ccaactggca cactacttgt cgattcagat cttaatgact
20881 tcgtctccga cgcagattct actttaattg gagactgtgc aacagtacat acggctaata
20941 aatgggacct tattattagc gatatgtatg accctaggac caaacatgtg acaaaagaga
21001 atgactctaa agaagggttt ttcacttatc tgtgtggatt tataaagcaa aaactagccc
21061 tgggtggttc tatagctgta aagataacag agcattcttg gaatgctgac ctttacaagc
21121 ttatgggcca tttctcatgg tggacagctt ttgttacaaa tgtaaatgca tcatcatcgg
21181 aagcatttt aattggggct aactatcttg gcaagccgaa ggaacaaatt gatggctata
21241 ccatgcatgc taactacatt ttctggagga cacaaatcc tatccagttg tcttcctatt
21301 cactctttga catgagcaaa tttcctctta aattaagagg aactgctgta atgtctctta
21361 aggagaatca aatcaatgat atgatttatt ctcttctgga aaaaggtagg cttatcatta
21421 gagaaaacaa cagagttgtg gtttcaagtg atattcttgt taacaactaa acgaacatgt
21481 ttattttctt attatttctt actctcacta gtggtagtga ccttgaccgg tgcaccactt
21541 ttgatgatgt tcaagctcct aattacactc aacatacttc atctatgagg ggggtttact
21601 atcctgatga aatttttaga tcagacactc tttatttaac tcaggattta tttcttccat
21661 tttattctaa tgttacaggg tttcatacta ttaatcatac gtttgacaac cctgtcatac
21721 cttttaagga tggtatttat tttgctgcca cagagaaatc aaatgttgtc cgtggttggg
21781 tttttggttc taccatgaac aacaagtcac agtcggtgat tattattaac aattctacta
21841 atgttgttat acgagcatgt aactttgaat tgtgtgacaa cccttttctt gctgtttcta
21901 aacccatggg tacacagaca catactatga tattcgataa tgcatttaat gcactttcg
21961 agtacatatc tgatgccttt cgcttgatg tttcagaaaa gtcaggtaat tttaaacact
22021 tacgagagtt tgtgtttaaa aataaagatg ggtttctcta tgtttataag ggctatcaac
22081 ctatagatgt agttcgtgat ctaccttctg gttttaacac tttgaaacct attttttaagt
22141 tgcctcttgg tattaacatt acaaatttta gagccattct tacagccttt tcacctgctc
22201 aagacacttg gggcacgtca gctgcagcct attttgttgg ctatttaaag ccaactacat
22261 ttatgctcaa gtatgatgaa aatggtacaa tcacagatgc tgttgattgt tctcaaaatc
22321 cacttgctga actcaaatgc tctgttaaga gctttgagat tgacaaagga atttaccaga
22381 cctctaattt cagggttgtt ccctcaggag atgttgtgag attccctaat attacaaact
22441 tgtgtccttt tggagaggtt tttaatgcta ctaaattccc ttctgtctat gcatgggaga
22501 gaaaaaaat ttctaattgt gttgctgatt actctgtgct ctacaactca acatttttt
22561 caacctttaa gtgctatggc gtttctgcca ctaagttgaa tgatctttgc ttctccaatg
22621 tctatgcaga ttcttttgta gtcaagggag atgatgtaag acaaatagcg ccaggacaaa
22681 ctggtgttat tgctgattat aattataaat tgccagatga tttcatgggt tgtgtccttg
22741 cttggaatac taggaacatt gatgctactt caactggtaa ttataattat aaatataggt
22801 atcttagaca tggcaagctt aggccctttg agagagacat atctaatgtg cctttctccc
22861 ctgatggcaa accttgcacc ccacctgctc ttaattgtta ttggccatta aatgattatg
22921 gttttacac cactactggc attggctacc aaccttacag agttgtagta cttcttttg
22981 aacttttaaa tgcaccggcc acggtttgtg gaccaaaatt atccactgac cttattaaga
23041 accagtgtgt caatttaat tttaatggac tcactggtac tggtgtgtta actccttctt
```

FIG. 3 CONT'D

```
23101 caaagagatt tcaaccattt caacaatttg gccgtgatgt ttctgatttc actgattccg
23161 ttcgagatcc taaaacatct gaaatattag acatttcacc ttgctctttt gggggtgtaa
23221 gtgtaattac acctggaaca aatgcttcat ctgaagttgc tgttctatat caagatgtta
23281 actgcactga tgtttctaca gcaattcatg cagatcaact cacaccagct tggcgcatat
23341 attctactgg aaacaatgta ttccagactc aagcaggctg tcttatagga gctgagcatg
23401 tcgacacttc ttatgagtgc gacattccta ttggagctgg catttgtgct agttaccata
23461 cagtttcttt attacgtagt actagccaaa aatctattgt ggcttatact atgtctttag
23521 gtgctgatag ttcaattgct tactctaata acaccattgc tatacctact aacttttcaa
23581 ttagcattac tacagaagta atgcctgttt ctatggctaa aacctccgta gattgtaata
23641 tgtacatctg cggagattct actgaatgtg ctaatttgct tctccaatat ggtagctttt
23701 gcacacaact aaatcgtgca ctctcaggta ttgctgctga acaggatcgc aacacacgtg
23761 aagtgttcgc tcaagtcaaa caaatgtaca aacccaac tttgaaatat tttggtggtt
23821 ttaatttttc acaaatatta cctgaccctc taaagccaac taagaggtct tttattgagg
23881 acttgctctt taataaggtg acactcgctg atgctggctt catgaagcaa tatggcgaat
23941 gcctaggtga tattaatgct agagatctca tttgtgcgca gaagttcaat ggacttacag
24001 tgttgccacc tctgctcact gatgatatga ttgctgccta cactgctgct ctagttagtg
24061 gtactgccac tgctggatgg acatttggtg ctggcgctgc tcttcaaata ccttttgcta
24121 tgcaaatggc ataggttc aatggcattg gagttaccca aaatgttctc tatgagaacc
24181 aaaaacaaat cgccaaccaa tttaacaagg cgattagtca aattcaagaa tcacttacaa
24241 caacatcaac tgcattgggc aagctgcaag acgttgttaa ccagaatgct caagcattaa
24301 acacacttgt taaacaactt agctctaatt ttggtgcaat ttcaagtgtg ctaaatgata
24361 tccttttcgcg acttgataaa gtcgaggcgg aggtacaaat tgacaggtta attacaggca
24421 gacttcaaag ccttcaaacc tatgtaacac aacaactaat cagggctgct gaaatcaggg
24481 cttctgctaa tcttgctgct actaaaatgt ctgagtgtgt tcttggacaa tcaaaaagag
24541 ttgacttttg tggaaagggc taccaccta tgtccttccc acaagcagcc ccgcatggtg
24601 ttgtcttcct acatgtcacg tatgtgccat cccaggagag gaacttcacc acagcgccag
24661 caatttgtca tgaaggcaaa gcatacttcc ctcgtgaagg tgttttttgtg tttaatggca
24721 cttcttggtt tattacacag aggaacttct tttctccaca ataattact acagacaata
24781 catttgtctc aggaaattgt gatgtcgtta ttggcatcat taacaacaca gtttatgatc
24841 ctctgcaacc tgagcttgac tcattcaaag aagagctgga caagtacttc aaaaatcata
24901 catcaccaga tgttgatctt ggcgacattt caggcattaa cgcttctgtc gtcaacattc
24961 aaaaagaaat tgaccgcctc aatgaggtcg ctaaaaattt aaatgaatca ctcattgacc
25021 ttcaagaatt gggaaaatat gagcaatata ttaaatggcc ttggtatgtt tggctcggct
25081 tcattgctgg actaattgcc atcgtcatgg ttacaatctt gctttgttgc atgactagtt
25141 gttgcagttg cctcaagggt gcatgctctt gtggttcttg ctgcaagttt gatgaggatg
25201 actctgagcc agttctcaag ggtgtcaaat tacattacac ataaacgaac ttatggattt
25261 gtttatgaga ttttttactc ttggatcaat tactgcacag ccagtaaaaa ttgacaatgc
25321 ttctcctgca agtactgttc atgctacagc aacgataccg ctacaagcct cactcccttt
25381 cggatggctt gttattggcg ttgcatttct tgctgttttt cagagcgcta ccaaaataat
25441 tgcgctgcaat aaaagatggc agctagccct ttataagggc ttccagttca tttgcaattt
25501 actgctgcta tttgttacca tctattcaca tcttttgctt gtcgctgcag gtatggaggc
25561 gcaatttttg tacctctatg ccttgatata ttttctacaa tgcatcaacg catgtagaat
25621 tattatgaca tgttggcttt gttggaagtg caaatccaag acccattac tttatgatgc
25681 caactacttt gtttgctggc acacacataa ctatgactac tgtataccat ataacagtgt
25741 cacagataca attgtcgtta ctgaaggtga cggcatttca acaccaaaac tcaaagaaga
25801 ctaccaaatt ggtggttatt ctgaggatag cactcaggt gttaaagact atgtcgttgt
25861 acatggctat ttcaccgaag tttactacca gcttgagtct acacaaatta ctacagacac
25921 tggtattgaa aatgctacat tcttcatctt taacaagctt gttaaagacc caccgaatgt
25981 gcaaatacac acaatcgacg gctcttcagg agttgctaat ccagcaatgg atccaattta
26041 tgatgagccg acgacgacta ctagcgtgcc tttgtaagca caagaaagtg agtacgaact
26101 tatgtactca ttcgtttcgg aagaaacagg tacgttaata gttaatagcg tacttctttt
26161 tcttgctttc gtggtattct tgctagtcac actagccatc cttactgcgc ttcgattgtg
26221 tgcgtactgc tgcaatattg ttaacgtgag tttagtaaaa ccaacggttt acgtctactc
26281 gcgtgttaaa aatctgaact cttctgaagg agttcctgat cttctggtct aaacgaacta
26341 actattatta ttattctgtt tggaacttta acattgctta tcatggcaga caacggtact
```

FIG. 3 CONT'D

```
26401 attaccgttg aggagcttaa acaactcctg gaacaatgga acctagtaat aggtttccta
26461 ttcctagcct ggattatgtt actacaattt gcctattcta atcggaacag gttttgtac
26521 ataataaagc ttgttttcct ctggctcttg tggccagtaa cacttgcttg ttttgtgctt
26581 gctgctgtct acagaattaa ttgggtgact ggcgggattg cgattgcaat ggcttgtatt
26641 gtaggcttga tgtggcttag ctacttcgtt gcttccttca ggctgtttgc tcgtacccgc
26701 tcaatgtggt cattcaaccc agaaacaaac attcttctca atgtgcctct ccgggggaca
26761 attgtgacca gaccgctcat ggaaagtgaa cttgtcattg gtgctgtgat cattcgtggt
26821 cacttgcgaa tggccggaca ctccctaggg cgctgtgaca ttaaggacct gccaaaagag
26881 atcactgtgg ctacatcacg aacgctttct tattacaaat taggagcgtc gcagcgtgta
26941 ggcactgatt caggttttgc tgcatacaac cgctaccgta ttggaaacta taaattaaat
27001 acagaccacg ccggtagcaa cgacaatatt gctttgctag tacagtaagt gacaacagat
27061 gtttcatctt gttgacttcc aggttacaat agcagagata ttgattatca ttatgaggac
27121 tttcaggatt gctatttgga atcttgacgt tataataagt tcaatagtga acaattatt
27181 taagcctcta actaagaaga attattcgga gttagatgat gaagaaccta tggagttaga
27241 ttatccataa aacgaacatg aaaattattc tcttcctgac attgattgta tttacatctt
27301 gcgagctata tcactatcag gagtgtgtta gaggtacgac tgtactacta aaagaacctt
27361 gcccatcagg aacatacgag ggcaattcac catttcaccc tcttgctgac aataaatttg
27421 cactaacttg cactagcaca cactttgctt ttgcttgtgc tgacggtact cgacataccct
27481 atcagctgcg tgcaagatca gtttcaccaa aactttcat cagacaagag gaggttcaac
27541 aagagctcta ctcgccactt tttctcattg ttgctgctct agtattttta atactttgct
27601 tcaccattaa gagaaagaca gaatgaatga gctcacttta attgacttct atttgtgctt
27661 tttagccttt ctgctattcc ttgttttaat aatgcttatt atattttggt tttcactcga
27721 aatccaggat ctagaagaac cttgtaccaa agtctaaacg aacatgaaac ttctcattgt
27781 tttgacttgt atttctctat gcagttgcat acgcactgta gtacagcgct gtgcatctaa
27841 taaacctcat gtgcttgaag atccttgtaa ggtacaacac taggggtaat acttatagca
27901 ctgcttggct ttgtgctcta ggaaaggttt tacctttttca tagatggcac actatggttc
27961 aaacatgcac acctaatgtt actatcaact gtcaagatcc agctggtggt gcgcttatag
28021 ctaggtgttg gtaccttcat gaaggtcacc aaactgctgc atttagagac gtacttgttg
28081 ttttaaataa acgaacaaat taaaatgtct gataatggac cccaatcaaa ccaacgtagt
28141 gccccccgca ttacatttgg tggacccaca gattcaactg acaataacca gaatggagga
28201 cgcaatgggg caaggccaaa acagcgccga ccccaaggtt tacccaataa tactgcgtct
28261 tggttcacag ctctcactca gcatggcaag gaggaactta gattccctcg aggccagggc
28321 gttccaatca acaccaatag tggtccagat gaccaaattg gctactaccg aagagctacc
28381 cgacgagttc gtggtggtga cggcaaaatg aaagagctca gccccagatg gtacttctat
28441 tacctaggaa ctggcccaga agcttcactt ccctacggcg ctaacaaaga aggcatcgta
28501 tgggttgcaa ctgagggagc cttgaataca cccaaagacc acattggcac ccgcaatcct
28561 aataacaatg ctgccaccgt gctacaactt cctcaaggaa caacattgcc aaaaggcttc
28621 tacgcagagg gaagcagagg cggcagtcaa gcctcttctc gctcctcatc acgtagtcgc
28681 ggtaattcaa gaaattcaac tcctggcagc agtaggggaa ttctcctgc tcgaatggct
28741 agcggaggtg gtgaaactgc cctcgcgcta ttgctgctag acagattgaa ccagcttgag
28801 agcaaagttt ctggtaaagg ccaacaacaa caaggccaaa ctgtcactaa gaaatctgct
28861 gctgaggcat ctaaaaagcc tcgccaaaaa cgtactgcca caaaacagta caacgtcact
28921 caagcatttg ggagacgtgg tccagaacaa acccaaggaa atttcggga ccaagaccta
28981 atcagacaag gaactgatta caaacattgg ccgcaaattg cacaatttgc tccaagtgcc
29041 tctgcattct ttggaatgtc acgcattggc atggaagtca caccttcggg aacatggctg
29101 acttatcatg gagccattaa attggatgac aaagatccac aattcaaaga caacgtcata
29161 ctgctgaaca agcacattga cgcatacaaa acattcccac caacagagcc taaaaaggac
29221 aaaaagaaaa agactgatga agctcagcct ttgccgcaga gacaaaagaa gcagccccact
29281 gtgactcttc ttcctgcggc tgacatggat gatttctcca gacaacttca aaattccatg
29341 agtggagctt ctgctgattc aactcaggca taaacactca tgatgaccac acaaggcaga
29401 tgggctatgt aaacgttttc gcaattccgt ttacgataca tagtctactc ttgtgcagaa
29461 tgaattctcg taactaaaca gcacaagtag gtttagttaa ctttaatctc acatagcaat
29521 ctttaatcaa tgtgtaacat tagggaggac ttgaaagagc caccacattt tcatcgaggc
29581 cacgcggagt acgatcgagg gtacagtgaa taatgctagg gagagctgcc tatatggaag
29641 agccctaatg tgtaaaatta attttagtag tgctatcccc atgtgatttt aatagcttct
29701 taggagaatg acaaaaaaaa aaaaaaaaa aaaaaa
```

FIG. 3 CONT'D

```
  1 - CTACCCAGGAAAAGCCAACCAACCTCGATCTCTTGTAGATCTGTTCTCTAAACGAACTTT -  60
    - L  P  R  K  S  Q  P  T  S  I  S  C  R  S  V  L  *  T  N  F
    -  Y  P  G  K  A  N  Q  P  R  S  L  V  D  L  F  S  K  R  T  L
    -   T  Q  E  K  P  T  N  L  D  L  L  *  I  C  S  L  N  E  L  *
 61 - AAAATCTGTGTAGCTGTCGCTCGGCTGCATGCCTAGTGCACCTACGCAGTATAAACAATA - 120
    - K  I  C  V  A  V  A  R  L  H  A  *  C  T  Y  A  V  *  T  I
    -  K  S  V  *  L  S  L  G  C  M  P  S  A  P  T  Q  Y  K  Q  *
    -   N  L  C  S  C  R  S  A  A  C  L  V  H  L  R  S  I  N  N  N
121 - ATAAATTTACTGTCGTTGACAAGAAACGAGTAACTCGTCCCTCTTCTGCAGACTGCTTA - 180
    - I  N  F  T  V  V  D  K  K  R  V  T  R  P  S  S  A  D  C  L
    -  *  I  L  L  S  L  T  R  N  E  *  L  V  P  L  L  Q  T  A  Y
    -   K  F  Y  C  R  *  Q  E  T  S  N  S  S  L  F  C  R  L  L  T
181 - CGGTTTCGTCCGTGTTGCAGTCGATCATCAGCATACCTAGGTTTCGTCCGGGTGTGACCG - 240
    - R  F  R  P  C  C  S  R  S  S  A  Y  L  G  F  V  R  V  *  P
    -  G  F  V  R  V  A  V  D  H  Q  H  T  *  V  S  S  G  C  D  R
    -   V  S  S  V  L  Q  S  I  I  S  I  P  R  F  R  P  G  V  T  E
241 - AAAGGTAAGATGGAGAGCCTTGTTCTTGGTGTCAACGAGAAAACACACGTCCAACTCAGT - 300
    - K  G  K  M  E  S  L  V  L  G  V  N  E  K  T  H  V  Q  L  S
    -  K  V  R  W  R  A  L  F  L  V  S  T  R  K  H  T  S  N  S  V
    -   R  *  D  G  E  P  C  S  W  C  Q  R  E  N  T  R  P  T  Q  F
301 - TTGCCTGTCCTTCAGGTTAGAGACGTGCTAGTGCGTGGCTTCGGGGACTCTGTGGAAGAG - 360
    - L  P  V  L  Q  V  R  D  V  L  V  R  G  F  G  D  S  V  E  E
    -  C  L  S  F  R  L  E  T  C  *  C  V  A  S  G  T  L  W  K  R
    -   A  C  P  S  G  *  R  R  A  S  A  W  L  R  G  L  C  G  R  G
361 - GCCCTATCGGAGGCACGTGAACACCTCAAAAATGGCACTTGTGGTCTAGTAGAGCTGGAA - 420
    - A  L  S  E  A  R  E  H  L  K  N  G  T  C  G  L  V  E  L  E
    -  P  Y  R  R  H  V  N  T  S  K  M  A  L  V  V  *  *  S  W  K
    -   P  I  G  G  T  *  T  P  Q  K  W  H  L  W  S  S  R  A  G  K
421 - AAAGGCGTACTGCCCCAGCTTGAACAGCCCTATGTGTTCATTAAACGTTCTGATGCCTTA - 480
    - K  G  V  L  P  Q  L  E  Q  P  Y  V  F  I  K  R  S  D  A  L
    -  K  A  Y  C  P  S  L  N  S  P  M  C  S  L  N  V  L  M  P  *
    -   R  R  T  A  P  A  *  T  A  L  C  V  H  *  T  F  *  C  L  K
481 - AGCACCAATCACGGCCACAAGGTCGTTGAGCTGGTTGCAGAAATGGACGGCATTCAGTAC - 540
    - S  T  N  H  G  H  K  V  V  E  L  V  A  E  M  D  G  I  Q  Y
    -  A  P  I  T  A  T  R  S  L  S  W  L  Q  K  W  T  A  F  S  T
    -   H  Q  S  R  P  Q  G  R  *  A  G  C  R  N  G  R  H  S  V  R
541 - GGTCGTAGCGGTATAACACTGGGAGTACTCGTGCCACATGTGGGCGAAACCCCAATTGCA - 600
    - G  R  S  G  I  T  L  G  V  L  V  P  H  V  G  E  T  P  I  A
    -  V  V  A  V  *  H  W  E  Y  S  C  H  M  W  A  K  P  Q  L  H
    -   S  *  R  Y  N  T  G  S  T  R  A  T  C  G  R  N  P  N  C  I
601 - TACCGCAATGTTCTTCTTCGTAAGAACGGTAATAAGGGAGCCGGTGGTCATAGCTATGGC - 660
    - Y  R  N  V  L  L  R  K  N  G  N  K  G  A  G  G  H  S  Y  G
    -  T  A  M  F  F  F  V  R  T  V  I  R  E  P  V  V  I  A  M  A
    -   P  Q  C  S  S  S  *  E  R  *  *  G  S  R  W  S  *  L  W  H
661 - ATCGATCTAAAGTCTTATGACTTAGGTGACGAGCTTGGCACTGATCCCATTGAAGATTAT - 720
    - I  D  L  K  S  Y  D  L  G  D  E  L  G  T  D  P  I  E  D  Y
    -  S  I  *  S  L  M  T  *  V  T  S  L  A  L  I  P  L  K  I  M
    -   R  S  K  V  L  *  L  R  *  R  A  W  H  *  S  H  *  R  L  *
721 - GAACAAAACTGGAACACTAAGCATGGCAGTGGTGCACTCCGTGAACTCACTCGTGAGCTC - 780
    - E  Q  N  W  N  T  K  H  G  S  G  A  L  R  E  L  T  R  E  L
    -  N  K  T  G  T  L  S  M  A  V  V  H  S  V  N  S  L  V  S  S
    -   T  K  L  E  H  *  A  W  Q  W  C  T  P  *  T  H  S  *  A  Q
781 - AATGGAGGTGCAGTCACTCGCTATGTCGACAACAATTTCTGTGGCCCAGATGGGTACCCT - 840
    - N  G  G  A  V  T  R  Y  V  D  N  N  F  C  G  P  D  G  Y  P
    -  M  E  V  Q  S  L  A  M  S  T  T  I  S  V  A  Q  M  G  T  L
    -   W  R  C  S  H  S  L  C  R  Q  Q  F  L  W  P  R  W  V  P  S
841 - CTTGATTGCATCAAAGATTTCTCGCACGCGCGGGCAAGTCAATGTGCACTCTTTCCGAA - 900
    - L  D  C  I  K  D  F  L  A  R  A  G  K  S  M  C  T  L  S  E
    -  L  I  A  S  K  I  F  S  H  A  R  A  S  Q  C  A  L  F  P  N
    -   *  L  H  Q  R  F  S  R  T  R  G  Q  V  N  V  H  S  F  R  T
```

FIG. 4

```
 901 - CAACTTGATTACATCGAGTCGAAGAGAGGTGTCTACTGCTGCCGTGACCATGAGCATGAA -  960
     -  Q  L  D  Y  I  E  S  K  R  G  V  Y  C  C  R  D  H  E  H  E
     -  N  L  I  T  S  S  R  R  E  V  S  T  A  A  V  T  M  S  M  K
     -  T  *  L  H  R  V  E  E  R  C  L  L  P  *  P  *  A  *  N
 961 - ATTGCCTGGTTCACTGAGCGCTCTGATAAGAGCTACGAGCACCAGACACCCTTCGAAATT - 1020
     -  I  A  W  F  T  E  R  S  D  K  S  Y  E  H  Q  T  P  F  E  I
     -  L  P  G  S  L  S  A  L  I  R  A  T  S  T  R  H  P  S  K  L
     -  C  L  V  H  *  A  L  *  *  E  L  R  A  P  D  T  L  R  N  *
1021 - AAGAGTGCCAAGAAATTTGACACTTTCAAAGGGGAATGCCCAAAGTTTGTGTTTCCTCTT - 1080
     -  K  S  A  K  K  F  D  T  F  K  G  E  C  P  K  F  V  F  P  L
     -  R  V  P  R  N  L  T  L  S  K  G  N  A  Q  S  L  C  F  L  L
     -  E  C  Q  E  I  *  H  F  Q  R  G  M  P  K  V  C  V  S  S  *
1081 - AACTCAAAAGTCAAAGTCATTCAACCACGTGTTGAAAAGAAAAAGACTGAGGGTTTCATG - 1140
     -  N  S  K  V  K  V  I  Q  P  R  V  E  K  K  K  T  E  G  F  M
     -  T  Q  K  S  K  S  F  N  H  V  L  K  R  K  R  L  R  V  S  W
     -  L  K  S  Q  S  H  S  T  T  C  *  K  E  K  D  *  G  F  H  G
1141 - GGGCGTATACGCTCTGTGTACCCTGTTGCATCTCCACAGGAGTGTAACAATATGCACTTG - 1200
     -  G  R  I  R  S  V  Y  P  V  A  S  P  Q  E  C  N  N  M  H  L
     -  G  V  Y  A  L  C  T  L  L  H  L  H  R  S  V  T  I  C  T  C
     -  A  Y  T  L  C  V  P  C  C  I  S  T  G  V  *  Q  Y  A  L  V
1201 - TCTACCTTGATGAAATGTAATCATTGCGATGAAGTTTCATGGCAGACGTGCGACTTTCTG - 1260
     -  S  T  L  M  K  C  N  H  C  D  E  V  S  W  Q  T  C  D  F  L
     -  L  P  *  *  N  V  I  I  A  M  K  F  H  G  R  R  A  T  F  *
     -  Y  L  D  E  M  *  S  L  R  *  S  F  M  A  D  V  R  L  S  E
1261 - AAAGCCACTTGTGAACATTGTGGCACTGAAAATTTAGTTATTGAAGGACCTACTACATGT - 1320
     -  K  A  T  C  E  H  C  G  T  E  N  L  V  I  E  G  P  T  T  C
     -  K  P  L  V  N  I  V  A  L  K  I  *  L  L  K  D  L  L  H  V
     -  S  H  L  *  T  L  W  H  *  K  F  S  Y  *  R  T  Y  Y  M  W
1321 - GGGTACCTACCTACTAATGCTGTAGTGAAAATGCCATGTCCTGCCTGTCAAGACCCAGAG - 1380
     -  G  Y  L  P  T  N  A  V  V  K  M  P  C  P  A  C  Q  D  P  E
     -  G  T  Y  L  L  M  L  *  *  K  C  H  V  L  P  V  K  T  Q  R
     -  V  P  T  Y  *  C  C  S  E  N  A  M  S  C  L  S  R  P  R  D
1381 - ATTGGACCTGAGCATAGTGTTGCAGATTATCACAACCACTCAAACATTGAAACTCGACTC - 1440
     -  I  G  P  E  H  S  V  A  D  Y  H  N  H  S  N  I  E  T  R  L
     -  L  D  L  S  I  V  L  Q  I  I  T  T  T  Q  T  L  K  L  D  S
     -  W  T  *  A  *  C  C  R  L  S  Q  P  L  K  H  *  N  S  T  P
1441 - CGCAAGGGAGGTAGGACTAGATGTTTTGGAGGCTGTGTGTTTGCCTATGTTGGCTGCTAT - 1500
     -  R  K  G  G  R  T  R  C  F  G  G  C  V  F  A  Y  V  G  C  Y
     -  A  R  E  V  G  L  D  V  L  E  A  V  C  L  P  M  L  A  A  I
     -  Q  G  R  *  D  *  M  F  W  R  L  C  V  C  L  C  W  L  L  *
1501 - AATAAGCGTGCCTACTGGGTTCCTCGTGCTAGTGCTGATATTGGCTCAGGCCATACTGGC - 1560
     -  N  K  R  A  Y  W  V  P  R  A  S  A  D  I  G  S  G  H  T  G
     -  I  S  V  P  T  G  F  L  V  L  V  L  I  L  A  Q  A  I  L  A
     -  *  A  C  L  L  G  S  S  C  *  C  *  Y  W  L  R  P  Y  W  H
1561 - ATTACTGGTGACAATGTGGAGACCTTGAATGAGGATCTCCTTGAGATACTGAGTCGTGAA - 1620
     -  I  T  G  D  N  V  E  T  L  N  E  D  L  L  E  I  L  S  R  E
     -  L  L  V  T  M  W  R  P  *  M  R  I  S  L  R  Y  *  V  V  N
     -  Y  W  *  Q  C  G  D  L  E  *  G  S  P  *  D  T  E  S  *  T
1621 - CGTGTTAACATTAACATTGTTGGCGATTTTCATTTGAATGAAGAGGTTGCCATCATTTTG - 1680
     -  R  V  N  I  N  I  V  G  D  F  H  L  N  E  E  V  A  I  I  L
     -  V  L  T  L  T  L  L  A  I  F  I  *  M  K  R  L  P  S  F  W
     -  C  *  H  *  H  C  W  R  F  S  F  E  *  R  G  C  H  H  F  G
1681 - GCATCTTTCTCTGCTTCTACAAGTGCCTTTATTGACACTATAAAGAGTCTTGATTACAAG - 1740
     -  A  S  F  S  A  S  T  S  A  F  I  D  T  I  K  S  L  D  Y  K
     -  H  L  S  L  L  L  Q  V  P  L  L  T  L  *  R  V  L  I  T  S
     -  I  F  L  C  F  Y  K  C  L  Y  *  H  Y  K  E  S  *  L  Q  V
1741 - TCTTTCAAAACCATTGTTGAGTCCTGCGGTAACTATAAAGTTACCAAGGGAAAGCCCGTA - 1800
     -  S  F  K  T  I  V  E  S  C  G  N  Y  K  V  T  K  G  K  P  V
     -  L  S  K  P  L  L  S  P  A  V  T  I  K  L  P  R  E  S  P  *
     -  F  Q  N  H  C  *  V  L  R  *  L  *  S  Y  Q  G  K  A  R  K
```

FIG. 4 Cont'd

```
1801 - AAAGGTGCTTGGAACATTGGACAACAGAGATCAGTTTTAACACCACTGTGTGGTTTTCCC - 1860
     -  K  G  A  W  N  I  G  Q  Q  R  S  V  L  T  P  L  C  G  F  P
     -  K  V  L  G  T  L  D  N  R  D  Q  F  *  H  H  C  V  V  F  P
     -  R  C  L  E  H  W  T  T  E  I  S  F  N  T  T  V  W  F  S  L
1861 - TCACAGGCTGCTGGTGTTATCAGATCAATTTTTGCGCGCACACTTGATGCAGCAAACCAC - 1920
     -  S  Q  A  A  G  V  I  R  S  I  F  A  R  T  L  D  A  A  N  H
     -  H  R  L  L  V  L  S  D  Q  F  L  R  A  H  L  M  Q  Q  T  T
     -  T  G  C  W  C  Y  Q  I  N  F  C  A  H  T  *  C  S  K  P  L
1921 - TCAATTCCTGATTTGCAAAGAGCAGCTGTCACCATACTTGATGGTATTTCTGAACAGTCA - 1980
     -  S  I  P  D  L  Q  R  A  A  V  T  I  L  D  G  I  S  E  Q  S
     -  Q  F  L  I  C  K  E  Q  L  S  P  Y  L  M  V  F  L  N  S  H
     -  N  S  *  F  A  K  S  S  C  H  H  T  *  W  Y  F  *  T  V  I
1981 - TTACGTCTTGTCGACGCCATGGTTTATACTTCAGACCTGCTCACCAACAGTGTCATTATT - 2040
     -  L  R  L  V  D  A  M  V  Y  T  S  D  L  L  T  N  S  V  I  I
     -  Y  V  L  S  T  P  W  F  I  L  Q  T  C  S  P  T  V  S  L  L
     -  T  S  C  R  R  H  G  L  Y  F  R  P  A  H  Q  Q  C  H  Y  Y
2041 - ATGGCATATGTAACTGGTGGTCTTGTACAACAGACTTCTCAGTGGTTGTCTAATCTTTTG - 2100
     -  M  A  Y  V  T  G  G  L  V  Q  Q  T  S  Q  W  L  S  N  L  L
     -  W  H  M  *  L  V  V  L  Y  N  R  L  L  S  G  C  L  I  F  W
     -  G  I  C  N  W  W  S  C  T  T  D  F  S  V  V  V  *  S  F  G
2101 - GGCACTACTGTTGAAAAACTCAGGCCTATCTTTGAATGGATTGAGGCGAAACTTAGTGCA - 2160
     -  G  T  T  V  E  K  L  R  P  I  F  E  W  I  E  A  K  L  S  A
     -  A  L  L  L  K  N  S  G  L  S  L  N  G  L  R  R  N  L  V  Q
     -  H  Y  C  *  K  T  Q  A  Y  L  *  M  D  *  G  E  T  *  C  R
2161 - GGAGTTGAATTTCTCAAGGATGCTTGGGAGATTCTCAAATTTCTCATTACAGGTGTTTTT - 2220
     -  G  V  E  F  L  K  D  A  W  E  I  L  K  F  L  I  T  G  V  F
     -  E  L  N  F  S  R  M  L  G  R  F  S  N  F  S  L  Q  V  F  L
     -  S  *  I  S  Q  G  C  L  G  D  S  Q  I  S  H  Y  R  C  F  *
2221 - GACATCGTCAAGGGTCAAATACAGGTTGCTTCAGATAACATCAAGGATTGTGTAAAATGC - 2280
     -  D  I  V  K  G  Q  I  Q  V  A  S  D  N  I  K  D  C  V  K  C
     -  T  S  S  R  V  K  Y  R  L  L  Q  I  T  S  R  I  V  *  N  A
     -  H  R  Q  G  S  N  T  G  C  F  R  *  H  Q  G  L  C  K  M  L
2281 - TTCATTGATGTTGTTAACAAGGCACTCGAAATGTGCATTGATCAAGTCACTATCGCTGGC - 2340
     -  F  I  D  V  V  N  K  A  L  E  M  C  I  D  Q  V  T  I  A  G
     -  S  L  M  L  L  T  R  H  S  K  C  A  L  I  K  S  L  S  L  A
     -  H  *  C  C  *  Q  G  T  R  N  V  H  *  S  S  H  Y  R  W  R
2341 - GCAAAGTTGCGATCACTCAACTTAGGTGAAGTCTTCATCGCTCAAAGCAAGGGACTTTAC - 2400
     -  A  K  L  R  S  L  N  L  G  E  V  F  I  A  Q  S  K  G  L  Y
     -  Q  S  C  D  H  S  T  *  V  K  S  S  S  L  K  A  R  D  F  T
     -  K  V  A  I  T  Q  L  R  *  S  L  H  R  S  K  Q  G  T  L  P
2401 - CGTCAGTGTATACGTGGCAAGGAGCAGCTGCAACTACTCATGCCTCTTAAGGCACCAAAA - 2460
     -  R  Q  C  I  R  G  K  E  Q  L  Q  L  L  M  P  L  K  A  P  K
     -  V  S  V  Y  V  A  R  S  S  C  N  Y  S  C  L  L  R  H  Q  K
     -  S  V  Y  T  W  Q  G  A  A  A  T  T  H  A  S  *  G  T  K  R
2461 - GAAGTAACCTTTCTTGAAGGTGATTCACATGACACAGTACTTACCTCTGAGGAGGTTGTT - 2520
     -  E  V  T  F  L  E  G  D  S  H  D  T  V  L  T  S  E  E  V  V
     -  K  *  P  F  L  K  V  I  H  M  T  Q  Y  L  P  L  R  R  L  F
     -  S  N  L  S  *  R  *  F  T  *  H  S  T  Y  L  *  G  G  C  S
2521 - CTCAAGAACGGTGAACTCGAAGCACTCGAGACGCCCGTTGATAGCTTCACAAATGGAGCT - 2580
     -  L  K  N  G  E  L  E  A  L  E  T  P  V  D  S  F  T  N  G  A
     -  S  R  T  V  N  S  K  H  S  R  R  P  L  I  A  S  Q  M  E  L
     -  Q  E  R  *  T  R  S  T  R  D  A  R  *  *  L  H  K  W  S  Y
2581 - ATCGTTGGCACACCAGTCTGTGTAAATGGCCTCATGCTCTTAGAGATTAAGGACAAAGAA - 2640
     -  I  V  G  T  P  V  C  V  N  G  L  M  L  L  E  I  K  D  K  E
     -  S  L  A  H  Q  S  V  *  M  A  S  C  S  *  R  L  R  T  K  N
     -  R  W  H  T  S  L  C  K  W  P  H  A  L  R  D  *  G  Q  R  T
2641 - CAATACTGCGCATTGTCTCCTGGTTTACTGGCTACAAACAATGTCTTTCGCTTAAAAGGG - 2700
     -  Q  Y  C  A  L  S  P  G  L  L  A  T  N  N  V  F  R  L  K  G
     -  N  T  A  H  C  L  L  V  Y  W  L  Q  T  M  S  F  A  *  K  G
     -  I  L  R  I  V  S  W  F  T  G  Y  K  Q  C  L  S  L  K  R  G
```

FIG. 4 Cont'd

```
2701 - GGTGCACCAATTAAAGGTGTAACCTTTGGAGAAGATACTGTTTGGGAAGTTCAAGGTTAC - 2760
     - G  A  P  I  K  G  V  T  F  G  E  D  T  V  W  E  V  Q  G  Y
     -  V  H  Q  L  K  V  *  P  L  E  K  I  L  F  G  K  F  K  V  T
     -   C  T  N  *  R  C  N  L  W  R  R  Y  C  L  G  S  S  R  L  Q
2761 - AAGAATGTGAGAATCACATTTGAGCTTGATGAACGTGTTGACAAAGTGCTTAATGAAAG - 2820
     - K  N  V  R  I  T  F  E  L  D  E  R  V  D  K  V  L  N  E  K
     -  R  M  *  E  S  H  L  S  L  M  N  V  L  T  K  C  L  M  K  S
     -   E  C  E  N  H  I  *  A  *  *  T  C  *  Q  S  A  *  *  K  V
2821 - TGCTCTGTCTACACTGTTGAATCCGGTACCGAAGTTACTGAGTTTGCATGTGTTGTAGCA - 2880
     - C  S  V  Y  T  V  E  S  G  T  E  V  T  E  F  A  C  V  V  A
     -  A  L  S  T  L  L  N  P  V  P  K  L  L  S  L  H  V  L  *  Q
     -   L  C  L  H  C  *  I  R  Y  R  S  Y  *  V  C  M  C  C  S  R
2881 - GAGGCTGTTGTGAAGACTTTACAACCAGTTTCTGATCTCCTTACCAACATGGGTATTGAT - 2940
     - E  A  V  V  K  T  L  Q  P  V  S  D  L  L  T  N  M  G  I  D
     -  R  L  L  *  R  L  Y  N  Q  F  L  I  S  L  P  T  W  V  L  I
     -   G  C  C  E  D  F  T  T  S  F  *  S  P  Y  Q  H  G  Y  *  S
2941 - CTTGATGAGTGGAGTGTAGCTACATTCTACTTATTTGATGATGCTGGTGAAGAAAACTTT - 3000
     - L  D  E  W  S  V  A  T  F  Y  L  F  D  D  A  G  E  E  N  F
     -  L  M  S  G  V  *  L  H  S  T  Y  L  M  M  L  V  K  K  T  F
     -   *  *  V  E  C  S  Y  I  L  L  I  *  *  C  W  *  R  K  L  F
3001 - TCATCACGTATGTATTGTTCCTTTTACCCTCCAGATGAGGAAGAAGAGGACGATGCAGAG - 3060
     - S  S  R  M  Y  C  S  F  Y  P  P  D  E  E  E  E  D  D  A  E
     -  H  H  V  C  I  V  P  F  T  L  Q  M  R  K  K  R  T  M  Q  S
     -   I  T  Y  V  L  F  L  L  P  S  R  *  G  R  R  G  R  C  R  V
3061 - TGTGAGGAAGAAGAAATTGATGAAACCTGTGAACATGAGTACGGTACAGAGGATGATTAT - 3120
     - C  E  E  E  E  I  D  E  T  C  E  H  E  Y  G  T  E  D  D  Y
     -  V  R  K  K  K  L  M  K  P  V  N  M  S  T  V  Q  R  M  I  I
     -   *  G  R  R  N  *  *  N  L  *  T  *  V  R  Y  R  G  *  L  S
3121 - CAAGGTCTCCCTCTGGAATTTGGTGCCTCAGCTGAAACAGTTCGAGTTGAGGAAGAAGAA - 3180
     - Q  G  L  P  L  E  F  G  A  S  A  E  T  V  R  V  E  E  E  E
     -  K  V  S  L  W  N  L  V  P  Q  L  K  Q  F  E  L  R  K  K  K
     -   R  S  P  S  G  I  W  C  L  S  *  N  S  S  S  *  G  R  R  R
3181 - GAGGAAGACTGGCTGGATGATACTACTGAGCAATCAGAGATTGAGCCAGAACCAGAACCT - 3240
     - E  E  D  W  L  D  D  T  T  E  Q  S  E  I  E  P  E  P  E  P
     -  R  K  T  G  W  M  I  L  L  S  N  Q  R  L  S  Q  N  Q  N  L
     -   G  R  L  A  G  *  Y  Y  *  A  I  R  D  *  A  R  T  R  T  Y
3241 - ACACCTGAAGAACCAGTTAATCAGTTTACTGGTTATTTAAAACTTACTGACAATGTTGCC - 3300
     - T  P  E  E  P  V  N  Q  F  T  G  Y  L  K  L  T  D  N  V  A
     -  H  L  K  N  Q  L  I  S  L  L  V  I  *  N  L  L  T  M  L  P
     -   T  *  R  T  S  *  S  V  Y  W  L  F  K  T  Y  *  Q  C  C  H
3301 - ATTAAATGTGTTGACATCGTTAAGGAGGCACAAAGTGCTAATCCTATGGTGATTGTAAAT - 3360
     - I  K  C  V  D  I  V  K  E  A  Q  S  A  N  P  M  V  I  V  N
     -  L  N  V  L  T  S  L  R  R  H  K  V  L  I  L  W  *  L  *  M
     -   *  M  C  *  H  R  *  G  G  T  K  C  *  S  Y  G  D  C  K  C
3361 - GCTGCTAACATACACCTGAAACATGGTGGTGGTGTAGCAGGTGCACTCAACAAGGCAACC - 3420
     - A  A  N  I  H  L  K  H  G  G  G  V  A  G  A  L  N  K  A  T
     -  L  L  T  Y  T  *  N  M  V  V  V  *  Q  V  H  S  T  R  Q  P
     -   C  *  H  T  P  E  T  W  W  W  C  S  R  C  T  Q  Q  G  N  Q
3421 - AATGGTGCCATGCAAAAGGAGAGTGATGATTACATTAAGCTAAATGGCCCTCTTACAGTA - 3480
     - N  G  A  M  Q  K  E  S  D  D  Y  I  K  L  N  G  P  L  T  V
     -  M  V  P  C  K  R  R  V  M  I  T  L  S  *  M  A  L  L  Q  *
     -   W  C  H  A  K  G  E  *  *  L  H  *  A  K  W  P  S  Y  S  R
3481 - GGAGGGTCTTGTTTGCTTTCTGGACATAATCTTGCTAAGAAGTGTCTGCATGTTGTTGGA - 3540
     - G  G  S  C  L  L  S  G  H  N  L  A  K  K  C  L  H  V  V  G
     -  E  G  L  V  C  F  L  D  I  I  L  L  R  S  V  C  M  L  L  D
     -   R  V  L  F  A  F  W  T  *  S  C  *  E  V  S  A  C  C  W  T
3541 - CCTAACCTAAATGCAGGTGAGGACATCCAGCTTCTTAAGGCAGCATATGAAAATTTCAAT - 3600
     - P  N  L  N  A  G  E  D  I  Q  L  L  K  A  A  Y  E  N  F  N
     -  L  T  *  M  Q  V  R  T  S  S  F  L  R  Q  H  M  K  I  S  I
     -   *  P  K  C  R  *  G  H  P  A  S  *  G  S  I  *  K  F  Q  F
```

FIG. 4 Cont'd

```
3601 - TCACAGGACATCTTACTTGCACCATTGTTGTCAGCAGGCATATTTGGTGCTAAACCACTT - 3660
     -  S  Q  D  I  L  L  A  P  L  L  S  A  G  I  F  G  A  K  P  L
     -  H  R  T  S  Y  L  H  H  C  C  Q  Q  A  Y  L  V  L  N  H  F
     -  T  G  H  L  T  C  T  I  V  V  S  R  H  I  W  C  *  T  T  S
3661 - CAGTCTTTACAAGTGTGCGTGCAGACGGTTCGTACACAGGTTTATATTGCAGTCAATGAC - 3720
     -  Q  S  L  Q  V  C  V  Q  T  V  R  T  Q  V  Y  I  A  V  N  D
     -  S  L  Y  K  C  A  C  R  R  F  V  H  R  F  I  L  Q  S  M  T
     -  V  F  T  S  V  R  A  D  G  S  Y  T  G  L  Y  C  S  Q  *  Q
3721 - AAAGCTCTTTATGAGCAGGTTGTCATGGATTATCTTGATAACCTGAAGCCTAGAGTGGAA - 3780
     -  K  A  L  Y  E  Q  V  V  M  D  Y  L  D  N  L  K  P  R  V  E
     -  K  L  F  M  S  R  L  S  W  I  I  L  I  T  *  S  L  E  W  K
     -  S  S  L  *  A  G  C  H  G  L  S  *  *  P  E  A  *  S  G  S
3781 - GCACCTAAACAAGAGGAGCCACCAAACACAGAAGATTCCAAAACTGAGGAGAAATCTGTC - 3840
     -  A  P  K  Q  E  E  P  P  N  T  E  D  S  K  T  E  E  K  S  V
     -  H  L  N  K  R  S  H  Q  T  Q  K  I  P  K  L  R  R  N  L  S
     -  T  *  T  R  G  A  T  K  H  R  R  F  Q  N  *  G  E  I  C  R
3841 - GTACAGAAGCCTGTCGATGTGAAGCCAAAAATTAAGGCCTGCATTGATGAGGTTACCACA - 3900
     -  V  Q  K  P  V  D  V  K  P  K  I  K  A  C  I  D  E  V  T  T
     -  Y  R  S  L  S  M  *  S  Q  K  L  R  P  A  L  M  R  L  P  Q
     -  T  E  A  C  R  C  E  A  K  N  *  G  L  H  *  *  G  Y  H  N
3901 - ACACTGGAAGAAACTAAGTTTCTTACCAATAAGTTACTCTTGTTTGCTGATATCAATGGT - 3960
     -  T  L  E  E  T  K  F  L  T  N  K  L  L  L  F  A  D  I  N  G
     -  H  W  K  K  L  S  F  L  P  I  S  Y  S  C  L  L  I  S  M  V
     -  T  G  R  N  *  V  S  Y  Q  *  V  T  L  V  C  *  Y  Q  W  *
3961 - AAGCTTTACCATGATTCTCAGAACATGCTTAGAGGTGAAGATATGTCTTTCCTTGAGAAG - 4020
     -  K  L  Y  H  D  S  Q  N  M  L  R  G  E  D  M  S  F  L  E  K
     -  S  F  T  M  I  L  R  T  C  L  E  V  K  I  C  L  S  L  R  R
     -  A  L  P  *  F  S  E  H  A  *  R  *  R  Y  V  F  P  *  E  G
4021 - GATGCACCTTACATGGTAGGTGATGTTATCACTAGTGGTGATATCACTTGTGTTGTAATA - 4080
     -  D  A  P  Y  M  V  G  D  V  I  T  S  G  D  I  T  C  V  V  I
     -  M  H  L  T  W  *  V  M  L  S  L  V  V  I  S  L  V  L  *  Y
     -  C  T  L  H  G  R  *  C  Y  H  *  W  *  Y  H  L  C  C  N  T
4081 - CCCTCCAAAAAGGCTGGTGGCACTACTGAGATGCTCTCAAGAGCTTTGAAGAAAGTGCCA - 4140
     -  P  S  K  K  A  G  G  T  T  E  M  L  S  R  A  L  K  K  V  P
     -  P  P  K  R  L  V  A  L  L  R  C  S  Q  E  L  *  R  K  C  Q
     -  L  Q  K  G  W  W  H  Y  *  D  A  L  K  S  F  E  E  S  A  S
4141 - GTTGATGAGTATATAACCACGTACCCTGGACAAGGATGTGCTGGTTATACACTTGAGGAA - 4200
     -  V  D  E  Y  I  T  T  Y  P  G  Q  G  C  A  G  Y  T  L  E  E
     -  L  M  S  I  *  P  R  T  L  D  K  D  V  L  V  I  H  L  R  K
     -  *  *  V  Y  N  H  V  P  W  T  R  M  C  W  L  Y  T  *  G  S
4201 - GCTAAGACTGCTCTTAAGAAATGCAAATCTGCATTTTATGTACTACCTTCAGAAGCACCT - 4260
     -  A  K  T  A  L  K  K  C  K  S  A  F  Y  V  L  P  S  E  A  P
     -  L  R  L  L  L  R  N  A  N  L  H  F  M  Y  Y  L  Q  K  H  L
     -  *  D  C  S  *  E  M  Q  I  C  I  L  C  T  T  F  R  S  T  *
4261 - AATGCTAAGGAAGAGATTCTAGGAACTGTATCCTGGAATTTGAGAGAAATGCTTGCTCAT - 4320
     -  N  A  K  E  E  I  L  G  T  V  S  W  N  L  R  E  M  L  A  H
     -  M  L  R  K  R  F  *  E  L  Y  P  G  I  *  E  K  C  L  L  M
     -  C  *  G  R  D  S  R  N  C  I  L  E  F  E  R  N  A  C  S  C
4321 - GCTGAAGAGACAAGAAAATTAATGCCTATATGCATGGATGTTAGAGCCATAATGGCAACC - 4380
     -  A  E  E  T  R  K  L  M  P  I  C  M  D  V  R  A  I  M  A  T
     -  L  K  R  Q  E  N  *  C  L  Y  A  W  M  L  E  P  *  W  Q  P
     -  *  R  D  K  K  I  N  A  Y  M  H  G  C  *  S  H  N  G  N  H
4381 - ATCCAACGTAAGTATAAAGGAATTAAAATTCAAGAGGGCATCGTTGACTATGGTGTCCGA - 4440
     -  I  Q  R  K  Y  K  G  I  K  I  Q  E  G  I  V  D  Y  G  V  R
     -  S  N  V  S  I  K  E  L  K  F  K  R  A  S  L  T  M  V  S  D
     -  P  T  *  V  *  R  N  *  N  S  R  G  H  R  *  L  W  C  P  I
4441 - TTCTTCTTTTATACTAGTAAAGAGCCTGTAGCTTCTATTATTACGAAGCTGAACTCTCTA - 4500
     -  F  F  F  Y  T  S  K  E  P  V  A  S  I  I  T  K  L  N  S  L
     -  S  S  F  I  L  V  K  S  L  *  L  L  L  R  S  *  T  L  *
     -  L  L  L  Y  *  *  R  A  C  S  F  Y  Y  Y  E  A  E  L  S  K
```

FIG. 4 Cont'd

```
4501 - AATGAGCCGCTTGTCACAATGCCAATTGGTTATGTGACACATGGTTTTAATCTTGAAGAG - 4560
     - N  E  P  L  V  T  M  P  I  G  Y  V  V  T  H  G  F  N  L  E  E
     -  M  S  R  L  S  Q  C  Q  L  V  M  *  H  M  V  L  I  L  K  R
     -   *  A  A  C  H  N  A  N  W  L  C  D  T  W  F  *  S  *  R  G
4561 - GCTGCGCGCTGTATGCGTTCTCTTAAAGCTCCTGCCGTAGTGTCAGTATCATCACCAGAT - 4620
     - A  A  R  C  M  R  S  L  K  A  P  A  V  V  S  V  S  S  P  D
     -  L  R  A  V  C  V  L  L  K  L  L  P  *  C  Q  Y  H  H  Q  M
     -   C  A  L  Y  A  F  S  *  S  S  C  R  S  V  S  I  I  T  R  C
4621 - GCTGTTACTACATATAATGGATACCTCACTTCGTCATCAAAGACATCTGAGGAGCACTTT - 4680
     - A  V  T  T  Y  N  G  Y  L  T  S  S  S  K  T  S  E  E  H  F
     -  L  L  L  H  I  M  D  T  S  L  R  H  Q  R  H  L  R  S  T  L
     -   C  Y  Y  I  *  W  I  P  H  F  V  I  K  D  I  *  G  A  L  C
4681 - GTAGAAACAGTTTCTTTGGCTGGCTCTTACAGAGATTGGTCCTATTCAGGACAGCGTACA - 4740
     - V  E  T  V  S  L  A  G  S  Y  R  D  W  S  Y  S  G  Q  R  T
     -  *  K  Q  F  L  W  L  A  L  T  E  I  G  P  I  Q  D  S  V  Q
     -   R  N  S  F  F  G  W  L  L  Q  R  L  V  L  F  R  T  A  Y  R
4741 - GAGTTAGGTGTTGAATTTCTTAAGCGTGGTGACAAAATTGTGTACCACACTCTGGAGAGC - 4800
     - E  L  G  V  E  F  L  K  R  G  D  K  I  V  Y  H  T  L  E  S
     -  S  *  V  L  N  F  L  S  V  V  T  K  L  C  T  T  L  W  R  A
     -   V  R  C  *  I  S  *  A  W  *  Q  N  C  V  P  H  S  G  E  P
4801 - CCCGTCGAGTTTCATCTTGACGGTGAGGTTCTTTCACTTGACAAACTAAAGAGTCTCTTA - 4860
     - P  V  E  F  H  L  D  G  E  V  L  S  L  D  K  L  K  S  L  L
     -  P  S  S  F  I  L  T  V  R  F  F  H  L  T  N  *  R  V  S  Y
     -   R  R  V  S  S  *  R  *  G  S  F  T  *  Q  T  K  E  S  L  I
4861 - TCCCTGCGGGAGGTTAAGACTATAAAAGTGTTCACAACTGTGGACAACACTAATCTCCAC - 4920
     - S  L  R  E  V  K  T  I  K  V  F  T  T  V  D  N  T  N  L  H
     -  P  C  G  R  L  R  L  *  K  C  S  Q  L  W  T  T  L  I  S  T
     -   P  A  G  G  *  D  Y  K  S  V  H  N  C  G  Q  H  *  S  P  H
4921 - ACACAGCTTGTGGATATGTCTATGACATATGGACAGCAGTTTGGTCCAACATACTTGGAT - 4980
     - T  Q  L  V  D  M  S  M  T  Y  G  Q  Q  F  G  P  T  Y  L  D
     -  H  S  L  W  I  C  L  *  H  M  D  S  S  L  V  Q  H  T  W  M
     -   T  A  C  G  Y  V  V  Y  D  I  W  T  A  V  W  S  N  I  L  G  W
4981 - GGTGCTGATGTTACAAAAATTAAACCTCATGTAAATCATGAGGGTAAGACTTTCTTTGTA - 5040
     - G  A  D  V  T  K  I  K  P  H  V  N  H  E  G  K  T  F  F  V
     -  V  L  M  L  Q  K  L  N  L  M  *  I  M  R  V  R  L  S  L  Y
     -   C  *  C  Y  K  N  *  T  S  C  K  S  *  G  *  D  F  L  C  T
5041 - CTACCTAGTGATGACACACTACGTAGTGAAGCTTTCGAGTACTACCATACTCTTGATGAG - 5100
     - L  P  S  D  D  T  L  R  S  E  A  F  E  Y  Y  H  T  L  D  E
     -  Y  L  V  M  T  H  Y  V  V  K  L  S  S  T  T  I  L  L  M  R
     -   T  *  *  *  H  T  T  *  *  S  F  R  V  L  P  Y  S  *  *  E
5101 - AGTTTTCTTGGTAGGTACATGTCTGCTTTAAACCACACAAAGAAATGGAAATTTCCTCAA - 5160
     - S  F  L  G  R  Y  M  S  A  L  N  H  T  K  K  W  K  F  P  Q
     -  V  F  L  V  G  T  C  L  L  *  T  T  Q  R  N  G  N  F  L  K
     -   F  S  W  *  V  H  V  C  F  K  P  H  K  E  M  E  I  S  S  S
5161 - GTTGGTGGTTTAACTTCAATTAAATGGGCTGATAACAATTGTTATTTGTCTAGTGTTTTA - 5220
     - V  G  G  L  T  S  I  K  W  A  D  N  N  C  Y  L  S  S  V  L
     -  L  V  V  *  L  Q  L  N  G  L  I  T  I  V  I  C  L  V  F  Y
     -   W  W  F  N  F  N  *  M  G  *  *  Q  L  L  F  V  *  C  F  I
5221 - TTAGCACTTCAACAGCTTGAAGTCAAATTCAATGCACCAGCACTTCAAGAGGCTTATTAT - 5280
     - L  A  L  Q  Q  L  E  V  K  F  N  A  P  A  L  Q  E  A  Y  Y
     -  *  H  F  N  S  L  K  S  N  S  M  H  Q  H  F  K  R  L  I  I
     -   S  T  S  T  A  *  S  Q  I  Q  C  T  S  T  S  R  G  L  L  *
5281 - AGAGCCCGTGCTGGTGATGCTGCTAACTTTTGTGCACTCATACTCGCTTACAGTAATAAA - 5340
     - R  A  R  A  G  D  A  A  N  F  C  A  L  I  L  A  Y  S  N  K
     -  E  P  V  L  V  M  L  L  T  F  V  H  S  Y  S  L  T  V  I  K
     -   S  P  C  W  *  C  C  *  L  L  C  T  H  T  R  L  Q  *  *  N
5341 - ACTGTTGGCGAGCTTGGTGATGTCAGAGAAACTATGACCCATCTTCTACAGCATGCTAAT - 5400
     - T  V  G  E  L  G  D  V  R  E  T  M  T  H  L  L  Q  H  A  N
     -  L  L  A  S  L  V  M  S  E  K  L  *  P  I  F  Y  S  M  L  I
     -   C  W  R  A  W  *  C  Q  R  N  Y  D  P  S  S  T  A  C  *  F
```

FIG. 4 Cont'd

```
5401 - TTGGAATCTGCAAAGCGAGTTCTTAATGTGGTGTGTAAACATTGTGGTCAGAAAACTACT - 5460
     - L  E  S  A  K  R  V  L  N  V  V  C  K  H  C  G  Q  K  T  T
     -  W  N  L  Q  S  E  F  L  M  W  C  V  N  I  V  V  R  K  L  L
     -   G  I  C  K  A  S  S  *  C  G  V  *  T  L  W  S  E  N  Y  Y
5461 - ACCTTAACGGTGTAGAAGCTGTGATGTATATGGGTACTCTATCTTATGATAATCTTAAG - 5520
     - T  L  T  G  V  E  A  V  M  Y  M  G  T  L  S  Y  D  N  L  K
     -  P  *  R  V  *  K  L  *  C  I  W  V  L  Y  L  M  I  I  L  R
     -   L  N  G  C  R  S  C  D  V  Y  G  Y  S  I  L  *  *  S  *  D
5521 - ACAGGTGTTTCCATTCCATGTGTGTGTGGTCGTGATGCTACACAATATCTAGTACAACAA - 5580
     - T  G  V  S  I  P  C  V  C  G  R  D  A  T  Q  Y  L  V  Q  Q
     -  Q  V  F  P  F  H  V  C  V  V  V  M  L  H  N  I  *  Y  N  K
     -   R  C  F  H  S  M  C  V  W  S  *  C  Y  T  I  S  S  T  T  R
5581 - GAGTCTTCTTTTGTTATGATGTCTGCACCACCTGCTGAGTATAAATTACAGCAAGGTACA - 5640
     - E  S  S  F  V  M  M  S  A  P  P  A  E  Y  K  L  Q  Q  G  T
     -  S  L  L  L  *  C  L  H  H  L  L  S  I  N  Y  S  K  V  H
     -   V  F  F  C  Y  D  V  C  T  T  C  *  V  *  I  T  A  R  Y  I
5641 - TTCTTATGTGCGAATGAGTACACTGGTAACTATCAGTGTGGTCATTACACTCATATAACT - 5700
     - F  L  C  A  N  E  Y  T  G  N  Y  Q  C  G  H  Y  T  H  I  T
     -  S  Y  V  R  M  S  T  L  V  T  I  S  V  V  I  T  L  I  *  L
     -   L  M  C  E  *  V  H  W  *  L  S  V  W  S  L  H  S  Y  N  C
5701 - GCTAAGGAGACCCTCTATCGTATTGACGGAGCTCACCTTACAAAGATGTCAGAGTACAAA - 5760
     - A  K  E  T  L  Y  R  I  D  G  A  H  L  T  K  M  S  E  Y  K
     -  L  R  R  P  S  I  V  L  T  E  L  T  L  Q  R  C  Q  S  T  K
     -   *  G  D  P  L  S  Y  *  R  S  S  P  Y  K  D  V  R  V  Q  R
5761 - GGACCAGTGACTGATGTTTTCTACAAGGAAACATCTTACACTACAACCATCAAGCCTGTG - 5820
     - G  P  V  T  D  V  F  Y  K  E  T  S  Y  T  T  T  I  K  P  V
     -  D  Q  *  L  M  F  S  T  R  K  H  L  T  L  Q  P  S  S  L  C
     -   T  S  D  *  C  F  L  Q  G  N  I  L  H  Y  N  H  Q  A  C  V
5821 - TCGTATAAACTCGATGGAGTTACTTACACAGAGATTGAACCAAAATTGGATGGGTATTAT - 5880
     - S  Y  K  L  D  G  V  T  Y  T  E  I  E  P  K  L  D  G  Y  Y
     -  R  I  N  S  M  E  L  L  T  Q  R  L  N  Q  N  W  M  G  I  I
     -   V  *  T  R  W  S  Y  L  H  R  D  *  T  K  I  G  W  V  L  *
5881 - AAAAAGGATAATGCTTACTATACAGAGCAGCCTATAGACCTTGTACCAACTCAACCATTA - 5940
     - K  K  D  N  A  Y  Y  T  E  Q  P  I  D  L  V  P  T  Q  P  L
     -  K  R  I  M  L  T  I  Q  S  S  L  *  T  L  Y  Q  L  N  H  Y
     -   K  G  *  C  L  L  Y  R  A  A  Y  R  P  C  T  N  S  T  I  T
5941 - CCAAATGCGAGTTTTGATAATTTCAAACTCACATGTTCTAACACAAAATTTGCTGATGAT - 6000
     - P  N  A  S  F  D  N  F  K  L  T  C  S  N  T  K  F  A  D  D
     -  Q  M  R  V  L  I  I  S  N  S  H  V  L  T  Q  N  L  L  M  I
     -   K  C  E  F  *  *  F  Q  T  H  M  F  *  H  K  I  C  *  *  F
6001 - TTAAATCAAATGACAGGCTTCACAAAGCCAGCTTCACGAGAGCTATCTGTCACATTCTTC - 6060
     - L  N  Q  M  T  G  F  T  K  P  A  S  R  E  L  S  V  T  F  F
     -  *  I  K  *  Q  A  S  Q  S  Q  L  H  E  S  Y  L  S  H  S  S
     -   K  S  N  D  R  L  H  K  A  S  F  T  R  A  I  C  H  I  L  P
6061 - CCAGACTTGAATGGCGATGTAGTGGCTATTGACTATAGACACTATTCAGCGAGTTTCAAG - 6120
     - P  D  L  N  G  D  V  V  A  I  D  Y  R  H  Y  S  A  S  F  K
     -  Q  T  *  M  A  M  *  W  L  L  T  I  D  T  I  Q  R  V  S  R
     -   R  L  E  W  R  C  S  G  Y  *  L  *  T  L  F  S  E  F  Q  E
6121 - AAAGGTGCTAAATTACTGCATAAGCCAATTGTTTGGCACATTAACCAGGCTACAACCAAG - 6180
     - K  G  A  K  L  L  H  K  P  I  V  W  H  I  N  Q  A  T  T  K
     -  K  V  L  N  Y  C  I  S  Q  L  F  G  T  L  T  R  L  Q  P  R
     -   R  C  *  I  T  A  *  A  N  C  L  A  H  *  P  G  Y  N  Q  D
6181 - ACAACGTTCAAACCAAACACTTGGTGTTTACGTTGTCTTTGGAGTACAAAGCCAGTAGAT - 6240
     - T  T  F  K  P  N  T  W  C  L  R  C  L  W  S  T  K  P  V  D
     -  Q  R  S  N  Q  T  L  G  V  Y  V  V  F  G  V  Q  S  Q  *  I
     -   N  V  Q  T  K  H  L  V  F  T  L  S  L  E  Y  K  A  S  R  Y
6241 - ACTTCAAATTCATTTGAAGTTCTGGCAGTAGAAGACACACAAGGAATGGACAATCTTGCT - 6300
     - T  S  N  S  F  E  V  L  A  V  E  D  T  Q  G  M  D  N  L  A
     -  L  Q  I  H  L  K  F  W  Q  *  K  T  H  K  E  W  T  I  L  L
     -   F  K  F  I  *  S  S  G  S  R  R  H  T  R  N  G  Q  S  C  L
```

FIG. 4 Cont'd

```
6301 - TGTGAAAGTCAACAACCCACCTCTGAAGAAGTAGTGGAAAATCCTACCATACAGAAGGAA - 6360
     -  C E S Q Q P T S E E V V E N P T I Q K E
     -   V K V N N P P L K K * W K I L P Y R R K
     -    * K S T T H L * R S S G K S Y H T E G S
6361 - GTCATAGAGTGTGACGTGAAAACTACCGAAGTTGTAGGCAATGTCATACTTAAACCATCA - 6420
     -  V I E C D V K T T E V V G N V I L K P S
     -   S * S V T * K L P K L * A M S Y L N H Q
     -    H R V * R E N Y R S C R Q C H T * T I R
6421 - GATGAAGGTGTTAAAGTAACACAAGAGTTAGGTCATGAGGATCTTATGGCTGCTTATGTG - 6480
     -  D E G V K V T Q E L G H E D L M A A Y V
     -   M K V L K * H K S * V M R I L W L L M W
     -    * R C * S N T R V R S * G S Y G C L C G
6481 - GAAAACACAAGCATTACCATTAAGAAACCTAATGAGCTTTCACTAGCCTTAGGTTTAAAA - 6540
     -  E N T S I T I K K P N E L S L A L G L K
     -   K T Q A L P L R N L M S F H * P * V * K
     -    K H K H Y H * E T * * A F T S L R F K N
6541 - ACAATTGCCACTCATGGTATTGCTGCAATTAATAGTGTTCCTTGGAGTAAAATTTTGGCT - 6600
     -  T I A T H G I A A I N S V P W S K I L A
     -   Q L P L M V L L Q L I V F L G V K F W L
     -    N C H S W Y C C N * * C S L E * N F G L
6601 - TATGTCAAACCATTCTTAGGACAAGCAGCAATTACAACATCAAATTGCGCTAAGAGATTA - 6660
     -  Y V K P F L G Q A A I T T S N C A K R L
     -   M S N H S * D K Q Q L Q H Q I A L R D *
     -    C Q T I L R T S S N Y N I K L R * E I S
6661 - GCACAACGTGTGTTTAACAATTATATGCCTTATGTGTTTACATTATTGTTCCAATTGTGT - 6720
     -  A Q R V F N N Y M P Y V F T L L F Q L C
     -   H N V C L T I I C L M C L H Y C S N C V
     -    T T C V * Q L Y A L C V Y I I V P I V Y
6721 - ACTTTTACTAAAAGTACCAATTCTAGAATTAGAGCTTCACTACCTACAACTATTGCTAAA - 6780
     -  T F T K S T N S R I R A S L P T T I A K
     -   L L L K V P I L E L E L H Y L Q L L L K
     -    F Y * K Y Q F * N * S F T T Y N Y C * K
6781 - AATAGTGTTAAGAGTGTTGCTAAATTATGTTTGGATGCCGGCATTAATTATGTGAAGTCA - 6840
     -  N S V K S V A K L C L D A G I N Y V K S
     -   I V L R V L L N Y V W M P A L I M * S H
     -    * C * E C C * I M F G C R H * L C E V T
6841 - CCCAAATTTTCTAAATTGTTCACAATCGCTATGTGGCTATTGTTGTTAAGTATTTGCTTA - 6900
     -  P K F S K L F T I A M W L L L L S I C L
     -   P N F L N C S Q S L C G Y C C * V F A *
     -    Q I F * I V H N R Y V A I V V K Y L L R
6901 - GGTTCTCTAATCTGTGTAACTGCTGCTTTTGGTGTACTCTTATCTAATTTTGGTGCTCCT - 6960
     -  G S L I C V T A A F G V L L S N F G A P
     -   V L * S V * L L L L V Y S Y L I L V L L
     -    F S N L C N C C F W C T L I * F W C S F
6961 - TCTTATTGTAATGGCGTTAGAGAATTGTATCTTAATTCGTCTAACGTTACTACTATGGAT - 7020
     -  S Y C N G V R E L Y L N S S N V T T M D
     -   L I V M A L E N C I L I R L T L L L W I
     -    L L * W R * R I V S * F V * R Y Y Y G F
7021 - TTCTGTGAAGGTTCTTTTCCTTGCAGCATTTGTTTAAGTGGATTAGACTCCCTTGATTCT - 7080
     -  F C E G S F P C S I C L S G L D S L D S
     -   S V K V L F L A A F V * V D * T P L I L
     -    L * R F F S L Q H L F K W I R L P * F L
7081 - TATCCAGCTCTTGAAACCATTCAGGTGACGATTTCATCGTACAAGCTAGACTTGACAATT - 7140
     -  Y P A L E T I Q V T I S S Y K L D L T I
     -   I Q L L K P F R * R F H R T S * T * Q F
     -    S S S * N H S G D D F I V Q A R L D N F
7141 - TTAGGTCTGGCCGCTGAGTGGGTTTTGGCATATATGTTGTTCACAAAATTCTTTTATTTA - 7200
     -  L G L A A E W V L A Y M L F T K F F Y L
     -   * V W P L S G F W H I C C S Q N S F I Y
     -    R S G R * V G F G I Y V V H K I L L F I
```

FIG. 4 Cont'd

```
7201 - TTAGGTCTTTCAGCTATAATGCAGGTGTTCTTTGGCTATTTTGCTAGTCATTTCATCAGC - 7260
     -   L  G  L  S  A  I  M  Q  V  F  F  G  Y  F  A  S  H  F  I  S
     -  *  V  F  Q  L  *  C  R  C  S  L  A  I  L  L  V  I  S  S  A
     -   R  S  F  S  Y  N  A  G  V  L  W  L  F  C  *  S  F  H  Q  Q
7261 - AATTCTTGGCTCATGTGGTTTATCATTAGTATTGTACAAATGGCACCCGTTTCTGCAATG - 7320
     -   N  S  W  L  M  W  F  I  I  S  I  V  Q  M  A  P  V  S  A  M
     -   I  L  G  S  C  G  L  S  L  V  L  Y  K  W  H  P  F  L  Q  W
     -   F  L  A  H  V  V  Y  H  *  Y  C  T  N  G  T  R  F  C  N  G
7321 - GTTAGGATGTACATCTTCTTTGCTTCTTTCTACTACATATGGAAGAGCTATGTTCATATC - 7380
     -   V  R  M  Y  I  F  F  A  S  F  Y  Y  I  W  K  S  Y  V  H  I
     -   L  G  C  T  S  S  L  L  L  S  T  T  Y  G  R  A  M  F  I  S
     -  *  D  V  H  L  L  C  F  F  L  L  H  M  E  E  L  C  S  Y  H
7381 - ATGGATGGTTGCACCTCTTCGACTTGCATGATGTGCTATAAGCGCAATCGTGCCACACGC - 7440
     -   M  D  G  C  T  S  S  T  C  M  M  C  Y  K  R  N  R  A  T  R
     -   W  M  V  A  P  L  R  L  A  *  C  A  I  S  A  I  V  P  H  A
     -   G  W  L  H  L  F  D  L  H  D  V  L  *  A  Q  S  C  H  T  R
7441 - GTTGAGTGTACAACTATTGTTAATGGCATGAAGAGATCTTTCTATGTCTATGCAAATGGA - 7500
     -   V  E  C  T  T  I  V  N  G  M  K  R  S  F  Y  V  Y  A  N  G
     -   L  S  V  Q  L  L  L  M  A  *  R  D  L  S  M  S  M  Q  M  E
     -  *  V  Y  N  Y  C  *  W  H  E  E  I  F  L  C  L  C  K  W  R
7501 - GGCCGTGGCTTCTGCAAGACTCACAATTGGAATTGTCTCAATTGTGACACATTTTGCACT - 7560
     -   G  R  G  F  C  K  T  H  N  W  N  C  L  N  C  D  T  F  C  T
     -   A  V  A  S  A  R  L  T  I  G  I  V  S  I  V  T  H  F  A  L
     -   P  W  L  L  Q  D  S  Q  L  E  L  S  Q  L  *  H  I  L  H  W
7561 - GGTAGTACATTCATTAGTGATGAAGTTGCTCGTGATTTGTCACTCCAGTTTAAAAGACCA - 7620
     -   G  S  T  F  I  S  D  E  V  A  R  D  L  S  L  Q  F  K  R  P
     -   V  V  H  S  L  V  M  K  L  L  V  I  C  H  S  S  L  K  D  Q
     -  *  Y  I  H  *  *  *  S  C  S  *  F  V  T  P  V  *  K  T  N
7621 - ATCAACCCTACTGACCAGTCATCGTATATTGTTGATAGTGTTGCTGTGAAAAATGGCGCG - 7680
     -   I  N  P  T  D  Q  S  S  Y  I  V  D  S  V  A  V  K  N  G  A
     -   S  T  L  L  T  S  H  R  I  L  L  I  V  L  L  *  K  M  A  R
     -   Q  P  Y  *  P  V  I  V  Y  C  *  *  C  C  C  E  K  W  R  A
7681 - CTTCACCTCTACTTTGACAAGGCTGGTCAAAAGACCTATGAGAGACATCCTCTCTCCCAT - 7740
     -   L  H  L  Y  F  D  K  A  G  Q  K  T  Y  E  R  H  P  L  S  H
     -   F  T  S  T  L  T  R  L  V  K  R  P  M  R  D  I  L  S  P  I
     -   S  P  L  L  *  Q  G  W  S  K  D  L  *  E  T  S  S  L  P  F
7741 - TTTGTCAATTTAGACAATTTGAGAGCTAACAACACTAAAGGTTCACTGCCTATTAATGTC - 7800
     -   F  V  N  L  D  N  L  R  A  N  N  T  K  G  S  L  P  I  N  V
     -   L  S  I  *  T  I  *  E  L  T  T  L  K  V  H  C  L  L  M  S
     -   C  Q  F  R  Q  F  E  S  *  Q  H  *  R  F  T  A  Y  *  C  H
7801 - ATAGTTTTTGATGGCAAGTCCAAATGCGACGAGTCTGCTTCTAAGTCTGCTTCTGTGTAC - 7860
     -   I  V  F  D  G  K  S  K  C  D  E  S  A  S  K  S  A  S  V  Y
     -  *  F  L  M  A  S  P  N  A  T  S  L  L  L  S  L  L  L  C  T
     -   S  F  *  W  Q  V  Q  M  R  R  V  C  F  *  V  C  F  C  V  L
7861 - TACAGTCAGCTGATGTGCCAACCTATTCTGTTGCTTGACCAAGCTCTTGTATCAGACGTT - 7920
     -   Y  S  Q  L  M  C  Q  P  I  L  L  L  D  Q  A  L  V  S  D  V
     -   T  V  S  *  C  A  N  L  F  C  C  L  T  K  L  L  Y  Q  T  L
     -   Q  S  A  D  V  P  T  Y  S  V  A  *  P  S  S  C  I  R  R  W
7921 - GGAGATAGTACTGAAGTTTCCGTTAAGATGTTTGATGCTTATGTCGACACCTTTTCAGCA - 7980
     -   G  D  S  T  E  V  S  V  K  M  F  D  A  Y  V  D  T  F  S  A
     -   E  I  V  L  K  F  P  L  R  C  L  M  L  S  M  T  P  F  Q  Q
     -   R  *  Y  *  S  F  R  *  D  V  *  C  L  C  R  H  L  F  S  N
7981 - ACTTTTAGTGTTCCTATGGAAAAACTTAAGGCACTTGTTGCTACAGCTCACAGCGAGTTA - 8040
     -   T  F  S  V  P  M  E  K  L  K  A  L  V  A  T  A  H  S  E  L
     -   L  L  V  F  L  W  K  N  L  R  H  L  L  L  Q  L  T  A  S  *
     -   F  *  C  S  Y  G  K  T  *  G  T  C  C  Y  S  S  Q  R  V  S
8041 - GCAAAGGGTGTAGCTTTAGATGGTGTCCTTTCTACATTCGTGTCAGCTGCCCGACAAGGT - 8100
     -   A  K  G  V  A  L  D  G  V  L  S  T  F  V  S  A  A  R  Q  G
     -   Q  R  V  *  L  *  M  V  S  F  L  H  S  C  Q  L  P  D  K  V
     -   K  G  C  S  F  R  W  C  P  F  Y  I  R  V  S  C  P  T  R  C
```

FIG. 4 Cont'd

```
8101 - GTTGTTGATACCGATGTTGACACAAAGGATGTTATTGAATGTCTCAAACTTTCACATCAC - 8160
     - V  V  D  T  D  V  D  T  K  D  V  I  E  C  L  K  L  S  H  H
     -  L  L  I  P  M  L  T  Q  R  M  L  L  N  V  S  N  F  H  I  T
     -   C  *  Y  R  C  *  H  K  G  C  Y  *  M  S  Q  T  F  T  S  L
8161 - TCTGACTTAGAAGTGACAGGTGACAGTTGTAACAATTTCATGCTCACCTATAATAAGGTT - 8220
     - S  D  L  E  V  T  G  D  S  C  N  N  F  M  L  T  Y  N  K  V
     -  L  T  *  K  *  Q  V  T  V  V  T  I  S  C  S  P  I  I  R  L
     -   *  L  R  S  D  R  *  Q  L  *  Q  F  H  A  H  L  *  *  G  *
8221 - GAAAACATGACGCCCAGAGATCTTGGCGCATGTATTGACTGTAATGCAAGGCATATCAAT - 8280
     - E  N  M  T  P  R  D  L  G  A  C  I  D  C  N  A  R  H  I  N
     -  K  T  *  R  P  E  I  L  A  H  V  L  T  V  M  Q  G  I  S  M
     -   K  H  D  A  Q  R  S  W  R  M  Y  *  L  *  C  K  A  Y  Q  C
8281 - GCCCAAGTAGCAAAAAGTCACAATGTTTCACTCATCTGGAATGTAAAAGACTACATGTCT - 8340
     - A  Q  V  A  K  S  H  N  V  S  L  I  W  N  V  K  D  Y  M  S
     -  P  K  *  Q  K  V  T  M  F  H  S  S  G  M  *  K  T  T  C  L
     -   P  S  S  K  K  S  Q  C  F  T  H  L  E  C  K  R  L  H  V  F
8341 - TTATCTGAACAGCTGCGTAAACAAATTCGTAGTGCTGCCAAGAAGAACAACATACCTTTT - 8400
     - L  S  E  Q  L  R  K  Q  I  R  S  A  A  K  K  N  N  I  P  F
     -  Y  L  N  S  C  V  N  K  F  V  V  L  P  R  R  T  T  Y  L  L
     -   I  *  T  A  A  *  T  N  S  *  C  C  Q  E  E  Q  H  T  F  *
8401 - AGACTAACTTGTGCTACAACTAGACAGGTTGTCAATGTCATAACTACTAAAATCTCACTC - 8460
     - R  L  T  C  A  T  T  R  Q  V  V  N  V  I  T  T  K  I  S  L
     -  D  *  L  V  L  Q  L  D  R  L  S  M  S  *  L  L  K  S  H  S
     -   T  N  L  C  Y  N  *  T  G  C  Q  C  H  N  Y  *  N  L  T  Q
8461 - AAGGGTGGTAAGATTGTTAGTACTTGTTTTAAACTTATGCTTAAGGCCACATTATTGTGC - 8520
     - K  G  G  K  I  V  S  T  C  F  K  L  M  L  K  A  T  L  L  C
     -  R  V  V  R  L  L  V  L  V  L  N  L  C  L  R  P  H  Y  C  A
     -   G  W  *  D  C  *  Y  L  F  *  T  Y  A  *  G  H  I  I  V  R
8521 - GTTCTTGCTGCATTGGTTTGTTATATCGTTATGCCAGTACATACATTGTCAATCCATGAT - 8580
     - V  L  A  A  L  V  C  Y  I  V  M  P  V  H  T  L  S  I  H  D
     -  F  L  L  H  W  F  V  I  S  L  C  Q  Y  I  H  C  Q  S  M  M
     -   S  C  C  I  G  L  L  Y  R  Y  A  S  T  Y  I  V  N  P  *  W
8581 - GGTTACACAAATGAAATCATTGGTTACAAAGCCATTCAGGATGGTGTCACTCGTGACATC - 8640
     - G  Y  T  N  E  I  I  G  Y  K  A  I  Q  D  G  V  T  R  D  I
     -  V  T  Q  M  K  S  L  V  T  K  P  F  R  M  V  S  L  V  T  S
     -   L  H  K  *  N  H  W  L  Q  S  H  S  G  W  C  H  S  *  H  H
8641 - ATTTCTACTGATGATTGTTTTGCAAATAAACATGCTGGTTTTGACGCATGGTTTAGCCAG - 8700
     - I  S  T  D  D  C  F  A  N  K  H  A  G  F  D  A  W  F  S  Q
     -  F  L  L  M  I  V  L  Q  I  N  M  L  V  L  T  H  G  L  A  S
     -   F  Y  *  *  L  F  C  K  *  T  C  W  F  *  R  M  V  *  P  A
8701 - CGTGGTGGTTCATACAAAAATGACAAAAGCTGCCCTGTAGTAGCTGCTATCATTACAAGA - 8760
     - R  G  G  S  Y  K  N  D  K  S  C  P  V  V  A  A  I  I  T  R
     -  V  V  V  H  T  K  M  T  K  A  A  L  *  *  L  L  S  L  Q  E
     -   W  W  F  I  Q  K  *  Q  K  L  P  C  S  S  C  Y  H  Y  K  R
8761 - GAGATTGGTTTCATAGTGCCTGGCTTACCGGGTACTGTGCTGAGAGCAATCAATGGTGAC - 8820
     - E  I  G  F  I  V  P  G  L  P  G  T  V  L  R  A  I  N  G  D
     -  R  L  V  S  *  C  L  A  Y  R  V  L  C  *  E  Q  S  M  V  T
     -   D  W  F  H  S  A  W  L  T  G  Y  C  A  E  S  N  Q  W  *  L
8821 - TTCTTGCATTTTCTACCTCGTGTTTTTAGTGCTGTTGGCAACATTTGCTACACACCTTCC - 8880
     - F  L  H  F  L  P  R  V  F  S  A  V  G  N  I  C  Y  T  P  S
     -  S  C  I  F  Y  L  V  F  L  V  L  L  A  T  F  A  T  H  L  P
     -   L  A  F  S  T  S  C  F  *  C  C  W  Q  H  L  L  H  T  F  Q
8881 - AAACTCATTGAGTATAGTGATTTTGCTACCTCTGCTTGCGTTCTTGCTGCTGAGTGTACA - 8940
     - K  L  I  E  Y  S  D  F  A  T  S  A  C  V  L  A  A  E  C  T
     -  N  S  L  S  I  V  I  L  L  P  L  L  A  F  L  L  L  S  V  Q
     -   T  H  *  V  *  *  F  C  Y  L  C  L  R  S  C  C  *  V  Y  N
8941 - ATTTTTAAGGATGCTATGGGCAAACCTGTGCCATATTGTTATGACACTAATTTGCTAGAG - 9000
     - I  F  K  D  A  M  G  K  P  V  P  Y  C  Y  D  T  N  L  L  E
     -  F  L  R  M  L  W  A  N  L  C  H  I  V  M  T  L  I  C  *  R
     -   F  *  G  C  Y  G  Q  T  C  A  I  L  L  *  H  *  F  A  R  G
```

FIG. 4 Cont'd

```
9001 - GGTTCTATTTCTTATAGTGAGCTTCGTCCAGACACTCGTTATGTGCTTATGGATGGTTCC - 9060
      -  G  S  I  S  Y  S  E  L  R  P  D  T  R  Y  V  L  M  D  G  S
      -    V  L  F  L  I  V  S  F  V  Q  T  L  V  M  C  L  W  M  V  P
      -      F  Y  F  L  *  *  A  S  S  R  H  S  L  C  A  Y  G  W  F  H
9061 - ATCATACAGTTCCTAACACTTACCTGGAGGGTTCTGTTAGAGTAGTAACAACTTTTGAT - 9120
      -  I  I  Q  F  P  N  T  Y  L  E  G  S  V  R  V  V  T  T  F  D
      -    S  Y  S  F  L  T  L  T  W  R  V  L  L  E  *  *  Q  L  L  M
      -      H  T  V  S  *  H  L  P  G  G  F  C  *  S  S  N  N  F  *  C
9121 - GCTGAGTACTGTAGACATGGTACATGCGAAAGGTCAGAAGTAGGTATTTGCCTATCTACC - 9180
      -  A  E  Y  C  R  H  G  T  C  E  R  S  E  V  G  I  C  L  S  T
      -    L  S  T  V  D  M  V  H  A  K  G  Q  K  *  V  F  A  Y  L  P
      -      *  V  L  *  T  W  Y  M  R  K  V  R  S  R  Y  L  P  I  Y  Q
9181 - AGTGGTAGATGGGTTCTTAATAATGAGCATTACAGAGCTCTATCAGGAGTTTTCTGTGGT - 9240
      -  S  G  R  W  V  L  N  N  E  H  Y  R  A  L  S  G  V  F  C  G
      -    V  V  D  G  F  L  I  M  S  I  T  E  L  Y  Q  E  F  S  V  V
      -      W  *  M  G  S  *  *  *  A  L  Q  S  S  I  R  S  F  L  W  C
9241 - GTTGATGCGATGAATCTCATAGCTAACATCTTTACTCCTCTTGTGCAACCTGTGGGTGCT - 9300
      -  V  D  A  M  N  L  I  A  N  I  F  T  P  L  V  Q  P  V  G  A
      -    L  M  R  *  I  S  *  L  T  S  L  L  L  C  N  L  W  V  L
      -      *  C  D  E  S  H  S  *  H  L  Y  S  S  C  A  T  C  G  C  F
9301 - TTAGATGTGTCTGCTTCAGTAGTGGCTGGTGGTATTATTGCCATATTGGTGACTTGTGCT - 9360
      -  L  D  V  S  A  S  V  V  A  G  G  I  I  A  I  L  V  T  C  A
      -    *  M  C  L  L  Q  *  W  L  V  V  L  L  P  Y  W  *  L  V  L
      -      R  C  V  C  F  S  S  G  W  W  Y  Y  C  H  I  G  D  L  C  C
9361 - GCCTACTACTTTATGAAATTCAGACGTGCTTTTGGTGAGTACAACCATGTTGTTGCTGCT - 9420
      -  A  Y  Y  F  M  K  F  R  R  A  F  G  E  Y  N  H  V  V  A  A
      -    P  T  T  L  *  N  S  D  V  L  L  V  S  T  T  M  L  L  L  L
      -      L  L  L  Y  E  I  Q  T  C  F  W  *  V  Q  P  C  C  C  C  *
9421 - AATGCACTTTTGTTTTTGATGTCTTTCACTATACTCTGTCTGGCACCAGCTTACAGCTTT - 9480
      -  N  A  L  L  F  L  M  S  F  T  I  L  C  L  A  P  A  Y  S  F
      -    M  H  F  C  F  *  C  L  S  L  Y  S  V  W  H  Q  L  T  A  F
      -      C  T  F  V  F  D  V  F  H  Y  T  L  S  G  T  S  L  Q  L  S
9481 - CTGCCGGGAGTCTACTCAGTCTTTTACTTGTACTTGACATTCTATTTCACCAATGATGTT - 9540
      -  L  P  G  V  Y  S  V  F  Y  L  Y  L  T  F  Y  F  T  N  D  V
      -    C  R  E  S  T  Q  S  F  T  C  T  *  H  S  I  S  P  M  M  F
      -      A  G  S  L  L  S  L  L  L  V  L  D  I  L  F  H  Q  *  C  F
9541 - TCATTCTTGGCTCACCTTCAATGGTTTGCCATGTTTTCTCCTATTGTGCCTTTTTGGATA - 9600
      -  S  F  L  A  H  L  Q  W  F  A  M  F  S  P  I  V  P  F  W  I
      -    H  S  W  L  T  F  N  G  L  P  C  F  L  L  L  C  L  F  G  *
      -      I  L  G  S  P  S  M  V  C  H  V  F  S  Y  C  A  F  L  D  N
9601 - ACAGCAATCTATGTATTCTGTATTTCTCTGAAGCACTGCCATTGGTTCTTTAACAACTAT - 9660
      -  T  A  I  Y  V  F  C  I  S  L  K  H  C  H  W  F  F  N  N  Y
      -    Q  Q  S  M  Y  S  V  F  L  *  S  T  A  I  G  S  L  T  T  I
      -      S  N  L  C  I  L  Y  F  S  E  A  L  P  L  V  L  *  Q  L  S
9661 - CTTAGGAAAAGAGTCATGTTTAATGGAGTTACATTTAGTACCTTCGAGGAGGCTGCTTTG - 9720
      -  L  R  K  R  V  M  F  N  G  V  T  F  S  T  F  E  E  A  A  L
      -    L  G  K  E  S  C  L  M  E  L  H  L  V  P  S  R  R  L  L  C
      -      *  E  K  S  H  V  *  W  S  Y  I  *  Y  L  R  G  G  C  F  V
9721 - TGTACCTTTTTGCTCAACAAGGAAATGTACCTAAAATTGCGTAGCGAGACACTGTTGCCA - 9780
      -  C  T  F  L  L  N  K  E  M  Y  L  K  L  R  S  E  T  L  L  P
      -    V  P  F  C  S  T  R  K  C  T  *  N  C  V  A  R  H  C  C  H
      -      Y  L  F  A  Q  Q  G  N  V  P  K  I  A  *  R  D  T  V  A  T
9781 - CTTACACAGTATAACAGGTATCTTGCTCTATATAACAAGTACAAGTATTTCAGTGGAGCC - 9840
      -  L  T  Q  Y  N  R  Y  L  A  L  Y  N  K  Y  K  Y  F  S  G  A
      -    L  H  S  I  T  G  I  L  L  Y  I  T  S  T  S  I  S  V  E  P
      -      Y  T  V  *  Q  V  S  C  S  I  *  Q  V  Q  V  F  Q  W  S  L
9841 - TTAGATACTACCAGCTATCGTGAAGCAGCTTGCTGCCACTTAGCAAAGGCTCTAAATGAC - 9900
      -  L  D  T  T  S  Y  R  E  A  A  C  C  H  L  A  K  A  L  N  D
      -    *  I  L  P  A  I  V  K  Q  L  A  A  T  *  Q  R  L  *  M  T
      -      R  Y  Y  Q  L  S  *  S  S  L  L  P  L  S  K  G  S  K  *  L
```

FIG. 4 Cont'd

```
9901  - TTTAGCAACTCAGGTGCTGATGTTCTCTACCAACCACCACAGACATCAATCACTTCTGCT  - 9960
      -  F  S  N  S  G  A  D  V  L  Y  Q  P  P  Q  T  S  I  T  S  A
      -  L  A  T  Q  V  L  M  F  S  T  N  H  H  R  H  Q  S  L  L  L
      -  *  Q  L  R  C  *  C  S  L  P  T  T  T  D  I  N  H  F  C  C
9961  - GTTCTGCAGAGTGGTTTTAGGAAAATGGCATTCCCGTCAGGCAAAGTTGAAGGGTGCATG  - 10020
      -  V  L  Q  S  G  F  R  K  M  A  F  P  S  G  K  V  E  G  C  M
      -  F  C  R  V  V  L  G  K  W  H  S  R  Q  A  K  L  K  G  A  W
      -  S  A  E  W  F  *  E  N  G  I  P  V  R  Q  S  *  R  V  H  G
10021 - GTACAAGTAACCTGTGGAACTACAACTCTTAATGGATTGTGGTTGGATGACACAGTATAC - 10080
      -  V  Q  V  T  C  G  T  T  T  L  N  G  L  W  L  D  D  T  V  Y
      -  Y  K  *  P  V  E  L  Q  L  L  M  D  C  G  W  M  T  Q  Y  T
      -  T  S  N  L  W  N  Y  N  S  *  W  I  V  V  G  *  H  S  I  L
10081 - TGTCCAAGACATGTCATTTGCACAGCAGAAGACATGCTTAATCCTAACTATGAAGATCTG - 10140
      -  C  P  R  H  V  I  C  T  A  E  D  M  L  N  P  N  Y  E  D  L
      -  V  Q  D  M  S  F  A  Q  Q  K  T  C  L  I  L  T  M  K  I  C
      -  S  K  T  C  H  L  H  S  R  R  H  A  *  S  *  L  *  R  S  A
10141 - CTCATTCGCAAATCCAACCATAGCTTTCTTGTTCAGGCTGGCAATGTTCAACTTCGTGTT - 10200
      -  L  I  R  K  S  N  H  S  F  L  V  Q  A  G  N  V  Q  L  R  V
      -  S  F  A  N  P  T  I  A  F  L  F  R  L  A  M  F  N  F  V  L
      -  H  S  Q  I  Q  P  *  L  S  C  S  G  W  Q  C  S  T  S  C  Y
10201 - ATTGGCCATTCTATGCAAAATTGTCTGCTTAGGCTTAAAGTTGATACTTCTAACCCTAAG - 10260
      -  I  G  H  S  M  Q  N  C  L  L  R  L  K  V  D  T  S  N  P  K
      -  L  A  I  L  C  K  I  V  C  L  G  L  K  L  I  L  L  T  L  R
      -  W  P  F  Y  A  K  L  S  A  *  A  *  S  *  Y  F  *  P  *  D
10261 - ACACCCAAGTATAAATTTGTCCGTATCCAACCTGGTCAAACATTTTCAGTTCTAGCATGC - 10320
      -  T  P  K  Y  K  F  V  R  I  Q  P  G  Q  T  F  S  V  L  A  C
      -  H  P  S  I  N  L  S  V  S  N  L  V  K  H  F  Q  F  *  H  A
      -  T  Q  V  *  I  C  P  Y  P  T  W  S  N  I  F  S  S  S  M  L
10321 - TACAATGGTTCACCATCTGGTGTTTATCAGTGTGCCATGAGACCTAATCATACCATTAAA - 10380
      -  Y  N  G  S  P  S  G  V  Y  Q  C  A  M  R  P  N  H  T  I  K
      -  T  M  V  H  H  L  V  F  I  S  V  P  *  D  L  I  I  P  L  K
      -  Q  W  F  T  I  W  C  L  S  V  C  H  E  T  *  S  Y  H  *  R
10381 - GGTTCTTTCCTTAATGGATCATGTGGTAGTGTTGGTTTTAACATTGATTATGATTGCGTG - 10440
      -  G  S  F  L  N  G  S  C  G  S  V  G  F  N  I  D  Y  D  C  V
      -  V  L  S  L  M  D  H  V  V  V  L  V  L  T  L  I  M  I  A  C
      -  F  F  P  *  W  I  M  W  *  C  W  F  *  H  *  L  *  L  R  V
10441 - TCTTTCTGCTATATGCATCATATGGAGCTTCCAACAGGAGTACACGCTGGTACTGACTTA - 10500
      -  S  F  C  Y  M  H  H  M  E  L  P  T  G  V  H  A  G  T  D  L
      -  L  S  A  I  C  I  I  W  S  F  Q  Q  E  Y  T  L  V  L  T  *
      -  F  L  L  Y  A  S  Y  G  A  S  N  R  S  T  R  W  Y  *  L  R
10501 - GAAGGTAAATTCTATGGTCCATTTGTTGACAGACAAACTGCACAGGCTGCAGGTACAGAC - 10560
      -  E  G  K  F  Y  G  P  F  V  D  R  Q  T  A  Q  A  A  G  T  D
      -  K  V  N  S  M  V  H  L  L  T  D  K  L  H  R  L  Q  V  Q  T
      -  R  *  I  L  W  S  I  C  *  Q  T  N  C  T  G  C  R  Y  R  H
10561 - ACAACCATAACATTAAATGTTTTGGCATGGCTGTATGCTGCTGTTATCAATGGTGATAGG - 10620
      -  T  T  I  T  L  N  V  L  A  W  L  Y  A  A  V  I  N  G  D  R
      -  Q  P  *  H  *  M  F  W  H  G  C  M  L  L  L  S  M  V  I  G
      -  N  H  N  I  K  C  F  G  M  A  V  C  C  C  Y  Q  W  *  *  V
10621 - TGGTTTCTTAATAGATTCACCACTACTTTGAATGACTTTAACCTTGTGGCAATGAAGTAC - 10680
      -  W  F  L  N  R  F  T  T  T  L  N  D  F  N  L  V  A  M  K  Y
      -  G  F  L  I  D  S  P  L  L  *  M  T  L  T  L  W  Q  *  S  T
      -  V  S  *  *  I  H  H  Y  F  E  *  L  *  P  C  G  N  E  V  Q
10681 - AACTATGAACCTTTGACACAAGATCATGTTGACATATTGGGACCTCTTTCTGCTCAAACA - 10740
      -  N  Y  E  P  L  T  Q  D  H  V  D  I  L  G  P  L  S  A  Q  T
      -  T  M  N  L  *  H  K  I  M  L  T  Y  W  D  L  F  L  L  K  Q
      -  L  *  T  F  D  T  R  S  C  *  H  I  G  T  S  F  C  S  N  R
10741 - GGAATTGCCGTCTTAGATATGTGTGCTGCTTTGAAAGAGCTGCTGCAGAATGGTATGAAT - 10800
      -  G  I  A  V  L  D  M  C  A  A  L  K  E  L  L  Q  N  G  M  N
      -  E  L  P  S  *  I  C  V  L  L  *  K  S  C  C  R  M  V  *  M
      -  N  C  R  L  R  Y  V  C  C  F  E  R  A  A  A  E  W  Y  E  W
```

FIG. 4 Cont'd

```
10801 - GGTCGTACTATCCTTGGTAGCACTATTTTAGAAGATGAGTTTACACCATTTGATGTTGTT - 10860
      - G  R  T  I  L  G  S  T  I  L  E  D  E  F  T  P  F  D  V  V
      - V  V  L  S  L  V  A  L  F  *  K  M  S  L  H  H  L  M  L  L
      - S  Y  Y  P  W  *  H  Y  F  R  R  *  V  Y  T  I  *  C  C  *
10861 - AGACAATGCTCTGGTGTTACCTTCCAAGGTAAGTTCAAGAAAATTGTTAAGGGCACTCAT - 10920
      - R  Q  C  S  G  V  T  F  Q  G  K  F  K  K  I  V  K  G  T  H
      - D  N  A  L  V  L  P  S  K  V  S  S  R  K  L  L  R  A  L  I
      - T  M  L  W  C  Y  L  P  R  *  V  Q  E  N  C  *  G  H  S  S
10921 - CATTGGATGCTTTTAACTTTCTTGACATCACTATTGATTCTTGTTCAAAGTACACAGTGG - 10980
      - H  W  M  L  L  T  F  L  T  S  L  L  I  L  V  Q  S  T  Q  W
      - I  G  C  F  *  L  S  *  H  H  Y  *  F  L  F  K  V  H  S  G
      - L  D  A  F  N  F  L  D  I  T  I  D  S  C  S  K  Y  T  V  V
10981 - TCACTGTTTTTCTTTGTTTACGAGAATGCTTTCTTGCCATTTACTCTTGGTATTATGGCA - 11040
      - S  L  F  F  F  V  Y  E  N  A  F  L  P  F  T  L  G  I  M  A
      - H  C  F  S  L  F  T  R  M  L  S  C  H  L  L  L  V  L  W  Q
      - T  V  F  L  C  L  R  E  C  F  L  A  I  Y  S  W  Y  Y  G  N
11041 - ATTGCTGCATGTGCTATGCTGCTTGTTAAGCATAAGCACGCATTCTTGTGCTTGTTTCTG - 11100
      - I  A  A  C  M  L  L  V  K  H  K  H  A  F  L  C  L  F  L
      - L  L  H  V  L  C  C  L  L  S  I  S  T  H  S  C  A  C  F  C
      - C  C  M  C  Y  A  A  C  *  A  *  A  R  I  L  V  L  V  S  V
11101 - TTACCTTCTCTTGCAACAGTTGCTTACTTTAATATGGTCTACATGCCTGCTAGCTGGGTG - 11160
      - L  P  S  L  A  T  V  A  Y  F  N  M  V  Y  M  P  A  S  W  V
      - Y  L  L  L  Q  Q  L  L  T  L  I  W  S  T  C  L  L  A  G  *
      - T  F  S  C  N  S  C  L  L  *  Y  G  L  H  A  C  *  L  G  D
11161 - ATGCGTATCATGACATGGCTTGAATTGGCTGACACTAGCTTGTCTGGTTATAGGCTTAAG - 11220
      - M  R  I  M  T  W  L  E  L  A  D  T  S  L  S  G  Y  R  L  K
      - C  V  S  *  H  G  L  N  W  L  T  L  A  C  L  V  I  G  L  R
      - A  Y  H  D  M  A  *  I  G  *  H  *  L  V  W  L  *  A  *  G
11221 - GATTGTGTTATGTATGCTTCAGCTTTAGTTTTGCTTATTCTCATGACAGCTCGCACTGTT - 11280
      - D  C  V  M  Y  A  S  A  L  V  L  L  I  L  M  T  A  R  T  V
      - I  V  L  C  M  L  Q  L  *  F  C  L  F  S  *  Q  L  A  L  F
      - L  C  Y  V  C  F  S  F  S  F  A  Y  S  H  D  S  S  H  C  L
11281 - TATGATGATGCTGCTAGACGTGTTTGGACACTGATGAATGTCATTACACTTGTTTACAAA - 11340
      - Y  D  D  A  A  R  R  V  W  T  L  M  N  V  I  T  L  V  Y  K
      - M  M  M  L  L  D  V  F  G  H  *  *  M  S  L  H  L  F  T  K
      - *  *  C  C  *  T  C  L  D  T  D  E  C  H  Y  T  C  L  Q  S
11341 - GTCTACTATGGTAATGCTTTAGATCAAGCTATTTCCATGTGGGCCTTAGTTATTTCTGTA - 11400
      - V  Y  Y  G  N  A  L  D  Q  A  I  S  M  W  A  L  V  I  S  V
      - S  T  M  V  M  L  *  I  K  L  F  P  C  G  P  *  L  F  L  *
      - L  L  W  *  C  F  R  S  S  Y  F  H  V  G  L  S  Y  F  C  N
11401 - ACCTCTAACTATTCTGGTGTCGTTACGACTATCATGTTTTTAGCTAGAGCTATAGTGTTT - 11460
      - T  S  N  Y  S  G  V  V  T  T  I  M  F  L  A  R  A  I  V  F
      - P  L  T  I  L  V  S  L  R  L  S  C  F  *  L  E  L  *  C  L
      - L  *  L  F  W  C  R  Y  D  Y  H  V  F  S  *  S  Y  S  V  C
11461 - GTGTGTGTTGAGTATTACCCATTGTTATTTATTACTGGCAACACCTTACAGTGTATCATG - 11520
      - V  C  V  E  Y  Y  P  L  L  F  I  T  G  N  T  L  Q  C  I  M
      - C  V  L  S  I  T  H  C  Y  L  L  A  T  P  Y  S  V  S  C
      - V  C  *  V  L  P  I  V  I  Y  Y  W  Q  H  L  T  V  Y  H  A
11521 - CTTGTTTATTGTTTCTTAGGCTATTGTTGCTGCTGCTACTTTGGCCTTTTCTGTTTACTC - 11580
      - L  V  Y  C  F  L  G  Y  C  C  C  C  Y  F  G  L  F  C  L  L
      - L  F  I  V  S  *  A  I  V  A  A  A  T  L  A  F  S  V  Y  S
      - C  L  L  F  L  R  L  L  L  L  L  L  W  P  F  L  F  T  Q
11581 - AACCGTTACTTCAGGCTTACTCTTGGTGTTTATGACTACTTGGTCTCTACACAAGAATTT - 11640
      - N  R  Y  F  R  L  T  L  G  V  Y  D  Y  L  V  S  T  Q  E  F
      - T  V  T  S  G  L  L  L  V  F  M  T  T  W  S  L  H  K  N  L
      - P  L  L  Q  A  Y  S  W  C  L  *  L  L  G  L  Y  T  R  I  *
11641 - AGGTATATGAACTCCCAGGGGCTTTTGCCTCCTAAGAGTAGTATTGATGCTTTCAAGCTT - 11700
      - R  Y  M  N  S  Q  G  L  L  P  P  K  S  S  I  D  A  F  K  L
      - G  I  *  T  P  R  G  F  C  L  L  R  V  V  L  M  L  S  S  L
      - V  Y  E  L  P  G  A  F  A  S  *  E  *  Y  *  C  F  Q  A  *
```

FIG. 4 Cont'd

```
11701 - AACATTAAGTTGTTGGGTATTGGAGGTAAACCATGTATCAAGGTTGCTACTGTACAGTCT - 11760
       - N  I  K  L  L  G  I  G  G  K  P  C  I  K  V  A  T  V  Q  S
       -  T  L  S  C  W  V  L  E  V  N  H  V  S  R  L  L  L  Y  S  L
       -   H  *  V  V  G  Y  W  R  *  T  M  Y  Q  G  C  Y  C  T  V  *
11761 - AAAATGTCTGACGTAAAGTGCACATCTGTGGTACTGCTCTCGGTTCTTCAACAACTTAGA - 11820
       - K  M  S  D  V  K  C  T  S  V  V  L  L  S  V  L  Q  Q  L  R
       -  K  C  L  T  *  S  A  H  L  W  Y  C  S  R  F  F  N  N  L  E
       -   N  V  *  R  K  V  H  I  C  G  T  A  L  G  S  S  T  T  *  S
11821 - GTAGAGTCATCTTCTAAATTGTGGGCACAATGTGTACAACTCCACAATGATATTCTTCTT - 11880
       - V  E  S  S  S  K  L  W  A  Q  C  V  Q  L  H  N  D  I  L  L
       -  *  S  H  L  L  N  C  G  H  N  V  Y  N  S  T  M  I  F  F  L
       -   R  V  I  F  *  I  V  G  T  M  C  T  T  P  Q  *  Y  S  S  C
11881 - GCAAAAGACACAACTGAAGCTTTCGAGAAGATGGTTTCTCTTTTGTCTGTTTTGCTATCC - 11940
       - A  K  D  T  T  E  A  F  E  K  M  V  S  L  L  S  V  L  L  S
       -  Q  K  T  Q  L  K  L  S  R  R  W  F  L  F  C  L  F  C  Y  P
       -   K  R  H  N  *  S  F  R  E  D  G  F  S  F  V  C  F  A  I  H
11941 - ATGCAGGGTGCTGTAGACATTAATAGGTTGTGCGAGGAAATGCTCGATAACCGTGCTACT - 12000
       - M  Q  G  A  V  D  I  N  R  L  C  E  E  M  L  D  N  R  A  T
       -  C  R  V  L  *  T  L  I  G  C  A  R  K  C  S  I  T  V  L  L
       -   A  G  C  C  R  H  *  *  V  V  R  G  N  A  R  *  P  C  Y  S
12001 - CTTCAGGCTATTGCTTCAGAATTTAGTTCTTTACCATCATATGCCGCTTATGCCACTGCC - 12060
       - L  Q  A  I  A  S  E  F  S  S  L  P  S  Y  A  A  Y  A  T  A
       -  F  R  L  L  L  Q  N  L  V  L  Y  H  H  M  P  L  M  P  L  P
       -   S  G  Y  C  F  R  I  *  F  F  T  I  I  C  R  L  C  H  C  P
12061 - CAGGAGGCCTATGAGCAGGCTGTAGCTAATGGTGATTCTGAAGTCGTTCTCAAAAAGTTA - 12120
       - Q  E  A  Y  E  Q  A  V  A  N  G  D  S  E  V  V  L  K  K  L
       -  R  R  P  M  S  R  L  *  L  M  V  I  L  K  S  F  S  K  S  *
       -   G  G  L  *  A  G  C  S  *  W  *  F  *  S  R  S  Q  K  V  K
12121 - AAGAAATCTTTGAATGTGGCTAAATCTGAGTTTGACCGTGATGCTGCCATGCAACGCAAG - 12180
       - K  K  S  L  N  V  A  K  S  E  F  D  R  D  A  A  M  Q  R  K
       -  R  N  L  *  M  W  L  N  L  S  L  T  V  M  L  P  C  N  A  S
       -   E  I  F  E  C  G  *  I  *  V  *  P  *  C  C  H  A  T  Q  V
12181 - TTGGAAAAGATGGCAGATCAGGCTATGACCCAAATGTACAAACAGGCAAGATCTGAGGAC - 12240
       - L  E  K  M  A  D  Q  A  M  T  Q  M  Y  K  Q  A  R  S  E  D
       -  W  K  R  W  Q  I  R  L  *  P  K  C  T  N  R  Q  D  L  R  T
       -   G  K  D  G  R  S  G  Y  D  P  N  V  Q  T  G  K  I  *  G  Q
12241 - AAGAGGGCAAAAGTAACTAGTGCTATGCAAACAATGCTCTTCACTATGCTTAGGAAGCTT - 12300
       - K  R  A  K  V  T  S  A  M  Q  T  M  L  F  T  M  L  R  K  L
       -  R  G  Q  K  *  L  V  L  C  K  Q  C  S  S  L  C  L  G  S  L
       -   E  G  K  S  N  *  C  Y  A  N  N  A  L  H  Y  A  *  E  A  *
12301 - GATAATGATGCACTTAACAACATTATCAACAATGCGCGTGATGGTTGTGTTCCACTCAAC - 12360
       - D  N  D  A  L  N  N  I  I  N  N  A  R  D  G  C  V  P  L  N
       -  I  M  M  H  L  T  T  L  S  T  M  R  V  M  V  V  F  H  S  T
       -   *  *  C  T  *  Q  H  Y  Q  Q  C  A  *  W  L  C  S  T  Q  H
12361 - ATCATACCATTGACTACAGCAGCCAAACTCATGGTTGTTGTCCCTGATTATGGTACCTAC - 12420
       - I  I  P  L  T  T  A  A  K  L  M  V  V  V  P  D  Y  G  T  Y
       -  S  Y  H  *  L  Q  Q  P  N  S  W  L  L  S  L  I  M  V  P  T
       -   H  T  I  D  Y  S  S  Q  T  H  G  C  C  P  *  L  W  Y  L  Q
12421 - AAGAACACTTGTGATGGTAACACCTTTACATATGCATCTGCACTCTGGGAAATCCAGCAA - 12480
       - K  N  T  C  D  G  N  T  F  T  Y  A  S  A  L  W  E  I  Q  Q
       -  R  T  L  V  M  V  T  P  L  H  M  H  L  S  G  K  S  S  K
       -   E  H  L  *  W  *  H  L  Y  I  C  I  C  T  L  G  N  P  A  S
12481 - GTTGTTGATGCGGATAGCAAGATTGTTCAACTTAGTGAAATTAACATGGACAATTCACCA - 12540
       - V  V  D  A  D  S  K  I  V  Q  L  S  E  I  N  M  D  N  S  P
       -  L  L  M  R  I  A  R  L  F  N  L  V  K  L  T  W  T  I  H  Q
       -   C  *  C  G  *  Q  D  C  S  T  *  *  N  *  H  G  Q  F  T  K
12541 - AATTTGGCTTGGCCTCTTATTGTTACAGCTCTAAGAGCCAACTCAGCTGTTAAACTACAG - 12600
       - N  L  A  W  P  L  I  V  T  A  L  R  A  N  S  A  V  K  L  Q
       -  I  W  L  G  L  L  L  L  Q  L  *  E  P  T  Q  L  L  N  Y  R
       -   F  G  L  A  S  Y  C  Y  S  S  K  S  Q  L  S  C  *  T  T  E
```

FIG. 4 Cont'd

```
12601 - AATAATGAACTGAGTCCAGTAGCACTACGACAGATGTCCTGTGCGGCTGGTACCACACAA - 12660
      -  N  N  E  L  S  P  V  A  L  R  Q  M  S  C  A  A  G  T  T  Q
      -  I  M  N  *  V  Q  *  H  Y  D  R  C  P  V  R  L  V  P  H  K
      -  *  *  T  E  S  S  S  T  T  T  D  V  L  C  G  W  Y  H  T  N
12661 - ACAGCTTGTACTGATGACAATGCACTTGCCTACTATAACAATTCGAAGGGAGGTAGGTTT - 12720
      -  T  A  C  T  D  D  N  A  L  A  Y  Y  N  N  S  K  G  G  R  F
      -  Q  L  V  L  M  T  M  H  L  P  T  I  T  I  R  R  E  V  G  L
      -  S  L  Y  *  *  Q  C  T  C  L  L  *  Q  F  E  G  R  *  V  C
12721 - GTGCTGGCATTACTATCAGACCACCAAGATCTCAAATGGGCTAGATTCCCTAAGAGTGAT - 12780
      -  V  L  A  L  L  S  D  H  Q  D  L  K  W  A  R  F  P  K  S  D
      -  C  W  H  Y  Y  Q  T  T  K  I  S  N  G  L  D  S  L  R  V  M
      -  A  G  I  T  I  R  P  P  R  S  Q  M  G  *  I  P  *  E  *  W
12781 - GGTACAGGTACAATTTACACAGAACTGGAACCACCTTGTAGGTTTGTTACAGACACACCA - 12840
      -  G  T  G  T  I  Y  T  E  L  P  P  C  R  F  V  T  D  T  P
      -  V  Q  V  Q  F  T  Q  N  W  N  H  L  V  G  L  L  Q  T  H  Q
      -  Y  R  Y  N  L  H  R  T  G  T  T  L  *  V  C  Y  R  H  T  K
12841 - AAAGGGCCTAAAGTGAAATACTTGTACTTCATCAAAGGCTTAAACAACCTAAATAGAGGT - 12900
      -  K  G  P  K  V  K  Y  L  Y  F  I  K  G  L  N  N  L  N  R  G
      -  K  G  L  K  *  N  T  C  T  S  S  K  A  *  T  T  *  I  E  V
      -  R  A  *  S  E  I  L  V  L  H  Q  R  L  K  Q  P  K  *  R  Y
12901 - ATGGTGCTGGGCAGTTTAGCTGCTACAGTACGTCTTCAGGCTGGAAATGCTACAGAAGTA - 12960
      -  M  V  L  G  S  L  A  A  T  V  R  L  Q  A  G  N  A  T  E  V
      -  W  C  W  A  V  *  L  L  Q  Y  V  F  R  L  E  M  L  Q  K  Y
      -  G  A  G  Q  F  S  C  Y  S  T  S  S  G  W  K  C  Y  R  S  T
12961 - CCTGCCAATTCAACTGTGCTTTCCTTCTGTGCTTTTGCAGTAGACCCTGCTAAAGCATAT - 13020
      -  P  A  N  S  T  V  L  S  F  C  A  F  A  V  D  P  A  K  A  Y
      -  L  P  I  Q  L  C  F  P  S  V  L  L  Q  *  T  L  L  K  H  I
      -  C  Q  F  N  C  A  F  L  L  C  F  C  S  R  P  C  *  S  I  *
13021 - AAGGATTACCTAGCAAGTGGAGGACAACCAATCACCAACTGTGTGAAGATGTTGTGTACA - 13080
      -  K  D  Y  L  A  S  G  G  Q  P  I  T  N  C  V  K  M  L  C  T
      -  R  I  T  *  Q  V  E  D  N  Q  S  P  T  V  *  R  C  C  V  H
      -  G  L  P  S  K  W  R  T  T  N  H  Q  L  C  E  D  V  V  Y  T
13081 - CACACTGGTACAGGACAGGCAATTACTGTAACACCAGAAGCTAACATGGACCAAGAGTCC - 13140
      -  H  T  G  T  G  Q  A  I  T  V  T  P  E  A  N  M  D  Q  E  S
      -  T  L  V  Q  D  R  Q  L  L  *  H  Q  K  L  T  W  T  K  S  P
      -  H  W  Y  R  T  G  N  Y  C  N  T  R  S  *  H  G  P  R  V  L
13141 - TTTGGTGGTGCTTCATGTTGTCTGTATTGTAGATGCCACATTGACCATCCAAATCCTAAA - 13200
      -  F  G  G  A  S  C  C  L  Y  C  R  C  H  I  D  H  P  N  P  K
      -  L  V  V  L  H  V  V  C  I  V  D  A  T  L  T  I  Q  I  L  K
      -  W  W  C  F  M  L  S  V  L  *  M  P  H  *  P  S  K  S  *  R
13201 - GGATTCTGTGACTTGAAAGGTAAGTACGTCCAAATACCTACCACTTGTGCTAATGACCCA - 13260
      -  G  F  C  D  L  K  G  K  Y  V  Q  I  P  T  T  C  A  N  D  P
      -  D  S  V  T  *  K  V  S  T  S  K  Y  L  P  L  V  L  M  T  Q
      -  I  L  *  L  E  R  *  V  R  P  N  T  Y  H  L  C  *  *  P  S
13261 - GTGGGTTTTACACTTAGAAACACAGTCTGTACCGTCTGCGGAATGTGGAAAGGTTATGGC - 13320
      -  V  G  F  T  L  R  N  T  V  C  T  V  C  G  M  W  K  G  Y  G
      -  W  V  L  H  L  E  T  Q  S  V  P  S  A  E  C  G  K  V  M  A
      -  G  F  Y  T  *  K  H  S  L  Y  R  L  R  N  V  E  R  L  W  L
13321 - TGTAGTTGTGACCAACTCCGCGAACCCTTGATGCAGTCTGCGGATGCATCAACGTTTTTA - 13380
      -  C  S  C  D  Q  L  R  E  P  L  M  Q  S  A  D  A  S  T  F  L
      -  V  V  V  T  N  S  A  N  P  *  C  S  L  R  M  H  Q  R  F  *
      -  *  L  *  P  T  P  R  T  L  D  A  V  C  G  C  I  N  V  F  K
13381 - AACGGGTTTGCGGTGTAAGTGCAGCCCGTCTTACACCGTGCGGCACAGGCACTAGTACTG - 13440
      -  N  G  F  A  V  *  V  Q  P  V  L  H  R  A  A  Q  A  L  V  L
      -  T  G  L  R  C  K  C  S  P  S  Y  T  V  R  H  R  H  *  Y  *
      -  R  V  C  G  V  S  A  A  R  L  T  P  C  G  T  G  T  S  T  D
13441 - ATGTCGTCTACAGGGCTTTTGATATTTACAACGAAAAAGTTGCTGGTTTTGCAAAGTTCC - 13500
      -  M  S  S  T  G  L  L  I  F  T  T  K  K  L  L  V  L  Q  S  S
      -  C  R  L  Q  G  F  *  Y  L  Q  R  K  S  C  W  F  C  K  V  P
      -  V  V  Y  R  A  F  D  I  Y  N  E  K  V  A  G  F  A  K  F  L
```

FIG. 4 Cont'd

```
13501 - TAAAAACTAATTGCTGTCGCTTCCAGGAGAAGGATGAGGAAGGCAATTTATTAGACTCTT - 13560
       - * K  L  I  A  V  A  S  R  R  R  M  R  K  A  I  Y  *  T  L
       -   K  N  *  L  L  S  L  P  G  E  G  *  G  R  Q  F  I  R  L  L
       -    K  T  N  C  C  R  F  Q  E  K  D  E  E  G  N  L  L  D  S  Y
13561 - ACTTTGTAGTTAAGAGGCATACTATGTCTAACTACCAACATGAAGAGACTATTTATAACT - 13620
       - T  L  *  L  R  G  I  L  C  L  T  T  N  M  K  R  L  F  I  T
       -   L  C  S  *  E  A  Y  Y  V  *  L  P  T  *  R  D  Y  L  *  L
       -    F  V  V  K  R  H  T  M  S  N  Y  Q  H  E  E  T  I  Y  N  L
13621 - TGGTTAAAGATTGTCCAGCGGTTGCTGTCCATGACTTTTTCAAGTTTAGAGTAGATGGTG - 13680
       - W  L  K  I  V  Q  R  L  L  S  M  T  F  S  S  L  E  *  M  V
       -   G  *  R  L  S  S  G  C  C  P  *  L  F  Q  V  *  S  R  W  *
       -    V  K  D  C  P  A  V  A  V  H  D  F  F  K  F  R  V  D  G  D
13681 - ACATGGTACCACATATATCACGTCAGCGTCTAACTAAATACACAATGGCTGATTTAGTCT - 13740
       - T  W  Y  H  I  Y  H  V  S  V  *  L  N  T  Q  W  L  I  *  S
       -   H  G  T  T  Y  I  T  S  A  S  N  *  I  H  N  G  *  F  S  L
       -    M  V  P  H  I  S  R  Q  R  L  T  K  Y  T  M  A  D  L  V  Y
13741 - ATGCTCTACGTCATTTTGATGAGGGTAATTGTGATACATTAAAAGAAATACTCGTCACAT - 13800
       - M  L  Y  V  I  L  M  R  V  I  V  I  H  *  K  K  Y  S  S  H
       -   C  S  T  S  F  *  *  G  *  L  *  Y  I  K  R  N  T  R  H  I
       -    A  L  R  H  F  D  E  G  N  C  D  T  L  K  E  I  L  V  T  Y
13801 - ACAATTGCTGTGATGATGATTATTTCAATAAGAAGGATTGGTATGACTTCGTAGAGAATC - 13860
       - T  I  A  V  M  M  I  I  S  I  R  R  I  G  M  T  S  *  R  I
       -   Q  L  L  *  *  *  L  F  Q  *  E  G  L  V  *  L  R  R  E  S
       -    N  C  C  D  D  D  Y  F  N  K  K  D  W  Y  D  F  V  E  N  P
13861 - CTGACATCTTACGCGTATATGCTAACTTAGGTGAGCGTGTACGCCAATCATTATTAAAGA - 13920
       - L  T  S  Y  A  Y  M  L  T  *  V  S  V  Y  A  N  H  Y  *  R
       -   *  H  L  T  R  I  C  *  L  R  *  A  C  T  P  I  I  I  K  D
       -    D  I  L  R  V  Y  A  N  L  G  E  R  V  R  Q  S  L  L  K  T
13921 - CTGTACAATTCTGCGATGCTATGCGTGATGCAGGCATTGTAGGCGTACTGACATTAGATA - 13980
       - L  Y  N  S  A  M  L  C  V  M  Q  A  L  *  A  Y  *  H  *  I
       -   C  T  I  L  R  C  Y  A  *  C  R  H  C  R  R  T  D  I  R  *
       -    V  Q  F  C  D  A  M  R  D  A  G  I  V  G  V  L  T  L  D  N
13981 - ATCAGGATCTTAATGGGAACTGGTACGATTTCGGTGATTTCGTACAAGTAGCACCAGGCT - 14040
       - I  R  I  L  M  G  T  G  T  I  S  V  I  S  Y  K  *  H  Q  A
       -   S  G  S  *  W  E  L  V  R  F  R  *  F  R  T  S  S  T  R  L
       -    Q  D  L  N  G  N  W  Y  D  F  G  D  F  V  Q  V  A  P  G  C
14041 - GCGGAGTTCCTATTGTGGATTCATATTACTCATTGCTGATGCCCATCCTCACTTTGACTA - 14100
       - A  E  F  L  L  W  I  H  I  T  H  C  *  C  P  S  S  L  *  L
       -   R  S  S  Y  C  G  F  I  L  L  I  A  D  A  H  P  H  F  D  *
       -    G  V  P  I  V  D  S  Y  Y  S  L  L  M  P  I  L  T  L  T  R
14101 - GGGCATTGGCTGCTGAGTCCCATATGGATGCTGATCTCGCAAAACCACTTATTAAGTGGG - 14160
       - G  H  W  L  L  S  P  I  W  M  L  I  S  Q  N  H  L  L  S  G
       -   G  I  G  C  *  V  P  Y  G  C  *  S  R  K  T  T  Y  *  V  G
       -    A  L  A  A  E  S  H  M  D  A  D  L  A  K  P  L  I  K  W  D
14161 - ATTTGCTGAAATATGATTTTACGGAAGAGAGACTTTGTCTCTTCGACCGTTATTTTAAAT - 14220
       - I  C  *  N  M  I  L  R  K  R  D  F  V  S  S  T  V  I  L  N
       -   F  A  E  I  *  F  Y  G  R  E  T  L  S  L  R  P  L  F  *  I
       -    L  L  K  Y  D  F  T  E  E  R  L  C  L  F  D  R  Y  F  K  Y
14221 - ATTGGGACCAGACATACCATCCCAATTGTATTAACTGTTTGGATGATAGGTGTATCCTTC - 14280
       - I  G  T  R  H  T  I  P  I  V  L  T  V  W  M  I  G  V  S  F
       -   L  G  P  D  I  P  S  Q  L  Y  *  L  F  G  *  *  V  Y  P  S
       -    W  D  Q  T  Y  H  P  N  C  I  N  C  L  D  D  R  C  I  L  H
14281 - ATTGTGCAAACTTTAATGTGTTATTTTCTACTGTGTTTCCACCTACAAGTTTTGGACCAC - 14340
       - I  V  Q  T  L  M  C  Y  F  L  L  C  F  H  L  Q  V  L  D  H
       -   L  C  K  L  *  C  V  I  F  Y  C  V  S  T  Y  K  F  W  T  T
       -    C  A  N  F  N  V  L  F  S  T  V  F  P  P  T  S  F  G  P  L
14341 - TAGTAAGAAAAATATTTGTAGATGGTGTTCCTTTTGTTGTTTCAACTGGATACCATTTTC - 14400
       - *  *  E  K  Y  L  *  M  V  F  L  L  L  F  Q  L  D  T  I  F
       -   S  K  K  N  I  C  R  W  C  S  F  C  C  F  N  W  I  P  F  S
       -    V  R  K  I  F  V  D  G  V  P  F  V  V  S  T  G  Y  H  F  R
```

FIG. 4 Cont'd

```
14401 - GTGAGTTAGGAGTCGTACATAATCAGGATGTAAACTTACATAGCTCGCGTCTCAGTTTCA - 14460
       - V S * E S Y I I R M * T Y I A R V S V S
       - * V R S R T * S G C K L T * L A S Q F Q
       - E L G V V H N Q D V N L H S S R L S F K
14461 - AGGAACTTTTAGTGTATGCTGCTGATCCAGCTATGCATGCAGCTTCTGGCAATTTATTGC - 14520
       - R N F * C M L L I Q L C M Q L L A I Y C
       - G T F S V C C * S S Y A C S F W Q F I A
       - E L L V Y A A D P A M H A A S G N L L L
14521 - TAGATAAACGCACTACATGCTTTTCAGTAGCTGCACTAACAAACAATGTTGCTTTTCAAA - 14580
       - * I N A L H A F Q * L H * Q T M L L F K
       - R * T H Y M L F S S C T N K Q C C F S N
       - D K R T T C F S V A A L T N N V A F Q T
14581 - CTGTCAAACCCGGTAATTTTAATAAAGACTTTTATGACTTTGCTGTGTCTAAAGGTTTCT - 14640
       - L S N P V I L I K T F M T L L C L K V S
       - C Q T R * F * * R L L * L C C V * R F L
       - V K P G N F N K D F Y D F A V S K G F F
14641 - TTAAGGAAGGAAGTTCTGTTGAACTAAAACACTTCTTCTTTGCTCAGGATGGCAACGCTG - 14700
       - L R K E V L L N * N T S S L L R M A T L
       - * G R K F C * T K T L L L C S G W Q R C
       - K E G S S V E L K H F F F A Q D G N A A
14701 - CTATCAGTGATTATGACTATTATCGTTATAATCTGCCAACAATGTGTGATATCAGACAAC - 14760
       - L S V I M T I I V I I C Q Q C V I S D N
       - Y Q * L * L L S L * S A N N V * Y Q T T
       - I S D Y D Y Y R Y N L P T M C D I R Q L
14761 - TCCTATTCGTAGTTGAAGTTGTTGATAAATACTTTGATTGTTACGATGGTGGCTGTATTA - 14820
       - S Y S * L K L L I N T L I V T M V A V L
       - P I R S * S C * * I L * L L R W W L Y *
       - L F V V E V V D K Y F D C Y D G G C I N
14821 - ATGCCAACCAAGTAATCGTTAACAATCTGGATAAATCAGCTGGTTTCCCATTTAATAAAT - 14880
       - M P T K * S L T I W I N Q L V S H L I N
       - C Q P S N R * Q S G * I S W F P I * * M
       - A N Q V I V N N L D K S A G F P F N K W
14881 - GGGGTAAGGCTAGACTTTATTATGACTCAATGAGTTATGAGGATCAAGATGCACTTTTCG - 14940
       - G V R L D F I M T Q * V M R I K M H F S
       - G * G * T L L * L N E L * G S R C T F R
       - G K A R L Y Y D S M S Y E D Q D A L F A
14941 - CGTATACTAAGCGTAATGTCATCCCTACTATAACTCAAATGAATCTTAAGTATGCCATTA - 15000
       - R I L S V M S S L L * L K * I L S M P L
       - V Y * A * C H P Y Y N S N E S * V C H *
       - Y T K R N V I P T I T Q M N L K Y A I S
15001 - GTGCAAAGAATAGAGCTCGCACCGTAGCTGGTGTCTCTATCTGTAGTACTATGACAAATA - 15060
       - V Q R I E L A P * L V S L S V V L * Q I
       - C K E * S S H R S W C L Y L * Y Y D K *
       - A K N R A R T V A G V S I C S T M T N R
15061 - GACAGTTTCATCAGAAATTATTGAAGTCAATAGCCGCCACTAGAGGAGCTACTGTGGTAA - 15120
       - D S F I R N Y * S Q * P P L E E L L W *
       - T V S S E I I E V N S R H * R S Y C G N
       - Q F H Q K L L K S I A A T R G A T V V I
15121 - TTGGAACAAGCAAGTTTTACGGTGGCTGGCATAATATGTTAAAAACTGTTTACAGTGATG - 15180
       - L E Q A S F T V A G I I C * K L F T V M
       - W N K Q V L R W L A * Y V K N C L Q * C
       - G T S K F Y G G W H N M L K T V Y S D V
15181 - TAGAAACTCCACACCTTATGGGTTGGGATTATCCAAAATGTGACAGAGCCATGCCTAACA - 15240
       - * K L H T L W V G I I Q N V T E P C L T
       - R N S T P Y G L G L S K M * Q S H A * H
       - E T P H L M G W D Y P K C D R A M P N M
15241 - TGCTTAGGATAATGGCCTCTCTTGTTCTTGCTCGCAAACATAACACTTGCTGTAACTTAT - 15300
       - C L G * W P L L F L L A N I T L A V T Y
       - A * D N G L S C S C S Q T * H L L * L I
       - L R I M A S L V L A R K H N T C C N L S
```

FIG. 4 Cont'd

```
15301 - CACACCGTTTCTACAGGTTAGCTAACGAGTGTGCGCAAGTATTAAGTGAGATGGTCATGT - 15360
       -  H  T  V  S  T  G  *  L  T  S  V  R  K  Y  *  V  R  W  S  C
       -    T  P  F  L  Q  V  S  *  R  V  C  A  S  I  K  *  D  G  H  V
       -      H  R  F  Y  R  L  A  N  E  C  A  Q  V  L  S  E  M  V  M  C
15361 - GTGGCGGCTCACTATATGTTAAACCAGGTGGAACATCATCCGGTGATGCTACAACTGCTT - 15420
       -  V  A  A  H  Y  M  L  N  Q  V  E  H  H  P  V  M  L  Q  L  L
       -    W  R  L  T  I  C  *  T  R  W  N  I  I  R  *  C  Y  N  C  L
       -      G  G  S  L  Y  V  K  P  G  G  T  S  S  G  D  A  T  T  A  Y
15421 - ATGCTAATAGTGTCTTTAACATTTGTCAAGCTGTTACAGCCAATGTAAATGCACTTCTTT - 15480
       -  M  L  I  V  S  L  T  F  V  K  L  L  Q  P  M  *  M  H  F  F
       -    C  *  *  C  L  *  H  L  S  S  C  Y  S  Q  C  K  C  T  S  F
       -      A  N  S  V  F  N  I  C  Q  A  V  T  A  N  V  N  A  L  L  S
15481 - CAACTGATGGTAATAAGATAGCTGACAAGTATGTCCGCAATCTACAACACAGGCTCTATG - 15540
       -  Q  L  M  V  I  R  *  L  T  S  M  S  A  I  Y  N  T  G  S  M
       -    N  *  W  *  *  D  S  *  Q  V  C  P  Q  S  T  T  Q  A  L  *
       -      T  D  G  N  K  I  A  D  K  Y  V  R  N  L  Q  H  R  L  Y  E
15541 - AGTGTCTCTATAGAAATAGGGATGTTGATCATGAATTCGTGGATGAGTTTTACGCTTACC - 15600
       -  S  V  S  I  E  I  G  M  L  I  M  N  S  W  M  S  F  T  L  T
       -    V  S  L  *  K  *  G  C  *  S  *  I  R  G  *  V  L  R  L  P
       -      C  L  Y  R  N  R  D  V  D  H  E  F  V  D  E  F  Y  A  Y  L
15601 - TGCGTAAACATTTCTCCATGATGATTCTTTCTGATGATGCCGTTGTGTGCTATAACAGTA - 15660
       -  C  V  N  I  S  P  *  *  F  F  L  M  M  P  L  C  A  I  T  V
       -    A  *  T  F  L  H  D  D  S  F  *  *  C  R  C  V  L  *  Q  *
       -      R  K  H  F  S  M  M  I  L  S  D  D  A  V  V  C  Y  N  S  N
15661 - ACTATGCGGCTCAAGGTTTAGTAGCTAGCATTAAGAACTTTAAGGCAGTTCTTTATTATC - 15720
       -  T  M  R  L  K  V  *  *  L  A  L  R  T  L  R  Q  F  F  I  I
       -    L  C  G  S  R  F  S  S  *  H  *  E  L  *  G  S  S  L  L  S
       -      Y  A  A  Q  G  L  V  A  S  I  K  N  F  K  A  V  L  Y  Y  Q
15721 - AAAATAATGTGTTCATGTCTGAGGCAAAATGTTGGACTGAGACTGACCTTACTAAAGGAC - 15780
       -  K  I  M  C  S  C  L  R  Q  N  V  G  L  R  L  T  L  L  K  D
       -    K  *  C  V  H  V  *  G  K  M  L  D  *  D  *  P  Y  *  R  T
       -      N  N  V  F  M  S  E  A  K  C  W  T  E  T  D  L  T  K  G  P
15781 - CTCACGAATTTTGCTCACAGCATACAATGCTAGTTAAACAAGGAGATGATTACGTGTACC - 15840
       -  L  T  N  F  A  H  S  I  Q  C  *  L  N  K  E  M  I  T  C  T
       -    S  R  I  L  L  T  A  Y  N  A  S  *  T  R  R  *  L  R  V  P
       -      H  E  F  C  S  Q  H  T  M  L  V  K  Q  G  D  D  Y  V  Y  L
15841 - TGCCTTACCCAGATCCATCAAGAATATTAGGCGCAGGCTGTTTTGTCGATGATATTGTCA - 15900
       -  C  L  T  Q  I  H  Q  E  Y  *  A  Q  A  V  L  S  M  I  L  S
       -    A  L  P  R  S  I  K  N  I  R  R  R  L  F  C  R  *  Y  C  Q
       -      P  Y  P  D  P  S  R  I  L  G  A  G  C  F  V  D  D  I  V  K
15901 - AAACAGATGGTACACTTATGATTGAAAGGTTCGTGTCACTGGCTATTGATGCTTACCCAC - 15960
       -  K  Q  M  V  H  L  *  L  K  G  S  C  H  W  L  L  M  L  T  H
       -    N  R  W  Y  T  Y  D  *  K  V  R  V  T  G  Y  *  C  L  P  T
       -      T  D  G  T  L  M  I  E  R  F  V  S  L  A  I  D  A  Y  P  L
15961 - TTACAAAACATCCTAATCAGGAGTATGCTGATGTCTTCACTTGTATTTACAATACATTA - 16020
       -  L  Q  N  I  L  I  R  S  M  L  M  S  F  T  C  I  Y  N  T  L
       -    Y  K  T  S  *  S  G  V  C  *  C  L  S  L  V  F  T  I  H  *
       -      T  K  H  P  N  Q  E  Y  A  D  V  F  H  L  Y  L  Q  Y  I  R
16021 - GAAAGTTACATGATGAGCTTACTGGCCACATGTTGGACATGTATTCCGTAATGCTAACTA - 16080
       -  E  S  Y  M  M  S  L  L  A  T  C  W  T  C  I  P  *  C  *  L
       -    K  V  T  *  *  A  Y  W  P  H  V  G  H  V  F  R  N  A  N  *
       -      K  L  H  D  E  L  T  G  H  M  L  D  M  Y  S  V  M  L  T  N
16081 - ATGATAACACCTCACGGTACTGGGAACCTGAGTTTTATGAGGCTATGTACACACCACATA - 16140
       -  M  I  T  P  H  G  T  G  N  L  S  F  M  R  L  C  T  H  H  I
       -    *  *  H  L  T  V  L  G  T  *  V  L  *  G  Y  V  H  T  T  Y
       -      D  N  T  S  R  Y  W  E  P  E  F  Y  E  A  M  Y  T  P  H  T
16141 - CAGTCTTGCAGGCTGTAGGTGCTTGTGTATTGTGCAATTCACAGACTTCACTTCGTTGCG - 16200
       -  Q  S  C  R  L  *  V  L  V  Y  C  A  I  H  R  L  H  F  V  A
       -    S  L  A  G  C  R  C  L  C  I  V  Q  F  T  D  F  T  S  L  R
       -      V  L  Q  A  V  G  A  C  V  L  C  N  S  Q  T  S  L  R  C  G
```

FIG. 4 Cont'd

```
16201 - GTGCCTGTATTAGGAGACCATTCCTATGTTGCAAGTGCTGCTATGACCATGTCATTTCAA - 16260
       - V  P  V  L  G  D  H  S  Y  V  A  S  A  A  M  T  M  S  F  Q
       - C  L  Y  *  E  T  I  P  M  L  Q  V  L  L  *  P  C  H  F  N
       -  A  C  I  R  R  P  F  L  C  C  K  C  C  Y  D  H  V  I  S  T
16261 - CATCACACAAATTAGTGTTGTCTGTTAATCCCTATGTTTGCAATGCCCCAGGTTGTGATG - 16320
       - H  H  T  N  *  C  C  L  L  I  P  M  F  A  M  P  Q  V  V  M
       - I  T  Q  I  S  V  V  C  *  S  L  C  L  Q  C  P  R  L  *  C
       -  S  H  K  L  V  L  S  V  N  P  Y  V  C  N  A  P  G  C  D  V
16321 - TCACTGATGTGACACAACTGTATCTAGGAGGTATGAGCTATTATTGCAAGTCACATAAGC - 16380
       - S  L  M  *  H  N  C  I  *  E  V  *  A  I  I  A  S  H  I  S
       - H  *  C  D  T  T  V  S  R  R  Y  E  L  L  L  L  Q  V  T  *  A
       -  T  D  V  T  Q  L  Y  L  G  G  M  S  Y  Y  C  K  S  H  K  P
16381 - CTCCCATTAGTTTTCCATTATGTGCTAATGGTCAGGTTTTTGGTTTATACAAAAACACAT - 16440
       - L  P  L  V  F  H  Y  V  L  M  V  R  F  L  V  Y  T  K  T  H
       - S  H  *  F  S  I  M  C  *  W  S  G  F  W  F  I  Q  K  H  M
       -  P  I  S  F  P  L  C  A  N  G  Q  V  F  G  L  Y  K  N  T  C
16441 - GTGTAGGCAGTGACAATGTCACTGACTTCAATGCGATAGCAACATGTGATTGGACTAATG - 16500
       - V  *  A  V  T  M  S  L  T  S  M  R  *  Q  H  V  I  G  L  M
       - C  R  Q  *  Q  C  H  *  L  Q  C  D  S  N  M  *  L  D  *  C
       -  V  G  S  D  N  V  T  D  F  N  A  I  A  T  C  D  W  T  N  A
16501 - CTGGCGATTACATACTTGCCAACACTTGTACTGAGAGACTCAAGCTTTTCGCAGCAGAAA - 16560
       - L  A  I  T  Y  L  P  T  L  V  L  R  D  S  S  F  S  Q  Q  K
       - W  R  L  H  T  C  Q  H  L  Y  *  E  T  Q  A  F  R  S  R  N
       -  G  D  Y  I  L  A  N  T  C  T  E  R  L  K  L  F  A  A  E  T
16561 - CGCTCAAAGCCACTGAGGAAACATTTAAGCTGTCATATGGTATTGCCACTGTACGCGAAG - 16620
       - R  S  K  P  L  R  K  H  L  S  C  H  M  V  L  P  L  Y  A  K
       - A  Q  S  H  *  G  N  I  *  A  V  I  W  Y  C  H  C  T  R  S
       -  L  K  A  T  E  E  T  F  K  L  S  Y  G  I  A  T  V  R  E  V
16621 - TACTCTCTGACAGAGAATTGCATCTTTCATGGAGGTTGGAAAACCTAGACCACCATTGA - 16680
       - Y  S  L  T  E  N  C  I  F  H  G  R  L  E  N  L  D  H  H  *
       - T  L  *  Q  R  I  A  S  F  M  G  G  W  K  T  *  T  T  I  E
       -  L  S  D  R  E  L  H  L  S  W  E  V  G  K  P  R  P  P  L  N
16681 - ACAGAAACTATGTCTTTACTGGTTACCGTGTAACTAAAAATAGTAAAGTACAGATTGGAG - 16740
       - T  E  T  M  S  L  L  V  T  V  *  L  K  I  V  K  Y  R  L  E
       - Q  K  L  C  L  Y  W  L  P  C  N  *  K  *  *  S  T  D  W  R
       -  R  N  Y  V  F  T  G  Y  R  V  T  K  N  S  K  V  Q  I  G  E
16741 - AGTACACCTTTGAAAAAGGTGACTATGGTGATGCTGTTGTGTACAGAGGTACTACGACAT - 16800
       - S  T  P  L  K  K  V  T  M  V  M  L  L  C  T  E  V  L  R  H
       - V  H  L  *  K  R  *  L  W  *  C  C  C  V  Q  R  Y  Y  D  I
       -  Y  T  F  E  K  G  D  Y  G  D  A  V  V  Y  R  G  T  T  T  Y
16801 - ACAAGTTGAATGTTGGTGATTACTTTGTGTTGACATCTCACACTGTAATGCCACTTAGTG - 16860
       - T  S  *  M  L  V  I  T  L  C  *  H  L  T  L  *  C  H  L  V
       - Q  V  E  C  W  *  L  L  C  V  D  I  S  H  C  N  A  T  *  C
       -  K  L  N  V  G  D  Y  F  V  L  T  S  H  T  V  M  P  L  S  A
16861 - CACCTACTCTAGTGCCACAAGAGCACTATGTGAGAATTACTGGCTTGTACCCAACACTCA - 16920
       - H  L  L  *  C  H  K  S  T  M  *  E  L  L  A  C  T  Q  H  S
       - T  Y  S  S  A  T  R  A  L  C  E  N  Y  W  L  V  P  N  T  Q
       -  P  T  L  V  P  Q  E  H  Y  V  R  I  T  G  L  Y  P  T  L  N
16921 - ACATCTCAGATGAGTTTTCTAGCAATGTTGCAAATTATCAAAAGGTCGGCATGCAAAAGT - 16980
       - T  S  Q  M  S  F  L  A  M  L  Q  I  I  K  R  S  A  C  K  S
       - H  L  R  *  V  F  *  Q  C  C  K  L  S  K  G  R  H  A  K  V
       -  I  S  D  E  F  S  S  N  V  A  N  Y  Q  K  V  G  M  Q  K  Y
16981 - ACTCTACACTCCAAGGACCACCTGGTACTGGTAAGAGTCATTTTGCCATCGGACTTGCTC - 17040
       - T  L  H  S  K  D  H  L  V  L  V  R  V  I  L  P  S  D  L  L
       - L  Y  T  P  R  T  T  W  Y  W  *  E  S  F  C  H  R  T  C  S
       -  S  T  L  Q  G  P  P  G  T  G  K  S  H  F  A  I  G  L  A  L
17041 - TCTATTACCCATCTGCTCGCATAGTGTATACGGCATGCTCTCATGCAGCTGTTGATGCCC - 17100
       - S  I  T  H  L  L  A  *  C  I  R  H  A  L  M  Q  L  L  M  P
       - L  L  P  I  C  S  H  S  V  Y  G  M  L  S  C  S  C  *  C  P
       -  Y  Y  P  S  A  R  I  V  Y  T  A  C  S  H  A  A  V  D  A  L
```

FIG. 4 Cont'd

```
17101 - TATGTGAAAAGGCATTAAAATATTTGCCCATAGATAAATGTAGTAGAATCATACCTGCGC - 17160
       - Y  V  K  R  H  *  N  I  C  P  *  I  N  V  V  E  S  Y  L  R
       - M  *  K  G  I  K  I  F  A  H  R  *  M  *  *  N  H  T  C  A
       - C  E  K  A  L  K  Y  L  P  I  D  K  C  S  R  I  I  P  A  R
17161 - GTGCGCGCGTAGAGTGTTTTGATAAATTCAAAGTGAATTCAACACTAGAACAGTATGTTT - 17220
       - V  R  A  *  S  V  L  I  N  S  K  *  I  Q  H  *  N  S  M  F
       - C  A  R  R  V  F  *  *  I  Q  S  E  F  N  T  R  T  V  C  F
       - A  R  V  E  C  F  D  K  F  K  V  N  S  T  L  E  Q  Y  V  F
17221 - TCTGCACTGTAAATGCATTGCCAGAAACAACTGCTGACATTGTAGTCTTTGATGAAATCT - 17280
       - S  A  L  *  M  H  C  Q  K  Q  L  L  T  L  *  S  L  M  K  S
       - L  H  C  K  C  I  A  R  N  N  C  *  H  C  S  L  *  *  N  L
       - C  T  V  N  A  L  P  E  T  T  A  D  I  V  V  F  D  E  I  S
17281 - CTATGGCTACTAATTATGACTTGAGTGTTGTCAATGCTAGACTTCGTGCAAAACACTACG - 17340
       - L  W  L  L  I  M  T  *  V  L  S  M  L  D  F  V  Q  N  T  T
       - Y  G  Y  *  L  *  L  E  C  C  Q  C  *  T  S  C  K  T  L  R
       - M  A  T  N  Y  D  L  S  V  V  N  A  R  L  R  A  K  H  Y  V
17341 - TCTATATTGGCGATCCTGCTCAATTACCAGCCCCCGCACATTGCTGACTAAAGGCACAC - 17400
       - S  I  L  A  I  L  L  N  Y  Q  P  P  A  H  C  *  L  K  A  H
       - L  Y  W  R  S  C  S  I  T  S  P  P  H  I  A  D  *  R  H  T
       - Y  I  G  D  P  A  Q  L  P  A  P  R  T  L  L  T  K  G  T  L
17401 - TAGAACCAGAATATTTTAATTCAGTGTGCAGACTTATGAAAACAATAGGTCCAGACATGT - 17460
       - *  N  Q  N  I  L  I  Q  C  A  D  L  *  K  Q  *  V  Q  T  C
       - R  T  R  I  F  *  F  S  V  Q  T  Y  E  N  N  R  S  R  H  V
       - E  P  E  Y  F  N  S  V  C  R  L  M  K  T  I  G  P  D  M  F
17461 - TCCTTGGAACTTGTCGCCGTTGTCCTGCTGAAATTGTTGACACTGTGAGTGCTTTAGTTT - 17520
       - S  L  E  L  V  A  V  V  L  L  K  L  L  T  L  *  V  L  *  F
       - P  W  N  L  S  P  L  S  C  *  N  C  *  H  C  E  C  F  S  L
       - L  G  T  C  R  R  C  P  A  E  I  V  D  T  V  S  A  L  V  Y
17521 - ATGACAATAAGCTAAAAGCACACAAGGAGAAGTCAGCTCAATGCTTCAAAATGTTCTACA - 17580
       - M  T  I  S  *  K  H  T  R  R  S  Q  L  N  A  S  K  C  S  T
       - *  Q  *  A  K  S  T  Q  G  E  V  S  S  M  L  Q  N  V  L  Q
       - D  N  K  L  K  A  H  K  E  K  S  A  Q  C  F  K  M  F  Y  K
17581 - AAGGTGTTATTACACATGATGTTTCATCTGCAATCAACAGACCTCAAATAGGCGTTGTAA - 17640
       - K  V  L  L  H  M  M  F  H  L  Q  S  T  D  L  K  *  A  L  *
       - R  C  Y  Y  T  *  C  F  I  C  N  Q  Q  T  S  N  R  R  C  K
       - G  V  I  T  H  D  V  S  S  A  I  N  R  P  Q  I  G  V  V  R
17641 - GAGAATTTCTTACACGCAATCCTGCTTGGAGAAAAGCTGTTTTTATCTCACCTTATAATT - 17700
       - E  N  F  L  H  A  I  L  L  G  E  K  L  F  L  S  H  L  I  I
       - R  I  S  Y  T  Q  S  C  L  E  K  S  C  F  Y  L  T  L  *  F
       - E  F  L  T  R  N  P  A  W  R  K  A  V  F  I  S  P  Y  N  S
17701 - CACAGAACGCTGTAGCTTCAAAAATCTTAGGATTGCCTACGCAGACTGTTGATTCATCAC - 17760
       - H  R  T  L  *  L  Q  K  S  *  D  C  L  R  R  L  L  I  H  H
       - T  E  R  C  S  F  K  N  L  R  I  A  Y  A  D  C  *  F  I  T
       - Q  N  A  V  A  S  K  I  L  G  L  P  T  Q  T  V  D  S  S  Q
17761 - AGGGTTCTGAATATGACTATGTCATATTCACACAAACTACTGAAACAGCACACTCTTGTA - 17820
       - R  V  L  N  M  T  M  S  Y  S  H  K  L  L  K  Q  H  T  L  V
       - G  F  *  I  *  L  C  H  I  H  T  N  Y  *  N  S  T  L  L  *
       - G  S  E  Y  D  Y  V  I  F  T  Q  T  T  E  T  A  H  S  C  N
17821 - ATGTCAACCGTTTCAATGTGGCTATCACAAGGGCAAAAATTGGCATTTTGTGCATAATGT - 17880
       - M  S  T  V  S  M  W  L  S  Q  G  Q  K  L  A  F  C  A  *  C
       - C  Q  P  F  Q  C  G  Y  H  K  G  K  N  W  H  F  V  H  N  V
       - V  N  R  F  N  V  A  I  T  R  A  K  I  G  I  L  C  I  M  S
17881 - CTGATAGAGATCTTTATGACAAACTGCAATTTACAAGTCTAGAAATACCACGTCGCAATG - 17940
       - L  I  E  I  F  M  T  N  C  N  L  Q  V  *  K  Y  H  V  A  M
       - *  *  R  S  L  *  Q  T  A  I  Y  K  S  R  N  T  T  S  Q  C
       - D  R  D  L  Y  D  K  L  Q  F  T  S  L  E  I  P  R  R  N  V
17941 - TGGCTACATTACAAGCAGAAAATGTAACTGGACTTTTTAAGGACTGTAGTAAGATCATTA - 18000
       - W  L  H  Y  K  Q  K  M  *  L  D  F  L  R  T  V  V  R  S  L
       - G  Y  I  T  S  R  K  C  N  W  T  F  *  G  L  *  *  D  H  Y
       - A  T  L  Q  A  E  N  V  T  G  L  F  K  D  C  S  K  I  I  T
```

FIG. 4 Cont'd

```
18001 - CTGGTCTTCATCCTACACAGGCACCTACACACCTCAGCGTTGATATAAAGTTCAAGACTG - 18060
       - L  V  F  I  L  H  R  H  L  H  T  S  A  L  I  *  S  S  R  L
       - W  S  S  Y  T  G  T  Y  T  P  Q  R  *  Y  K  V  Q  D  *
       - G  L  H  P  T  Q  A  P  T  H  L  S  V  D  I  K  F  K  T  E
18061 - AAGGATTATGTGTTGACATACCAGGCATACCAAAGGACATGACCTACCGTAGACTCATCT - 18120
       - K  D  Y  V  L  T  Y  Q  A  Y  Q  R  T  *  P  T  V  D  S  S
       - R  I  M  C  *  H  T  R  H  T  K  G  H  D  L  P  *  T  H  L
       - G  L  C  V  D  I  P  G  I  P  K  D  M  T  Y  R  R  L  I  S
18121 - CTATGATGGGTTCAAAATGAATTACCAAGTCAATGGTTACCCTAATATGTTTATCACCC - 18180
       - L  *  W  V  S  K  *  I  T  K  S  M  V  T  L  I  C  L  S  P
       - Y  D  G  F  Q  N  E  L  P  S  Q  W  L  P  *  Y  V  Y  H  P
       - M  M  G  F  K  M  N  Y  Q  V  N  G  Y  P  N  M  F  I  T  R
18181 - GCGAAGAAGCTATTCGTCACGTTCGTGCGTGGATTGGCTTTGATGTAGAGGGCTGTCATG - 18240
       - A  K  K  L  F  V  T  F  V  R  G  L  A  L  M  *  R  A  V  M
       - R  R  S  Y  S  S  R  S  C  V  D  W  L  *  C  R  G  L  S  C
       - E  E  A  I  R  H  V  R  A  W  I  G  F  D  V  E  G  C  H  A
18241 - CAACTAGAGATGCTGTGGGTACTAACCTACCTCTCCAGCTAGGATTTTCTACAGGTGTTA - 18300
       - Q  L  E  M  L  W  V  L  T  Y  L  S  S  *  D  F  L  Q  V  L
       - N  *  R  C  C  G  Y  *  P  T  S  P  A  R  I  F  Y  R  C  *
       - T  R  D  A  V  G  T  N  L  P  L  Q  L  G  F  S  T  G  V  N
18301 - ACTTAGTAGCTGTACCGACTGGTTATGTTGACACTGAAAATAACACAGAATTCACCAGAG - 18360
       - T  *  *  L  Y  R  L  V  M  L  T  L  K  I  T  Q  N  S  P  E
       - L  S  S  C  T  D  W  L  C  *  H  *  K  *  H  R  I  H  Q  S
       - L  V  A  V  P  T  G  Y  V  D  T  E  N  N  T  E  F  T  R  V
18361 - TTAATGCAAAACCTCCACCAGGTGACCAGTTTAAACATCTTATACCACTCATGTATAAAG - 18420
       - L  M  Q  N  L  H  Q  V  T  S  L  N  I  L  Y  H  S  C  I  K
       - *  C  K  T  S  T  R  *  P  V  *  T  S  Y  T  T  H  V  *  R
       - N  A  K  P  P  P  G  D  Q  F  K  H  L  I  P  L  M  Y  K  G
18421 - GCTTGCCCTGGAATGTAGTGCGTATTAAGATAGTACAAATGCTCAGTGATACACTGAAAG - 18480
       - A  C  P  G  M  *  C  V  L  R  *  Y  K  C  S  V  I  H  *  K
       - L  A  L  E  C  S  A  Y  *  D  S  T  N  A  Q  *  Y  T  E  R
       - L  P  W  N  V  V  R  I  K  I  V  Q  M  L  S  D  T  L  K  G
18481 - GATTGTCAGACAGAGTCGTGTTCGTCCTTTGGGCGCATGGCTTTGAGCTTACATCAATGA - 18540
       - D  C  Q  T  E  S  C  S  S  F  G  R  M  A  L  S  L  H  Q  *
       - I  V  R  Q  S  R  V  R  P  L  G  A  W  L  *  A  Y  I  N  E
       - L  S  D  R  V  V  F  V  L  W  A  H  G  F  E  L  T  S  M  K
18541 - AGTACTTTGTCAAGATTGGACCTGAAAGAACGTGTTGTCTGTGTGACAAACGTGCAACTT - 18600
       - S  T  L  S  R  L  D  L  K  E  R  V  V  C  V  T  N  V  Q  L
       - V  L  C  Q  D  W  T  *  K  N  V  L  S  V  *  Q  T  C  N  L
       - Y  F  V  K  I  G  P  E  R  T  C  C  L  C  D  K  R  A  T  C
18601 - GCTTTTCTACTTCATCAGATACTTATGCCTGCTGGAATCATTCTGTGGGTTTTGACTATG - 18660
       - A  F  L  L  H  Q  I  L  M  P  A  G  I  I  L  W  V  L  T  M
       - L  F  Y  F  I  R  Y  L  C  L  L  E  S  F  C  G  F  *  L  C
       - F  S  T  S  S  D  T  Y  A  C  W  N  H  S  V  G  F  D  Y  V
18661 - TCTATAACCCATTTATGATTGATGTTCAGCAGTGGGGCTTTACGGGTAACCTTCAGAGTA - 18720
       - S  I  T  H  L  *  L  M  F  S  S  G  A  L  R  V  T  F  R  V
       - L  *  P  I  Y  D  *  C  S  A  V  G  L  Y  G  *  P  S  E  *
       - Y  N  P  F  M  I  D  V  Q  Q  W  G  F  T  G  N  L  Q  S  N
18721 - ACCATGACCAACATTGCCAGGTACATGGAAATGCACATGTGGCTAGTTGTGATGCTATCA - 18780
       - T  M  T  N  I  A  R  Y  M  E  M  H  M  W  L  V  V  M  L  S
       - P  *  P  T  L  P  G  T  W  K  C  T  C  G  *  L  *  C  Y  H
       - H  D  Q  H  C  Q  V  H  G  N  A  H  V  A  S  C  D  A  I  M
18781 - TGACTAGATGTTAGCAGTCCATGAGTGCTTTGTTAAGCGCGTTGATTGGTCTGTTGAAT - 18840
       - *  L  D  V  *  Q  S  M  S  A  L  L  S  A  L  I  G  L  L  N
       - D  *  M  F  S  S  P  *  V  L  C  *  A  R  *  L  V  C  *  I
       - T  R  C  L  A  V  H  E  C  F  V  K  R  V  D  W  S  V  E  Y
18841 - ACCCTATTATAGGAGATGAACTGAGGGTTAATTCTGCTTGCAGAAAAGTACAACACATGG - 18900
       - T  L  L  *  E  M  N  *  G  L  I  L  L  A  E  K  Y  N  T  W
       - P  Y  Y  R  R  *  T  E  G  *  F  C  L  Q  K  S  T  T  H  G
       - P  I  I  G  D  E  L  R  V  N  S  A  C  R  K  V  Q  H  M  V
```

FIG. 4 Cont'd

```
18901 - TTGTGAAGTCTGCATTGCTTGCTGATAAGTTTCCAGTTCTTCATGACATTGGAAATCCAA - 18960
      - L * S L H C L L I S F Q F F M T L E I Q
      - C E V C I A C * * V S S S * H W K S K
      - V K S A L L A D K F P V L H D I G N P K
18961 - AGGCTATCAAGTGTGTGCCTCAGGCTGAAGTAGAATGGAAGTTCTACGATGCTCAGCCAT - 19020
      - R L S S V C L R L K * N G S S T M L S H
      - G Y Q V C A S G * S R M E V L R C S A M
      - A I K C V P Q A E V E W K F Y D A Q P C
19021 - GTAGTGACAAAGCTTACAAAATAGAGGAGCTCTTCTATTCTTATGCTACACATCACGATA - 19080
      - V V T K L T K * R S S S I L M L H I T I
      - * * Q S L Q N R G A L L F L C Y T S R *
      - S D K A Y K I E E L F Y S Y A T H H D K
19081 - AATTCACTGATGGTGTTTGTTTGTTTGGAATTGTAACGTTGATCGTTACCCAGCCAATG - 19140
      - N S L M V F V C F G I V T L I V T Q P M
      - I H * W C L F V L E L * R * S L P S Q C
      - F T D G V C L F W N C N V D R Y P A N A
19141 - CAATTGTGTGTAGGTTTGACACAAGAGTCTTGTCAAACTTGAACTTACCAGGCTGTGATG - 19200
      - Q L C V G L T Q E S C Q T * T Y Q A V M
      - N C V * V * H K S L V K L E L T R L * W
      - I V C R F D T R V L S N L N L P G C D G
19201 - GTGGTAGTTTGTATGTGAATAAGCATGCATTCCACACTCCAGCTTTCGATAAAAGTGCAT - 19260
      - V V V C M * I S M H S T L Q L S I K V H
      - W * F V C E * A C I P H S S F R * K C I
      - G S L Y V N K H A F H T P A F D K S A F
19261 - TTACTAATTTAAAGCAATTGCCTTTCTTTTACTATTCTGATAGTCCTTGTGAGTCTCATG - 19320
      - L L I * S N C L S F T I L I V L V S L M
      - Y * F K A I A F L L L F * * S L * V S W
      - T N L K Q L P F F Y Y S D S P C E S H G
19321 - GCAAACAAGTAGTGTCGGATATTGATTATGTTCCACTCAAATCTGCTACGTGTATTACAC - 19380
      - A N K * C R I L I M F H S N L L R V L H
      - Q T S S V G Y * L C S T Q I C Y V Y T
      - K Q V V S D I D Y V P L K S A T C I T R
19381 - GATGCAATTTAGGTGGTGCTGTTTGCAGACACCATGCAAATGAGTACCGACAGTACTTGG - 19440
      - D A I * V V L F A D T M Q M S T D S T W
      - M Q F R W C C L Q T P C K * V P T V L G
      - C N L G G A V C R H H A N E Y R Q Y L D
19441 - ATGCATATAATATGATGATTTCTGCTGGATTTAGCCTATGGATTTACAAACAATTTGATA - 19500
      - M H I I * * F L L D L A Y G F T N N L I
      - C I * Y D D F C W I * P M D L Q T I * Y
      - A Y N M M I S A G F S L W I Y K Q F D T
19501 - CTTATAACCTGTGGAATACATTTACCAGGTTACAGAGTTTAGAAAATGTGGCTTATAATG - 19560
      - L I T C G I H L P G Y R V * K M W L I M
      - L * P V E Y I Y Q V T E F R K C G L * C
      - Y N L W N T F T R L Q S L E N V A Y N V
19561 - TTGTTAATAAAGGACACTTTGATGGACACGCCGGCGAAGCACCTGTTTCCATCATTAATA - 19620
      - L L I K D T L M D T P A K H L F P S L I
      - C * * R T L * W T R R S T C F H H * *
      - V N K G H F D G H A G E A P V S I I N N
19621 - ATGCTGTTTACACAAAGGTAGATGGTATTGATGTGGAGATCTTTGAAAATAAGACAACAC - 19680
      - M L F T Q R * M V L M W R S L K I R Q H
      - C C L H K G R W Y * C G D L * K * D N T
      - A V Y T K V D G I D V E I F E N K T T L
19681 - TTCCTGTTAATGTTGCATTTGAGCTTTGGGCTAAGCGTAACATTAAACCAGTGCCAGAGA - 19740
      - F L L M L H L S F G L S V T L N Q C Q R
      - S C * C C I * A L G * A * H * T S A R D
      - P V N V A F E L W A K R N I K P V P E I
19741 - TTAAGATACTCAATAATTTGGGTGTTGATATCGCTGCTAATACTGTAATCTGGGACTACA - 19800
      - L R Y S I I W V L I S L L I L * S G T T
      - * D T Q * F G C * Y R C * Y C N L G L Q
      - K I L N N L G V D I A A N T V I W D Y K
```

FIG. 4 Cont'd

```
19801 - AAAGAGAAGCCCCAGCACATGTATCTACAATAGGTGTCTGCACAATGACTGACATTGCCA - 19860
      - K E K P Q H M Y L Q * V S A Q * L T L P
      - K R S P S T C I Y N R C L H N D * H C Q
      - R E A P A H V S T I G V C T M T D I A K
19861 - AGAAACCTACTGAGAGTGCTTGTTCTTCACTTACTGTCTTGTTTGATGGTAGAGTGGAAG - 19920
      - R N L L R V L V L H L L S C L M V E W K
      - E T Y * E C L F F T Y C L V * W * S G R
      - K P T E S A C S S L T V L F D G R V E G
19921 - GACAGGTAGACCTTTTTAGAAACGCCCGTAATGGTGTTTTAATAACAGAAGGTTCAGTCA - 19980
      - D R * T F L E T P V M V F * * Q K V Q S
      - T G R P F * K R P * W C F N N R R F S Q
      - Q V D L F R N A R N G V L I T E G S V K
19981 - AAGGTCTAACACCTTCAAAGGGACCAGCACAAGCTAGCGTCAATGGAGTCACATTAATTG - 20040
      - K V * H L Q R D Q H K L A S M E S H * L
      - R S N T F K G T S T S * R Q W S H I N W
      - G L T P S K G P A Q A S V N G V T L I G
20041 - GAGAATCAGTAAAAACACAGTTTAACTACTTTAAGAAAGTAGACGGCATTATTCAACAGT - 20100
      - E N Q * K H S L T T L R K * T A L F N S
      - R I S K N T V * L L * E S R R H Y S T V
      - E S V K T Q F N Y F K K V D G I I Q Q L
20101 - TGCCTGAAACCTACTTTACTCAGAGCAGAGACTTAGAGGATTTTAAGCCCAGATCACAAA - 20160
      - C L K P T L L R A E T * R I L S P D H K
      - A * N L L Y S E Q R L R G F * A Q I T N
      - P E T Y F T Q S R D L E D F K P R S Q M
20161 - TGGAAACTGACTTTCTCGAGCTCGCTATGGATGAATTCATACAGCGATATAAGCTCGAGG - 20220
      - W K L T F S S S L W M N S Y S D I S S R
      - G N * L S R A R Y G * I H T A I * A R G
      - E T D F L E L A M D E F I Q R Y K L E G
20221 - GCTATGCCTTCGAACACATCGTTTATGGAGATTTCAGTCATGGACAACTTGGCGGTCTTC - 20280
      - A M P S N T S F M E I S V M D N L A V F
      - L C L R T H R L W R F Q S W T T W R S S
      - Y A F E H I V Y G D F S H G Q L G G L H
20281 - ATTTAATGATAGGCTTAGCCAAGCGCTCACAAGATTCACCACTTAAATTAGAGGATTTTA - 20340
      - I * * * A * P S A H K I H H L N * R I L
      - F N D R L S Q A L T R F T T * I R G F Y
      - L M I G L A K R S Q D S P L K L E D F I
20341 - TCCCTATGGACAGCACAGTGAAAAATTACTTCATAACAGATGCGCAAACAGGTTCATCAA - 20400
      - S L W T A Q * K I T S * Q M R K Q V H Q
      - P Y G Q H S E K L L H N R C A N R F I K
      - P M D S T V K N Y F I T D A Q T G S S K
20401 - AATGTGTGTGTTCTGTGATTGATCTTTTACTTGATGACTTTGTCGAGATAATAAAGTCAC - 20460
      - N V C V L * L I F Y L M T L S R * * S H
      - M C V F C D * S F T * * L C R D N K V T
      - C V C S V I D L L L D D F V E I I K S Q
20461 - AAGATTTGTCAGTGATTTCAAAAGTGGTCAAGGTTACAATTGACTATGCTGAAATTTCAT - 20520
      - K I C Q * F Q K W S R L Q L T M L K F H
      - R F V S D F K S G Q G Y N * L C * N F I
      - D L S V I S K V V K V T I D Y A E I S F
20521 - TCATGCTTTGGTGTAAGGATGGACATGTTGAAACCTTCTACCCAAAACTACAAGCAAGTC - 20580
      - S C F G V R M D M L K P S T Q N Y K Q V
      - H A L V * G W T C * N L L P K T T S K S
      - M L W C K D G H V E T F Y P K L Q A S Q
20581 - AAGCGTGGCAACCAGGTGTTGCGATGCCTAACTTGTACAAGATGCAAAGAATGCTTCTTG - 20640
      - K R G N Q V L R C L T C T R C K E C F L
      - S V A T R C C D A * L V Q D A K N A S *
      - A W Q P G V A M P N L Y K M Q R M L L E
20641 - AAAAGTGTGACCTTCAGAATTATGGTGAAAATGCTGTTATACCAAAAGGAATAATGATGA - 20700
      - K S V T F R I M V K M L L Y Q K E * * *
      - K V * P S E L W * K C C Y T K R N N D E
      - K C D L Q N Y G E N A V I P K G I M M N
```

FIG. 4 Cont'd

```
20701 - ATGTCGCAAAGTATACTCAACTGTGTCAATACTTAAATACACTTACTTTAGCTGTACCCT - 20760
      - M  S  Q  S  I  L  N  C  V  N  T  *  I  H  L  L  *  L  Y  P
      -  C  R  K  V  Y  S  T  V  S  I  L  K  Y  T  Y  F  S  C  T  L
      -   V  A  K  Y  T  Q  L  C  Q  Y  L  N  T  L  T  L  A  V  P  Y
20761 - ACAACATGAGAGTTATTCACTTTGGTGCTGGCTCTGATAAAGGAGTTGCACCAGGTACAG - 20820
      - T  T  *  E  L  F  T  L  V  L  A  L  I  K  E  L  H  Q  V  Q
      -  Q  H  E  S  Y  S  L  W  C  W  L  *  *  R  S  C  T  R  Y  S
      -   N  M  R  V  I  H  F  G  A  G  S  D  K  G  V  A  P  G  T  A
20821 - CTGTGCTCAGACAATGGTTGCCAACTGGCACACTACTTGTCGATTCAGATCTTAATGACT - 20880
      - L  C  S  D  N  G  C  Q  L  A  H  Y  L  S  I  Q  I  L  M  T
      -  C  A  Q  T  M  V  A  N  W  H  T  T  C  R  F  R  S  *  *  L
      -   V  L  R  Q  W  L  P  T  G  T  L  L  V  D  S  D  L  N  D  F
20881 - TCGTCTCCGACGCAGATTCTACTTTAATTGGAGACTGTGCAACAGTACATACGGCTAATA - 20940
      - S  S  P  T  Q  I  L  L  *  L  E  T  V  Q  Q  Y  I  R  L  I
      -  R  L  R  R  R  F  Y  F  N  W  R  L  C  N  S  T  Y  G  *  *
      -   V  S  D  A  D  S  T  L  I  G  D  C  A  T  V  H  T  A  N  K
20941 - AATGGGACCTTATTATTAGCGATATGTATGACCCTAGGACCAAACATGTGACAAAAGAGA - 21000
      - N  G  T  L  L  L  A  I  C  M  T  L  G  P  N  M  *  Q  K  R
      -  M  G  P  Y  Y  *  R  Y  V  *  P  *  D  Q  T  C  D  K  R  E
      -   W  D  L  I  I  S  D  M  Y  D  P  R  T  K  H  V  T  K  E  N
21001 - ATGACTCTAAAGAAGGGTTTTTTCACTTATCTGTGTGGATTTATAAAGCAAAAACTAGCCC - 21060
      - M  T  L  K  K  G  F  S  L  I  C  V  D  L  *  S  K  N  *  P
      -  *  L  *  R  R  V  F  H  L  S  V  W  I  Y  K  A  K  T  S  P
      -   D  S  K  E  G  F  F  T  Y  L  C  G  F  I  K  Q  K  L  A  L
21061 - TGGGTGGTTCTATAGCTGTAAAGATAACAGAGCATTCTTGGAATGCTGACCTTTACAAGC - 21120
      - W  V  V  L  *  L  *  R  *  Q  S  I  L  G  M  L  T  F  T  S
      -  G  W  F  Y  S  C  K  D  N  R  A  F  L  E  C  *  P  L  Q  A
      -   G  G  S  I  A  V  K  I  T  E  H  S  W  N  A  D  L  Y  K  L
21121 - TTATGGGCCATTTCTCATGGTGGACAGCTTTTGTTACAAATGTAAATGCATCATCATCGG - 21180
      - L  W  A  I  S  H  G  G  Q  L  L  L  Q  M  *  M  H  H  H  R
      -  Y  G  P  F  L  M  V  D  S  F  C  Y  K  C  K  C  I  I  I  G
      -   M  G  H  F  S  W  W  T  A  F  V  T  N  V  N  A  S  S  S  E
21181 - AAGCATTTTTAATTGGGGCTAACTATCTTGGCAAGCCGAAGGAACAAATTGATGGCTATA - 21240
      - K  H  F  *  L  G  L  T  I  L  A  S  R  R  N  K  L  M  A  I
      -  S  I  F  N  W  G  *  L  S  W  Q  A  E  G  T  N  *  W  L  Y
      -   A  F  L  I  G  A  N  Y  L  G  K  P  K  E  Q  I  D  G  Y  T
21241 - CCATGCATGCTAACTACATTTTCTGGAGGAACACAAATCCTATCCAGTTGTCTTCCTATT - 21300
      - P  C  M  L  T  T  F  S  G  G  T  Q  I  L  S  S  C  L  P  I
      -  H  A  C  *  L  H  F  L  E  E  H  K  S  Y  P  V  V  L  L  F
      -   M  H  A  N  Y  I  F  W  R  N  T  N  P  I  Q  L  S  S  Y  S
21301 - CACTCTTTGACATGAGCAAATTTCCTCTTAAATTAAGAGGAACTGCTGTAATGTCTCTTA - 21360
      - H  S  L  T  *  A  N  F  L  L  N  *  E  E  L  L  *  C  L  L
      -  T  L  *  H  E  Q  I  S  S  *  I  K  R  N  C  C  N  V  S  *
      -   L  F  D  M  S  K  F  P  L  K  L  R  G  T  A  V  M  S  L  K
21361 - AGGAGAATCAAATCAATGATATGATTTATTCTCTTCTGGAAAAAGGTAGGCTTATCATTA - 21420
      - R  R  I  K  S  M  I  *  F  I  L  F  W  K  K  V  G  L  S  L
      -  G  E  S  N  Q  *  Y  D  L  F  S  S  G  K  R  *  A  Y  H  *
      -   E  N  Q  I  N  D  M  I  Y  S  L  L  E  K  G  R  L  I  I  R
21421 - GAGAAAACAACAGAGTTGTGGTTTCAAGTGATATTCTTGTTAACAACTAAACGAACATGT - 21480
      - E  K  T  T  E  L  W  F  Q  V  I  F  L  L  T  T  K  R  T  C
      -  R  K  Q  Q  S  C  G  F  K  *  Y  S  C  *  Q  L  N  E  H  V
      -   E  N  N  R  V  V  V  S  S  D  I  L  V  N  N  *  T  N  M  F
21481 - TTATTTCTTATTATTTCTTACTCTCACTAGTGGTAGTGACCTTGACCGGTGCACCACTT - 21540
      - L  F  S  Y  Y  F  L  L  S  L  V  V  V  T  L  T  G  A  P  L
      -  Y  F  L  I  I  S  Y  S  H  *  W  *  *  P  *  P  V  H  H  F
      -   I  F  L  L  F  L  T  L  T  S  G  S  D  L  D  R  C  T  T  F
21541 - TTGATGATGTTCAAGCTCCTAATTACACTCAACATACTTCATCTATGAGGGGGGTTTACT - 21600
      - L  M  M  F  K  L  L  I  T  L  N  I  L  H  L  *  G  G  F  T
      -  *  *  C  S  S  S  *  L  H  S  T  Y  F  I  Y  E  G  G  L  L
      -   D  D  V  Q  A  P  N  Y  T  Q  H  T  S  S  M  R  G  V  Y  Y
```

FIG. 4 Cont'd

```
21601 - ATCCTGATGAAATTTTTAGATCAGACACTCTTTATTTAACTCAGGATTTATTTCTTCCAT - 21660
       - I  L  M  K  F  L  D  Q  T  L  F  I  *  L  R  I  Y  F  F  H
       - S  *  *  N  F  *  I  R  H  S  L  F  N  S  G  F  I  S  S  I
       - P  D  E  I  F  R  S  D  T  L  Y  L  T  Q  D  L  F  L  P  F
21661 - TTTATTCTAATGTTACAGGGTTTCATACTATTAATCATACGTTTGACAACCCTGTCATAC - 21720
       - F  I  L  M  L  Q  G  F  I  L  L  I  I  R  L  T  T  L  S  Y
       - L  F  *  C  Y  R  V  S  Y  Y  *  S  Y  V  *  Q  P  C  H  T
       - Y  S  N  V  T  G  F  H  T  I  N  H  T  F  D  N  P  V  I  P
21721 - CTTTTAAGGATGGTATTTATTTTGCTGCCACAGAGAAATCAAATGTTGTCCGTGGTTGGG - 21780
       - L  L  R  M  V  F  I  L  L  P  Q  R  N  Q  M  L  S  V  V  G
       - F  *  G  W  Y  L  F  C  C  H  R  E  I  K  C  C  P  W  L  G
       - F  K  D  G  I  Y  F  A  A  T  E  K  S  N  V  V  R  G  W  V
21781 - TTTTTGGTTCTACCATGAACAACAAGTCACAGTCGGTGATTATTATTAACAATTCTACTA - 21840
       - F  L  V  L  P  *  T  T  S  H  S  R  *  L  L  L  T  I  L  L
       - F  W  F  Y  H  E  Q  Q  V  T  V  G  D  Y  Y  *  Q  F  Y  *
       - F  G  S  T  M  N  N  K  S  Q  S  V  I  I  I  N  N  S  T  N
21841 - ATGTTGTTATACGAGCATGTAACTTTGAATTGTGTGACAACCCTTTCTTTGCTGTTTCTA - 21900
       - M  L  L  Y  E  H  V  T  L  N  C  V  T  T  L  S  L  L  F  L
       - C  C  Y  T  S  M  *  L  *  I  V  *  Q  P  F  L  C  C  F  *
       - V  V  I  R  A  C  N  F  E  L  C  D  N  P  F  F  A  V  S  K
21901 - AACCCATGGGTACACAGACACATACTATGATATTCGATAATGCATTTAATTGCACTTTCG - 21960
       - N  P  W  V  H  R  H  I  L  *  Y  S  I  M  H  L  I  A  L  S
       - T  H  G  Y  T  D  T  Y  Y  D  I  R  *  C  I  *  L  H  F  R
       - P  M  G  T  Q  T  H  T  M  I  F  D  N  A  F  N  C  T  F  E
21961 - AGTACATATCTGATGCCTTTTCGCTTGATGTTTCAGAAAAGTCAGGTAATTTTAAACACT - 22020
       - S  T  Y  L  M  P  F  R  L  M  F  Q  K  S  Q  V  I  L  N  T
       - V  H  I  *  C  L  F  A  *  C  F  R  K  V  R  *  F  *  T  L
       - Y  I  S  D  A  F  S  L  D  V  S  E  K  S  G  N  F  K  H  L
22021 - TACGAGAGTTTGTGTTTAAAAATAAAGATGGGTTTCTCTATGTTTATAAGGGCTATCAAC - 22080
       - Y  E  S  L  C  L  K  I  K  M  G  F  S  M  F  I  R  A  I  N
       - T  R  V  C  V  *  K  *  R  W  V  S  L  C  L  *  G  L  S  T
       - R  E  F  V  F  K  N  K  D  G  F  L  Y  V  Y  K  G  Y  Q  P
22081 - CTATAGATGTAGTTCGTGATCTACCTTCTGGTTTTAACACTTTGAAACCTATTTTTAAGT - 22140
       - L  *  M  *  F  V  I  Y  L  L  V  L  T  L  *  N  L  F  L  S
       - Y  R  C  S  S  *  S  T  F  W  F  *  H  F  E  T  Y  F  *  V
       - I  D  V  V  R  D  L  P  S  G  F  N  T  L  K  P  I  F  K  L
22141 - TGCCTCTTGGTATTAACATTACAAATTTTAGAGCCATTCTTACAGCCTTTTCACCTGCTC - 22200
       - C  L  L  V  L  T  L  Q  I  L  E  P  F  L  Q  P  F  H  L  L
       - A  S  W  Y  *  H  Y  K  F  *  S  H  S  Y  S  L  F  T  C  S
       - P  L  G  I  N  I  T  N  F  R  A  I  L  T  A  F  S  P  A  Q
22201 - AAGACACTTGGGGCACGTCAGCTGCAGCCTATTTTGTTGGCTATTTAAAGCCAACTACAT - 22260
       - K  T  L  G  A  R  Q  L  Q  P  I  L  L  A  I  *  S  Q  L  H
       - R  H  L  G  H  V  S  C  S  L  F  C  W  L  F  K  A  N  Y  I
       - D  T  W  G  T  S  A  A  A  Y  F  V  G  Y  L  K  P  T  T  F
22261 - TTATGCTCAAGTATGATGAAAATGGTACAATCACAGATGCTGTTGATTGTTCTCAAAATC - 22320
       - L  C  S  S  M  M  K  M  V  Q  S  Q  M  L  L  I  V  L  K  I
       - Y  A  Q  V  *  *  K  W  Y  N  H  R  C  C  *  L  F  S  K  S
       - M  L  K  Y  D  E  N  G  T  I  T  D  A  V  D  C  S  Q  N  P
22321 - CACTTGCTGAACTCAAATGCTCTGTTAAGAGCTTTGAGATTGACAAAGGAATTTACCAGA - 22380
       - H  L  L  N  S  N  A  L  L  R  A  L  R  L  T  K  E  F  T  R
       - T  C  *  T  Q  M  L  C  *  E  L  *  D  *  Q  R  N  L  P  D
       - L  A  E  L  K  C  S  V  K  S  F  E  I  D  K  G  I  Y  Q  T
22381 - CCTCTAATTTCAGGGTTGTTCCCTCAGGAGATGTTGTGAGATTCCCTAATATTACAAACT - 22440
       - P  L  I  S  G  L  F  P  Q  E  M  L  *  D  S  L  I  L  Q  T
       - L  *  F  Q  G  C  S  L  R  R  C  C  E  I  P  *  Y  Y  K  L
       - S  N  F  R  V  V  P  S  G  D  V  V  R  F  P  N  I  T  N  L
22441 - TGTGTCCTTTTGGAGAGGTTTTTAATGCTACTAAATTCCCTTCTGTCTATGCATGGGAGA - 22500
       - C  V  L  L  E  R  F  L  M  L  L  N  S  L  L  S  M  H  G  R
       - V  S  F  W  R  G  F  *  C  Y  *  I  P  F  C  L  C  M  G  E
       - C  P  F  G  E  V  F  N  A  T  K  F  P  S  V  Y  A  W  E  R
```

FIG. 4 Cont'd

```
22501 - GAAAAAAAATTTCTAATTGTGTTGCTGATTACTCTGTGCTCTACAACTCAACATTTTTTT - 22560
      - E  K  K  F  L  I  V  L  L  I  T  L  C  S  T  T  Q  H  F  F
      - K  K  N  F  *  L  C  C  *  L  L  C  A  L  Q  L  N  I  F  F
      - K  K  I  S  N  C  V  A  D  Y  S  V  L  Y  N  S  T  F  F  S
22561 - CAACCTTTAAGTGCTATGGCGTTTCTGCCACTAAGTTGAATGATCTTTGCTTCTCCAATG - 22620
      - Q  P  L  S  A  M  A  F  L  P  L  S  *  M  I  F  A  S  P  M
      - N  L  *  V  L  W  R  F  C  H  *  V  E  *  S  L  L  L  Q  C
      - T  F  K  C  Y  G  V  S  A  T  K  L  N  D  L  C  F  S  N  V
22621 - TCTATGCAGATTCTTTTGTAGTCAAGGGAGATGATGTAAGACAAATAGCGCCAGGACAAA - 22680
      - S  M  Q  I  L  L  *  S  R  E  M  M  *  D  K  *  R  Q  D  K
      - L  C  R  F  F  C  S  Q  G  R  *  C  K  T  N  S  A  R  T  N
      - Y  A  D  S  F  V  V  K  G  D  D  V  R  Q  I  A  P  G  Q  T
22681 - CTGGTGTTATTGCTGATTATAATTATAAATTGCCAGATGATTTCATGGGTTGTGTCCTTG - 22740
      - L  V  L  L  L  I  I  I  *  L  P  D  D  F  M  G  C  V  L
      - W  C  Y  C  *  L  *  L  *  I  A  R  *  F  H  G  L  C  P  C
      - G  V  I  A  D  Y  N  Y  K  L  P  D  D  F  M  G  C  V  L  A
22741 - CTTGGAATACTAGGAACATTGATGCTACTTCAACTGGTAATTATAATTATAAATATAGGT - 22800
      - L  G  I  L  G  T  L  M  L  L  Q  L  V  I  I  I  N  I  G
      - L  E  Y  *  E  H  *  C  Y  F  N  W  *  L  *  L  *  I  *  V
      - W  N  T  R  N  I  D  A  T  S  T  G  N  Y  N  Y  K  Y  R  Y
22801 - ATCTTAGACATGGCAAGCTTAGGCCCTTTGAGAGAGACATATCTAATGTGCCTTTCTCCC - 22860
      - I  L  D  M  A  S  L  G  P  L  R  E  T  Y  L  M  C  L  S  P
      - S  *  T  W  Q  A  *  A  L  *  E  R  H  I  *  C  A  F  L  P
      - L  R  H  G  K  L  R  P  F  E  R  D  I  S  N  V  P  F  S  P
22861 - CTGATGGCAAACCTTGCACCCCACCTGCTCTTAATTGTTATTGGCCATTAAATGATTATG - 22920
      - L  M  A  N  L  A  P  H  L  L  L  I  V  I  G  H  *  M  I  M
      - *  W  Q  T  L  H  P  T  C  S  *  L  L  L  A  I  K  *  L  W
      - D  G  K  P  C  T  P  P  A  L  N  C  Y  W  P  L  N  D  Y  G
22921 - GTTTTTACACCACTACTGGCATTGGCTACCAACCTTACAGAGTTGTAGTACTTTCTTTTG - 22980
      - V  F  T  P  L  L  A  L  A  T  N  L  T  E  L  *  Y  F  L  L
      - F  L  H  H  Y  W  H  W  L  P  T  L  Q  S  C  S  T  F  F  *
      - F  Y  T  T  T  G  I  G  Y  Q  P  Y  R  V  V  V  L  S  F  E
22981 - AACTTTTAAATGCACCGGCCACGGTTTGTGGACCAAAATTATCCACTGACCTTATTAAGA - 23040
      - N  F  *  M  H  R  P  R  F  V  D  Q  N  Y  P  L  T  L  L  R
      - T  F  K  C  T  G  H  G  L  W  T  K  I  I  H  *  P  Y  *  E
      - L  L  N  A  P  A  T  V  C  G  P  K  L  S  T  D  L  I  K  N
23041 - ACCAGTGTGTCAATTTTAATTTTAATGGACTCACTGGTACTGGTGTGTTAACTCCTTCTT - 23100
      - T  S  V  S  I  L  I  L  M  D  S  L  V  L  V  C  *  L  L  L
      - P  V  C  Q  F  *  F  *  W  T  H  W  Y  W  C  V  N  S  F  F
      - Q  C  V  N  F  N  F  N  G  L  T  G  T  G  V  L  T  P  S  S
23101 - CAAAGAGATTTCAACCATTTCAACAATTTGGCCGTGATGTTTCTGATTTCACTGATTCCG - 23160
      - Q  R  D  F  N  H  F  N  N  L  A  V  M  F  L  I  S  L  I  P
      - K  E  I  S  T  I  S  T  I  W  P  *  C  F  *  F  H  *  F  R
      - K  R  F  Q  P  F  Q  Q  F  G  R  D  V  S  D  F  T  D  S  V
23161 - TTCGAGATCCTAAAACATCTGAAATATTAGACATTTCACCTTGCTCTTTTGGGGGTGTAA - 23220
      - F  E  I  L  K  H  L  K  Y  *  T  F  H  L  A  L  L  G  V  *
      - S  R  S  *  N  I  *  N  I  R  H  F  T  L  L  F  W  G  C  K
      - R  D  P  K  T  S  E  I  L  D  I  S  P  C  S  F  G  G  V  S
23221 - GTGTAATTACACCTGGAACAAATGCTTCATCTGAAGTTGCTGTTCTATATCAAGATGTTA - 23280
      - V  *  L  H  L  E  Q  M  L  H  L  K  L  L  F  Y  I  K  M  L
      - C  N  Y  T  W  N  K  C  F  I  *  S  C  C  S  I  S  R  C  *
      - V  I  T  P  G  T  N  A  S  S  E  V  A  V  L  Y  Q  D  V  N
23281 - ACTGCACTGATGTTTCTACAGCAATTCATGCAGATCAACTCACACCAGCTTGGCGCATAT - 23340
      - T  A  L  M  F  L  Q  Q  F  M  Q  I  N  S  H  Q  L  G  A  Y
      - L  H  *  C  F  Y  S  N  S  C  R  S  T  H  T  S  L  A  H  I
      - C  T  D  V  S  T  A  I  H  A  D  Q  L  T  P  A  W  R  I  Y
23341 - ATTCTACTGGAAACAATGTATTCCAGACTCAAGCAGGCTGTCTTATAGGAGCTGAGCATG - 23400
      - I  L  L  E  T  M  Y  S  R  L  K  Q  A  V  L  *  E  L  S  M
      - F  Y  W  K  Q  C  I  P  D  S  S  R  L  S  Y  R  S  *  A  C
      - S  T  G  N  N  V  F  Q  T  Q  A  G  C  L  I  G  A  E  H  V
```

FIG. 4 Cont'd

```
23401 - TCGACACTTCTTATGAGTGCGACATTCCTATTGGAGCTGGCATTTGTGCTAGTTACCATA - 23460
       - S  T  L  L  M  S  A  T  F  L  L  E  L  A  F  V  L  V  T  I
       - R  H  F  L  *  V  R  H  S  Y  W  S  W  H  L  C  *  L  P  Y
       -  D  T  S  Y  E  C  D  I  P  I  G  A  G  I  C  A  S  Y  H  T
23461 - CAGTTTCTTTATTACGTAGTACTAGCCAAAAATCTATTGTGGCTTATACTATGTCTTTAG - 23520
       - Q  F  L  Y  Y  V  V  L  A  K  N  L  L  W  L  I  L  C  L  *
       -  S  F  F  I  T  *  Y  *  P  K  I  Y  C  G  L  Y  Y  V  F  R
       -   V  S  L  L  R  S  T  S  Q  K  S  I  V  A  Y  T  M  S  L  G
23521 - GTGCTGATAGTTCAATTGCTTACTCTAATAACACCATTGCTATACCTACTAACTTTTCAA - 23580
       - V  L  I  V  Q  L  L  T  L  I  T  P  L  L  Y  L  L  T  F  Q
       -  C  *  *  F  N  C  L  L  *  *  H  H  C  Y  T  Y  *  L  F  N
       -   A  D  S  S  I  A  Y  S  N  N  T  I  A  I  P  T  N  F  S  I
23581 - TTAGCATTACTACAGAAGTAATGCCTGTTTCTATGGCTAAAACCTCCGTAGATTGTAATA - 23640
       - L  A  L  L  Q  K  *  C  L  F  L  W  L  K  P  P  *  I  V  I
       -  *  H  Y  Y  R  S  N  A  C  F  Y  G  *  N  L  R  R  L  *  Y
       -   S  I  T  T  E  V  M  P  V  S  M  A  K  T  S  V  D  C  N  M
23641 - TGTACATCTGCGGAGATTCTACTGAATGTGCTAATTTGCTTCTCCAATATGGTAGCTTTT - 23700
       - C  T  S  A  E  I  L  L  N  V  L  I  C  F  S  N  M  V  A  F
       -  V  H  L  R  R  F  Y  *  M  C  *  F  A  S  P  I  W  *  L  L
       -   Y  I  C  G  D  S  T  E  C  A  N  L  L  L  Q  Y  G  S  F  C
23701 - GCACACAACTAAATCGTGCACTCTCAGGTATTGCTGCTGAACAGGATCGCAACACACGTG - 23760
       - A  H  N  *  I  V  H  S  Q  V  L  L  L  N  R  I  A  T  H  V
       -  H  T  T  K  S  C  T  L  R  Y  C  C  *  T  G  S  Q  H  T  *
       -   T  Q  L  N  R  A  L  S  G  I  A  A  E  Q  D  R  N  T  R  E
23761 - AAGTGTTCGCTCAAGTCAAACAAATGTACAAAACCCCAACTTTGAAATATTTTGGTGGTT - 23820
       - K  C  S  L  K  S  N  K  C  T  K  P  Q  L  *  N  I  L  V  V
       -  S  V  R  S  S  Q  T  N  V  Q  N  P  N  F  E  I  F  W  W  F
       -   V  F  A  Q  V  K  Q  M  Y  K  T  P  T  L  K  Y  F  G  G  F
23821 - TTAATTTTTCACAAATATTACCTGACCCTCTAAAGCCAACTAAGAGGTCTTTTATTGAGG - 23880
       - L  I  F  H  K  Y  Y  L  T  L  *  S  Q  L  R  G  L  L  R
       -  *  F  F  T  N  I  T  *  P  S  K  A  N  *  E  V  F  Y  *  G
       -   N  F  S  Q  I  L  P  D  P  L  K  P  T  K  R  S  F  I  E  D
23881 - ACTTGCTCTTTAATAAGGTGACACTCGCTGATGCTGGCTTCATGAAGCAATATGGCGAAT - 23940
       - T  C  S  L  I  R  *  H  S  L  M  L  A  S  *  S  N  M  A  N
       -  L  A  L  *  *  G  D  T  R  *  C  W  L  H  E  A  I  W  R  M
       -   L  L  F  N  K  V  T  L  A  D  A  G  F  M  K  Q  Y  G  E  C
23941 - GCCTAGGTGATATTAATGCTAGAGATCTCATTTGTGCGCAGAAGTTCAATGGACTTACAG - 24000
       - A  *  V  I  L  M  L  E  I  S  F  V  R  R  S  S  M  D  L  Q
       -  P  R  *  Y  *  C  *  R  S  H  L  C  A  E  V  Q  W  T  Y  S
       -   L  G  D  I  N  A  R  D  L  I  C  A  Q  K  F  N  G  L  T  V
24001 - TGTTGCCACCTCTGCTCACTGATGATATGATTGCTGCCTACACTGCTGCTCTAGTTAGTG - 24060
       - C  C  H  L  C  S  L  M  I  *  L  L  P  T  L  L  L  *  L  V
       -  V  A  T  S  A  H  *  *  Y  D  C  C  L  H  C  C  S  S  *  W
       -   L  P  P  L  L  T  D  D  M  I  A  A  Y  T  A  A  L  V  S  G
24061 - GTACTGCCACTGCTGGATGGACATTTGGTGCTGGCGCTGCTCTTCAAATACCTTTTGCTA - 24120
       - V  L  P  L  L  D  G  H  L  V  L  A  L  L  F  K  Y  L  L  L
       -  Y  C  H  C  W  M  D  I  W  C  W  R  C  S  S  N  T  F  C  Y
       -   T  A  T  A  G  W  T  F  G  A  G  A  A  L  Q  I  P  F  A  M
24121 - TGCAAATGGCATATAGGTTCAATGGCATTGGAGTTACCCAAAATGTTCTCTATGAGAACC - 24180
       - C  K  W  H  I  G  S  M  A  L  E  L  P  K  M  F  S  M  R  T
       -  A  N  G  I  *  V  Q  W  H  W  S  Y  P  K  C  S  L  *  E  P
       -   Q  M  A  Y  R  F  N  G  I  G  V  T  Q  N  V  L  Y  E  N  Q
24181 - AAAAACAAATCGCCAACCAATTTAACAAGGCGATTAGTCAAATTCAAGAATCACTTACAA - 24240
       - K  N  K  S  P  T  N  L  T  R  R  L  V  K  F  K  N  H  L  Q
       -  K  T  N  R  Q  P  I  *  Q  G  D  *  S  N  S  R  I  T  Y  N
       -   K  Q  I  A  N  Q  F  N  K  A  I  S  Q  I  Q  E  S  L  T  T
24241 - CAACATCAACTGCATTGGGCAAGCTGCAAGACGTTGTTAACCAGAATGCTCAAGCATTAA - 24300
       - Q  H  Q  L  H  W  A  S  C  K  T  L  L  T  R  M  L  K  H  *
       -  N  I  N  C  I  G  Q  A  A  R  R  C  *  P  E  C  S  S  I  K
       -   T  S  T  A  L  G  K  L  Q  D  V  V  N  Q  N  A  Q  A  L  N
```

FIG. 4 Cont'd

```
24301 - ACACACTTGTTAAACAACTTAGCTCTAATTTTGGTGCAATTTCAAGTGTGCTAAATGATA - 24360
       - T  H  L  L  N  N  L  A  L  I  L  V  Q  F  Q  V  C  *  M  I
       - H  T  C  *  T  T  *  L  *  F  W  C  N  F  K  C  A  K  *  Y
       -   T  L  V  K  Q  L  S  S  N  F  G  A  I  S  S  V  L  N  D  I
24361 - TCCTTTCGCGACTTGATAAAGTCGAGGCGGAGGTACAAATTGACAGGTTAATTACAGGCA - 24420
       - S  F  R  D  L  I  K  S  R  R  R  Y  K  L  T  G  *  L  Q  A
       - P  F  A  T  *  *  S  R  G  G  G  T  N  *  Q  V  N  Y  R  Q
       -   L  S  R  L  D  K  V  E  A  E  V  Q  I  D  R  L  I  T  G  R
24421 - GACTTCAAAGCCTTCAAACCTATGTAACACAACAACTAATCAGGGCTGCTGAAATCAGGG - 24480
       - D  F  K  A  F  K  P  M  *  H  N  N  *  S  G  L  L  K  S  G
       - T  S  K  P  S  N  L  C  N  T  T  T  N  Q  G  C  *  N  Q  G
       -   L  Q  S  L  Q  T  Y  V  T  Q  Q  L  I  R  A  A  E  I  R  A
24481 - CTTCTGCTAATCTTGCTGCTACTAAAATGTCTGAGTGTGTTCTTGGACAATCAAAAAGAG - 24540
       - L  L  L  I  L  L  L  L  K  C  L  S  V  F  L  D  N  Q  K  E
       - F  C  *  S  C  C  Y  *  N  V  *  V  C  S  W  T  I  K  K  S
       -   S  A  N  L  A  A  T  K  M  S  E  C  V  L  G  Q  S  K  R  V
24541 - TTGACTTTTGTGGAAAGGGCTACCACCTTATGTCCTTCCCACAAGCAGCCCCGCATGGTG - 24600
       - L  T  F  V  E  R  A  T  T  L  C  P  S  H  K  Q  P  R  M  V
       - *  L  L  W  K  G  L  P  P  Y  V  L  P  T  S  S  P  A  W  C
       -   D  F  C  G  K  G  Y  H  L  M  S  F  P  Q  A  A  P  H  G  V
24601 - TTGTCTTCCTACATGTCACGTATGTGCCATCCCAGGAGAGGAACTTCACCACAGCGCCAG - 24660
       - L  S  S  Y  M  S  R  M  C  H  P  R  R  G  T  S  P  Q  R  Q
       - C  L  P  T  C  H  V  C  A  I  P  G  E  E  L  H  H  S  A  S
       -   V  F  L  H  V  T  Y  V  P  S  Q  E  R  N  F  T  T  A  P  A
24661 - CAATTTGTCATGAAGGCAAAGCATACTTCCCTCGTGAAGGTGTTTTTGTGTTTAATGGCA - 24720
       - Q  F  V  M  K  A  K  H  T  S  L  V  K  V  F  L  C  L  M  A
       - N  L  S  *  R  Q  S  I  L  P  S  *  R  C  F  C  V  *  W  H
       -   I  C  H  E  G  K  A  Y  F  P  R  E  G  V  F  V  F  N  G  T
24721 - CTTCTTGGTTTATTACACAGAGGAACTTCTTTTCTCCACAAATAATTACTACAGACAATA - 24780
       - L  L  G  L  L  H  R  G  T  S  F  L  H  K  *  L  L  Q  T  I
       - F  L  V  Y  Y  T  E  E  L  L  F  S  T  N  N  Y  Y  R  Q  Y
       -   S  W  F  I  T  Q  R  N  F  F  S  P  Q  I  I  T  T  D  N  T
24781 - CATTTGTCTCAGGAAATTGTGATGTCGTTATTGGCATCATTAACAACACAGTTTATGATC - 24840
       - H  L  S  Q  E  I  V  M  S  L  L  A  S  L  T  T  Q  F  M  I
       - I  C  L  R  K  L  *  C  R  Y  W  H  H  *  Q  H  S  L  *  S
       -   F  V  S  G  N  C  D  V  V  I  G  I  I  N  N  T  V  Y  D  P
24841 - CTCTGCAACCTGAGCTTGACTCATTCAAAGAAGAGCTGGACAAGTACTTCAAAAATCATA - 24900
       - L  C  N  L  S  L  T  H  S  K  K  S  W  T  S  T  S  K  I  I
       - S  A  T  *  A  *  L  I  Q  R  R  A  G  Q  V  L  Q  K  S  Y
       -   L  Q  P  E  L  D  S  F  K  E  E  L  D  K  Y  F  K  N  H  T
24901 - CATCACCAGATGTTGATCTTGGCGACATTTCAGGCATTAACGCTTCTGTCGTCAACATTC - 24960
       - H  H  Q  M  L  I  L  A  T  F  Q  A  L  T  L  L  S  S  T  F
       - I  T  R  C  *  S  W  R  H  F  R  H  *  R  F  C  R  Q  H  S
       -   S  P  D  V  D  L  G  D  I  S  G  I  N  A  S  V  V  N  I  Q
24961 - AAAAAGAAATTGACCGCCTCAATGAGGTCGCTAAAAATTTAAATGAATCACTCATTGACC - 25020
       - K  K  K  L  T  A  S  M  R  S  L  K  I  *  M  N  H  S  L  T
       - K  R  N  *  P  P  Q  *  G  R  *  K  F  K  *  I  T  H  *  P
       -   K  E  I  D  R  L  N  E  V  A  K  N  L  N  E  S  L  I  D  L
25021 - TTCAAGAATTGGGAAAATATGAGCAATATATTAAATGGCCTTGGTATGTTTGGCTCGGCT - 25080
       - F  K  N  W  E  N  M  S  N  I  L  N  G  L  G  M  F  G  S  A
       - S  R  I  G  K  I  *  A  I  Y  *  M  A  L  V  C  L  A  R  L
       -   Q  E  L  G  K  Y  E  Q  Y  I  K  W  P  W  Y  V  W  L  G  F
25081 - TCATTGCTGGACTAATTGCCATCGTCATGGTTACAATCTTGCTTTGTTGCATGACTAGTT - 25140
       - S  L  L  D  *  L  P  S  S  W  L  Q  S  C  F  V  A  *  L  V
       - H  C  W  T  N  C  H  R  H  G  Y  N  L  A  L  L  H  D  *  L
       -   I  A  G  L  I  A  I  V  M  V  T  I  L  L  C  C  M  T  S  C
25141 - GTTGCAGTTGCCTCAAGGGTGCATGCTCTTGTGGTTCTTGCTGCAAGTTTGATGAGGATG - 25200
       - V  A  V  A  S  R  V  H  A  L  V  V  L  A  A  S  L  M  R  M
       - L  Q  L  P  Q  G  C  M  L  L  W  F  L  L  Q  V  *  *  G  *
       -   C  S  C  L  K  G  A  C  S  C  G  S  C  C  K  F  D  E  D  D
```

FIG. 4 Cont'd

```
25201 - ACTCTGAGCCAGTTCTCAAGGGTGTCAAATTACATTACACATAAACGAACTTATGGATTT - 25260
      -   T  L  S  Q  F  S  R  V  S  N  Y  I  T  H  K  R  T  Y  G  F
      - L  *  A  S  S  Q  G  C  Q  I  T  L  H  I  N  E  L  M  D  L
      -    S  E  P  V  L  K  G  V  K  L  H  Y  T  *  T  N  L  W  I  C
25261 - GTTTATGAGATTTTTTACTCTTGGATCAATTACTGCACAGCCAGTAAAAATTGACAATGC - 25320
      -   V  Y  E  I  F  Y  S  W  I  N  Y  C  T  A  S  K  N  *  Q  C
      - F  M  R  F  F  T  L  G  S  I  T  A  Q  P  V  K  I  D  N  A
      -    L  *  D  F  L  L  L  D  Q  L  L  H  S  Q  *  K  L  T  M  L
25321 - TTCTCCTGCAAGTACTGTTCATGCTACAGCAACGATACCGCTACAAGCCTCACTCCCTTT - 25380
      -   F  S  C  K  Y  C  S  C  Y  S  N  D  T  A  T  S  L  T  P  F
      - S  P  A  S  T  V  H  A  T  A  T  I  P  L  Q  A  S  L  P  F
      -    L  L  Q  V  L  F  M  L  Q  Q  R  Y  R  Y  K  P  H  S  L  S
25381 - CGGATGGCTTGTTATTGGCGTTGCATTTCTTGCTGTTTTCAGAGCGCTACCAAAATAAT - 25440
      -   R  M  A  C  Y  W  R  C  I  S  C  C  F  S  E  R  Y  Q  N  N
      - G  W  L  V  I  G  V  A  F  L  A  V  F  Q  S  A  T  K  I  I
      -    D  G  L  L  L  A  L  H  F  L  L  F  F  R  A  L  P  K  *  L
25441 - TGCGCTCAATAAAAGATGGCAGCTAGCCCTTTATAAGGGCTTCCAGTTCATTTGCAATTT - 25500
      -   C  A  Q  *  K  M  A  A  S  P  L  *  G  L  P  V  H  L  Q  F
      - A  L  N  K  R  W  Q  L  A  L  Y  K  G  F  Q  F  I  C  N  L
      -    R  S  I  K  D  G  S  *  P  F  I  R  A  S  S  S  F  A  I  Y
25501 - ACTGCTGCTATTTGTTACCATCTATTCACATCTTTTGCTTGTCGCTGCAGGTATGGAGGC - 25560
      -   T  A  A  I  C  Y  H  L  F  T  S  F  A  C  R  C  R  Y  G  G
      - L  L  L  F  V  T  I  Y  S  H  L  L  L  V  A  A  G  M  E  A
      -    C  C  Y  L  L  P  S  I  H  I  F  C  L  S  L  Q  V  W  R  R
25561 - GCAATTTTTGTACCTCTATGCCTTGATATATTTTCTACAATGCATCAACGCATGTAGAAT - 25620
      -   A  I  F  V  P  L  C  L  D  I  F  S  T  M  H  Q  R  M  *  N
      - Q  F  L  Y  L  Y  A  L  I  Y  F  L  Q  C  I  N  A  C  R  I
      -    N  F  C  T  S  M  P  *  Y  I  F  Y  N  A  S  T  H  V  E  L
25621 - TATTATGAGATGTTGGCTTTGTTGGAAGTGCAAATCCAAGAACCCATTACTTTATGATGC - 25680
      -   Y  Y  E  M  L  A  L  L  E  V  Q  I  Q  E  P  I  T  L  *  C
      - I  M  R  C  W  L  C  W  K  C  K  S  K  N  P  L  L  Y  D  A
      -    L  *  D  V  G  F  V  G  S  A  N  P  R  T  H  Y  F  M  M  P
25681 - CAACTACTTTGTTTGCTGGCACACACATAACTATGACTACTGTATACCATATAACAGTGT - 25740
      -   Q  L  L  C  L  L  A  H  T  *  L  *  L  L  Y  T  I  *  Q  C
      - N  Y  F  V  C  W  H  T  H  N  Y  D  Y  C  I  P  Y  N  S  V
      -    T  T  L  F  A  G  T  H  I  T  M  T  T  V  Y  H  I  T  V  S
25741 - CACAGATACAATTGTCGTTACTGAAGGTGACGGCATTTCAACACCAAAACTCAAAGAAGA - 25800
      -   H  R  Y  N  C  R  Y  *  R  *  R  H  F  N  T  K  T  Q  R  R
      - T  D  T  I  V  V  T  E  G  D  G  I  S  T  P  K  L  K  E  D
      -    Q  I  Q  L  S  L  L  K  V  T  A  F  Q  H  Q  N  S  K  K  T
25801 - CTACCAAATTGGTGGTTATTCTGAGGATAGGCACTCAGGTGTTAAAGACTATGTCGTTGT - 25860
      -   L  P  N  W  W  L  F  *  G  *  A  L  R  C  *  R  L  C  R  C
      - Y  Q  I  G  G  Y  S  E  D  R  H  S  G  V  K  D  Y  V  V  V
      -    T  K  L  V  V  I  L  R  I  G  T  Q  V  L  K  T  M  S  L  Y
25861 - ACATGGCTATTTCACCGAAGTTTACTACCAGCTTGAGTCTACACAAATTACTACAGACAC - 25920
      -   T  W  L  F  H  R  S  L  L  P  A  *  V  Y  T  N  Y  Y  R  H
      - H  G  Y  F  T  E  V  Y  Y  Q  L  E  S  T  Q  I  T  T  D  T
      -    M  A  I  S  P  K  F  T  T  S  L  S  L  H  K  L  L  Q  T  L
25921 - TGGTATTGAAAATGCTACATTCTTCATCTTTAACAAGCTTGTTAAAGACCCACCGAATGT - 25980
      -   W  Y  *  K  C  Y  I  L  H  L  *  Q  A  C  *  R  P  T  E  C
      - G  I  E  N  A  T  F  F  I  F  N  K  L  V  K  D  P  P  N  V
      -    V  L  K  M  L  H  S  S  S  L  T  S  L  L  K  T  H  R  M  C
25981 - GCAAATACACACAATCGACGGCTCTTCAGGAGTTGCTAATCCAGCAATGGATCCAATTTA - 26040
      -   A  N  T  H  N  R  R  L  F  R  S  C  *  S  S  N  G  S  N  L
      - Q  I  H  T  I  D  G  S  S  G  V  A  N  P  A  M  D  P  I  Y
      -    K  Y  T  Q  S  T  A  L  Q  E  L  L  I  Q  Q  W  I  Q  F  M
26041 - TGATGAGCCGACGACGACTACTAGCGTGCCTTTGTAAGCACAAGAAAGTGAGTACGAACT - 26100
      -   *  *  A  D  D  D  Y  *  R  A  F  V  S  T  R  K  *  V  R  T
      - D  E  P  T  T  T  T  S  V  P  L  *  A  Q  E  S  E  Y  E  L
      -    M  S  R  R  R  L  L  A  C  L  C  K  H  K  K  V  S  T  N  L
```

FIG. 4 Cont'd

```
26101 - TATGTACTCATTCGTTTCGGAAGAAACAGGTACGTTAATAGTTAATAGCGTACTTCTTTT - 26160
       - Y V L I R F G R N R Y V N S * * R T S F
       - M Y S F V S E E T G T L I V N S V L L F
       -   C T H S F R K K Q V R * * L I A Y F F F
26161 - TCTTGCTTTCGTGGTATTCTTGCTAGTCACACTAGCCATCCTTACTGCGCTTCGATTGTG - 26220
       - S C F R G I L A S H T S H P Y C A S I V
       - L A F V V F L L V T L A I L T A L R L C
       -   L L S W Y S C * S H * P S L L R F D C V
26221 - TGCGTACTGCTGCAATATTGTTAACGTGAGTTTAGTAAAACCAACGGTTTACGTCTACTC - 26280
       - C V L L Q Y C * R E F S K T N G L R L L
       - A Y C C N I V N V S L V K P T V Y V Y S
       -   R T A A I L L T * V * * N Q R F T S T R
26281 - GCGTGTTAAAAATCTGAACTCTTCTGAAGGAGTTCCTGATCTTCTGGTCTAAACGAACTA - 26340
       - A C * K S E L F * R S S * S S G L N E L
       - R V K N L N S S E G V P D L L V * T N *
       -   V L K I * T L L K E F L I F W S K R T N
26341 - ACTATTATTATTATTCTGTTTGGAACTTTAACATTGCTTATCATGGCAGACAACGGTACT - 26400
       - T I I I L F G T L T L L I M A D N G T
       - L L L L F C L E L * H C L S W Q T T V L
       -   Y Y Y Y S V W N F N I A Y H G R Q R Y Y
26401 - ATTACCGTTGAGGAGCTTAAACAACTCCTGGAACAATGGAACCTAGTAATAGGTTTCCTA - 26460
       - I T V E E L K Q L L E Q W N L V I G F L
       - L P L R S L N N S W N N G T * * * V S Y
       -   Y R * G A * T T P G T M E P S N R F P I
26461 - TTCCTAGCCTGGATTATGTTACTACAATTTGCCTATTCTAATCGGAACAGGTTTTTGTAC - 26520
       - F L A W I M L L Q F A Y S N R N R F L Y
       - S * P G L C Y Y N L P I L I G T G F C T
       -   P S L D Y V T T I C L F * S E Q V F V H
26521 - ATAATAAAGCTTGTTTTCCTCTGGCTCTTGTGGCCAGTAACACTTGCTTGTTTTGTGCTT - 26580
       - I I K L V F L W L L W P V T L A C F V L
       - * * S L F S S G S C G Q * H L L V L C L
       -   N K A C F P L A L V A S N T C L F C A C
26581 - GCTGCTGTCTACAGAATTAATTGGGTGACTGGCGGGATTGCGATTGCAATGGCTTGTATT - 26640
       - A A V Y R I N W V T G G I A I A M A C I
       - L L S T E L I G * L A G L R L Q W L V L
       -   C C L Q N * L G D W R D C D C N G L Y C
26641 - GTAGGCTTGATGTGGCTTAGCTACTTCGTTGCTTCCTTCAGGCTGTTTGCTCGTACCCGC - 26700
       - V G L M W L S Y F V A S F R L F A R T R
       - * A * C G L A T S L L P S G C L L V P A
       -   R L D V A * L L R C F L Q A V C S Y P L
26701 - TCAATGTGGTCATTCAACCCAGAAACAAACATTCTTCTCAATGTGCCTCTCCGGGGGACA - 26760
       - S M W S F N P E T N I L L N V P L R G T
       - Q C G H S T Q K Q T F F S M C L S G G Q
       -   N V V I Q P R N K H S S Q C A S P G D N
26761 - ATTGTGACCAGACCGCTCATGGAAAGTGAACTTGTCATTGGTGCTGTGATCATTCGTGGT - 26820
       - I V T R P L M E S E L V I G A V I I R G
       - L * P D R S W K V N L S L V L * S F V V
       -   C D Q T A H G K * T C H W C C D H S W S
26821 - CACTTGCGAATGGCCGGACACTCCCTAGGGCGCTGTGACATTAAGGACCTGCCAAAAGAG - 26880
       - H L R M A G H S L G R C D I K D L P K E
       - T C E W P D T P * G A V T L R T C Q K R
       -   L A N G R T L P R A L * H * G P A K R D
26881 - ATCACTGTGGCTACATCACGAACGCTTTCTTATTACAAATTAGGAGCGTCGCAGCGTGTA - 26940
       - I T V A T S R T L S Y Y K L G A S Q R V
       - S L W L H H E R F L I T N * E R R S V *
       -   H C G Y I T N A F L L Q I R S V A A C R
26941 - GGCACTGATTCAGGTTTTGCTGCATACAACCGCTACCGTATTGGAAACTATAAATTAAAT - 27000
       - G T D S G F A A Y N R Y R I G N Y K L N
       - A L I Q V L L H T T A T V L E T I N * I
       -   H * F R F C C I Q P L P Y W K L * I K Y
```

FIG. 4 Cont'd

```
27001 - ACAGACCACGCCGGTAGCAACGACAATATTGCTTTGCTAGTACAGTAAGTGACAACAGAT - 27060
       -  T  D  H  A  G  S  N  D  N  I  A  L  L  V  Q  *  V  T  T  D
       -  Q  T  T  P  V  A  T  T  I  L  L  C  *  Y  S  K  *  Q  Q  M
       -  R  P  R  R  *  Q  R  Q  Y  C  F  A  S  T  V  S  D  N  R  C
27061 - GTTTCATCTTGTTGACTTCCAGGTTACAATAGCAGAGATATTGATTATCATTATGAGGAC - 27120
       -  V  S  S  C  *  L  P  G  Y  N  S  R  D  I  D  Y  H  Y  E  D
       -  F  H  L  V  D  F  Q  V  T  I  A  E  I  L  I  I  I  M  R  T
       -  F  I  L  L  T  S  R  L  Q  *  Q  R  Y  *  L  S  L  *  G  L
27121 - TTTCAGGATTGCTATTTGGAATCTTGACGTTATAATAAGTTCAATAGTGAGACAATTATT - 27180
       -  F  Q  D  C  Y  L  E  S  *  R  Y  N  K  F  N  S  E  T  I  I
       -  F  R  I  A  I  W  N  L  D  V  I  I  S  S  I  V  R  Q  L  F
       -  S  G  L  L  F  G  I  L  T  L  *  *  V  Q  *  *  D  N  Y  L
27181 - TAAGCCTCTAACTAAGAAGAATTATTCGGAGTTAGATGATGAAGAACCTATGGAGTTAGA - 27240
       -  *  A  S  N  *  E  E  L  F  G  V  R  *  *  R  T  Y  G  V  R
       -  K  P  L  T  K  K  N  Y  S  E  L  D  D  E  E  P  M  E  L  D
       -  S  L  *  L  R  R  I  I  R  S  *  M  M  K  N  L  W  S  *  I
27241 - TTATCCATAAAACGAACATGAAAATTATTCTCTTCCTGACATTGATTGTATTTACATCTT - 27300
       -  L  S  I  K  R  T  *  K  L  F  S  S  *  H  *  L  Y  L  H  L
       -  Y  P  *  N  E  H  E  N  Y  S  L  P  D  I  D  C  I  Y  I  L
       -  I  H  K  T  N  M  K  I  I  L  F  L  T  L  I  V  F  T  S  C
27301 - GCGAGCTATATCACTATCAGGAGTGTGTTAGAGGTACGACTGTACTACTAAAAGAACCTT - 27360
       -  A  S  Y  I  T  I  R  S  V  L  E  V  R  L  Y  Y  *  K  N  L
       -  R  A  I  S  L  S  G  V  C  *  R  Y  D  C  T  T  K  R  T  L
       -  E  L  Y  H  Y  Q  E  C  V  R  G  T  T  V  L  L  K  E  P  C
27361 - GCCCATCAGGAACATACGAGGGCAATTCACCATTTCACCCTCTTGCTGACAATAAATTTG - 27420
       -  A  H  Q  E  H  T  R  A  I  H  H  F  T  L  L  T  I  N  L
       -  P  I  R  N  I  R  G  Q  F  T  I  S  P  S  C  *  Q  *  I  C
       -  P  S  G  T  Y  E  G  N  S  P  F  H  P  L  A  D  N  K  F  A
27421 - CACTAACTTGCACTAGCACACACTTTGCTTTTGCTTGTGCTGACGGTACTCGACATACCT - 27480
       -  H  *  L  A  L  A  H  T  L  L  L  V  L  T  V  L  D  I  P
       -  T  N  L  H  *  H  T  L  C  F  C  L  C  *  R  Y  S  T  Y  L
       -  L  T  C  T  S  T  H  F  A  F  A  C  A  D  G  T  R  H  T  Y
27481 - ATCAGCTGCGTGCAAGATCAGTTTCACCAAAACTTTTCATCAGACAAGAGGAGGTTCAAC - 27540
       -  I  S  C  V  Q  D  Q  F  H  Q  N  F  S  S  D  K  R  R  F  N
       -  S  A  A  C  K  I  S  F  T  K  T  F  H  Q  T  R  G  G  S  T
       -  Q  L  R  A  R  S  V  S  P  K  L  F  I  R  Q  E  E  V  Q  Q
27541 - AAGAGCTCTACTCGCCACTTTTTCTCATTGTTGCTGCTCTAGTATTTTTAATACTTTGCT - 27600
       -  K  S  S  T  R  H  F  F  S  L  L  L  L  *  Y  F  *  Y  F  A
       -  R  A  L  L  A  T  F  S  H  C  C  C  S  S  I  F  N  T  L  L
       -  E  L  Y  S  P  L  F  L  I  V  A  A  L  V  F  L  I  L  C  F
27601 - TCACCATTAAGAGAAAGACAGAATGAATGAGCTCACTTTAATTGACTTCTATTTGTGCTT - 27660
       -  S  P  L  R  E  R  Q  N  E  *  A  H  F  N  *  L  L  F  V  L
       -  H  H  *  E  K  D  R  M  N  E  L  T  L  I  D  F  Y  L  C  F
       -  T  I  K  R  K  T  E  *  M  S  S  L  *  L  T  S  I  C  A  F
27661 - TTTAGCCTTTCTGCTATTCCTTGTTTTAATAATGCTTATTATATTTTGGTTTTCACTCGA - 27720
       -  F  S  L  S  A  I  P  C  F  N  N  A  Y  Y  I  L  V  F  T  R
       -  L  A  F  L  L  P  L  V  L  I  M  L  I  I  F  W  F  S  L  E
       -  *  P  F  C  Y  S  L  F  *  *  C  L  L  Y  F  G  F  H  S  K
27721 - AATCCAGGATCTAGAAGAACCTTGTACCAAAGTCTAAACGAACATGAAACTTCTCATTGT - 27780
       -  N  P  G  S  R  R  T  L  Y  Q  S  L  N  E  H  E  T  S  H  C
       -  I  Q  D  L  E  E  P  C  T  K  V  *  T  N  M  K  L  L  I  V
       -  S  R  I  *  K  N  L  V  P  K  S  K  R  T  *  N  F  S  L  F
27781 - TTTGACTTGTATTTCTCTATGCAGTTGCATACGCACTGTAGTACAGCGCTGTGCATCTAA - 27840
       -  F  D  L  Y  F  S  M  Q  L  H  T  H  C  S  T  A  L  C  I  *
       -  L  T  C  I  S  L  C  S  C  I  R  T  V  V  Q  R  C  A  S  N
       -  *  L  V  F  L  Y  A  V  A  Y  A  L  *  Y  S  A  V  H  L  I
27841 - TAAACCTCATGTGCTTGAAGATCCTTGTAAGGTACAACACTAGGGGTAATACTTATAGCA - 27900
       -  *  T  S  C  A  *  R  S  L  *  G  T  T  L  G  V  I  L  I  A
       -  K  P  H  V  L  E  D  P  C  K  V  Q  H  *  G  *  Y  L  *  H
       -  N  L  M  C  L  K  I  L  V  R  Y  N  T  R  G  N  T  Y  S  T
```

FIG. 4 Cont'd

```
27901 - CTGCTTGGCTTTGTGCTCTAGGAAAGGTTTTACCTTTTCATAGATGGCACACTATGGTTC - 27960
      - L  L  G  F  V  L  *  E  R  F  Y  L  F  I  D  G  T  L  W  F
      -  C  L  A  L  C  S  R  K  G  F  T  F  S  *  M  A  H  Y  G  S
      -   A  W  L  C  A  L  G  K  V  L  P  F  H  R  W  H  T  M  V  Q
27961 - AAACATGCACACCTAATGTTACTATCAACTGTCAAGATCCAGCTGGTGGTGCGCTTATAG - 28020
      - K  H  A  H  L  M  L  L  S  T  V  K  I  Q  L  V  V  R  L  *
      -  N  M  H  T  *  C  Y  Y  Q  L  S  R  S  S  W  W  C  A  Y  S
      -   T  C  T  P  N  V  T  I  N  C  Q  D  P  A  G  G  A  L  I  A
28021 - CTAGGTGTTGGTACCTTCATGAAGGTCACCAAACTGCTGCATTTAGAGACGTACTTGTTG - 28080
      - L  G  V  G  T  F  M  K  V  T  K  L  L  H  L  E  T  Y  L  L
      -  *  V  L  V  P  S  *  R  S  P  N  C  C  I  *  R  R  T  C  C
      -   R  C  W  Y  L  H  E  G  H  Q  T  A  A  F  R  D  V  L  V  V
28081 - TTTTAAATAAACGAACAAATTAAAATGTCTGATAATGGACCCCAATCAAACCAACGTAGT - 28140
      - F  *  I  N  E  Q  I  K  M  S  D  N  G  P  Q  S  N  Q  R  S
      -  F  K  *  T  N  K  L  K  C  L  I  M  D  P  N  Q  T  N  V  V
      -   L  N  K  R  T  N  *  N  V  *  *  W  T  P  I  K  P  T  *  C
28141 - GCCCCCCGCATTACATTTGGTGGACCCACAGATTCAACTGACAATAACCAGAATGGAGGA - 28200
      - A  P  R  I  T  F  G  G  P  T  D  S  T  D  N  N  Q  N  G  G
      -  P  P  A  L  H  L  V  D  P  Q  I  Q  L  T  I  T  R  M  E  D
      -   P  P  H  Y  I  W  W  T  H  R  F  N  *  Q  *  P  E  W  R  T
28201 - CGCAATGGGGCAAGGCCAAAACAGCGCCGACCCCAAGGTTTACCCAATAATACTGCGTCT - 28260
      - R  N  G  A  R  P  K  Q  R  R  P  Q  G  L  P  N  N  T  A  S
      -  A  M  G  Q  G  Q  N  S  A  D  P  K  V  Y  P  I  I  L  R  L
      -   Q  W  G  K  A  K  T  A  P  T  P  R  F  T  Q  *  Y  C  V  L
28261 - TGGTTCACAGCTCTCACTCAGCATGGCAAGGAGGAACTTAGATTCCCTCGAGGCCAGGGC - 28320
      - W  F  T  A  L  T  Q  H  G  K  E  E  L  R  F  P  R  G  Q  G
      -  G  S  Q  L  S  L  S  M  A  R  R  N  L  D  S  L  E  A  R  A
      -   V  H  S  S  H  S  A  W  Q  G  G  T  *  I  P  S  R  P  G  R
28321 - GTTCCAATCAACACCAATAGTGGTCCAGATGACCAAATTGGCTACTACCGAAGAGCTACC - 28380
      - V  P  I  N  T  N  S  G  P  D  D  Q  I  G  Y  Y  R  R  A  T
      -  F  Q  S  T  P  I  V  V  Q  M  T  K  L  A  T  T  E  E  L  P
      -   S  N  Q  H  Q  *  W  S  R  *  P  N  W  L  L  P  K  S  Y  P
28381 - CGACGAGTTCGTGGTGGTGACGGCAAAATGAAAGAGCTCAGCCCCAGATGGTACTTCTAT - 28440
      - R  R  V  R  G  G  D  G  K  M  K  E  L  S  P  R  W  Y  F  Y
      -  D  E  F  V  V  V  T  A  K  *  K  S  S  A  P  D  G  T  S  I
      -   T  S  S  W  W  *  R  Q  N  E  R  A  Q  P  Q  M  V  L  L  L
28441 - TACCTAGGAACTGGCCCAGAAGCTTCACTTCCCTACGGCGCTAACAAAGAAGGCATCGTA - 28500
      - Y  L  G  T  G  P  E  A  S  L  P  Y  G  A  N  K  E  G  I  V
      -  T  *  E  L  A  Q  K  L  H  F  P  T  A  L  T  K  K  A  S  Y
      -   P  R  N  W  P  R  S  F  T  S  L  R  R  *  Q  R  R  H  R  M
28501 - TGGGTTGCAACTGAGGGAGCCTTGAATACACCCAAAGACCACATTGGCACCCGCAATCCT - 28560
      - W  V  A  T  E  G  A  L  N  T  P  K  D  H  I  G  T  R  N  P
      -  G  L  Q  L  R  E  P  *  I  H  P  K  T  T  L  A  P  A  I  L
      -   G  C  N  *  G  S  L  E  Y  T  Q  R  P  H  W  H  P  Q  S  *
28561 - AATAACAATGCTGCCACCGTGCTACAACTTCCTCAAGGAACAACATTGCCAAAAGGCTTC - 28620
      - N  N  N  A  A  T  V  L  Q  L  P  Q  G  T  T  L  P  K  G  F
      -  I  T  M  L  P  P  C  Y  N  F  L  K  E  Q  H  C  Q  K  A  S
      -   *  Q  C  C  H  R  A  T  T  S  S  R  N  N  I  A  K  R  L  L
28621 - TACGCAGAGGGAAGCAGAGGCGGCAGTCAAGCCTCTTCTCGCTCCTCATCACGTAGTCGC - 28680
      - Y  A  E  G  S  R  G  G  S  Q  A  S  S  R  S  S  S  R  S  R
      -  T  Q  R  E  A  E  A  A  V  K  P  L  L  A  P  H  H  V  V  A
      -   R  R  G  K  Q  R  R  Q  S  S  L  F  S  L  L  I  T  *  S  R
28681 - GGTAATTCAAGAAATTCAACTCCTGGCAGCAGTAGGGGAAATTCTCCTGCTCGAATGGCT - 28740
      - G  N  S  R  N  S  T  P  G  S  S  R  G  N  S  P  A  R  M  A
      -  V  I  Q  E  I  Q  L  L  A  A  V  G  E  I  L  L  L  E  W  L
      -   *  F  K  K  F  N  S  W  Q  Q  *  G  K  F  S  C  S  N  G  *
28741 - AGCGGAGGTGGTGAAACTGCCCTCGCGCTATTGCTGCTAGACAGATTGAACCAGCTTGAG - 28800
      - S  G  G  G  E  T  A  L  A  L  L  L  L  D  R  L  N  Q  L  E
      -  A  E  V  V  K  L  P  S  R  Y  C  C  *  T  D  *  T  S  L  R
      -   R  R  W  *  N  C  P  R  A  I  A  A  R  Q  I  E  P  A  *  E
```

FIG. 4 Cont'd

```
28801 - AGCAAAGTTTCTGGTAAAGGCCAACAACAACAAGGCCAAACTGTCACTAAGAAATCTGCT - 28860
       - S  K  V  S  G  K  G  Q  Q  Q  Q  G  Q  T  V  T  K  K  S  A
       -  A  K  F  L  V  K  A  N  N  N  K  A  K  L  S  L  R  N  L  L
       -   Q  S  F  W  *  R  P  T  T  T  R  P  N  C  H  *  E  I  C  C
28861 - GCTGAGGCATCTAAAAAGCCTCGCCAAAAACGTACTGCCACAAAACAGTACAACGTCACT - 28920
       - A  E  A  S  K  K  P  R  Q  K  R  T  A  T  K  Q  Y  N  V  T
       -  L  R  H  L  K  S  L  A  K  N  V  L  P  Q  N  S  T  T  S  L
       -   *  G  I  *  K  A  S  P  K  T  Y  C  H  K  T  V  Q  R  H  S
28921 - CAAGCATTTGGGAGACGTGGTCCAGAACAAACCCAAGGAAATTTCGGGGACCAAGACCTA - 28980
       - Q  A  F  G  R  R  G  P  E  Q  T  Q  G  N  F  G  D  Q  D  L
       -  K  H  L  G  D  V  V  Q  N  K  P  K  E  I  S  G  T  K  T  *
       -   S  I  W  E  T  W  S  R  T  N  P  R  K  F  R  G  R  P  N
28981 - ATCAGACAAGGAACTGATTACAAACATTGGCCGCAAATTGCACAATTTGCTCCAAGTGCC - 29040
       - I  R  Q  G  T  D  Y  K  H  W  P  Q  I  A  Q  F  A  P  S  A
       -  S  D  K  E  L  I  T  N  I  G  R  K  L  H  N  L  L  Q  V  X
       -   Q  T  R  N  *  L  Q  T  L  A  A  N  C  T  I  C  S  K  C  X
29041 - TCTGCATTCTTTGGAATGTCACGCATTGGCATGGAAGTCACACCTTCGGGAACATGGCTG - 29100
       - S  A  F  F  G  M  S  R  I  G  M  E  V  T  P  S  G  T  W  L
       -  L  H  S  L  E  C  H  A  L  A  W  K  S  H  L  R  E  H  G  *
       -   C  I  L  W  N  V  T  H  W  H  G  S  H  T  F  G  N  M  A  D
29101 - ACTTATCATGGAGCCATTAAATTGGATGACAAAGATCCACAATTCAAAGACAACGTCATA - 29160
       - T  Y  H  G  A  I  K  L  D  D  K  D  P  Q  F  K  D  N  V  I
       -  L  I  M  E  P  L  N  W  M  T  K  I  H  N  S  K  T  T  S  Y
       -   L  S  W  S  H  *  I  G  *  Q  R  S  T  I  Q  R  Q  R  H  T
29161 - CTGCTGAACAAGCACATTGACGCATACAAAACATTCCCACCAACAGAGCCTAAAAAGGAC - 29220
       - L  L  N  K  H  I  D  A  Y  K  T  F  P  P  T  E  P  K  K  D
       -  C  *  T  S  T  L  T  H  T  K  H  S  H  Q  Q  S  L  K  R  T
       -   A  E  Q  A  H  *  R  I  Q  N  I  P  T  N  R  A  *  K  G  Q
29221 - AAAAAGAAAAAGACTGATGAAGCTCAGCCTTTGCCGCAGAGACAAAAGAAGCAGCCCACT - 29280
       - K  K  K  K  T  D  E  A  Q  P  L  P  Q  R  Q  K  K  Q  P  T
       -  K  R  K  R  L  M  K  L  S  L  C  R  R  D  K  R  S  S  P  L
       -   K  E  K  D  *  *  S  S  A  F  A  A  E  T  K  E  A  A  H  C
29281 - GTGACTCTTCTTCCTGCGGCTGACATGGATGATTTCTCCAGACAACTTCAAAATTCCATG - 29340
       - V  T  L  L  P  A  A  D  M  D  D  F  S  R  Q  L  Q  N  S  M
       -  *  L  F  F  L  R  L  T  W  M  I  S  P  D  N  F  K  I  P  *
       -   D  S  S  S  C  G  *  H  G  *  F  L  Q  T  T  S  K  F  H  E
29341 - AGTGGAGCTTCTGCTGATTCAACTCAGGCATAAACACTCATGATGACCACACAAGGCAGA - 29400
       - S  G  A  S  A  D  S  T  Q  A  *  T  L  M  M  T  T  Q  G  R
       -  V  E  L  L  L  I  Q  L  R  H  K  H  S  *  *  P  H  K  A  D
       -   W  S  F  C  *  F  N  S  G  I  N  T  H  D  D  H  T  R  Q  M
29401 - TGGGCTATGTAAACGTTTTCGCAATTCCGTTTACGATACATAGTCTACTCTTGTGCAGAA - 29460
       - W  A  M  *  T  F  S  Q  F  R  L  R  Y  I  V  Y  S  C  A  E
       -  G  L  C  K  R  F  R  N  S  V  Y  D  T  *  S  T  L  V  Q  N
       -   G  Y  V  N  V  F  A  I  P  F  T  I  H  S  L  L  L  C  R  M
29461 - TGAATTCTCGTAACTAAACAGCACAAGTAGGTTTAGTTAACTTTAATCTCACATAGCAAT - 29520
       - *  I  L  V  T  K  Q  H  K  *  V  *  L  T  L  I  S  H  S  N
       -  E  F  S  *  L  N  S  T  S  R  F  S  *  L  *  S  H  I  A  I
       -   N  S  R  N  *  T  A  Q  V  G  L  V  N  F  N  L  T  *  Q  S
29521 - CTTTAATCAATGTGTAACATTAGGGAGGACTTGAAAGAGCCACCACATTTTCATCGAGGC - 29580
       - L  *  S  M  C  N  I  R  E  D  L  K  E  P  P  H  F  H  R  G
       -  F  N  Q  C  V  T  L  G  R  T  *  K  S  H  H  I  F  I  E  A
       -   L  I  N  V  *  H  *  G  G  L  E  R  A  T  T  F  S  S  R  P
29581 - CACGCGGAGTACGATCGAGGGTACAGTGAATAATGCTAGGGAGAGCTGCCTATATGGAAG - 29640
       - H  A  E  Y  D  R  G  Y  S  E  *  C  *  G  E  L  P  I  W  K
       -  T  R  S  T  I  E  G  T  V  N  N  A  R  E  S  C  L  Y  G  R
       -   R  G  V  R  S  R  V  Q  *  I  M  L  G  R  A  A  Y  M  E  E
29641 - AGCCCTAATGTGTAAAATTAATTTTAGTAGTGCTATCCCCATGTGATTTTAATAGCTTCT - 29700
       - S  P  N  V  *  N  *  F  *  *  C  Y  P  H  V  I  L  I  A  S
       -  A  L  M  C  K  I  N  F  S  S  A  I  P  M  *  F  *  *  L  L
```

FIG. 4 Cont'd

```
            -     P  *  C  V  K  L  I  L  V  V  L  S  P  C  D  F  N  S  F  L
    29701   - TAGGAGAATGACAAAAAAAAAAAAAAAAAAAAAAAA - 29736
            -  *  E  N  D  K  K  K  K  K  K  K  K  X
            -  R  R  M  T  K  K  K  K  K  K  K  X
            -  G  E  *  Q  K  K  K  K  K  K  K  X
```

FIG. 4 Cont'd

```
  1 - GATGGGTCCTTTTCGGTTGGTTGGAGCTAGAGAACATCTAGACAAGAGATTTGCTTGAAA -  60
    - D  G  S  F  S  V  G  W  S  *  R  T  S  R  Q  E  I  C  L  K
    -  M  G  P  F  R  L  V  G  A  R  E  H  L  D  K  R  F  A  *  N
    -   W  V  L  F  G  W  L  E  L  E  N  I  *  T  R  D  L  L  E  I
 61 - TTTTAGACACATCGACAGCGAGCCGACGTACGGATCACGTGGATGCGTCATATTTGTTAT - 120
    - F  *  T  H  R  Q  R  A  D  V  R  I  T  W  M  R  H  I  C  Y
    -  F  R  H  I  D  S  E  P  T  Y  G  S  R  G  C  V  I  F  V  I
    -   L  D  T  S  T  A  S  R  R  T  D  H  V  D  A  S  Y  L  L  L
121 - TATTTAAAATGACAGCAACTGTTCTTTGCTCATTGAGCAGGGAGAAGACGTCTGACGAAT - 180
    - Y  L  K  *  Q  Q  L  F  F  A  H  *  A  G  R  R  R  L  T  N
    -  I  *  N  D  S  N  C  S  L  L  I  E  Q  G  E  D  V  *  R  M
    -   F  K  M  T  A  T  V  L  C  S  L  S  R  E  K  T  S  D  E  C
181 - GCCAAAGCAGGCACAACGTCAGCTAGTAGTCGTATGGATCCAAAGCAGGCCCACACTGGC - 240
    - A  K  A  G  T  T  S  A  S  S  R  M  D  P  K  Q  A  H  T  G
    -  P  K  Q  A  Q  R  Q  L  V  V  V  W  I  Q  S  R  P  T  L  A
    -   Q  S  R  H  N  V  S  *  *  S  Y  G  S  K  A  G  P  H  W  L
241 - TTTCCATTCTACCTCTCGGAACAAGAACCACAGTTGCTCTTTTGTGTGCAGGTTGAGTCA - 300
    - F  P  F  Y  L  S  E  Q  E  P  Q  L  L  F  C  V  Q  V  E  S
    -  F  H  S  T  S  R  N  K  N  H  S  C  S  F  V  C  R  L  S  Q
    -   S  I  L  P  L  G  T  R  T  T  V  A  L  L  C  A  G  *  V  K
301 - AACGGACAGGAAGTCCAATCTCTGCACGATCACGCACCGAAGCCCCTGAGACACCTTCTC - 360
    - N  G  Q  E  V  Q  S  L  H  D  H  A  P  K  P  L  R  H  L  L
    -  T  D  R  K  S  N  L  C  T  I  T  H  R  S  P  *  D  T  F  S
    -   R  T  G  S  P  I  S  A  R  S  R  T  E  A  P  E  T  P  S  P
361 - CGGGATAGCCTCCGTGCACTTGTGGAGTTTTTACCGTGAACACCAGATCATCTCGACCTT - 420
    - R  D  S  L  R  A  L  V  E  F  L  P  *  T  P  D  H  L  D  L
    -  G  I  A  S  V  H  L  W  S  F  Y  R  E  H  Q  I  I  S  T  F
    -   G  *  P  P  C  T  C  G  V  F  T  V  N  T  R  S  S  R  P  F
421 - TTTCCGCATGACGGGGTCGAACTTGTCGGGATACACAAGTAATTTGCAAGACTACGGAAT - 480
    - F  P  H  D  G  V  E  L  V  G  I  H  K  *  F  A  R  L  R  N
    -  F  R  M  T  G  S  N  L  S  G  Y  T  S  N  L  Q  D  Y  G  I
    -   S  A  *  R  G  R  T  C  R  D  T  Q  V  I  C  K  T  T  E  F
481 - TCGTGGTTAGTGCCGGTGTTCCAGCAACTCGACCAACGTCTTTACCTGCCGTAAGTCATG - 540
    - S  W  L  V  P  V  F  Q  Q  L  D  Q  R  L  Y  L  P  *  V  M
    -  R  G  *  C  R  C  S  S  N  S  T  N  V  F  T  C  R  K  S  C
    -   V  V  S  A  G  V  P  A  T  R  P  T  S  L  P  A  V  S  H  A
541 - CCAGCATCGCCATATTGTGACCCTCATGAGCACGGTGTACACCCGCTTTGGGGTTAACGT - 600
    - P  A  S  P  Y  C  D  P  H  E  H  G  V  H  P  L  W  G  *  R
    -  Q  H  R  H  I  V  T  L  M  S  T  V  Y  T  R  F  G  V  N  V
    -   S  I  A  I  L  *  P  S  *  A  R  C  T  P  A  L  G  L  T  Y
601 - ATGGCGTTACAAGAAGAAGCATTCTTGCCATTATTCCCTCGGCCACCAGTATCGATACCG - 660
    - M  A  L  Q  E  E  A  F  L  P  L  F  P  R  P  P  V  S  I  P
    -  W  R  Y  K  K  K  H  S  C  H  Y  S  L  G  H  Q  Y  R  Y  R
    -   G  V  T  R  R  S  I  L  A  I  I  P  S  A  T  S  I  D  T  V
661 - TAGCTAGATTTCAGAATACTGAATCCACTGCTCGAACCGTGACTAGGGTAACTTCTAATA - 720
    - *  L  D  F  R  I  L  N  P  L  L  E  P  *  L  G  *  L  L  I
    -  S  *  I  S  E  Y  *  I  H  C  S  N  R  D  *  G  N  F  *  Y
    -   A  R  F  Q  N  T  E  S  T  A  R  T  V  T  R  V  T  S  N  T
721 - CTTGTTTTGACCTTGTGATTCGTACCGTCACCACGTGAGGCACTTGAGTGAGCACTCGAG - 780
    - L  V  L  T  L  *  F  V  P  S  P  R  E  A  L  E  *  A  L  E
    -  L  F  *  P  C  D  S  Y  R  H  H  V  R  H  L  S  E  H  S  S
    -   C  F  D  L  V  I  R  T  V  T  T  *  G  T  *  V  S  T  R  V
781 - TTACCTCCACGTCAGTGAGCGATACAGCTGTTGTTAAAGACACCGGGTCTACCCATGGGA - 840
    - L  P  P  R  Q  *  A  I  Q  L  L  L  K  T  P  G  L  P  M  G
    -  Y  L  H  V  S  E  R  Y  S  C  C  *  R  H  R  V  Y  P  W  E
    -   T  S  T  S  V  S  D  T  A  V  V  K  D  T  G  S  T  H  G  R
841 - GAACTAACGTAGTTTCTAAAAGAGCGTGCGCGCCCGTTCAGTTACACGTGAGAAAGGCTT - 900
    - E  L  T  *  F  L  K  E  R  A  R  P  F  S  Y  T  *  E  R  L
    -  N  *  R  S  F  *  K  S  V  R  A  R  S  V  T  R  E  K  G  L
    -   T  N  V  V  S  K  R  A  C  A  P  V  Q  L  H  V  R  K  A  C
```

FIG. 5

```
 901 - GTTGAACTAATGTAGCTCAGCTTCTCTCCACAGATGACGACGGCACTGGTACTCGTACTT - 960
     -  V  E  L  M  *  L  S  F  S  P  Q  M  T  T  A  L  V  L  V  L
     -   L  N  *  C  S  S  A  S  L  H  R  *  R  R  H  W  Y  S  Y  F
     -    *  T  N  V  A  Q  L  L  S  T  D  D  D  G  T  G  T  R  T  L
 961 - TAACGGACCAAGTGACTCGCGAGACTATTCTCGATGCTCGTGGTCTGTGGGAAGCTTTAA - 1020
     -  *  R  T  K  *  L  A  R  L  F  S  M  L  V  V  C  G  K  L  *
     -   N  G  P  S  D  S  R  D  Y  S  R  C  S  W  S  V  G  S  F  N
     -    T  D  Q  V  T  R  E  T  I  L  D  A  R  G  L  W  E  A  L  I
1021 - TTCTCACGGTTCTTTAAACTGTGAAAGTTTCCCCTTACGGGTTTCAAACACAAAGGAGAA - 1080
     -  F  S  R  F  F  K  L  *  K  F  P  L  T  G  F  K  H  K  G  E
     -   S  H  G  S  L  N  C  E  S  F  P  L  R  V  S  N  T  K  E  N
     -    L  T  V  L  *  T  V  K  V  S  P  Y  G  F  Q  T  Q  R  R  I
1081 - TTGAGTTTTCAGTTTCAGTAAGTTGGTGCACAACTTTTCTTTTTCTGACTCCCAAAGTAC - 1140
     -  L  S  F  Q  F  Q  *  V  G  A  Q  L  F  F  F  *  L  P  K  Y
     -   *  V  F  S  F  S  K  L  V  H  N  F  S  F  S  D  S  Q  S  T
     -    E  F  S  V  S  V  S  W  C  T  T  F  L  F  L  T  P  K  V  P
1141 - CCCGCATATGCGAGACACATGGGACAACGTAGAGGTGTCCTCACATTGTTATACGTGAAC - 1200
     -  P  A  Y  A  R  H  M  G  Q  R  R  G  V  L  T  L  L  Y  V  N
     -   P  H  M  R  D  T  W  D  N  V  E  V  S  S  H  C  Y  T  *  T
     -    R  I  C  E  T  H  G  T  T  *  R  C  P  H  I  V  I  R  E  Q
1201 - AGATGGAACTACTTTACATTAGTAACGCTACTTCAAAGTACCGTCTGCACGCTGAAAGAC - 1260
     -  R  W  N  Y  F  T  L  V  T  L  L  Q  S  T  V  C  T  L  K  D
     -   D  G  T  T  L  H  *  *  R  Y  F  K  V  P  S  A  R  *  K  T
     -    M  E  L  L  Y  I  S  N  A  T  S  K  Y  R  L  H  A  E  R  L
1261 - TTTCGGTGAACACTTGTAACACCGTGACTTTTAAATCAATAACTTCCTGGATGATGTACA - 1320
     -  F  R  *  T  L  V  T  P  *  L  L  N  Q  *  L  P  G  *  C  T
     -   F  G  E  H  L  *  H  R  D  F  *  I  N  N  F  L  D  D  V  H
     -    S  V  N  T  C  N  T  V  T  F  K  S  I  T  S  W  M  M  Y  T
1321 - CCCATGGATGGATGATTACGACATCACTTTTACGGTACAGGACGGACAGTTCTGGGTCTC - 1380
     -  P  M  D  G  *  L  R  H  H  F  Y  G  T  G  R  T  V  L  G  L
     -   P  W  M  D  D  Y  D  I  T  F  T  V  Q  D  G  Q  F  W  V  S
     -    H  G  W  M  I  T  T  S  L  L  R  Y  R  T  D  S  S  G  S  L
1381 - TAACCTGGACTCGTATCACAACGTCTAATAGTGTTGGTGAGTTTGTAACTTTGAGCTGAG - 1440
     -  *  P  G  L  V  S  Q  R  L  I  V  L  V  S  L  *  L  *  A  E
     -   N  L  D  S  Y  H  N  V  *  *  C  W  *  V  C  N  F  E  L  R
     -    T  W  T  R  I  T  T  S  N  S  V  G  E  F  V  T  L  S  *  G
1441 - GCGTTCCCTCCATCCTGATCTACAAAACCTCCGACACACAAACGGATACAACCGACGATA - 1500
     -  A  F  P  P  S  *  S  T  K  P  P  T  H  K  R  I  Q  P  T  I
     -   R  S  L  H  P  D  L  Q  N  L  R  H  T  N  G  Y  N  R  R  Y
     -    V  P  S  I  L  I  Y  K  T  S  D  T  Q  T  D  T  T  D  D  I
1501 - TTATTCGCACGGATGACCCAAGGAGCACGATCACGACTATAACCGAGTCCGGTATGACCG - 1560
     -  L  F  A  R  M  T  Q  G  A  R  S  R  L  *  P  S  P  V  *  P
     -   Y  S  H  G  *  P  K  E  H  D  H  D  Y  N  R  V  R  Y  D  R
     -    I  R  T  D  D  P  R  S  T  I  T  T  I  T  E  S  G  M  T  V
1561 - TAATGACCACTGTTACACCTCTGGAACTTACTCCTAGAGGAACTCTATGACTCAGCACTT - 1620
     -  *  *  P  L  L  H  L  W  N  L  L  L  E  E  L  Y  D  S  A  L
     -   N  D  H  C  Y  T  S  G  T  Y  S  *  R  N  S  M  T  Q  H  L
     -    M  T  T  V  T  P  L  E  L  T  P  R  G  T  L  *  L  S  T  C
1621 - GCACAATTGTAATTGTAACAACCGCTAAAAGTAAACTTACTTCTCCAACGGTAGTAAAAC - 1680
     -  A  Q  L  *  L  *  Q  P  L  K  V  N  L  L  L  Q  R  *  *  N
     -   H  N  C  N  C  N  N  R  *  K  *  T  Y  F  S  N  G  S  K  T
     -    T  I  V  I  V  T  T  A  K  S  K  L  T  S  P  T  V  V  K  P
1681 - CGTAGAAAGAGACGAAGATGTTCACGGAAATAACTGTGATATTTCTCAGAACTAATGTTC - 1740
     -  R  R  K  R  R  R  C  S  R  K  *  L  *  Y  F  S  E  L  M  F
     -   V  E  R  D  E  D  V  H  G  N  N  C  D  I  S  Q  N  *  C  S
     -    *  K  E  T  K  M  F  T  E  I  T  V  I  F  L  R  T  N  V  Q
1741 - AGAAAGTTTTGGTAACAACTCAGGACGCCATTGATATTTCAATGGTTCCCTTTCGGGCAT - 1800
     -  R  K  F  W  *  Q  L  R  T  P  L  I  F  Q  W  F  P  F  G  H
     -   E  S  F  G  N  N  S  G  R  H  *  Y  F  N  G  S  L  S  G  I
     -    K  V  L  V  T  T  Q  D  A  I  D  I  S  M  V  P  F  R  A  F
```

FIG. 5 Cont'd

```
1801 - TTTCCACGAACCTTGTAACCTGTTGTCTCTAGTCAAAATTGTGGTGACACACCAAAAGGG - 1860
     -  F  P  R  T  L  *  P  V  V  S  S  Q  N  C  G  D  T  P  K  G
     -  F  H  E  P  C  N  L  L  S  L  V  K  I  V  V  T  H  Q  K  G
     -  S  T  N  L  V  T  C  C  L  *  S  K  L  W  *  H  T  K  R  E
1861 - AGTGTCCGACGACCACAATAGTCTAGTTAAAAACGCGCGTGTGAACTACGTCGTTGGTG - 1920
     -  S  V  R  R  P  Q  *  S  S  *  K  R  A  C  E  L  R  R  L  V
     -  V  S  D  D  H  N  S  L  V  K  N  A  R  V  N  Y  V  V  W  *
     -  C  P  T  T  T  I  V  *  L  K  T  R  V  *  T  T  S  F  G  E
1921 - AGTTAAGGACTAAACGTTTCTCGTCGACAGTGGTATGAACTACCATAAAGACTTGTCAGT - 1980
     -  S  *  G  L  N  V  S  R  R  Q  W  Y  E  L  P  *  R  L  V  S
     -  V  K  D  *  T  F  L  V  D  S  G  M  N  Y  H  K  D  L  S  V
     -  L  R  T  K  R  F  S  S  T  V  V  *  T  T  I  K  T  C  Q  *
1981 - AATGCAGAACAGCTGCGGTACCAAATATGAAGTCTGGACGAGTGGTTGTCACAGTAATAA - 2040
     -  N  A  E  Q  L  R  Y  Q  I  *  S  L  D  E  W  L  S  Q  *  *
     -  M  Q  N  S  C  G  T  K  Y  E  V  W  T  S  G  C  H  S  N  N
     -  C  R  T  A  A  V  P  N  M  K  S  G  R  V  V  V  T  V  I  I
2041 - TACCGTATACATTGACCACCAGAACATGTTGTCTGAAGAGTCACCAACAGATTAGAAAAC - 2100
     -  Y  R  I  H  *  P  P  E  H  V  V  *  R  V  T  N  R  L  E  N
     -  T  V  Y  I  D  H  Q  N  M  L  S  E  E  S  P  T  D  *  K  T
     -  P  Y  T  L  T  T  R  T  C  C  L  K  S  H  Q  Q  I  R  K  P
2101 - CCGTGATGACAACTTTTTGAGTCCGGATAGAAACTTACCTAACTCCGCTTTGAATCACGT - 2160
     -  P  *  *  Q  L  F  E  S  G  *  K  L  T  *  L  R  F  E  S  R
     -  R  D  D  N  F  L  S  P  D  R  N  L  P  N  S  A  L  N  H  V
     -  V  M  T  T  F  *  V  R  I  E  T  Y  L  T  P  L  *  I  T  S
2161 - CCTCAACTTAAAGAGTTCCTACGAACCCTCTAAGAGTTTAAAGAGTAATGTCCACAAAAA - 2220
     -  P  Q  L  K  E  F  L  R  T  L  *  E  F  K  E  *  C  P  Q  K
     -  L  N  L  K  S  S  Y  E  P  S  K  S  L  K  S  N  V  H  K  N
     -  S  T  *  R  V  P  T  N  P  L  R  V  *  R  V  M  S  T  K  T
2221 - CTGTAGCAGTTCCCAGTTTATGTCCAACGAAGTCTATTGTAGTTCCTAACACATTTTACG - 2280
     -  L  *  Q  F  P  V  Y  V  Q  R  S  L  L  *  F  L  T  H  F  T
     -  C  S  S  S  Q  F  M  S  N  E  V  Y  C  S  S  *  H  I  L  R
     -  V  A  V  P  S  L  C  P  T  K  S  I  V  V  P  N  T  F  Y  E
2281 - AAGTAACTACAACAATTGTTCCGTGAGCTTTACACGTAACTAGTTCAGTGATAGCGACCG - 2340
     -  K  *  L  Q  Q  L  F  R  E  L  Y  T  *  L  V  Q  *  *  R  P
     -  S  N  Y  N  N  C  S  V  S  F  T  R  N  *  F  S  D  S  D  R
     -  V  T  T  T  I  V  P  *  A  L  H  V  T  S  S  V  I  A  T  A
2341 - CGTTTCAACGCTAGTGAGTTGAATCCACTTCAGAAGTAGCGAGTTTCGTTCCCTGAAATG - 2400
     -  R  F  N  A  S  E  L  N  P  L  Q  K  *  R  V  S  F  P  E  M
     -  V  S  T  L  V  S  *  I  H  F  R  S  S  E  F  R  S  L  K  W
     -  F  Q  R  *  *  V  E  S  T  S  E  V  A  S  F  V  P  *  N  G
2401 - GCAGTCACATATGCACCGTTCCTCGTCGACGTTGATGAGTACGGAGAATTCCGTGGTTTT - 2460
     -  A  V  T  Y  A  P  F  L  V  D  V  D  E  Y  G  E  F  R  G  F
     -  Q  S  H  M  H  R  S  S  S  T  L  M  S  T  E  N  S  V  V  F
     -  S  H  I  C  T  V  P  R  R  R  *  *  V  R  R  I  P  W  F  S
2461 - CTTCATTGGAAAGAACTTCCACTAAGTGTACTGTGTCATGAATGGAGACTCCTCCAACAA - 2520
     -  L  H  W  K  E  L  P  L  S  V  L  C  H  E  W  R  L  L  Q  Q
     -  F  I  G  K  N  F  H  *  V  Y  C  V  M  N  G  D  S  S  N  K
     -  S  L  E  R  T  S  T  K  C  T  V  S  *  M  E  T  P  P  T  R
2521 - GAGTTCTTGCCACTTGAGCTTCGTGAGCTCTGCGGGCAACTATCGAAGTGTTTACCTCGA - 2580
     -  E  F  L  P  L  E  L  R  E  L  C  G  Q  L  S  K  C  L  P  R
     -  S  S  C  H  L  S  F  V  S  S  A  G  N  Y  R  S  V  Y  L  D
     -  V  L  A  T  *  A  S  *  A  L  R  A  T  I  E  V  F  T  S  I
2581 - TAGCAACCGTGTGGTCAGACACATTTACCGGAGTACGAGAATCTCTAATTCCTGTTTCTT - 2640
     -  *  Q  P  C  G  Q  T  H  L  P  E  Y  E  N  L  *  F  L  F  L
     -  S  N  R  V  V  R  H  I  Y  R  S  T  R  I  S  N  S  C  F  L
     -  A  T  V  W  S  D  T  F  T  G  V  R  E  S  L  I  P  V  S  C
2641 - GTTATGACGCGTAACAGAGGACCAAATGACCGATGTTTGTTACAGAAAGCGAATTTTCCC - 2700
     -  V  M  T  R  N  R  G  P  N  D  R  C  L  L  Q  K  A  N  F  P
     -  L  *  R  V  T  E  D  Q  M  T  D  V  C  Y  R  K  R  I  F  P
     -  Y  D  A  *  Q  R  T  K  *  P  M  F  V  T  E  S  E  F  S  P
```

FIG. 5 Cont'd

```
2701 - CCACGTGGTTAATTTCCACATTGGAAACCTCTTCTATGACAAACCCTTCAAGTTCCAATG - 2760
     - P  R  G  *  F  P  H  W  K  P  L  L  *  Q  T  L  Q  V  P  M
     -  H  V  V  N  F  H  I  G  N  L  F  Y  D  K  P  F  K  F  Q  C
     -   T  W  L  I  S  T  L  E  T  S  S  M  T  N  P  S  S  S  N  V
2761 - TTCTTACACTCTTAGTGTAAACTCGAACTACTTGCACAACTGTTTCACGAATTACTTTTC - 2820
     - F  L  H  S  *  C  K  L  E  L  L  A  Q  L  F  H  E  L  L  F
     -  S  Y  T  L  S  V  N  S  N  Y  L  H  N  C  F  T  N  Y  F  S
     -   L  T  L  L  V  *  T  R  T  T  C  T  T  V  S  R  I  T  F  H
2821 - ACGAGACAGATGTGACAACTTAGGCCATGGCTTCAATGACTCAAACGTACACAACATCGT - 2880
     - T  R  Q  M  *  Q  L  R  P  W  L  Q  *  L  K  R  T  Q  H  R
     -  R  D  R  C  D  N  L  G  H  G  F  N  D  S  N  V  H  N  I  V
     -   E  T  D  V  T  T  *  A  M  A  S  M  T  Q  T  Y  T  T  S  S
2881 - CTCCGACAACACTTCTGAAATGTTGGTCAAAGACTAGAGGAATGGTTGTACCCATAACTA - 2940
     - L  R  Q  H  F  *  N  V  G  Q  R  L  E  E  W  L  Y  P  *  L
     -  S  D  N  T  S  E  M  L  V  K  D  *  R  N  G  C  T  H  N  *
     -   P  T  T  L  L  K  C  W  S  K  T  R  G  M  V  V  P  I  T  R
2941 - GAACTACTCACCTCACATCGATGTAAGATGAATAAACTACTACGACCACTTCTTTTGAAA - 3000
     - E  L  L  T  S  H  R  C  K  M  N  K  L  L  R  P  L  L  L  K
     -  N  Y  S  P  H  I  D  V  R  *  I  N  Y  Y  D  H  F  F  *  K
     -   T  T  H  L  T  S  M  *  D  E  *  T  T  T  T  T  S  F  E  K
3001 - AGTAGTGCATACATAACAAGGAAAATGGGAGGTCTACTCCTTCTTCTCCTGCTACGTCTC - 3060
     - S  S  A  Y  I  T  R  K  M  G  G  L  L  L  L  L  L  R  L
     -  V  V  H  T  *  Q  G  K  W  E  V  Y  S  F  F  S  C  Y  V  S
     -   *  C  I  H  N  K  E  N  G  R  S  T  P  S  S  P  A  T  S  H
3061 - ACACTCCTTCTTCTTTAACTACTTTGGACACTTGTACTCATGCCATGTCTCCTACTAATA - 3120
     - T  L  L  L  L  *  L  L  W  T  L  V  L  M  P  C  L  L  L  I
     -  H  S  F  F  F  N  Y  F  G  H  L  Y  S  C  H  V  S  Y  *  *
     -   T  P  S  S  L  T  T  L  D  T  C  T  H  A  M  S  P  T  N  S
3121 - GTTCCAGAGGGAGACCTTAAACCACGGAGTCGACTTTGTCAAGCTCAACTCCTTCTTCTT - 3180
     - V  P  E  G  D  L  K  P  R  S  R  L  C  Q  A  Q  L  L  L  L
     -  F  Q  R  E  T  L  N  H  G  V  D  F  V  K  L  N  S  F  F  F
     -   S  R  G  R  P  *  T  T  E  S  T  L  S  S  S  T  P  S  S  S
3181 - CTCCTTCTGACCGACCTACTATGATGACTCGTTAGTCTCTAACTCGGTCTTGGTCTTGGA - 3240
     - L  L  L  T  D  L  L  *  *  L  V  S  L  *  L  G  L  G  L  G
     -  S  F  *  P  T  Y  Y  D  D  S  L  V  S  N  S  V  L  V  L  D
     -   P  S  D  R  P  T  M  M  T  R  *  S  L  T  R  S  W  S  W  M
3241 - TGTGGACTTCTTGGTCAATTAGTCAAATGACCAATAAATTTTGAATGACTGTTACAACGG - 3300
     - C  G  L  L  G  Q  L  V  K  *  P  I  N  F  E  *  L  L  Q  R
     -  V  D  F  L  V  N  *  S  N  D  Q  *  I  L  N  D  C  Y  N  G
     -   W  T  S  W  S  I  S  Q  M  T  N  K  F  *  M  T  V  T  T  V
3301 - TAATTTACACAACTGTAGCAATTCCTCCGTGTTTCACGATTAGGATACCACTAACATTTA - 3360
     - *  F  T  Q  L  *  Q  F  L  R  V  S  R  L  G  Y  H  *  H  L
     -  N  L  H  N  C  S  N  S  S  V  F  H  D  *  D  T  T  N  I  Y
     -   I  Y  T  T  V  A  I  P  P  C  F  T  I  R  I  P  L  T  F  T
3361 - CGACGATTGTATGTGGACTTTGTACCACCACCACATCGTCCACGTGAGTTGTTCCGTTGG - 3420
     - R  R  L  Y  V  D  F  V  P  P  P  H  R  P  R  E  L  F  R  W
     -  D  D  C  M  W  T  L  Y  H  H  H  I  V  H  V  S  C  S  V  G
     -   T  I  V  C  G  L  C  T  T  T  T  S  S  T  *  V  V  P  L  V
3421 - TTACCACGGTACGTTTTCCTCTCACTACTAATGTAATTCGATTTACCGGGAGAATGTCAT - 3480
     - L  P  R  Y  V  F  L  S  L  L  M  *  F  D  L  P  G  E  C  H
     -  Y  H  G  T  F  S  S  H  Y  *  C  N  S  I  Y  R  E  N  V  I
     -   T  T  V  R  F  P  L  T  T  N  V  I  R  F  T  G  R  M  S  S
3481 - CCTCCCAGAACAAACGAAAGACCTGTATTAGAACGATTCTTCACAGACGTACAACAACCT - 3540
     - P  P  R  T  N  E  R  P  V  L  E  R  F  F  T  D  V  Q  Q  P
     -  L  P  E  Q  T  K  D  L  Y  *  N  D  S  S  Q  T  Y  N  N  L
     -   S  Q  N  K  R  K  T  C  I  R  T  I  L  H  R  R  T  T  T  W
3541 - GGATTGGATTTACGTCCACTCCTGTAGGTCGAAGAATTCCGTCGTATACTTTTAAAGTTA - 3600
     - G  L  D  L  R  P  L  L  *  V  E  E  F  R  R  I  L  L  K  L
     -  D  W  I  Y  V  H  S  C  R  S  K  N  S  V  V  Y  F  *  S  *
     -   I  G  F  T  S  T  P  V  G  R  R  I  P  S  Y  T  F  K  V  K
```

FIG. 5 Cont'd

```
3601 - AGTGTCCTGTAGAATGAACGTGGTAACAACAGTCGTCCGTATAAACCACGATTTGGTGAA - 3660
      - S  V  L  *  N  E  R  G  N  N  S  R  P  Y  K  P  R  F  G  E
      - V  S  C  R  M  N  V  V  T  T  V  V  R  I  N  H  D  L  V  K
      - C  P  V  E  *  T  W  *  Q  Q  S  S  V  *  T  T  I  W  *  S
3661 - GTCAGAAATGTTCACACGCACGTCTGCCAAGCATGTGTCCAAATATAACGTCAGTTACTG - 3720
      - V  R  N  V  H  T  H  V  C  Q  A  C  V  Q  I  *  R  Q  L  L
      - S  E  M  F  T  R  T  S  A  K  H  V  S  K  Y  N  V  S  Y  C
      - Q  K  C  S  H  A  R  L  P  S  M  C  P  N  I  T  S  V  T  V
3721 - TTTCGAGAAATACTCGTCCAACAGTACCTAATAGAACTATTGGACTTCGGATCTCACCTT - 3780
      - F  R  E  I  L  V  Q  Q  Y  L  I  E  L  L  D  F  G  S  H  L
      - F  E  K  Y  S  S  N  S  T  *  *  N  Y  W  T  S  D  L  T  F
      - S  R  N  T  R  P  T  V  P  N  R  T  I  G  L  R  I  S  P  S
3781 - CGTGGATTTGTTCTCCTCGGTGGTTTGTGTCTTCTAAGGTTTTGACTCCTCTTTAGACAG - 3840
      - R  G  F  V  L  L  G  G  L  C  L  L  R  F  *  L  L  F  R  Q
      - V  D  L  F  S  S  V  V  C  V  F  *  G  F  D  S  S  L  D  S
      - W  I  C  S  P  R  W  F  V  S  S  K  V  L  T  P  L  *  T  A
3841 - CATGTCTTCGGACAGCTACACTTCGGTTTTTAATTCCGGACGTAACTACTCCAATGGTGT - 3900
      - H  V  F  G  Q  L  H  F  G  F  *  F  R  T  *  L  L  Q  W  C
      - M  S  S  D  S  Y  T  S  V  F  N  S  G  R  N  Y  S  N  G  V
      - C  L  R  T  A  T  L  R  F  L  I  P  D  V  T  T  P  M  V  L
3901 - TGTGACCTTCTTTGATTCAAAGAATGGTTATTCAATGAGAACAAACGACTATAGTTACCA - 3960
      - C  D  L  L  *  F  K  E  W  L  F  N  E  N  K  R  L  *  L  P
      - V  T  F  F  D  S  K  N  G  Y  S  M  R  T  N  D  Y  S  Y  H
      - *  P  S  L  I  Q  R  M  V  I  Q  *  E  Q  T  T  I  V  T  I
3961 - TTCGAAATGGTACTAAGAGTCTTGTACGAATCTCCACTTCTATACAGAAAGGAACTCTTC - 4020
      - F  E  M  V  L  R  V  L  Y  E  S  P  L  L  Y  R  K  E  L  F
      - S  K  W  Y  *  E  S  C  T  N  L  H  F  Y  T  E  R  N  S  S
      - R  N  G  T  K  S  L  V  R  I  S  T  S  I  Q  K  G  T  L  P
4021 - CTACGTGGAATGTACCATCCACTACAATAGTGATCACCACTATAGTGAACACAACATTAT - 4080
      - L  R  G  M  Y  H  P  L  Q  *  *  S  P  L  *  *  T  Q  H  Y
      - Y  V  E  C  T  I  H  Y  N  S  D  H  H  Y  S  E  H  N  I  M
      - T  W  N  V  P  S  T  T  I  V  I  T  T  I  V  N  T  T  L  W
4081 - GGGAGGTTTTTCCGACCACCGTGATGACTCTACGAGAGTTCTCGAAACTTCTTTCACGGT - 4140
      - G  R  F  F  R  P  P  *  *  L  Y  E  S  S  R  N  F  F  H  G
      - G  G  F  S  D  H  R  D  D  S  T  R  V  L  E  T  S  F  T  V
      - E  V  F  P  T  T  V  M  T  L  R  E  F  S  K  L  L  S  R  S
4141 - CAACTACTCATATATTGGTGCATGGGACCTGTTCCTACACGACCAATATGTGAACTCCTT - 4200
      - Q  L  L  I  Y  W  C  M  G  P  V  P  T  R  P  I  C  E  L  L
      - N  Y  S  Y  I  G  A  W  D  L  F  L  H  D  Q  Y  V  N  S  F
      - T  T  H  I  L  V  H  G  T  C  S  Y  T  T  N  M  *  T  P  S
4201 - CGATTCTGACGAGAATTCTTTACGTTTAGACGTAAAATACATGATGGAAGTCTTCGTGGA - 4260
      - R  F  *  R  E  F  F  T  F  R  R  K  I  H  D  G  S  L  R  G
      - D  S  D  E  N  S  L  R  L  D  V  K  Y  M  M  E  V  F  V  D
      - I  L  T  R  I  L  Y  V  *  T  *  N  T  *  W  K  S  S  W  I
4261 - TTACGATTCCTTCTCTAAGATCCTTGACATAGGACCTTAAACTCTCTTTACGAACGAGTA - 4320
      - L  R  F  L  L  *  D  P  *  H  R  T  L  N  S  L  Y  E  R  V
      - Y  D  S  F  S  K  I  L  D  I  G  P  *  T  L  F  T  N  E  Y
      - T  I  P  S  L  R  S  L  T  *  D  L  K  L  S  L  R  T  S  T
4321 - CGACTTCTCTGTTCTTTTAATTACGGATATACGTACCTACAATCTCGGTATTACCGTTGG - 4380
      - R  L  L  C  S  F  N  Y  G  Y  T  Y  L  Q  S  R  Y  Y  R  W
      - D  F  S  V  L  L  I  T  D  I  R  T  Y  N  L  G  I  T  V  G
      - T  S  L  F  F  *  L  R  I  Y  V  P  T  I  S  V  L  P  L  V
4381 - TAGGTTGCATTCATATTTCCTTAATTTTAAGTTCTCCCGTAGCAACTGATACCACAGGCT - 4440
      - *  V  A  F  I  F  P  *  F  *  V  L  P  *  Q  L  I  P  Q  A
      - R  L  H  S  Y  F  L  N  F  K  F  S  R  S  N  *  Y  H  R  L
      - G  C  I  H  I  S  L  I  L  S  S  P  V  A  T  D  T  T  G  *
4441 - AAGAAGAAAATATGATCATTTCTCGGACATCGAAGATAATAATGCTTCGACTTGAGAGAT - 4500
      - K  K  K  I  *  S  F  L  G  H  R  R  *  *  C  F  D  L  R  D
      - R  R  K  Y  D  H  F  S  D  I  E  D  N  N  A  S  T  *  E  I
      - E  E  N  M  I  I  S  R  T  S  K  I  I  M  L  R  L  E  R  F
```

FIG. 5 Cont'd

```
4501 - TTACTCGGCGAACAGTGTTACGGTTAACCAATACACTGTGTACCAAAATTAGAACTTCTC - 4560
     - L  L  G  E  Q  C  Y  G  *  P  I  H  C  V  P  K  L  E  L  L
     - Y  S  A  N  S  V  T  V  N  Q  Y  T  V  Y  Q  N  *  N  F  S
     - T  R  R  T  V  L  R  L  T  N  T  L  C  T  K  I  R  T  S  P
4561 - CGACGCGCGACATACGCAAGAGAATTTCGAGGACGGCATCACAGTCATAGTAGTGGTCTA - 4620
     - R  R  A  T  Y  A  R  E  F  R  G  R  H  H  S  H  S  S  G  L
     - D  A  R  H  T  Q  E  N  F  E  D  G  I  T  V  I  V  V  V  Y
     - T  R  D  I  R  K  R  I  S  R  T  A  S  Q  S  *  *  W  S  T
4621 - CGACAATGATGTATATTACCTATGGAGTGAAGCAGTAGTTTCTGTAGACTCCTCGTGAAA - 4680
     - R  Q  *  C  I  L  P  M  E  *  S  S  S  F  C  R  L  L  V  K
     - D  N  D  V  Y  Y  L  W  S  E  A  V  V  S  V  D  S  S  *  N
     - T  M  M  Y  I  T  Y  G  V  K  Q  *  F  L  *  T  P  R  E  T
4681 - CATCTTTGTCAAAGAAACCGACCGAGAATGTCTCTAACCAGGATAAGTCCTGTCGCATGT - 4740
     - H  L  C  Q  R  N  R  P  R  M  S  L  T  R  I  S  P  V  A  C
     - I  F  V  K  E  T  D  R  E  C  L  *  P  G  *  V  L  S  H  V
     - S  L  S  K  K  P  T  E  N  V  S  N  Q  D  K  S  C  R  M  S
4741 - CTCAATCCACAACTTAAAGAATTCGCACCACTGTTTTAACACATGGTGTGAGACCTCTCG - 4800
     - L  N  P  Q  L  K  E  F  A  P  L  F  *  H  M  V  *  D  L  S
     - S  I  H  N  L  K  N  S  H  H  C  F  N  T  W  C  E  T  S  R
     - Q  S  T  T  *  R  I  R  T  T  V  L  T  H  G  V  R  P  L  G
4801 - GGGCAGCTCAAAGTAGAACTGCCACTCCAAGAAAGTGAACTGTTTGATTTCTCAGAGAAT - 4860
     - G  Q  L  K  V  E  L  P  L  Q  E  S  E  L  F  D  F  S  E  N
     - G  S  S  K  *  N  C  H  S  K  K  V  N  C  L  I  S  Q  R  I
     - A  A  Q  S  R  T  A  T  P  R  K  *  T  V  *  F  L  R  E  *
4861 - AGGGACGCCCTCCAATTCTGATATTTTCACAAGTGTTGACACCTGTTGTGATTAGAGGTG - 4920
     - R  D  A  L  Q  F  *  Y  F  H  K  C  *  H  L  L  *  L  E  V
     - G  T  P  S  N  S  D  I  F  T  S  V  D  T  C  C  D  *  R  C
     - G  R  P  P  I  L  I  F  S  Q  V  L  T  P  V  V  I  R  G  V
4921 - TGTGTCGAACACCTATACAGATACTGTATACCTGTCGTCAAACCAGGTTGTATGAACCTA - 4980
     - C  V  E  H  L  Y  R  Y  C  I  P  V  V  K  P  G  C  M  N  L
     - V  S  N  T  Y  T  D  T  V  Y  L  S  S  N  Q  V  V  *  T  Y
     - C  R  T  P  I  Q  I  L  Y  T  C  R  Q  T  R  L  Y  E  P  T
4981 - CCACGACTACAATGTTTTTAATTTGGAGTACATTTAGTACTCCCATTCTGAAAGAAACAT - 5040
     - P  R  L  Q  C  F  *  F  G  V  H  L  V  L  P  F  *  K  K  H
     - H  D  Y  N  V  F  N  L  E  Y  I  *  Y  S  H  S  E  R  N  M
     - T  T  T  M  F  L  I  W  S  T  F  S  T  P  I  L  K  E  T  *
5041 - GATGGATCACTACTGTGTGATGCATCACTTCGAAAGCTCATGATGGTATGAGAACTACTC - 5100
     - D  G  S  L  L  C  D  A  S  L  R  K  L  M  M  V  *  E  L  L
     - M  D  H  Y  C  V  M  H  H  F  E  S  S  *  W  Y  E  N  Y  S
     - W  I  T  T  V  *  C  I  T  S  K  A  H  D  G  M  R  T  T  L
5101 - TCAAAAGAACCATCCATGTACAGACGAAATTTGGTGTGTTTCTTTACCTTTAAAGGAGTT - 5160
     - S  K  E  P  S  M  Y  R  R  N  L  V  C  F  F  T  F  K  G  V
     - Q  K  N  H  P  C  T  D  E  I  W  C  V  S  L  P  L  K  E  F
     - K  R  T  I  H  V  Q  T  K  F  G  V  F  L  Y  L  *  R  S  S
5161 - CAACCACCAAATTGAAGTTAATTTACCCGACTATTGTTAACAATAAACAGATCACAAAAT - 5220
     - Q  P  P  N  *  S  *  F  T  R  L  L  L  T  I  N  R  S  Q  N
     - N  H  Q  I  E  V  N  L  P  D  Y  C  *  Q  *  T  D  H  K  I
     - T  T  K  L  K  L  I  Y  P  T  I  V  N  N  K  Q  I  T  K  *
5221 - AATCGTGAAGTTGTCGAACTTCAGTTTAAGTTACGTGGTCGTGAAGTTCTCCGAATAATA - 5280
     - N  R  E  V  V  E  L  Q  F  K  L  R  G  R  E  V  L  R  I  I
     - I  V  K  L  S  N  F  S  L  S  Y  V  V  V  K  F  S  E  *  Y
     - S  *  S  C  R  T  S  V  *  V  T  W  S  *  S  S  P  N  N  I
5281 - TCTCGGGCACGACCACTACGACGATTGAAAACACGTGAGTATGAGCGAATGTCATTATTT - 5340
     - S  R  A  R  P  L  R  R  L  K  T  R  E  Y  E  R  M  S  L  F
     - L  G  H  D  H  Y  D  D  *  K  H  V  S  M  S  E  C  H  Y  F
     - S  G  T  T  T  T  T  I  E  N  T  *  V  *  A  N  V  I  I  L
5341 - TGACAACCGCTCGAACCACTACAGTCTCTTTGATACTGGGTAGAAGATGTCGTACGATTA - 5400
     - *  Q  P  L  E  P  L  Q  S  L  *  Y  W  V  E  D  V  V  R  L
     - D  N  R  S  N  H  Y  S  L  F  D  T  G  *  K  M  S  Y  D  *
     - T  T  A  R  T  T  T  V  S  L  I  L  G  R  R  C  R  T  I  K
```

FIG. 5 Cont'd

```
5401 - AACCTTAGACGTTTCGCTCAAGAATTACACCACACATTTGTAACACCAGTCTTTTGATGA - 5460
     - N  L  R  R  F  A  Q  E  L  H  H  T  F  V  T  P  V  F  *  *
     -  T  L  D  V  S  L  K  N  Y  T  T  H  L  *  H  Q  S  F  D  D
     -   P  *  T  F  R  S  R  I  T  P  H  I  C  N  T  S  L  L  M  M
5461 - TGGAATTGCCCACATCTTCGACACTACATATACCCATGAGATAGAATACTATTAGAATTC - 5520
     - W  N  C  P  H  L  R  H  Y  I  Y  P  *  D  R  I  L  L  E  F
     -  G  I  A  H  I  F  D  T  T  Y  T  H  E  I  E  Y  Y  *  N  S
     -   E  L  P  T  S  S  T  L  H  I  P  M  R  *  N  T  I  R  I  L
5521 - TGTCCACAAAGGTAAGGTACACACACACCAGCACTACGATGTGTTATAGATCATGTTGTT - 5580
     - C  P  Q  R  *  G  T  H  T  P  A  L  R  C  V  I  D  H  V  V
     -  V  H  K  G  K  V  H  T  H  Q  H  Y  D  V  L  *  I  M  L  F
     -   S  T  K  V  R  Y  T  H  T  S  T  T  M  C  Y  R  S  C  C  S
5581 - CTCAGAAGAAAACAATACTACAGACGTGGTGGACGACTCATATTTAATGTCGTTCCATGT - 5640
     - L  R  R  K  Q  Y  Y  R  R  G  G  R  L  I  F  N  V  V  P  C
     -  S  E  E  N  N  T  T  D  V  V  D  D  S  Y  L  M  S  F  H  V
     -   Q  K  K  T  I  L  Q  T  W  W  T  T  H  I  *  C  R  S  M  *
5641 - AAGAATACACGCTTACTCATGTGACCATTGATAGTCACACCAGTAATGTGAGTATATTGA - 5700
     - K  N  T  R  L  L  M  *  P  L  I  V  T  P  V  M  *  V  Y  *
     -  R  I  H  A  Y  S  C  D  H  *  *  S  H  Q  *  C  E  Y  I  D
     -   E  Y  T  L  T  H  V  T  I  D  S  H  T  S  N  V  S  I  L  T
5701 - CGATTCCTCTGGGAGATAGCATAACTGCCTCGAGTGGAATGTTTCTACAGTCTCATGTTT - 5760
     - R  F  L  W  E  I  A  *  L  P  R  V  E  C  F  Y  S  L  M  F
     -  D  S  S  G  R  *  H  N  C  L  E  W  N  V  S  T  V  S  C  F
     -   I  P  L  G  D  S  I  T  A  S  S  G  M  F  L  Q  S  H  V  S
5761 - CCTGGTCACTGACTACAAAAGATGTTCCTTTGTAGAATGTGATGTTGGTAGTTCGGACAC - 5820
     - P  G  H  *  L  Q  K  M  F  L  C  R  M  *  C  W  *  F  G  H
     -  L  V  T  D  Y  K  R  C  S  F  V  E  C  D  V  G  S  S  D  T
     -   W  S  L  T  T  K  D  V  P  L  *  N  V  M  L  V  V  R  T  Q
5821 - AGCATATTTGAGCTACCTCAATGAATGTGTCTCTAACTTGGTTTTAACCTACCCATAATA - 5880
     - S  I  F  E  L  P  Q  *  M  C  L  *  L  G  F  N  L  P  I  I
     -  A  Y  L  S  Y  L  N  E  C  V  S  N  L  V  L  T  Y  P  *  Y
     -   H  I  *  A  T  S  M  N  V  S  L  T  W  F  *  P  T  H  N  I
5881 - TTTTTCCTATTACGAATGATATGTCTCGTCGGATATCTGGAACATGGTTGAGTTGGTAAT - 5940
     - F  F  L  L  R  M  I  C  L  V  G  Y  L  E  H  G  *  V  G  N
     -  F  S  Y  Y  E  *  Y  V  S  S  D  I  W  N  M  V  E  L  V  M
     -   F  P  I  T  N  D  M  S  R  R  I  S  G  T  W  L  S  W  *  W
5941 - GGTTTACGCTCAAAACTATTAAAGTTTGAGTGTACAAGATTGTGTTTTAAACGACTACTA - 6000
     - G  L  R  S  K  L  L  K  F  E  C  T  R  L  C  F  K  R  L  L
     -  V  Y  A  Q  N  Y  *  S  L  S  V  Q  D  C  V  L  N  D  Y  *
     -   F  T  L  K  T  I  K  V  *  V  Y  K  I  V  F  *  T  T  T  K
6001 - AATTTAGTTTACTGTCCGAAGTGTTTCGGTCGAAGTGCTCTCGATAGACAGTGTAAGAAG - 6060
     - N  L  V  Y  C  P  K  C  F  G  R  S  A  L  D  R  Q  C  K  K
     -  I  *  F  T  V  R  S  V  S  V  E  V  L  S  I  D  S  V  R  R
     -   F  S  L  L  S  E  V  F  R  S  K  C  S  R  *  T  V  *  E  G
6061 - GGTCTGAACTTACCGCTACATCACCGATAACTGATATCTGTGATAAGTCGCTCAAAGTTC - 6120
     - G  L  N  L  P  L  H  H  R  *  L  I  S  V  I  S  R  S  K  F
     -  V  *  T  Y  R  Y  I  T  D  N  *  Y  L  *  *  V  A  Q  S  S
     -   S  E  L  T  A  T  S  P  I  T  D  I  C  D  K  S  L  K  V  L
6121 - TTTCCACGATTTAATGACGTATTCGGTTAACAAACCGTGTAATTGGTCCGATGTTGGTTC - 6180
     - F  P  R  F  N  D  V  F  G  *  Q  T  V  *  L  V  R  C  W  F
     -  F  H  D  L  M  T  Y  S  V  N  K  P  C  N  W  S  D  V  G  S
     -   S  T  I  *  *  R  I  R  L  T  N  R  V  I  G  P  M  L  V  L
6181 - TGTTGCAAGTTTGGTTTGTGAACCACAAATGCAACAGAAACCTCATGTTTCGGTCATCTA - 6240
     - C  C  K  F  G  L  *  T  T  N  A  T  E  T  S  C  F  G  H  L
     -  V  A  S  L  V  C  E  P  Q  M  Q  Q  K  P  H  V  S  V  I  Y
     -   L  Q  V  W  F  V  N  H  K  C  N  R  N  L  M  F  R  S  S  M
6241 - TGAAGTTTAAGTAAACTTCAAGACCGTCATCTTCTGTGTGTTCCTTACCTGTTAGAACGA - 6300
     - *  S  L  S  K  L  Q  D  R  H  L  L  C  V  P  Y  L  L  E  R
     -  E  V  *  V  N  F  K  T  V  I  F  C  V  F  L  T  C  *  N  E
     -   K  F  K  *  T  S  R  P  S  S  S  V  C  S  L  P  V  R  T  N
```

FIG. 5 Cont'd

```
6301 - ACACTTTCAGTTGTTGGGTGGAGACTTCTTCATCACCTTTTAGGATGGTATGTCTTCCTT - 6360
       - T  L  S  V  V  G  W  R  L  L  H  H  L  L  G  W  Y  V  F  L
       - H  F  Q  L  L  G  G  D  F  F  I  T  F  *  D  G  M  S  S  F
       -  T  F  S  C  W  V  E  T  S  S  P  F  R  M  V  C  L  P  S
6361 - CAGTATCTCACACTGCACTTTTGATGGCTTCAACATCCGTTACAGTATGAATTTGGTAGT - 6420
       - Q  Y  L  T  L  H  F  *  W  L  Q  H  P  L  Q  Y  E  F  G  S
       - S  I  S  H  C  T  F  D  G  F  N  I  R  Y  S  M  N  L  V  V
       -  V  S  H  T  A  L  L  M  A  S  T  S  V  T  V  *  I  W  *  S
6421 - CTACTTCCACAATTTCATTGTGTTCTCAATCCAGTACTCCTAGAATACCGACGAATACAC - 6480
       - L  L  P  Q  F  H  C  V  L  N  P  V  L  L  E  Y  R  R  I  H
       - Y  F  H  N  F  I  V  F  S  I  Q  Y  S  *  N  T  D  E  Y  T
       -  T  S  T  I  S  L  C  S  Q  S  S  T  P  R  I  P  T  N  T  P
6481 - CTTTTGTGTTCGTAATGGTAATTCTTTGGATTACTCGAAAGTGATCGGAATCCAAATTTT - 6540
       - L  L  C  S  *  W  *  F  F  G  L  L  E  S  D  R  N  P  N  F
       - F  C  V  R  N  G  N  S  L  D  Y  S  K  V  I  G  I  Q  I  F
       -  F  V  F  V  M  V  I  L  W  I  T  R  K  *  S  E  S  K  F  L
6541 - TGTTAACGGTGAGTACCATAACGACGTTAATTATCACAAGGAACCTCATTTTAAAACCGA - 6600
       - C  *  R  *  V  P  *  R  R  *  L  S  Q  G  T  S  F  *  N  R
       - V  N  G  E  Y  H  N  D  V  N  Y  H  K  E  P  H  F  K  T  E
       -  L  T  V  S  T  I  T  T  L  I  I  T  R  N  L  I  L  K  P  N
6601 - ATACAGTTTGGTAAGAATCCTGTTCGTCGTTAATGTTGTAGTTTAACGCGATTCTCTAAT - 6660
       - I  Q  F  G  K  N  P  V  R  R  *  C  C  S  L  T  R  F  S  N
       - Y  S  L  V  R  I  L  F  V  V  N  V  V  V  *  R  D  S  L  I
       -  T  V  W  *  E  S  C  S  S  L  M  L  *  F  N  A  I  L  *  S
6661 - CGTGTTGCACACACAAATTGTTAATATACGGAATACACAAATGTAATAACAAGGTTAACACA - 6720
       - R  V  A  H  K  L  L  I  Y  G  I  H  K  C  N  N  K  V  N  T
       - V  L  H  T  N  C  *  Y  T  E  Y  T  N  V  I  T  R  L  T  H
       -  C  C  T  Q  I  V  N  I  R  N  T  Q  M  *  *  Q  G  *  H  M
6721 - TGAAAATGATTTTCATGGTTAAGATCTTAATCTCGAAGTGATGGATGTTGATAACGATTT - 6780
       - *  K  *  F  S  W  L  R  S  *  S  R  S  D  G  C  *  *  R  F
       - E  N  D  F  H  G  *  D  L  N  L  E  V  M  D  V  D  N  D  F
       -  K  M  I  F  M  V  K  I  L  I  S  K  *  W  M  L  I  T  I  F
6781 - TTATCACAATTCTCACAACGATTTAATACAAACCTACGGCCGTAATTAATACACTTCAGT - 6840
       - L  S  Q  F  S  Q  R  F  N  T  N  L  R  P  *  L  I  H  F  S
       - Y  H  N  S  H  N  D  L  I  Q  T  Y  G  R  N  *  Y  T  S  V
       -  I  T  I  L  T  T  I  *  Y  K  P  T  A  V  I  N  T  L  Q  W
6841 - GGGTTTAAAAGATTTAACAAGTGTTAGCGATACACCGATAACAACAATTCATAAACGAAT - 6900
       - G  F  K  R  F  N  K  C  *  R  Y  T  D  N  N  N  S  *  T  N
       - G  L  K  D  L  T  S  V  S  D  T  P  I  T  T  I  H  K  R  I
       -  V  *  K  I  *  Q  V  L  A  I  H  R  *  Q  Q  F  I  N  E  S
6901 - CCAAGAGATTAGACACATTGACGACGAAAACCACATGAGAATAGATTAAAACCACGAGGA - 6960
       - P  R  D  *  T  H  *  R  R  K  P  H  E  N  R  L  K  P  R  G
       - Q  E  I  R  H  I  D  D  E  N  H  M  R  I  D  *  N  H  E  E
       -  K  R  L  D  T  L  T  T  K  T  T  *  E  *  I  K  T  T  R  K
6961 - AGAATAACATTACCGCAATCTCTTAACATAGAATTAAGCAGATTGCAATGATGATACCTA - 7020
       - R  I  T  L  P  Q  S  L  N  I  E  L  S  R  L  Q  *  *  Y  L
       - E  *  H  Y  R  N  L  L  T  *  N  *  A  D  C  N  D  D  T  *
       -  N  N  I  T  A  I  S  *  H  R  I  K  Q  I  A  M  M  I  P  K
7021 - AAGACACTTCCAAGAAAAGGAACGTCGTAAACAAATTCACCTAATCTGAGGGAACTAAGA - 7080
       - K  T  L  P  R  K  G  T  S  *  T  N  S  P  N  L  R  E  L  R
       - R  H  F  Q  E  K  E  R  R  K  Q  I  H  L  I  *  G  N  *  E
       -  D  T  S  K  K  R  N  V  V  N  K  F  T  *  S  E  G  T  K  N
7081 - ATAGGTCGAGAACTTTGGTAAGTCCACTGCTAAAGTAGCATGTTCGATCTGAACTGTTAA - 7140
       - I  G  R  E  L  W  *  V  H  C  *  S  S  M  F  D  L  N  C  *
       - *  V  E  N  F  G  K  S  T  A  K  V  A  C  S  I  *  T  V  K
       -  R  S  R  T  L  V  S  P  L  L  K  *  H  V  R  S  E  L  L  K
7141 - AATCCAGACCGGCGACTCACCCAAAACCGTATATACAACAAGTGTTTTAAGAAAATAAAT - 7200
       - N  P  D  R  R  L  T  Q  N  R  I  Y  N  K  C  F  K  K  I  N
       - I  Q  T  G  D  S  P  K  T  V  Y  T  T  S  V  L  R  K  *  I
       -  S  R  P  A  T  H  P  K  P  Y  I  Q  Q  V  F  *  E  N  K  *
```

FIG. 5 Cont'd

```
7201 - AATCCAGAAAGTCGATATTACGTCCACAAGAAACCGATAAAACGATCAGTAAAGTAGTCG - 7260
     - N  P  E  S  R  Y  Y  V  H  K  K  P  I  K  R  S  V  K  *  S
     -  I  Q  K  V  D  I  T  S  T  R  N  R  *  N  D  Q  *  S  S  R
     -   S  R  K  S  I  L  R  P  Q  E  T  D  K  T  I  S  K  V  V  V
7261 - TTAAGAACCGAGTACACCAAATAGTAATCATAACATGTTTACCGTGGGCAAAGACGTTAC - 7320
     - L  R  T  E  Y  T  K  *  *  S  *  H  V  Y  R  G  Q  R  R  Y
     -  *  E  P  S  T  P  N  S  N  H  N  M  F  T  V  G  K  D  V  T
     -   K  N  R  V  H  Q  I  V  I  I  T  C  L  P  W  A  K  T  L  P
7321 - CAATCCTACATGTAGAAGAAACGAAGAAAGATGATGTATACCTTCTCGATACAAGTATAG - 7380
     - Q  S  Y  M  *  K  K  R  R  K  M  M  Y  T  F  S  I  Q  V  *
     -  N  P  T  C  R  R  N  E  E  R  *  C  I  P  S  R  Y  K  Y  S
     -   I  L  H  V  E  E  T  K  K  D  D  V  Y  L  L  D  T  S  I  V
7381 - TACCTACCAACGTGGAGAAGCTGAACGTACTACACGATATTCGCGTTAGCACGGTGTGCG - 7440
     - Y  L  P  T  W  R  S  *  T  Y  Y  T  I  F  A  L  A  R  C  A
     -  T  Y  Q  R  G  E  A  E  R  T  T  R  Y  S  R  *  H  G  V  R
     -   P  T  N  V  E  K  L  N  V  L  H  D  I  R  V  S  T  V  C  A
7441 - CAACTCACATGTTGATAACAATTACCGTACTTCTCTAGAAAGATACAGATACGTTTACCT - 7500
     - Q  L  T  C  *  *  Q  L  P  Y  F  S  R  K  I  Q  I  R  L  P
     -  N  S  H  V  D  N  N  Y  R  T  S  L  E  R  Y  R  Y  V  Y  L
     -   T  H  M  L  I  T  I  T  V  L  L  *  K  D  T  D  T  F  T  S
7501 - CCGGCACCGAAGACGTTCTGAGTGTTAACCTTAACAGAGTTAACACTGTGTAAAACGTGA - 7560
     - P  A  P  K  T  F  *  V  L  T  L  T  E  L  T  L  C  K  T  *
     -  R  H  R  R  R  S  E  C  *  P  *  Q  S  *  H  C  V  K  R  D
     -   G  T  E  D  V  L  S  V  N  L  N  R  V  N  T  V  *  N  V  T
7561 - CCATCATGTAAGTAATCACTACTTCAACGAGCACTAAACAGTGAGGTCAAATTTTCTGGT - 7620
     - P  S  C  K  *  S  L  L  Q  R  A  L  N  S  E  V  K  F  S  G
     -  H  H  V  S  N  H  Y  F  N  E  H  *  T  V  R  S  N  F  L  V
     -   I  M  *  V  I  T  T  S  T  S  T  K  Q  *  G  Q  I  F  W  L
7621 - TAGTTGGGATGACTGGTCAGTAGCATATAACAACTATCACAACGACACTTTTTACCGCGC - 7680
     - *  L  G  *  L  V  S  S  I  *  Q  L  S  Q  R  H  F  L  P  R
     -  S  W  D  D  W  S  V  A  Y  N  N  Y  H  N  D  T  F  Y  R  A
     -   V  G  M  T  G  Q  *  H  I  T  T  I  T  T  T  L  P  T  A  R
7681 - GAAGTGGAGATGAAACTGTTCCGACCAGTTTTCTGGATACTCTCTGTAGGAGAGAGGGTA - 7740
     - E  V  E  M  K  L  F  R  P  V  F  W  I  L  S  V  G  E  R  V
     -  K  W  R  *  N  C  S  D  Q  F  S  G  Y  S  L  *  E  R  G  *
     -   S  G  D  E  T  V  P  T  S  F  L  D  T  L  C  R  R  E  G  K
7741 - AAACAGTTAAATCTGTTAAACTCTCGATTGTTGTGATTTCCAAGTGACGGATAATTACAG - 7800
     - K  Q  L  N  L  L  N  S  R  L  L  *  F  P  S  D  G  *  L  Q
     -  N  S  *  I  C  *  T  L  D  C  C  D  F  Q  V  T  D  N  Y  S
     -   T  V  K  S  V  K  L  S  I  V  V  I  S  K  *  R  I  I  T  V
7801 - TATCAAAAACTACCGTTCAGGTTTACGCTGCTCAGACGAAGATTCAGACGAAGACACATG - 7860
     - Y  Q  K  L  P  F  R  F  T  L  L  R  R  R  F  R  R  R  H  M
     -  I  K  N  Y  R  S  G  L  R  C  S  D  E  D  S  D  E  D  T  *
     -   S  K  T  T  V  Q  V  Y  A  A  Q  T  K  I  Q  T  K  T  H  D
7861 - ATGTCAGTCGACTACACGGTTGGATAAGACAACGAACTGGTTCGAGAACATAGTCTGCAA - 7920
     - M  S  V  D  Y  T  V  G  *  D  N  E  L  V  R  E  H  S  L  Q
     -  C  Q  S  T  T  R  L  D  K  T  T  N  W  F  E  N  I  V  C  N
     -   V  S  R  L  H  G  W  I  R  Q  R  T  G  S  R  T  *  S  A  T
7921 - CCTCTATCATGACTTCAAAGGCAATTCTACAAACTACGAATACAGCTGTGGAAAAGTCGT - 7980
     - P  L  S  *  L  Q  R  Q  F  Y  K  L  R  I  Q  L  W  K  S  R
     -  L  Y  H  D  F  K  G  N  S  T  N  Y  E  Y  S  C  G  K  V  V
     -   S  I  M  T  S  K  A  I  L  Q  T  T  N  T  A  V  E  K  S  L
7981 - TGAAAATCACAAGGATACCTTTTTGAATTCCGTGAACAACGATGTCGAGTGTCGCTCAAT - 8040
     - *  K  S  Q  G  Y  L  F  E  F  R  E  Q  R  C  R  V  S  L  N
     -  E  N  H  K  D  T  F  L  N  S  V  N  N  D  V  E  C  R  S  I
     -   K  I  T  R  I  P  F  *  I  P  *  T  T  M  S  S  V  A  Q  S
8041 - CGTTTCCCACATCGAAATCTACCACAGGAAAGATGTAAGCACAGTCGACGGGCTGTTCCA - 8100
     - R  F  P  H  R  N  L  P  Q  E  R  C  K  H  S  R  R  A  V  P
     -  V  S  H  I  E  I  Y  H  R  K  D  V  S  T  V  D  G  L  F  H
     -   F  P  T  S  K  S  T  T  G  K  M  *  A  Q  S  T  G  C  S  T
```

FIG. 5 Cont'd

```
8101 - CAACAACTATGGCTACAACTGTGTTTCCTACAATAACTTACAGAGTTTGAAAGTGTAGTG - 8160
     -  Q  Q  L  W  L  Q  L  C  F  L  Q  *  L  T  E  F  E  S  V  V
     -   N  N  Y  G  Y  N  C  V  S  Y  N  N  L  Q  S  L  K  V  *  *
     -    T  T  M  A  T  T  V  F  P  T  I  T  Y  R  V  *  K  C  S  E
8161 - AGACTGAATCTTCACTGTCCACTGTCAACATTGTTAAAGTACGAGTGGATATTATTCCAA - 8220
     -  R  L  N  L  H  C  P  L  S  T  L  L  K  Y  E  W  I  L  F  Q
     -   D  *  I  F  T  V  H  C  Q  H  C  *  S  T  S  G  Y  Y  S  N
     -    T  E  S  S  L  S  T  V  N  I  V  K  V  R  V  D  I  I  P  T
8221 - CTTTTGTACTGCGGGTCTCTAGAACCGCGTACATAACTGACATTACGTTCCGTATAGTTA - 8280
     -  L  L  Y  C  G  S  L  E  P  R  T  *  L  T  L  R  S  V  *  L
     -   F  C  T  A  G  L  *  N  R  V  H  N  *  H  Y  V  P  Y  S  Y
     -    F  V  L  R  V  S  R  T  A  Y  I  T  D  I  T  F  R  I  V  T
8281 - CGGGTTCATCGTTTTTCAGTGTTACAAAGTGAGTAGACCTTACATTTCTGATGTACAGA - 8340
     -  R  V  H  R  F  S  V  L  Q  S  E  *  T  L  H  F  L  M  Y  R
     -   G  F  I  V  F  Q  C  Y  K  V  S  R  P  Y  I  F  *  C  T  E
     -    G  S  S  F  F  S  V  T  K  *  V  D  L  T  F  S  D  V  Q  K
8341 - AATAGACTTGTCGACGCATTTGTTTAAGCATCACGACGGTTCTTCTTGTTGTATGGAAAA - 8400
     -  N  R  L  V  D  A  F  V  *  A  S  R  R  F  L  L  Y  G  K
     -   I  D  L  S  T  H  L  F  K  H  H  D  G  S  S  C  C  M  E  N
     -    *  T  C  R  R  I  C  L  S  I  T  T  V  L  L  V  V  W  K  I
8401 - TCTGATTGAACACGATGTTGATCTGTCCAACAGTTACAGTATTGATGATTTTAGAGTGAG - 8460
     -  S  D  *  T  R  C  *  S  V  Q  Q  L  Q  Y  *  *  F  *  S  E
     -   L  I  E  H  D  V  D  L  S  N  S  Y  S  I  D  D  F  R  V  S
     -    *  L  N  T  M  L  I  C  P  T  V  T  V  L  M  I  L  E  *  V
8461 - TTCCCACCATTCTAACAATCATGAACAAAATTTGAATACGAATTCCGGTGTAATAACACG - 8520
     -  F  P  P  F  *  Q  S  *  T  K  F  E  Y  E  F  R  C  N  N  T
     -   S  H  H  S  N  N  H  E  Q  N  L  N  T  N  S  G  V  I  T  R
     -    P  T  I  L  T  I  M  N  K  I  *  I  R  I  P  V  *  *  H  A
8521 - CAAGAACGACGTAACCAAACAATATAGCAATACGGTCATGTATGTAACAGTTAGGTACTA - 8580
     -  Q  E  R  R  N  Q  T  I  *  Q  Y  G  H  V  C  N  S  *  V  L
     -   K  N  D  V  T  K  Q  Y  S  N  T  V  M  Y  V  T  V  R  Y  Y
     -    R  T  T  *  P  N  N  I  A  I  R  S  C  M  *  Q  L  G  T  T
8581 - CCAATGTGTTTACTTTAGTAACCAATGTTTCGGTAAGTCCTACCACAGTGAGCACTGTAG - 8640
     -  P  M  C  L  L  *  *  P  M  F  R  *  V  L  P  Q  *  A  L  *
     -   Q  C  V  Y  F  S  N  Q  C  F  G  K  S  Y  H  S  E  H  C  S
     -    N  V  F  T  L  V  T  N  V  S  V  S  P  T  T  V  S  T  V  V
8641 - TAAAGATGACTACTAACAAAACGTTTATTTGTACGACCAAAACTGCGTACCAAATCGGTC - 8700
     -  *  R  *  L  L  T  K  R  L  F  V  R  P  K  L  R  T  K  S  V
     -   K  D  D  Y  *  Q  N  V  Y  L  Y  D  Q  N  C  V  P  N  R  S
     -    K  M  T  T  N  K  T  F  I  C  T  T  K  T  A  Y  Q  I  G  R
8701 - GCACCACCAAGTATGTTTTTACTGTTTTCGACGGGACATCATCGACGATAGTAATGTTCT - 8760
     -  A  P  P  S  M  F  L  L  F  S  T  G  H  H  R  R  *  *  C  S
     -   H  H  Q  V  C  F  Y  C  F  R  R  D  I  I  D  D  S  N  V  L
     -    T  T  K  Y  V  F  T  V  F  D  G  T  S  S  T  I  V  M  F  S
8761 - CTCTAACCAAAGTATCACGGACCGAATGGCCCATGACACGACTCTCGTTAGTTACCACTG - 8820
     -  L  *  P  K  Y  H  G  P  N  G  P  *  H  D  S  R  *  L  P  L
     -   S  N  Q  S  I  T  D  R  M  A  H  D  T  T  L  V  S  Y  H  *
     -    L  T  K  V  S  R  T  E  W  P  M  T  R  L  S  L  V  T  T  E
8821 - AAGAACGTAAAAGATGGAGCACAAAAATCACGACAACCGTTGTAAACGATGTGTGGAAGG - 8880
     -  K  N  V  K  D  G  A  Q  K  S  R  Q  P  L  *  T  M  C  G  R
     -   R  T  *  K  M  E  H  K  N  H  D  N  R  C  K  R  C  V  E  G
     -    E  R  K  W  S  T  K  I  T  T  T  V  V  N  D  V  W  K  V
8881 - TTTGAGTAACTCATATCACTAAAACGATGGAGACGAACGCAAGAACGACGACTCACATGT - 8940
     -  F  E  *  L  I  S  L  K  R  W  R  R  T  Q  E  R  R  L  T  C
     -   L  S  N  S  Y  H  *  N  D  G  D  E  R  K  N  D  D  S  H  V
     -    *  V  T  H  I  T  K  T  M  E  T  N  A  R  T  T  T  H  M  L
8941 - TAAAAATTCCTACGATACCCGTTTGGACACGGTATAACAATACTGTGATTAAACGATCTC - 9000
     -  *  K  F  L  R  Y  P  F  G  H  G  I  T  I  L  *  L  N  D  L
     -   K  N  S  Y  D  T  R  L  D  T  V  *  Q  Y  C  D  *  T  I  S
     -    K  I  P  T  I  P  V  W  T  R  Y  N  N  T  V  I  K  R  S  P
```

FIG. 5 Cont'd

```
9001 - CCAAGATAAAGAATATCACTCGAAGCAGGTCTGTGAGCAATACACGAATACCTACCAAGG - 9060
     -   P R * R I S L E A G L * A I H E Y L P R
     - Q D K E Y H S K Q V C E Q Y T N T Y Q G
     -  K I K N I T R S R S V S N T R I P T K V
9061 - TAGTATGTCAAAGGATTGTGAATGGACCTCCCAAGACAATCTCATCATTGTTGAAAACTA - 9120
     -  * Y V K G L * M D L P R Q S H H C * K L
     -  S M S K D C E W T S Q D N L I I V E N Y
     - V C Q R I V N G P P P K T I S S L L K T T
9121 - CGACTCATGACATCTGTACCATGTACGCTTTCCAGTCTTCATCCATAAACGGATAGATGG - 9180
     - R L M T S V P C T L S S L H P * T D R W
     - D S * H L Y H V R F P V F I H K R I D G
     -  T H D I C T M Y A F Q S S S I N G * M V
9181 - TCACCATCTACCCAAGAATTATTACTCGTAATGTCTCGAGATAGTCCTCAAAAGACACCA - 9240
     - S P S T Q E L L L V M S R D S P Q K T P
     -  H H L P K N Y Y S * C L E I V L K R H H
     -   T I Y P R I I T R N V S R * S S K D T T
9241 - CAACTACGCTACTTAGAGTATCGATTGTAGAAATGAGGAGAACACGTTGGACACCCACGA - 9300
     - Q L R Y L E Y R L * K * G E H V G H P R
     -  N Y A T * S I D C R N E E N T L D T H E
     -   T T L L R V S I V E M R R T R W T P T K
9301 - AATCTACACGACGAAGTCATCACCGACCACCATAATAACGGTATAACCACTGAACACGA - 9360
     - N L H R R S H H R P P * * R Y N H * T R
     -  I Y T D E V I T D H H N G I T T E H D
     -   S T Q T K S S P T T I I T V * P L N T T
9361 - CGGATGATGAAATACTTTAAGTCTGCACGAAAACCACTCATGTTGGTACAACAACGACGA - 9420
     - R M M K Y F K S A R K P L M L V Q Q R R
     -  G * * N T L S L H E N H S C W Y N N D D
     -   D D E I L * V C T K T T H V G T T T T I
9421 - TTACGTGAAAACAAAAACTACAGAAAGTGATATGAGACAGACCGTGGTCGAATGTCGAAA - 9480
     - L R E N K N Y R K * Y E T D R G R M S K
     -  Y V K T K T T E S D M R Q T V V E C R K
     -   T * K Q K L Q K V I * D R P W S N V E R
9481 - GACGGCCCTCAGATGAGTCAGAAAATGAACATGAACTGTAAGATAAAGTGGTTACTACAA - 9540
     - D G P Q M S Q K M N M N C K I K W L L Q
     -  T A L R * V R K * T * T V R * S G Y Y K
     -   R P S D E S E N E H E L * D K V V T T K
9541 - AGTAAGAACCGAGTGGAAGTTACCAAACGGTACAAAAGAGGATAACACGGAAAAACCTAT - 9600
     - S K N R V E V T K R Y K R G * H G K T Y
     -  V R T E W K L P N G T K E D N T E K P I
     -   * E P S G S Y Q T V Q K R I T R K N L L
9601 - TGTCGTTAGATACATAAGACATAAAGAGACTTCGTGACGGTAACCAAGAAATTGTTGATA - 9660
     - C R * I H K T * R D F V T V T K K L L I
     -  V V R Y I R H K E T S * R * P R N C * *
     -   S L D T * D I K R L R D G N Q E I V D R
9661 - GAATCCTTTTCTCAGTACAAATTACCTCAATGTAAATCATGGAAGCTCCTCCGACGAAAC - 9720
     - E S F S Q Y K L P Q C K S W K L L R R N
     -  N P F L S T N Y L N V N H G S S S D E T
     -   I L F S V Q I T S M * I M E A P P T K H
9721 - ACATGGAAAAACGAGTTGTTCCTTTACATGGATTTTAACGCATCGCTCTGTGACAACGGT - 9780
     - T W K N E L F L Y M D F N A S L C D N G
     -  H G K T S C S F T W I L T H R S V T T V
     -   M E K R V V P L H G F * R I A L * Q R *
9781 - GAATGTGTCATATTGTCCATAGAACGAGATATATTGTTCATGTTCATAAAGTCACCTCGG - 9840
     - E C V I L S I E R D I L F M F I K S P R
     -  N V S Y C P * N E I Y C S C S * S H L G
     -   M C H I V H R T R Y I V H V H K V T S E
9841 - AATCTATGATGGTCGATAGCACTTCGTCGAACGACGGTGAATCGTTTCCGAGATTTACTG - 9900
     - N L * W S I A L R R T T V N R F R D L L
     -  I Y D G R * H F V E R R * I V S E I Y *
     -   S M M V D S T S S N D G E S F P R F T E
```

FIG. 5 Cont'd

```
9901  - AAATCGTTGAGTCCACGACTACAAGAGATGGTTGGTGGTGTCTGTAGTTAGTGAAGACGA - 9960
      - K  S  L  S  P  R  L  Q  E  M  V  G  G  V  C  S  *  *  R  R
      -  N  R  *  V  H  D  Y  K  R  W  L  V  V  S  V  V  S  E  D  D
      -   I  V  E  S  T  T  T  R  D  G  W  W  C  L  *  L  V  K  T  T
9961  - CAAGACGTCTCACCAAAATCCTTTTACCGTAAGGGCAGTCCGTTTCAACTTCCCACGTAC - 10020
      - Q  D  V  S  P  K  S  F  Y  R  K  G  S  P  F  Q  L  P  T  Y
      -  K  T  S  H  Q  N  P  F  T  V  R  A  V  R  F  N  F  P  R  T
      -   R  R  L  T  K  I  L  L  P  *  G  Q  S  V  S  T  S  H  V  P
10021 - CATGTTCATTGGACACCTTGATGTTGAGAATTACCTAACACCAACCTACTGTGTCATATG - 10080
      - H  V  H  W  T  P  *  C  *  E  L  P  N  T  N  L  L  C  H  M
      -  M  F  I  G  H  L  D  V  E  N  Y  L  T  P  T  Y  C  V  I  *
      -   C  S  L  D  T  L  M  L  R  I  T  *  H  Q  P  T  V  S  Y  D
10081 - ACAGGTTCTGTACAGTAAACGTGTCGTCTTCTGTACGAATTAGGATTGATACTTCTAGAC - 10140
      - T  G  S  V  Q  *  T  C  R  L  L  Y  E  L  G  L  I  L  L  D
      -  Q  V  L  Y  S  K  R  V  V  F  C  T  N  *  D  *  Y  F  *  T
      -   R  F  C  T  V  N  V  S  S  S  V  R  I  R  I  D  T  S  R  R
10141 - GAGTAAGCGTTTAGGTTGGTATCGAAAGAACAAGTCCGACCGTTACAAGTTGAAGCACAA - 10200
      - E  *  A  F  R  L  V  S  K  E  Q  V  R  P  L  Q  V  E  A  Q
      -  S  K  R  L  G  W  Y  R  K  N  K  S  D  R  Y  K  L  K  H  N
      -   V  S  V  *  V  G  I  E  R  T  S  P  T  V  T  S  *  S  T  I
10201 - TAACCGGTAAGATACGTTTTAACAGACGAATCCGAATTTCAACTATGAAGATTGGGATTC - 10260
      - *  P  V  R  Y  V  L  T  D  E  S  E  F  Q  L  *  R  L  G  F
      -  N  R  *  D  T  F  *  Q  T  N  P  N  F  N  Y  E  D  W  D  S
      -   T  G  K  I  R  F  N  R  R  I  R  I  S  T  M  K  I  G  I  L
10261 - TGTGGGTTCATATTTAAACAGGCATAGGTTGGACCAGTTTGTAAAAGTCAAGATCGTACG - 10320
      - C  G  F  I  F  K  Q  A  *  V  G  P  V  C  K  S  Q  D  R  T
      -  V  G  S  Y  L  N  R  H  R  L  D  Q  F  V  K  V  K  I  V  R
      -   W  V  H  I  *  T  G  I  G  W  T  S  L  *  K  S  R  S  Y  D
10321 - ATGTTACCAAGTGGTAGACCACAAATAGTCACACGGTACTCTGGATTAGTATGGTAATTT - 10380
      - M  L  P  S  G  R  P  Q  I  V  T  R  Y  S  G  L  V  W  *  F
      -  C  Y  Q  V  V  D  H  K  *  S  H  G  T  L  D  *  Y  G  N  F
      -   V  T  K  W  *  T  T  N  S  H  T  V  L  W  I  S  M  V  I  S
10381 - CCAAGAAAGGAATTACCTAGTACACCATCACAACCAAAATTGTAACTAATACTAACGCAC - 10440
      - P  R  K  E  L  P  S  T  P  S  Q  P  K  L  *  L  I  L  T  H
      -  Q  E  R  N  Y  L  V  H  H  H  N  Q  N  C  N  *  Y  *  R  T
      -   K  K  G  I  T  *  Y  T  I  T  T  K  I  V  T  N  T  N  A  Q
10441 - AGAAAGACGATATACGTAGTATACCTCGAAGGTTGTCCTCATGTGCGACCATGACTGAAT - 10500
      - R  K  T  I  Y  V  V  Y  L  E  G  C  P  H  V  R  P  *  L  N
      -  E  R  R  Y  T  *  Y  T  S  K  V  V  L  M  C  D  H  D  *  I
      -   K  D  D  I  R  S  I  P  R  R  L  S  S  C  A  T  M  T  E  S
10501 - CTTCCATTTAAGATACCAGGTAAACAACTGTCTGTTTGACGTGTCCGACGTCCATGTCTG - 10560
      - L  P  F  K  I  P  G  K  Q  L  S  V  *  R  V  R  R  P  C  L
      -  F  H  L  R  Y  Q  V  N  N  C  L  F  D  V  S  D  V  H  V  C
      -   S  I  *  D  T  R  *  T  T  V  C  L  T  C  P  T  S  M  S  V
10561 - TGTTGGTATTGTAATTTACAAAACCGTACCGACATACGACGACAATAGTTACCACTATCC - 10620
      - C  W  Y  C  N  L  Q  N  R  T  D  I  R  R  Q  *  L  P  L  S
      -  V  G  I  V  I  Y  K  T  V  P  T  Y  D  D  N  S  Y  H  Y  P
      -   L  V  L  *  F  T  K  P  Y  R  H  T  T  T  I  V  T  T  I  H
10621 - ACCAAAGAATTATCTAAGTGGTGATGAAACTTACTGAAATTGGAACACCGTTACTTCATG - 10680
      - T  K  E  L  S  K  W  *  *  N  L  L  K  L  E  H  R  Y  F  M
      -  P  K  N  Y  L  S  G  D  E  T  Y  *  N  W  N  T  V  T  S  C
      -   Q  R  I  I  *  V  V  M  K  L  T  E  I  G  T  P  L  L  H  V
10681 - TTGATACTTGGAAACTGTGTTCTAGTACAACTGTATAACCCTGGAGAAAGACGAGTTTGT - 10740
      - L  I  L  G  N  C  V  L  V  Q  L  Y  N  P  G  E  R  R  V  C
      -  *  Y  L  E  T  V  F  *  Y  N  C  I  T  L  E  K  D  E  F  V
      -   D  T  W  K  L  C  S  S  T  T  V  *  P  W  R  K  T  S  L  S
10741 - CCTTAACGGCAGAATCTATACACACGACGAAACTTTCTCGACGACGTCTTACCATACTTA - 10800
      - P  *  R  Q  N  L  Y  T  R  R  N  F  L  D  D  V  L  P  Y  L
      -  L  N  G  R  I  Y  T  H  D  E  T  F  S  T  T  S  Y  H  T  Y
      -   L  T  A  E  S  I  H  T  T  K  L  S  R  R  R  L  T  I  L  T
```

FIG. 5 Cont'd

```
10801 - CCAGCATGATAGGAACCATCGTGATAAAATCTTCTACTCAAATGTGGTAAACTACAACAA - 10860
       - P  A  *  *  E  P  S  *  *  N  L  L  L  K  C  G  K  L  Q  Q
       - Q  H  D  R  N  H  R  D  K  I  F  Y  S  N  V  V  N  Y  N  N
       -    S  M  I  G  T  I  V  I  K  S  S  T  Q  M  W  *  T  T  T  I
10861 - TCTGTTACGAGACCACAATGGAAGGTTCCATTCAAGTTCTTTTAACAATTCCCGTGAGTA - 10920
       - S  V  T  R  P  Q  W  K  V  P  F  K  F  F  *  Q  F  P  *  V
       - L  L  R  D  H  N  G  R  F  H  S  S  S  F  N  N  S  R  E  *
       -    C  Y  E  T  T  M  E  G  S  I  Q  V  L  L  T  I  P  V  S  S
10921 - GTAACCTACGAAAATTGAAAGAACTGTAGTGATAACTAAGAACAAGTTTCATGTGTCACC - 10980
       - V  T  Y  E  N  *  K  N  C  S  D  N  *  E  Q  V  S  C  V  T
       - *  P  T  K  I  E  R  T  V  V  I  T  K  N  K  F  H  V  S  P
       -    N  L  R  K  L  K  E  L  *  *  *  L  R  T  S  F  M  C  H  Q
10981 - AGTGACAAAAAGAAACAAATGCTCTTACGAAAGAACGGTAAATGAGAACCATAATACCGT - 11040
       - S  D  K  K  K  Q  M  L  L  R  K  N  G  K  *  E  P  *  Y  R
       - V  T  K  R  N  K  C  S  Y  E  R  T  V  N  E  N  H  N  T  V
       -    *  Q  K  E  T  N  A  L  T  K  E  R  *  M  R  T  I  I  P  L
11041 - TAACGACGTACACGATACGACGAACAATTCGTATTCGTGCGTAAGAACACGAACAAAGAC - 11100
       - *  R  R  T  R  Y  D  E  Q  F  V  F  V  R  K  N  T  N  K  D
       - N  D  V  H  D  T  T  N  N  S  Y  S  C  V  R  T  R  T  K  T
       -    T  T  Y  T  I  R  R  T  I  R  I  R  A  *  E  H  E  Q  R  Q
11101 - AATGGAAGAGAACGTTGTCAACGAATGAAATTATACCAGATGTACGGACGATCGACCCAC - 11160
       - N  G  R  E  R  C  Q  R  M  K  L  Y  Q  M  Y  G  R  S  T  H
       - M  E  E  N  V  V  N  E  *  N  Y  T  R  C  T  D  D  R  P  T
       -    W  K  R  T  L  S  T  N  E  I  I  P  D  V  R  T  I  D  P  L
11161 - TACGCATAGTACTGTACCGAACTTAACCGACTGTGATCGAACAGACCAATATCCGAATTC - 11220
       - Y  A  *  Y  C  T  E  L  N  R  L  *  S  N  R  P  I  S  E  F
       - T  H  S  T  V  P  N  L  T  D  C  D  R  T  D  Q  Y  P  N  S
       -    R  I  V  L  Y  R  T  *  P  T  V  I  E  Q  T  N  I  R  I  P
11221 - CTAACACAATACATACGAAGTCGAAATCAAAACGAATAAGAGTACTGTCGAGCGTGACAA - 11280
       - L  T  Q  Y  I  R  S  R  N  Q  N  E  *  E  Y  C  R  A  *  Q
       - *  H  N  T  Y  E  V  E  I  K  T  N  K  S  T  V  E  R  D  K
       -    N  T  I  H  T  K  S  K  S  K  R  I  R  V  L  S  S  V  T  N
11281 - ATACTACTACGACGATCTGCACAAACCTGTGACTACTTACAGTAATGTGAACAAATGTTT - 11340
       - I  L  L  R  R  S  A  Q  T  C  D  Y  L  Q  *  C  E  Q  M  F
       - Y  Y  Y  D  D  L  H  K  P  V  T  T  Y  S  N  V  N  K  C  F
       -    T  T  T  T  I  C  T  N  L  *  L  L  T  V  M  *  T  N  V  S
11341 - CAGATGATACCATTACGAAATCTAGTTCGATAAAGGTACACCCGGAATCAATAAAGACAT - 11400
       - Q  M  I  P  L  R  N  L  V  R  *  R  Y  T  R  N  Q  *  R  H
       - R  *  Y  H  Y  E  I  *  F  D  K  G  T  P  G  I  N  K  D  I
       -    D  D  T  I  T  K  S  S  S  I  K  V  H  P  E  S  I  K  T  L
11401 - TGGAGATTGATAAGACCACAGCAATGCTGATAGTACAAAAATCGATCTCGATATCACAAA - 11460
       - W  R  L  I  R  P  Q  Q  C  *  *  Y  K  N  R  S  R  Y  H  K
       - G  D  *  *  D  H  S  N  A  D  S  T  K  I  D  L  D  I  T  N
       -    E  I  D  K  T  T  A  M  L  I  V  Q  K  S  I  S  I  S  Q  T
11461 - CACACACAACTCATAATGGGTAACAATAAATAATGACCGTTGTGGAATGTCACATAGTAC - 11520
       - H  T  Q  L  I  M  G  N  N  K  *  *  P  L  W  N  V  T  *  Y
       - T  H  N  S  *  W  V  T  I  N  N  D  R  C  G  M  S  H  S  T
       -    H  T  T  H  N  G  *  Q  *  I  M  T  V  V  E  C  H  I  V  R
11521 - GAACAAATAACAAAGAATCCGATAACAACGACGACGATGAAACCGGAAAAGACAAATGAG - 11580
       - E  Q  I  T  K  N  P  I  T  T  T  T  M  K  P  E  K  T  N  E
       - N  K  *  Q  R  I  R  *  Q  R  R  R  *  N  R  K  R  Q  M  S
       -    T  N  N  K  E  S  D  N  N  D  D  D  E  T  G  K  D  K  *  V
11581 - TTGGCAATGAAGTCCGAATGAGAACCACAAATACTGATGAACCAGAGATGTGTTCTTAAA - 11640
       - L  A  M  K  S  E  *  E  P  Q  I  L  M  N  Q  R  C  V  L  K
       - W  Q  *  S  P  N  E  N  H  K  Y  *  *  T  R  D  V  F  L  N
       -    G  N  E  V  R  M  R  T  T  N  T  D  E  P  E  M  C  S  *  I
11641 - TCCATATACTTGAGGGTCCCCGAAAACGGAGGATTCTCATCATAACTACGAAAGTTCGAA - 11700
       - S  I  Y  L  R  V  P  E  N  G  G  F  S  S  *  L  R  K  F  E
       - P  Y  T  *  G  S  P  K  T  E  D  S  H  H  N  Y  E  S  S  N
       -    H  I  L  E  G  P  R  K  R  R  I  L  I  I  T  T  K  V  R  I
```

FIG. 5 Cont'd

```
11701 - TTGTAATTCAACAACCCATAACCTCCATTTGGTACATAGTTCCAACGATGACATGTCAGA - 11760
       - L * F N N P * P P F G T * F Q R * H V R
       - C N S T T H N L H L V H S S N D D M S D
       - V I Q Q P I T S I W Y I V P T M T C Q I
11761 - TTTTACAGACTGCATTTCACGTGTAGACACCATGACGAGAGCCAAGAAGTTGTTGAATCT - 11820
       - F Y R L H F T C R H H D E S Q E V V E S
       - F T D C I S R V D T M T R A K K L L N L
       - L Q T A F H V * T P * R E P R S C * I S
11821 - CATCTCAGTAGAAGATTTAACACCCGTGTTACACATGTGAGGTGTTACTATAAGAAGAA - 11880
       - H L S R R F N T R V T H V E V L L * E E
       - I S V E D L T P V L H M L R C Y Y K K N
       - S Q * K I * H P C Y T C * G V T I R R T
11881 - CGTTTTCTGTGTTGACTTCGAAAGCTCTTCTACCAAAGAGAAAACAGACAAAACGATAGG - 11940
       - R F L C * L R K L F Y Q R E N R Q N D R
       - V F C V D F E S S S T K E K T D K T I G
       - F S V L T S K A L L P K R K Q T K R * V
11941 - TACGTCCCACGACATCTGTAATTATCCAACACGCTCCTTTACGAGCTATTGGCACGATGA - 12000
       - Y V P R H L * L S N T L L Y E L L A R *
       - T S H D I C N Y P T R S F T S Y W H D E
       - R P T T S V I I Q H A P L R A I G T M R
12001 - GAAGTCCGATAACGAAGTCTTAAATCAAGAAATGGTAGTATACGGCGAATACGGTGACGG - 12060
       - E V R * R S L K S R N G S I R R I R * R
       - K S D N E V L N Q E M V V Y G E Y G D G
       - S P I T K S * I K K W * Y T A N T V T G
12061 - GTCCTCCGGATACTCGTCCGACATCGATTACCACTAAGACTTCAGCAAGAGTTTTTCAAT - 12120
       - V L R I L V R H R L P L R L Q Q E F F N
       - S S G Y S S D I D Y H * D F S K S F S I
       - P P D T R P T S I T T K T S A R V F Q F
12121 - TTCTTTAGAAACTTACACCGATTTAGACTCAAACTGGCACTACGACGGTACGTTGCGTTC - 12180
       - F F R N L H R F R L K L A L R R Y V A F
       - S L E T Y T D L D S N W H Y D G T L R S
       - L * K L T P I * T Q T G T T T V R C V Q
12181 - AACCTTTTCTACCGTCTAGTCCGATACTGGGTTTACATGTTTGTCCGTTCTAGACTCCTG - 12240
       - N L F Y R L V R Y W V Y M F V R S R L L
       - T F S T V * S D T G F T C L S V L D S C
       - P F L P S S P I L G L H V C P F * T P V
12241 - TTCTCCCGTTTTCATTGATCACGATACGTTTGTTACGAGAAGTGATACGAATCCTTCGAA - 12300
       - F S R F H * S R Y V C Y E K * Y E S F E
       - S P V F I D H D T F V T R S D T N P S N
       - L P F S L I T I R L L R E V I R I L R T
12301 - CTATTACTACGTGAATTGTTGTAATAGTTGTTACGCGCACTACCAACACAAGGTGAGTTG - 12360
       - L L L R E L L * * L L R A L P T Q G E L
       - Y Y Y V N C C N S C Y A H Y Q H K V S C
       - I T T * I V V I V V T R T T N T R * V V
12361 - TAGTATGGTAACTGATGTCGTCGGTTTGAGTACCAACAACAGGGACTAATACCATGGATG - 12420
       - * Y G N * C R R F E Y Q Q Q G L I P W M
       - S M V T D V V G L S T N N R D * Y H G C
       - V W * L M S S V * V P T T G T N T M D V
12421 - TTCTTGTGAACACTACCATTGTGGAAATGTATACGTAGACGTGAGACCCTTTAGGTCGTT - 12480
       - F L * T L P L W K C I R R R E T L * V V
       - S C E H Y H C G N V Y V D V R P F R S F
       - L V N T T I V E M Y T * T * D P L G R S
12481 - CAACAACTACGCCTATCGTTCTAACAAGTTGAATCACTTTAATTGTACCTGTTAAGTGGT - 12540
       - Q Q L R L S F * Q V E S L * L Y L L S G
       - N N Y A Y R S N K L N H F N C T C * V V
       - T T T P I V L T S * I T L I V P V K W F
12541 - TTAAACCGAACCGGAGAATAACAATGTCGAGATTCTCGGTTGAGTCGACAATTTGATGTC - 12600
       - L N R T G E * Q C R D S R L S R Q F D V
       - * T E P E N N N V E I L G * V D N L M S
       - K P N R R I T M S R F S V E S T I * C L
```

FIG. 5 Cont'd

```
12601 - TTATTACTTGACTCAGGTCATCGTGATGCTGTCTACAGGACACGCCGACCATGGTGTGTT - 12660
      - L  L  L  D  S  G  H  R  D  A  V  Y  R  T  R  R  P  W  C  V
      -  Y  Y  L  T  Q  V  I  V  M  L  S  T  G  H  A  D  H  G  V  F
      -   I  T  *  L  R  S  S  *  C  C  L  Q  D  T  P  T  M  V  C  L
12661 - TGTCGAACATGACTACTGTTACGTGAACGGATGATATTGTTAAGCTTCCCTCCATCCAAA - 12720
      - C  R  T  *  L  L  L  R  E  R  M  I  L  L  S  F  P  P  S  K
      -  V  E  H  D  Y  C  Y  V  N  G  *  Y  C  *  A  S  L  H  P  N
      -   S  N  M  T  T  V  T  *  T  D  D  I  V  K  L  P  S  I  Q  T
12721 - CACGACCGTAATGATAGTCTGGTGGTTCTAGAGTTTACCCGATCTAAGGGATTCTCACTA - 12780
      - H  D  R  N  D  S  L  V  V  L  E  F  T  R  S  K  G  F  S  L
      -  T  T  V  M  I  V  W  W  F  *  S  L  P  D  L  R  D  S  H  Y
      -   R  P  *  *  *  S  G  G  S  R  V  Y  P  I  *  G  I  L  T  T
12781 - CCATGTCCATGTTAAATGTGTCTTGACCTTGGTGGAACATCCAAACAATGTCTGTGTGGT - 12840
      - P  C  P  C  *  M  C  L  D  L  G  G  T  S  K  Q  C  L  C  G
      -  H  V  H  V  K  C  V  L  T  L  V  E  H  P  N  N  V  C  V  V
      -   M  S  M  L  N  V  S  *  P  W  W  N  I  Q  T  M  S  V  W  F
12841 - TTTCCCGGATTTCACTTTATGAACATGAAGTAGTTTCCGAATTTGTTGGATTTATCTCCA - 12900
      - F  P  G  F  H  F  M  N  M  K  *  F  P  N  L  L  D  L  S  P
      -  F  P  D  F  T  L  *  T  *  S  S  F  R  I  C  W  I  Y  L  H
      -   S  R  I  S  L  Y  E  H  E  V  V  S  E  F  V  G  F  I  S  I
12901 - TACCACGACCCGTCAAATCGACGATGTCATGCAGAAGTCCGACCTTTACGATGTCTTCAT - 12960
      - Y  H  D  P  S  N  R  R  C  H  A  E  V  R  P  L  R  C  L  H
      -  T  T  T  R  Q  I  D  D  V  M  Q  K  S  D  L  Y  D  V  F  M
      -   P  R  P  V  K  S  T  M  S  C  R  S  P  T  F  T  M  S  S  W
12961 - GGACGGTTAAGTTGACACGAAAGGAAGACACGAAAACGTCATCTGGGACGATTTCGTATA - 13020
      - G  R  L  S  *  H  E  R  K  T  R  K  R  H  L  G  R  F  R  I
      -  D  G  *  V  D  T  K  G  R  H  E  N  V  I  W  D  D  F  V  Y
      -   T  V  K  L  T  R  K  E  D  T  K  T  S  S  G  T  I  S  Y  I
13021 - TTCCTAATGGATCGTTCACCTCCTGTTGGTTAGTGGTTGACACACTTCTACAACACATGT - 13080
      - F  L  M  D  R  S  P  P  V  G  *  W  L  T  H  F  Y  N  T  C
      -  S  *  W  I  V  H  L  L  L  V  S  G  *  H  T  S  T  T  H  V
      -   P  N  G  S  F  T  S  C  W  L  V  V  D  T  L  L  Q  H  M  C
13081 - GTGTGACCATGTCCTGTCCGTTAATGACATTGTGGTCTTCGATTGTACCTGGTTCTCAGG - 13140
      - V  *  P  C  P  V  R  *  *  H  C  G  L  R  L  Y  L  V  L  R
      -  C  D  H  V  L  S  V  N  D  I  V  V  F  D  C  T  W  F  S  G
      -   V  T  M  S  C  P  L  M  T  L  W  S  S  I  V  P  G  S  Q  E
13141 - AAACCACCACGAAGTACAACAGACATAACATCTACGGTGTAACTGGTAGGTTTAGGATTT - 13200
      - K  P  P  R  S  T  T  D  I  T  S  T  V  *  L  V  G  L  G  F
      -  N  H  H  E  V  Q  Q  T  *  H  L  R  C  N  W  *  V  *  D  F
      -   T  T  T  K  Y  N  R  H  N  I  Y  G  V  T  G  R  F  R  I  S
13201 - CCTAAGACACTGAACTTTCCATTCATGCAGGTTTATGGATGGTGAACACGATTACTGGGT - 13260
      - P  K  T  L  N  F  P  F  M  Q  V  Y  G  W  *  T  R  L  L  G
      -  L  R  H  *  T  F  H  S  C  R  F  M  D  G  E  H  D  Y  W  V
      -   *  D  T  E  L  S  I  H  A  G  L  W  M  V  N  T  I  T  G  S
13261 - CACCCAAAATGTGAATCTTTGTGTCAGACATGGCAGACGCCTTACACCTTTCCAATACCG - 13320
      - H  P  K  C  E  S  L  C  Q  T  W  Q  T  P  Y  T  F  P  I  P
      -  T  Q  N  V  N  L  C  V  R  H  G  R  R  L  T  P  F  Q  Y  R
      -   P  K  M  *  I  F  V  S  D  M  A  D  A  L  H  L  S  N  T  D
13321 - ACATCAACACTGGTTGAGGCGCTTGGGAACTACGTCAGACGCCTACGTAGTTGCAAAAAT - 13380
      - T  S  T  L  V  E  A  L  G  N  Y  V  R  R  L  R  S  C  K  N
      -  H  Q  H  W  L  R  R  L  G  T  T  S  D  A  Y  V  V  A  K  I
      -   I  N  T  G  *  G  A  W  E  L  R  Q  T  P  T  *  L  Q  K  F
13381 - TTGCCCAAACGCCACATTCACGTCGGGCAGAATGTGGCACGCCGTGTCCGTGATCATGAC - 13440
      - L  P  K  R  H  I  H  V  G  Q  N  V  A  R  R  V  R  D  H  D
      -  C  P  N  A  T  F  T  S  G  R  M  W  H  A  V  S  V  I  M  T
      -   A  Q  T  P  H  S  R  R  A  E  C  G  T  P  C  P  *  S  *  L
13441 - TACAGCAGATGTCCCGAAAACTATAAATGTTGCTTTTTCAACGACCAAAACGTTTCAAGG - 13500
      - Y  S  R  C  P  E  N  Y  K  C  C  F  F  N  D  Q  N  V  S  R
      -  T  A  D  V  P  K  T  I  N  V  A  F  S  T  T  K  T  F  Q  G
      -   Q  Q  M  S  R  K  L  *  M  L  L  F  Q  R  P  K  R  F  K  D
```

FIG. 5 Cont'd

```
13501 - ATTTTTGATTAACGACAGCGAAGGTCCTCTTCCTACTCCTTCCGTTAAATAATCTGAGAA - 13560
       - I  F  D  *  R  Q  R  R  S  S  S  Y  S  F  R  *  I  I  *  E
       - F  L  I  N  D  S  E  G  P  L  P  T  P  S  V  K  *  S  E  N
       - F  *  L  T  T  A  K  V  L  F  L  L  L  P  L  N  N  L  R  M
13561 - TGAAACATCAATTCTCCGTATGATACAGATTGATGGTTGTACTTCTCTGATAAATATTGA - 13620
       - *  N  I  N  S  P  Y  D  T  D  *  W  L  Y  F  S  D  K  Y  *
       - E  T  S  I  L  R  M  I  Q  I  D  G  C  T  S  L  I  N  I  E
       - K  H  Q  F  S  V  *  Y  R  L  M  V  V  L  L  *  *  I  L  N
13621 - ACCAATTTCTAACAGGTCGCCAACGACAGGTACTGAAAAAGTTCAAATCTCATCTACCAC - 13680
       - T  N  F  *  Q  V  A  N  D  R  Y  *  K  S  S  N  L  I  Y  H
       - P  I  S  N  R  S  P  T  T  G  T  E  K  V  Q  I  S  S  T  T
       - Q  F  L  T  G  R  Q  R  Q  V  L  K  K  F  K  S  H  L  P  L
13681 - TGTACCATGGTGTATATAGTGCAGTCGCAGATTGATTTATGTGTTACCGACTAAATCAGA - 13740
       - C  T  M  V  Y  I  V  Q  S  Q  I  D  L  C  V  T  D  *  I  R
       - V  P  W  C  I  *  C  S  R  R  L  I  Y  V  L  P  T  K  S  D
       - Y  H  G  V  Y  S  A  V  A  D  *  F  M  C  Y  R  L  N  Q  I
13741 - TACGAGATGCAGTAAAACTACTCCCATTAACACTATGTAATTTTCTTTATGAGCAGTGTA - 13800
       - Y  E  M  Q  *  N  Y  S  H  *  H  Y  V  I  F  F  M  S  S  V
       - T  R  C  S  K  T  T  P  I  N  T  M  *  F  S  L  *  A  V  Y
       - R  D  A  V  K  L  L  P  L  T  L  C  N  F  L  Y  E  Q  C  M
13801 - TGTTAACGACACTACTACTAATAAAGTTATTCTTCCTAACCATACTGAAGCATCTCTTAG - 13860
       - C  *  R  H  Y  Y  *  *  S  Y  S  S  *  P  Y  *  S  I  S  *
       - V  N  D  T  T  T  N  K  V  I  L  P  N  H  T  E  A  S  L  R
       - L  T  T  L  L  L  I  K  L  F  F  L  T  I  L  K  H  L  L  G
13861 - GACTGTAGAATGCGCATATACGATTGAATCCACTCGCACATGCGGTTAGTAATAATTTCT - 13920
       - D  C  R  M  R  I  Y  D  *  I  H  S  H  M  R  L  V  I  I  S
       - T  V  E  C  A  Y  T  I  E  S  T  R  T  C  G  *  *  *  F  L
       - L  *  N  A  H  I  R  L  N  P  L  A  H  A  V  S  N  N  F  *
13921 - GACATGTTAAGACGCTACGATACGCACTACGTCCGTAACATCCGCATGACTGTAATCTAT - 13980
       - D  M  L  R  R  Y  D  T  H  Y  V  R  N  I  R  M  T  V  I  Y
       - T  C  *  D  A  T  I  R  T  T  S  V  T  S  A  *  L  *  S  I
       - H  V  K  T  L  R  Y  A  L  R  P  *  H  P  H  D  C  N  L  L
13981 - TAGTCCTAGAATTACCCTTGACCATGCTAAAGCCACTAAAGCATGTTCATCGTGGTCCGA - 14040
       - *  S  *  N  Y  P  *  P  C  *  S  H  *  S  M  F  I  V  V  R
       - S  P  R  I  T  L  D  H  A  K  A  T  K  A  C  S  S  W  S  D
       - V  L  E  L  P  L  T  M  L  K  P  L  K  H  V  H  R  G  P  T
14041 - CGCCTCAAGGATAACACCTAAGTATAATGAGTAACGACTACGGGTAGGAGTGAAACTGAT - 14100
       - R  L  K  D  N  T  *  V  *  *  V  T  T  T  G  R  S  E  T  D
       - A  S  R  I  T  P  K  Y  N  E  *  R  L  R  V  G  V  K  L  I
       - P  Q  G  *  H  L  S  I  M  S  N  D  Y  G  *  E  *  N  *  S
14101 - CCCGTAACCGACGACTCAGGGTATACCTACGACTAGAGCGTTTTGGTGAATAATTCACCC - 14160
       - P  V  T  D  D  S  G  Y  T  Y  D  *  S  V  L  V  N  N  S  P
       - P  *  P  T  T  Q  G  I  P  T  T  R  A  F  W  *  I  I  H  P
       - R  N  R  R  L  R  V  Y  L  R  L  E  R  F  G  E  *  F  T  L
14161 - TAAACGACTTTATACTAAAATGCCTTCTCTCTGAAACAGAGAAGCTGGCAATAAAATTTA - 14220
       - *  T  T  L  Y  *  N  A  F  S  L  K  Q  R  S  W  Q  *  N  L
       - K  R  L  Y  T  K  M  P  S  L  *  N  R  E  A  G  N  K  I  Y
       - N  D  F  I  L  K  C  L  L  S  E  T  E  K  L  A  I  K  F  I
14221 - TAACCCTGGTCTGTATGGTAGGGTTAACATAATTGACAAACCTACTATCCACATAGGAAG - 14280
       - *  P  W  S  V  W  *  G  *  H  N  *  Q  T  Y  Y  P  H  R  K
       - N  P  G  L  Y  G  R  V  N  I  I  D  K  P  T  I  H  I  G  S
       - T  L  V  C  M  V  G  L  T  *  L  T  N  L  L  S  T  *  E  V
14281 - TAACACGTTTGAAATTACACAATAAAAGATGACACAAAGGTGGATGTTCAAAACCTGGTG - 14340
       - *  H  V  *  N  Y  T  I  K  D  D  T  K  V  D  V  Q  N  L  V
       - N  T  F  E  I  T  Q  *  K  M  T  Q  R  W  M  F  K  T  W  *
       - T  R  L  K  L  H  N  K  R  *  H  K  G  G  C  S  K  P  G  D
14341 - ATCATTCTTTTTATAAACATCTACCACAAGGAAAACAACAAAGTTGACCTATGGTAAAAG - 14400
       - I  I  L  F  I  N  I  Y  H  K  E  N  N  K  V  D  L  W  *  K
       - S  F  F  L  *  T  S  T  T  R  K  T  T  K  L  T  Y  G  K  S
       - H  S  F  Y  K  H  L  P  Q  G  K  Q  Q  S  *  P  M  V  K  A
```

FIG. 5 Cont'd

```
14401 - CACTCAATCCTCAGCATGTATTAGTCCTACATTTGAATGTATCGAGCGCAGAGTCAAAGT - 14460
       - H  S  I  L  S  M  Y  *  S  Y  I  *  M  Y  R  A  Q  S  Q  S
       - T  Q  S  S  A  C  I  S  P  T  F  E  C  I  E  R  R  V  K  V
       - L  N  P  Q  H  V  L  V  L  H  L  N  V  S  S  A  E  S  K  F
14461 - TCCTTGAAAATCACATACGACGACTAGGTCGATACGTACGTCGAAGACCGTTAAATAACG - 14520
       - S  L  K  I  T  Y  D  D  *  V  D  T  Y  V  E  D  R  *  I  T
       - P  *  K  S  H  T  T  T  R  S  I  R  T  S  K  T  V  K  *  R
       - L  E  N  H  I  R  R  L  G  R  Y  V  R  R  R  P  L  N  N  D
14521 - ATCTATTTGCGTGATGTACGAAAAGTCATCGACGTGATTGTTTGTTACAACGAAAAGTTT - 14580
       - I  Y  L  R  D  V  R  K  V  I  D  V  I  V  C  Y  N  E  K  F
       - S  I  C  V  M  Y  E  K  S  S  T  *  L  F  V  T  T  K  S  L
       - L  F  A  *  C  T  K  S  H  R  R  D  C  L  L  Q  R  K  V  *
14581 - GACAGTTTGGGCCATTAAAATTATTTCTGAAAATACTGAAACGACACAGATTTCCAAAGA - 14640
       - D  S  L  G  H  *  N  Y  F  *  K  Y  *  N  D  T  D  F  Q  R
       - T  V  W  A  I  K  I  I  S  E  N  T  E  T  T  Q  I  S  K  E
       - Q  F  G  P  L  K  L  F  L  K  I  L  K  R  H  R  F  P  K  K
14641 - AATTCCTTCCTTCAAGACAACTTGATTTTGTGAAGAAGAAACGAGTCCTACCGTTGCGAC - 14700
       - N  S  F  L  Q  D  N  L  I  L  *  R  R  N  E  S  Y  R  C  D
       - I  P  S  F  K  T  T  *  F  C  E  E  E  T  S  P  T  V  A  T
       - F  L  P  S  R  Q  L  D  F  V  K  K  K  R  V  L  P  L  R  R
14701 - GATAGTCACTAATACTGATAATAGCAATATTAGACGGTTGTTACACACTATAGTCTGTTG - 14760
       - D  S  H  *  Y  *  *  *  Q  Y  *  T  V  V  T  H  Y  S  L  L
       - I  V  T  N  T  D  N  S  N  I  R  R  L  L  H  T  I  V  C  *
       - *  S  L  I  L  I  I  A  I  L  D  G  C  Y  T  L  *  S  V  E
14761 - AGGATAAGCATCAACTTCAACAACTATTTATGAAACTAACAATGCTACCACCGACATAAT - 14820
       - R  I  S  I  N  F  N  N  Y  L  *  N  *  Q  C  Y  H  R  H  N
       - G  *  A  S  T  S  T  T  I  Y  E  T  N  N  A  T  T  D  I  I
       - D  K  H  Q  L  Q  Q  L  F  M  K  L  T  M  L  P  P  T  *  L
14821 - TACGGTTGGTTCATTAGCAATTGTTAGACCTATTTAGTCGACCAAAGGGTAAATTATTTA - 14880
       - Y  G  W  F  I  S  N  C  *  T  Y  L  V  D  Q  R  V  N  Y  L
       - T  V  G  S  L  A  I  V  R  P  I  *  S  T  K  G  *  I  I  Y
       - R  L  V  H  *  Q  L  L  D  L  F  S  R  P  K  G  K  L  F  T
14881 - CCCCATTCCGATCTGAAATAATACTGAGTTACTCAATACTCCTAGTTCTACGTGAAAAGC - 14940
       - P  H  S  D  L  K  *  Y  *  V  T  Q  Y  S  *  F  Y  V  K  S
       - P  I  P  I  *  N  N  T  E  L  L  N  T  P  S  S  T  *  K  A
       - P  F  R  S  E  I  I  L  S  Y  S  I  L  L  V  L  R  E  K  R
14941 - GCATATGATTCGCATTACAGTAGGGATGATATTGAGTTTACTTAGAATTCATACGGTAAT - 15000
       - A  Y  D  S  H  Y  S  R  D  D  I  E  F  T  *  N  S  Y  G  N
       - H  M  I  R  I  T  V  G  M  I  L  S  L  L  R  I  H  T  V  I
       - I  *  F  A  L  Q  *  G  *  Y  *  V  Y  L  E  F  I  R  *  S
15001 - CACGTTTCTTATCTCGAGCGTGGCATCGACCACAGAGATAGACATCATGATACTGTTTAT - 15060
       - H  V  S  Y  L  E  R  G  I  D  H  R  D  R  H  H  D  T  V  Y
       - T  F  L  I  S  S  V  A  S  T  T  E  I  D  I  M  I  L  F  I
       - R  F  L  S  R  A  W  H  R  P  Q  R  *  T  S  *  Y  C  L  S
15061 - CTGTCAAAGTAGTCTTTAATAACTTCAGTTATCGGCGGTGATCTCCTCGATGACACCATT - 15120
       - L  S  K  *  S  L  I  T  S  V  I  G  G  D  L  L  D  D  T  I
       - C  Q  S  S  L  *  *  L  Q  L  S  A  V  I  S  S  M  T  P  L
       - V  K  V  V  F  N  N  F  S  Y  R  R  *  S  P  R  *  H  H  *
15121 - AACCTTGTTCGTTCAAAATGCCACCGACCGTATTATACAATTTTTGACAAATGTCACTAC - 15180
       - N  L  V  R  S  K  C  H  R  P  Y  Y  T  I  F  D  K  C  H  Y
       - T  L  F  V  Q  N  A  T  D  R  I  I  Q  F  L  T  N  V  T  T
       - P  C  S  F  K  M  P  P  T  V  L  Y  N  F  *  Q  M  S  L  H
15181 - ATCTTTGAGGTGTGGAATACCCAACCCTAATAGGTTTTACACTGTCTCGGTACGGATTGT - 15240
       - I  F  E  V  W  N  T  Q  P  *  *  V  L  H  C  L  G  T  D  C
       - S  L  R  C  G  I  P  N  P  N  R  F  Y  T  V  S  V  R  I  V
       - L  *  G  V  E  Y  P  T  L  I  G  F  T  L  S  R  Y  G  L  Y
15241 - ACGAATCCTATTACCGGAGAGAACAAGAACGAGCGTTTGTATTGTGAACGACATTGAATA - 15300
       - T  N  P  I  T  G  E  N  K  N  E  R  L  Y  C  E  R  H  *  I
       - R  I  L  L  P  E  R  T  R  T  S  V  C  I  V  N  D  I  E  *
       - E  S  Y  Y  R  R  E  Q  E  R  A  F  V  L  *  T  T  L  N  S
```

FIG. 5 Cont'd

```
15301 - GTGTGGCAAAGATGTCCAATCGATTGCTCACACGCGTTCATAATTCACTCTACCAGTACA - 15360
       - V  W  Q  R  C  P  I  D  C  S  H  A  F  I  I  H  S  T  S  T
       -  C  G  K  D  V  Q  S  I  A  H  T  R  S  *  F  T  L  P  V  H
       -   V  A  K  M  S  N  R  L  L  T  R  V  H  N  S  L  Y  Q  Y  T
15361 - CACCGCCGAGTGATATACAATTTGGTCCACCTTGTAGTAGGCCACTACGATGTTGACGAA - 15420
       - H  R  R  V  I  Y  N  L  V  H  L  V  V  G  H  Y  D  V  D  E
       -  T  A  E  *  Y  T  I  W  S  T  L  *  *  A  T  T  M  L  T  N
       -   P  P  S  D  I  Q  F  G  P  P  C  S  R  P  L  R  C  *  R  I
15421 - TACGATTATCACAGAAATTGTAAACAGTTCGACAATGTCGGTTACATTTACGTGAAGAAA - 15480
       - Y  D  Y  H  R  N  C  K  Q  F  D  N  V  G  Y  I  Y  V  K  K
       -  T  I  I  T  E  I  V  N  S  S  T  M  S  V  T  F  T  *  R  K
       -   R  L  S  Q  K  L  *  T  V  R  Q  C  R  L  H  L  R  E  E  S
15481 - GTTGACTACCATTATTCTATCGACTGTTCATACAGGCGTTAGATGTTGTGTCCGAGATAC - 15540
       - V  D  Y  H  Y  S  I  D  C  S  Y  R  R  *  M  L  C  P  R  Y
       -  L  T  T  I  I  L  S  T  V  H  T  G  V  R  C  C  V  R  D  T
       -   *  L  P  L  F  Y  R  L  F  I  Q  A  L  D  V  V  S  E  I  L
15541 - TCACAGAGATATCTTTATCCCTACAACTAGTACTTAAGCACCTACTCAAAATGCGAATGG - 15600
       - S  Q  R  Y  L  Y  P  Y  N  *  Y  L  S  T  Y  S  K  C  E  W
       -  H  R  D  I  F  I  P  T  T  S  T  *  A  P  T  Q  N  A  N  G
       -   T  E  I  S  L  S  L  Q  L  V  L  K  H  L  L  K  M  R  M  D
15601 - ACGCATTTGTAAAGAGGTACTACTAAGAAAGACTACTACGGCAACACACGATATTGTCAT - 15660
       - T  H  L  *  R  G  T  T  K  K  D  Y  Y  G  N  T  R  Y  C  H
       -  R  I  C  K  E  V  L  L  R  K  T  T  T  A  T  H  D  I  V  I
       -   A  F  V  K  R  Y  Y  *  E  R  L  L  R  Q  H  T  I  L  S  L
15661 - TGATACGCCGAGTTCCAAATCATCGATCGTAATTCTTGAAATTCCGTCAAGAAATAATAG - 15720
       - *  Y  A  E  F  Q  I  I  D  R  N  S  *  N  S  V  K  K  *  *
       -  D  T  P  S  S  K  S  S  I  V  I  L  E  I  P  S  R  N  N  S
       -   I  R  R  V  P  N  H  R  S  *  F  L  K  F  R  Q  E  I  I  V
15721 - TTTTATTACACAAGTACAGACTCCGTTTTACAACCTGACTCTGACTGGAATGATTTCCTG - 15780
       - F  Y  Y  T  S  T  D  S  V  L  Q  P  D  S  D  W  N  D  F  L
       -  F  I  T  Q  V  Q  T  P  F  Y  N  L  T  L  T  G  M  I  S  W
       -   L  L  H  K  Y  R  L  R  F  T  T  *  L  *  L  E  *  F  P  G
15781 - GAGTGCTTAAAACGAGTGTCGTATGTTACGATCAATTTGTTCCTCTACTAATGCACATGG - 15840
       - E  C  L  K  R  V  S  Y  V  T  I  N  L  F  L  Y  *  C  T  W
       -  S  A  *  N  E  C  R  M  L  R  S  I  C  S  S  T  N  A  H  G
       -   V  L  K  T  S  V  V  C  Y  D  Q  F  V  P  L  L  M  H  M  D
15841 - ACGGAATGGGTCTAGGTAGTTCTTATAATCCGCGTCCGACAAAACAGCTACTATAACAGT - 15900
       - T  E  W  V  *  V  V  L  I  I  R  V  R  Q  N  S  Y  Y  N  S
       -  R  N  G  S  R  *  F  L  *  S  A  S  D  K  T  A  T  I  T  V
       -   G  M  G  L  G  S  S  Y  N  P  R  P  T  K  Q  L  L  *  Q  F
15901 - TTTGTCTACCATGTGAATACTAACTTTCCAAGCACAGTGACCGATAACTACGAATGGGTG - 15960
       - F  V  Y  H  V  N  T  N  F  P  S  T  V  T  D  N  Y  E  W  V
       -  L  S  T  M  *  I  L  T  F  Q  A  Q  *  P  I  T  T  N  G  *
       -   C  L  P  C  E  Y  *  L  S  K  H  S  D  R  *  L  R  M  G  E
15961 - AATGTTTTGTAGGATTAGTCCTCATACGACTACAGAAAGTGAACATAAATGTTATGTAAT - 16020
       - N  V  L  *  D  *  S  S  Y  D  Y  R  K  *  T  *  M  L  C  N
       -  M  F  C  R  I  S  P  H  T  T  T  E  S  E  H  K  C  Y  V  I
       -   C  F  V  G  L  V  L  I  R  L  Q  K  V  N  I  N  V  M  *  S
16021 - CTTTCAATGTACTACTCGAATGACCGGTGTACAACCTGTACATAAGGCATTACGATTGAT - 16080
       - L  S  M  Y  Y  S  N  D  R  C  T  T  C  T  *  G  I  T  I  D
       -  F  Q  C  T  T  R  M  T  G  V  Q  P  V  H  K  A  L  R  L  I
       -   F  N  V  L  L  E  *  P  V  Y  N  L  Y  I  R  H  Y  D  *  L
16081 - TACTATTGTGGAGTGCCATGACCCTTGGACTCAAAATACTCCGATACATGTGTGGTGTAT - 16140
       - Y  Y  C  G  V  P  *  P  L  D  S  K  Y  S  D  T  C  V  V  Y
       -  T  I  V  E  C  H  D  P  W  T  Q  N  T  P  I  H  V  W  C  M
       -   L  L  W  S  A  M  T  L  G  L  K  I  L  R  Y  M  C  G  V  C
16141 - GTCAGAACGTCCGACATCCACGAACACATAACACGTTAAGTGTCTGAAGTGAAGCAACGC - 16200
       - V  R  T  S  D  I  H  E  H  I  T  R  *  V  S  E  V  K  Q  R
       -  S  E  R  P  T  S  T  N  T  *  H  V  K  C  L  K  *  S  N  A
       -   Q  N  V  R  H  P  R  T  H  N  T  L  S  V  *  S  E  A  T  P
```

FIG. 5 Cont'd

```
16201 - CACGGACATAATCCTCTGGTAAGGATACAACGTTCACGACGATACTGGTACAGTAAAGTT - 16260
       - H G H N P L V R I Q R R R Y W Y S K V
       - T D I I L W * G Y N V H D D T G V K L
       - R T * S S G K D T T F T T I L V Q * S C
16261 - GTAGTGTGTTTAATCACAACAGACAATTAGGGATACAAACGTTACGGGGTCCAACACTAC - 16320
       - V V C L I T T D N * G Y K R Y G V Q H Y
       - * C V * S Q Q T I R D T N V T G S N T T
       - S V F N H N R Q L G I Q T L R G P T L Q
16321 - AGTGACTACACTGTGTTGACATAGATCCTCCATACTCGATAATAACGTTCAGTGTATTCG - 16380
       - S D Y T V L T * I L H T R * * R S V Y S
       - V T T L C * H R S S I L D N N V Q C I R
       - * L H C V D I D P P Y S I I T F S V F G
16381 - GAGGGTAATCAAAAGGTAATACACGATTACCAGTCCAAAAACCAAATATGTTTTGTGTA - 16440
       - E G N Q K V I H D Y Q S K N Q I C F C V
       - R V I K R * Y T I T S P K T K Y V F V Y
       - G * S K G N T R L P V Q K P N M F L C T
16441 - CACATCCGTCACTGTTACAGTGACTGAAGTTACGCTATCGTTGTACACTAACCTGATTAC - 16500
       - H I R H C Y S D * S Y A I V V H * P D Y
       - T S V T V T V T E V T L S L Y T N L I T
       - H P S L L Q * L K L R Y R C T L T * L R
16501 - GACCGCTAATGTATGAACGGTTGTGAACATGACTCTCTGAGTTCGAAAAGCGTCGTCTTT - 16560
       - D R * C M N G C E H D S L S S K S V V F
       - T A N V * T V V N M T L * V R K A S S L
       - P L M Y E R L * T * L S E F E K R R L C
16561 - GCGAGTTTCGGTGACTCCTTTGTAAATTCGACAGTATACCATAACGGTGACATGCGCTTC - 16620
       - A S F G D S F V N S T V Y H N G D M R F
       - R V S V T P L * I R Q Y T I T V T C A S
       - E F R * L L C K F D S I P * R * H A L H
16621 - ATGAGAGACTGTCTCTTAACGTAGAAAGTACCCTCCAACCTTTTGGATCTGGTGGTAACT - 16680
       - M R D C L L T * K V P S N L L D L V V T
       - * E T V S * R R K Y P P T F W I W W * L
       - E R L S L N V E S T L Q P F G S G G N L
16681 - TGTCTTTGATACAGAAATGACCAATGGCACATTGATTTTTATCATTTCATGTCTAACCTC - 16740
       - C L * Y R N D Q W H I D F Y H F M S N L
       - V F D T E M T N G T L I F I I S C L T S
       - S L I Q K * P M A H * F L S F H V * P L
16741 - TCATGTGGAAACTTTTTCCACTGATACCACTACGACAACACATGTCTCCATGATGCTGTA - 16800
       - S C G N F F H * Y H Y D N T C L H D A V
       - H V E T F S T D T T T T H V S M M L Y
       - M W K L F P L I P L R Q H M S P * C C M
16801 - TGTTCAACTTACAACCACTAATGAAACACAACTGTAGAGTGTGACATTACGGTGAATCAC - 16860
       - C S T Y N H * * N T T V E C D I T V N H
       - V Q L T T T N E T Q L * S V T L R * I T
       - F N L Q P L M K H N C R V * H Y G E S R
16861 - GTGGATGAGATCACGGTGTTCTCGTGATACACTCTTAATGACCGAACATGGGTTGTGAGT - 16920
       - V D E I T V F S * Y T L N D R T W V V S
       - W M R S R C S R D T L L M T E H G L * V
       - G * D H G V L V I H S * * P N M G C E L
16921 - TGTAGAGTCTACTCAAAAGATCGTTACAACGTTTAATAGTTTTCCAGCCGTACGTTTTCA - 16980
       - C R V Y S K D R Y N V * * F S S R T F S
       - V E S T Q K I V T T F N S F P A V R F H
       - * S L L K R S L Q R L I V F Q P Y V F M
16981 - TGAGATGTGAGGTTCCTGGTGGACCATGACCATTCTCAGTAAAACGGTAGCCTGAACGAG - 17040
       - * D V R F L V D H D H S Q * N G S L N E
       - E M * G S W W T M T I L S K T V A * T R
       - R C E V P G G P * P F S V K R * P E R E
17041 - AGATAATGGGTAGACGAGCGTATCACATATGCCGTACGAGAGTACGTCGACAACTACGGG - 17100
       - R * W V D E R I T Y A V R E Y V D N Y G
       - D N G * T S V S H M P Y E S T S T T T G
       - I M G R R A Y H I C R T R V R R Q L R D
```

FIG. 5 Cont'd

```
17101 - ATACACTTTTCCGTAATTTTATAAACGGGTATCTATTTACATCATCTTAGTATGGACGCG - 17160
      - I  H  F  S  V  I  L  *  T  G  I  Y  L  H  H  L  S  M  D  A
      -  Y  T  F  P  *  F  Y  K  R  V  S  I  Y  I  I  L  V  W  T  R
      -   T  L  F  R  N  F  I  N  G  Y  L  F  T  S  S  *  Y  G  R  A
17161 - CACGCGCGCATCTCACAAAACTATTTAAGTTTCACTTAAGTTGTGATCTTGTCATACAAA - 17220
      - H  A  R  I  S  Q  N  Y  L  S  F  T  *  V  V  I  L  S  Y  K
      -  T  R  A  S  H  K  T  I  *  V  S  L  K  L  *  S  C  H  T  K
      -   R  A  H  L  T  K  L  F  K  F  H  L  S  C  D  L  V  I  Q  K
17221 - AGACGTGACATTTACGTAACGGTCTTTGTTGACGACTGTAACATCAGAAACTACTTTAGA - 17280
      - R  R  D  I  Y  V  T  V  F  V  D  D  C  N  I  R  N  Y  F  R
      -  D  V  T  F  T  *  R  S  L  L  T  T  V  T  S  E  T  T  L  E
      -   T  *  H  L  R  N  G  L  C  *  R  L  *  H  Q  K  L  L  *  R
17281 - GATACCGATGATTAATACTGAACTCACAACAGTTACGATCTGAAGCACGTTTTGTGATGC - 17340
      - D  T  D  D  *  Y  *  T  H  N  S  Y  D  L  K  H  V  L  *  C
      -  I  P  M  I  N  T  E  L  T  T  V  T  I  *  S  T  F  C  D  A
      -   Y  R  *  L  I  L  N  S  Q  Q  L  R  S  E  A  R  F  V  M  Q
17341 - AGATATAACCGCTAGGACGAGTTAATGGTCGGGGGGCGTGTAACGACTGATTTCCGTGTG - 17400
      - R  Y  N  R  *  D  E  L  M  V  G  G  R  V  T  T  D  F  R  V
      -  D  I  T  A  R  T  S  *  W  S  G  G  V  *  R  L  I  S  V  *
      -   I  *  P  L  G  R  V  N  G  R  G  A  C  N  D  *  F  P  C  D
17401 - ATCTTGGTCTTATAAAATTAAGTCACACGTCTGAATACTTTTGTTATCCAGGTCTGTACA - 17460
      - I  L  V  L  *  N  *  V  T  R  L  N  T  F  V  I  Q  V  C  T
      -  S  W  S  Y  K  I  K  S  H  V  *  I  L  L  L  S  R  S  V  Q
      -   L  G  L  I  K  L  S  H  T  S  E  Y  F  C  Y  P  G  L  Y  K
17461 - AGGAACCTTGAACAGCGGCAACAGGACGACTTTAACAACTGTGACACTCACGAAATCAAA - 17520
      - R  N  L  E  Q  R  Q  Q  D  D  F  N  N  C  D  T  H  E  I  K
      -  G  T  L  N  S  G  N  R  T  T  L  T  T  V  T  L  T  K  S  N
      -   E  P  *  T  A  A  T  G  R  L  *  Q  L  *  H  S  R  N  Q  I
17521 - TACTGTTATTCGATTTTCGTGTGTTCCTCTTCAGTCGAGTTACGAAGTTTTACAAGATGT - 17580
      - Y  C  Y  S  I  F  V  C  S  S  S  V  E  L  R  S  F  T  R  C
      -  T  V  I  R  F  S  C  V  P  L  Q  S  S  Y  E  V  L  Q  D  V
      -   L  L  F  D  F  R  V  F  L  F  S  R  V  T  K  F  Y  K  M  F
17581 - TTCCACAATAATGTGTACTACAAAGTAGACGTTAGTTGTCTGGAGTTTATCCGCAACATT - 17640
      - F  H  N  N  V  Y  Y  K  V  D  V  S  C  L  E  F  I  R  N  I
      -  S  T  I  M  C  T  T  K  *  T  L  V  V  W  S  L  S  A  T  F
      -   P  Q  *  C  V  L  Q  S  R  R  *  L  S  G  V  Y  P  Q  H  S
17641 - CTCTTAAAGAATGTGCGTTAGGACGAACCTCTTTTCGACAAAAATAGAGTGGAATATTAA - 17700
      - L  L  K  N  V  R  *  D  E  P  L  F  D  K  N  R  V  E  Y  *
      -  S  *  R  M  C  V  R  T  N  L  F  S  T  K  I  E  W  N  I  K
      -   L  K  E  C  A  L  G  R  T  S  F  R  Q  K  *  S  G  I  L  S
17701 - GTGTCTTGCGACATCGAAGTTTTTAGAATCCTAACGGATGCGTCTGACAACTAAGTAGTG - 17760
      - V  S  C  D  I  E  V  F  R  I  L  T  D  A  S  D  N  *  V  V
      -  C  L  A  T  S  K  F  L  E  S  *  R  M  R  L  T  T  K  *  C
      -   V  L  R  H  R  S  F  *  N  P  N  G  C  V  *  Q  L  S  S  V
17761 - TCCCAAGACTTATACTGATACAGTATAAGTGTGTTTGATGACTTTGTCGTGTGAGAACAT - 17820
      - S  Q  D  L  Y  *  Y  S  I  S  V  F  D  D  F  V  V  *  E  H
      -  P  K  T  Y  T  D  T  V  *  V  C  L  M  T  L  S  C  E  N  I
      -   P  R  L  I  L  I  Q  Y  K  C  V  *  *  L  C  R  V  R  T  L
17821 - TACAGTTGGCAAAGTTACACCGATAGTGTTCCCGTTTTTAACCGTAAAACACGTATTACA - 17880
      - Y  S  W  Q  S  Y  T  D  S  V  P  V  F  N  R  K  T  R  I  T
      -  T  V  G  K  V  T  P  I  V  F  P  F  L  T  V  K  H  V  L  Q
      -   Q  L  A  K  L  H  R  *  C  S  R  F  *  P  *  N  T  Y  Y  R
17881 - GACTATCTCTAGAAATACTGTTTGACGTTAAATGTTCAGATCTTTATGGTGCAGCGTTAC - 17940
      - D  Y  L  *  K  Y  C  L  T  L  N  V  Q  I  F  M  V  Q  R  Y
      -  T  I  S  R  N  T  V  *  R  *  M  F  R  S  L  W  C  S  V  T
      -   L  S  L  E  I  L  F  D  V  K  C  S  D  L  Y  G  A  A  L  H
17941 - ACCGATGTAATGTTCGTCTTTTACATTGACCTGAAAAATTCCTGACATCATTCTAGTAAT - 18000
      - T  D  V  M  F  V  F  Y  I  D  L  K  N  S  *  H  H  S  S  N
      -  P  M  *  C  S  S  F  T  L  T  *  K  I  P  D  I  I  L  V  M
      -   R  C  N  V  R  L  L  H  *  P  E  K  F  L  T  S  F  *  *  *
```

FIG. 5 Cont'd

```
18001 - GACCAGAAGTAGGATGTGTCCGTGGATGTGTGGAGTCGCAACTATATTTCAAGTTCTGAC - 18060
       - D  Q  K  *  D  V  S  V  D  V  W  S  R  N  Y  I  S  S  S  D
       -  T  R  S  R  M  C  P  W  M  C  G  V  A  T  I  F  Q  V  L  T
       -   P  E  V  G  C  V  R  G  C  V  E  S  Q  L  Y  F  K  F  *  L
18061 - TTCCTAATACACAACTGTATGGTCCGTATGGTTTCCTGTACTGGATGGCATCTGAGTAGA - 18120
       - F  L  I  H  N  C  M  V  R  M  V  S  C  T  G  W  H  L  S  R
       -  S  *  Y  T  T  V  W  S  V  W  F  P  V  L  D  G  I  *  V  E
       -   P  N  T  Q  L  Y  G  P  Y  G  F  L  Y  W  M  A  S  E  *  R
18121 - GATACTACCCAAAGTTTTACTTAATGGTTCAGTTACCAATGGGATTATACAAATAGTGGG - 18180
       - D  T  T  Q  S  F  T  *  W  F  S  Y  Q  W  D  Y  T  N  S  G
       -  I  L  P  K  V  L  L  N  G  S  V  T  N  G  I  I  Q  I  V  G
       -   Y  Y  P  K  F  Y  L  M  V  Q  L  P  M  G  L  Y  K  *  W  A
18181 - CGCTTCTTCGATAAGCAGTGCAAGCACGCACCTAACCGAAACTACATCTCCCGACAGTAC - 18240
       - R  F  F  D  K  Q  C  K  H  A  P  N  R  N  Y  I  S  R  Q  Y
       -  A  S  S  I  S  S  A  S  T  H  L  T  E  T  T  S  P  D  S  T
       -   L  L  R  *  A  V  Q  A  R  T  *  P  K  L  H  L  P  T  V  R
18241 - GTTGATCTCTACGACACCCATGATTGGATGGAGAGGTCGATCCTAAAAGATGTCCACAAT - 18300
       - V  D  L  Y  D  T  H  D  W  M  E  R  S  I  L  K  D  V  H  N
       -  L  I  S  T  T  P  M  I  G  W  R  G  R  S  *  K  M  S  T  I
       -   *  S  L  R  H  P  *  L  D  G  E  V  D  P  K  R  C  P  Q  L
18301 - TGAATCATCGACATGGCTGACCAATACAACTGTGACTTTTATTGTGTCTTAAGTGGTCTC - 18360
       - *  I  I  D  M  A  D  Q  Y  N  C  D  F  Y  C  V  L  S  G  L
       -  E  S  S  T  W  L  T  N  T  T  V  T  F  I  V  S  *  V  V  S
       -   N  H  R  H  G  *  P  I  Q  L  *  L  L  L  C  L  K  W  S  Q
18361 - AATTACGTTTTGGAGGTGGTCCACTGGTCAAATTTGTAGAATATGGTGAGTACATATTTC - 18420
       - N  Y  V  L  E  V  V  H  W  S  N  L  *  N  M  V  S  T  Y  F
       -  I  T  F  W  R  W  S  T  G  Q  I  C  R  I  W  *  V  H  I  S
       -   L  R  F  G  G  G  P  L  V  K  F  V  E  Y  G  E  Y  I  F  P
18421 - CGAACGGGACCTTACATCACGCATAATTCTATCATGTTTACGAGTCACTATGTGACTTTC - 18480
       - R  T  G  P  Y  I  T  H  N  S  I  M  F  T  S  H  Y  V  T  F
       -  E  R  D  L  T  S  R  I  I  L  S  C  L  R  V  T  M  *  L  S
       -   N  G  T  L  H  H  A  *  F  Y  H  V  Y  E  S  L  C  D  F  P
18481 - CTAACAGTCTGTCTCAGCACAAGCAGGAAACCCGCGTACCGAAACTCGAATGTAGTTACT - 18540
       - L  T  V  C  L  S  T  S  R  K  P  A  Y  R  N  S  N  V  V  T
       -  *  Q  S  V  S  A  Q  A  G  N  P  R  T  E  T  R  M  *  L  L
       -   N  S  L  S  Q  H  K  Q  E  T  R  V  P  K  L  E  C  S  Y  F
18541 - TCATGAAACAGTTCTAACCTGGACTTTCTTGCACAACAGACACACTGTTTGCACGTTGAA - 18600
       - S  *  N  S  S  N  L  D  F  L  A  Q  Q  T  H  C  L  H  V  E
       -  H  E  T  V  L  T  W  T  F  L  H  N  R  H  T  V  C  T  L  N
       -   M  K  Q  F  *  P  G  L  S  C  T  T  D  T  L  F  A  R  *  T
18601 - CGAAAAGATGAAGTAGTCTATGAATACGGACGACCTTAGTAAGACACCCAAAACTGATAC - 18660
       - R  K  D  E  V  V  Y  E  Y  G  R  P  *  *  D  T  Q  N  *  Y
       -  E  K  M  K  *  S  M  N  T  D  D  L  S  K  T  P  K  T  D  T
       -   K  R  *  S  S  L  *  I  R  T  T  L  V  R  H  P  K  L  I  Q
18661 - AGATATTGGGTAAATACTAACTACAAGTCGTCACCCCGAAATGCCCATTGGAAGTCTCAT - 18720
       - R  Y  W  V  N  T  N  Y  K  S  S  P  R  N  A  H  W  K  S  H
       -  D  I  G  *  I  L  T  T  S  R  H  P  E  M  P  I  G  S  L  I
       -   I  L  G  K  Y  *  L  Q  V  V  T  P  K  C  P  L  E  V  S  L
18721 - TGGTACTGGTTGTAACGGTCCATGTACCTTTACGTGTACACCGATCAACACTACGATAGT - 18780
       - W  Y  W  L  *  R  S  M  Y  L  Y  V  Y  T  D  Q  H  Y  D  S
       -  G  T  G  C  N  G  P  C  T  F  T  C  T  P  I  N  T  T  I  V
       -   V  L  V  V  T  V  H  V  P  L  R  V  H  R  S  T  L  R  *  Y
18781 - ACTGATCTACAAATCGTCAGGTACTCACGAAACAATTCGCGCAACTAACCAGACAACTTA - 18840
       - T  D  L  Q  I  V  R  Y  S  R  N  N  S  R  N  *  P  D  N  L
       -  L  I  Y  K  S  S  G  T  H  E  T  I  R  A  T  N  Q  T  T  Y
       -   *  S  T  N  R  Q  V  L  T  K  Q  F  A  Q  L  T  R  Q  L  M
18841 - TGGGATAATATCCTCTACTTGACTCCCAATTAAGACGAACGTCTTTTCATGTTGTGTACC - 18900
       - W  D  N  I  L  Y  L  T  P  N  *  D  E  R  L  F  M  L  C  T
       -  G  I  I  S  S  T  *  L  P  I  K  T  N  V  F  S  C  C  V  P
       -   G  *  Y  P  L  L  D  S  Q  L  R  R  T  S  F  H  V  V  Y  Q
```

FIG. 5 Cont'd

```
18901 - AACACTTCAGACGTAACGAACGACTATTCAAAGGTCAAGAAGTACTGTAACCTTTAGGTT - 18960
      - N T S D V T N D Y S K V K K Y C N L * V
      -  T L Q T * R T T I Q R S R S T V T F R F
      -   H F R R N E R L F K G Q E V L * P L G F
18961 - TCCGATAGTTCACACACGGAGTCCGACTTCATCTTACCTTCAAGATGCTACGAGTCGGTA - 19020
      - S D S S H T E S D F I L P S R C Y E S V
      -  P I V H T R S P T S S Y L Q D A T S R Y
      -   R * F T H G V R L H L T F K M L R V G T
19021 - CATCACTGTTTCGAATGTTTTATCTCCTCGAAGAAGATAAGAATACGATGTGTAGTGCTAT - 19080
      - H H C F E C F I S S R R * E Y D V * C Y
      -  I T V S N V L S P R E D K N T M C S A I
      -   S L F R M F Y L L E K I R I R C V V L F
19081 - TTAAGTGACTACCACAAACAAACAAAACCTTAACATTGCAACTAGCAATGGGTCGGTTAC - 19140
      - L S D Y H K Q T K P * H C N * Q W V G Y
      -  * V T T T N K Q N L N I A T S N G S V T
      -   K * L P Q T N K T L T L Q L A M G R L R
19141 - GTTAACACACATCCAAACTGTGTTCTCAGAACAGTTTGAACTTGAATGGTCCGACACTAC - 19200
      - V N T H P N C V L R T V * T * M V R H Y
      -  L T H I Q T V F S E Q F E L E W S D T T
      -   * H T S K L C S Q N S L N L N G P T L P
19201 - CACCATCAAACATACACTTATTCGTACGTAAGGTGTGAGGTCGAAAGCTATTTTCACGTA - 19260
      - H H Q T Y T Y S Y V R C E V E S Y F H V
      -  T I K H T L I R T * G V R S K A I F T *
      -   P S N I H L F V R K V * G R K L F S R K
19261 - AATGATTAAATTTCGTTAACGGAAAGAAAATGATAAGACTATCAGGAACACTCAGAGTAC - 19320
      - N D * I S L T E R K * * D Y Q E H S E Y
      -  M I K F R * R K E N D K T I R N T Q S T
      -   * L N F V N G K K M I R L S G T L R V P
19321 - CGTTTGTTCATCACAGCCTATAACTAATACAAGGTGAGTTTAGACGATGCACATAATGTG - 19380
      - R L F I T A Y N * Y K V S L D D A H N V
      -  V C S S Q P I T N T R * V * T M H I M C
      -   F V H H S L * L I Q G E F R R C T * C A
19381 - CTACGTTAAATCCACCACGACAAACGTCTGTGGTACGTTTACTCATGGCTGTCATGAACC - 19440
      - L R * I H H D K R L W Y V Y S W L S * T
      -  Y V K S T T T N V C G T F T H G C H E P
      -   T L N P P R Q T S V V R L L M A V M N L
19441 - TACGTATATTATACTACTAAAGACGACCTAAATCGGATACCTAAATGTTTGTTAAACTAT - 19500
      - Y V Y Y T T K D D L N R I P K C L L N Y
      -  T Y I I L L K T T * I G Y L N V C * T M
      -   R I L Y Y * R R P K S D T * M F V K L *
19501 - GAATATTGGACACCTTATGTAAATGGTCCAATGTCTCAAATCTTTTACACCGAATATTAC - 19560
      - E Y W T P Y V N G P M S Q I F Y T E Y Y
      -  N I G H L M * M V Q C L K S F T P N I T
      -   I L D T L C K W S N V S N L L H R I L Q
19561 - AACAATTATTTCCTGTGAAACTACCTGTGCGGCCGCTTCGTGGACAAAGGTAGTAATTAT - 19620
      - N N Y F L * N Y L C G R F V D K G S N Y
      -  T I I S C E T T C A A A S W T K V V I I
      -   Q L F P V K L P V R P L R G Q R * * L L
19621 - TACGACAAATGTGTTTCCATCTACCATAACTACACCTCTAGAAACTTTTATTCTGTTGTG - 19680
      - Y D K C V S I Y H N Y T S R N F Y S V V
      -  T T N V F P S T I T T P L E T F I L L *
      -   R Q M C F H L P * L H L * K L L F C C E
19681 - AAGGACAATTACAACGTAAACTCGAAACCCGATTCGCATTGTAATTTGGTCACGGTCTCT - 19740
      - K D N Y N V N S K P D S H C N L V T V S
      -  R T I T T * T R N P I R I V I W S R S L
      -   G Q L Q R K L E T R F A L * F G H G L *
19741 - AATTCTATGAGTTATTAAACCCACAACTATAGCGACGATTATGACATTAGACCCTGATGT - 19800
      - N S M S Y * T H N Y S D D Y D I R P * C
      -  I L * V I K P T T I A T I M T L D P D V
      -   F Y E L L N P Q L * R R L * H * T L M F
```

FIG. 5 Cont'd

```
19801 - TTTCTCTTCGGGGTCGTGTACATAGATGTTATCCACAGACGTGTTACTGACTGTAACGGT - 19860
      - F  L  F  G  V  V  Y  I  D  V  I  H  R  R  V  T  D  C  N  G
      -  F  S  S  G  S  C  T  *  M  L  S  T  D  V  L  L  T  V  T  V
      -   S  L  R  G  R  V  H  R  C  Y  P  Q  T  C  Y  *  L  *  R  F
19861 - TCTTTGGATGACTCTCACGAACAAGAAGTGAATGACAGAACAAACTACCATCTCACCTTC - 19920
      - S  L  D  D  S  H  E  Q  E  V  N  D  R  T  N  Y  H  L  T  F
      -  L  W  M  T  L  T  N  K  K  *  M  T  E  Q  T  T  I  S  P  S
      -   F  G  *  L  S  R  T  R  S  E  *  Q  N  K  L  P  S  H  L  P
19921 - CTGTCCATCTGGAAAAATCTTTGCGGGCATTACCACAAAATTATTGTCTTCCAAGTCAGT - 19980
      - L  S  I  W  K  N  L  C  G  H  Y  H  K  I  I  V  F  Q  V  S
      -  C  P  S  G  K  I  F  A  G  I  T  T  K  L  L  S  S  K  S  V
      -   V  H  L  E  K  S  L  R  A  L  P  Q  N  Y  C  L  P  S  Q  F
19981 - TTCCAGATTGTGGAAGTTTCCCTGGTCGTGTTCGATCGCAGTTACCTCAGTGTAATTAAC - 20040
      - F  Q  I  V  E  V  S  L  V  V  F  D  R  S  Y  L  S  V  I  N
      -  S  R  L  W  K  F  P  W  S  C  S  I  A  V  T  S  V  *  L  T
      -   P  D  C  G  S  F  P  G  R  V  R  S  Q  L  P  Q  C  N  *  P
20041 - CTCTTAGTCATTTTTGTGTCAAATTGATGAAATTCTTTCATCTGCCGTAATAAGTTGTCA - 20100
      - L  L  V  I  F  V  S  N  *  *  N  S  F  I  C  R  N  K  L  S
      -  S  *  S  F  L  C  Q  I  D  E  I  L  S  S  A  V  I  S  C  Q
      -   L  S  H  F  C  V  K  L  M  K  F  F  H  L  P  *  *  V  V  N
20101 - ACGGACTTTGGATGAAATGAGTCTCGTCTCTGAATCTCCTAAAATTCGGGTCTAGTGTTT - 20160
      - T  D  F  G  *  N  E  S  R  L  *  I  S  *  N  S  G  L  V  F
      -  R  T  L  D  E  M  S  L  V  S  E  S  P  K  I  R  V  *  C  L
      -   G  L  W  M  K  *  V  S  S  L  N  L  L  K  F  G  S  S  V  Y
20161 - ACCTTTGACTGAAAGAGCTCGAGCGATACCTACTTAAGTATGTCGCTATATTCGAGCTCC - 20220
      - T  F  D  *  K  S  S  S  D  T  Y  L  S  M  S  L  Y  S  S  S
      -  P  L  T  E  R  A  R  A  I  P  T  *  V  C  R  Y  I  R  A  P
      -   L  *  L  K  E  L  E  R  Y  L  L  K  Y  V  A  I  F  E  L  P
20221 - CGATACGGAAGCTTGTGTAGCAAATACCTCTAAAGTCAGTACCTGTTGAACCGCCAGAAG - 20280
      - R  Y  G  S  L  C  S  K  Y  L  *  S  Q  Y  L  L  N  R  Q  K
      -  D  T  E  A  C  V  A  N  T  S  K  V  S  T  C  *  T  A  R  S
      -   I  R  K  L  V  *  Q  I  P  L  K  S  V  P  V  E  P  P  E  V
20281 - TAAATTACTATCCGAATCGGTTCGCGAGTGTTCTAAGTGGTGAATTTAATCTCCTAAAAT - 20340
      - *  I  T  I  R  I  G  S  R  V  F  *  V  V  N  L  I  S  *  N
      -  K  L  L  S  E  S  V  R  E  C  S  K  W  *  I  *  S  P  K  I
      -   N  Y  Y  P  N  R  F  A  S  V  L  S  G  E  F  N  L  L  K  *
20341 - AGGGATACCTGTCGTGTCACTTTTTAATGAAGTATTGTCTACGCGTTTGTCCAAGTAGTT - 20400
      - R  D  T  C  R  V  T  F  *  *  S  I  V  Y  A  F  V  Q  V  V
      -  G  I  P  V  V  S  L  F  N  E  V  L  S  T  R  L  S  K  *  F
      -   G  Y  L  S  C  H  F  L  M  K  Y  C  L  R  V  C  P  S  S  F
20401 - TTACACACACAAGACACTAACTAGAAAATGAACTACTGAAACAGCTCTATTATTTCAGTG - 20460
      - L  H  T  Q  D  T  N  *  K  M  N  Y  *  N  S  S  I  I  S  V
      -  Y  T  H  K  T  L  T  R  K  *  T  T  E  T  A  L  L  F  Q  C
      -   T  H  T  R  H  *  L  E  N  E  L  L  K  Q  L  Y  Y  F  S  V
20461 - TTCTAAACAGTCACTAAAGTTTTCACCAGTTCCAATGTTAACTGATACGACTTTAAAGTA - 20520
      - F  *  T  V  T  K  V  F  T  S  S  N  V  N  *  Y  D  F  K  V
      -  S  K  Q  S  L  K  F  S  P  V  P  M  L  T  D  T  T  L  K  *
      -   L  N  S  H  *  S  F  H  Q  F  Q  C  *  L  I  R  L  *  S  K
20521 - AGTACGAAACCACATTCCTACCTGTACAACTTTGGAAGATGGGTTTTGATGTTCGTTCAG - 20580
      - S  T  K  P  H  S  Y  L  Y  N  F  G  R  W  V  L  M  F  V  Q
      -  V  R  N  H  I  P  T  C  T  T  L  E  D  G  F  *  C  S  F  S
      -   Y  E  T  T  F  L  P  V  Q  L  W  K  M  G  F  D  V  R  S  V
20581 - TTCGCACCGTTGGTCCACAACGCTACGGATTGAACATGTTCTACGTTTCTTACGAAGAAC - 20640
      - F  A  P  L  V  H  N  A  T  D  *  T  C  S  T  F  L  T  K  N
      -  S  H  R  W  S  T  T  L  R  I  E  H  V  L  R  F  L  R  R  T
      -   R  T  V  G  P  Q  R  Y  G  L  N  M  F  Y  V  S  Y  E  E  L
20641 - TTTTCACACTGGAAGTCTTAATACCACTTTTACGACAATATGGTTTTCCTTATTACTACT - 20700
      - F  S  H  W  K  S  *  Y  H  F  Y  D  N  M  V  F  L  I  T  T
      -  F  H  T  G  S  L  N  T  T  F  T  T  I  W  F  S  L  L  L  L
      -   F  T  L  E  V  L  I  P  L  L  R  Q  Y  G  F  P  Y  Y  Y  L
```

FIG. 5 Cont'd

```
20701 - TACAGCGTTTCATATGAGTTGACACAGTTATGAATTTATGTGAATGAAATCGACATGGGA - 20760
      - Y S V S Y E L T Q L * I Y V N E I D M G
      - T A F H M S * H S Y E F M * M K S T W D
      - Q R F I * V D T V M N L C E * N R H G M
20761 - TGTTGTACTCTCAATAAGTGAAACCACGACCGAGACTATTTCCTCAACGTGGTCCATGTC - 20820
      - C C T L N K * N H D R D Y F L N V V H V
      - V V L S I S E T T T E T I S S T W S M S
      - L Y S Q * V K P R P R L F P Q R G P C R
20821 - GACACGAGTCTGTTACCAACGGTTGACCGTGTGATGAACAGCTAAGTCTAGAATTACTGA - 20880
      - D T S L L P T V D R V M N S * V * N Y *
      - T R V C Y Q R L T V * * T A K S R I T E
      - H E S V T N G * P C D E Q L S L E L L K
20881 - AGCAGAGGCTGCGTCTAAGATGAAATTAACCTCTGACACGTTGTCATGTATGCCGATTAT - 20940
      - S R G C V * D E I N L * H V V M Y A D Y
      - A E A A S K M K L T S D T L S C M P I I
      - Q R L R L R * N * P L T R C H V C R L F
20941 - TTACCCTGGAATAATAATCGCTATACATACTGGGATCCTGGTTTGTACACTGTTTTCTCT - 21000
      - L P W N N N R Y T Y W D P G L Y T V F S
      - Y P G I I I A I H T G I L V C T L F S L
      - T L E * * S L Y I L G S W F V H C F L L
21001 - TACTGAGATTTCTTCCCAAAAAGTGAATAGACACACCTAAATATTTCGTTTTTGATCGGG - 21060
      - Y * D F F P K S E * T H L N I S F L I G
      - T E I S S Q K V N R H T * I F R F * S G
      - L R F L P K K * I D T P K Y F V F D R D
21061 - ACCCACCAAGATATCGACATTTCTATTGTCTCGTAAGAACCTTACGACTGGAAATGTTCG - 21120
      - T H Q D I D I S I V S * E P Y D W K C S
      - P T K I S T F L L S R K N L T T G N V R
      - P P R Y R H F Y C L V R T L R L E M F E
21121 - AATACCCGGTAAAGAGTACCACCTGTCGAAAACAATGTTTACATTTACGTAGTAGTAGCC - 21180
      - N T R * R V P P V E N N V Y I Y V V V A
      - I P G K E Y H L S K T M F T F T * * * P
      - Y P V K S T T C R K Q C L H L R S S S L
21181 - TTCGTAAAAATTAACCCCGATTGATAGAACCGTTCGGCTTCCTTGTTTAACTACCGATAT - 21240
      - F V K I N P D * * N R S A S L F N Y R Y
      - S * K L T P I D R T V R L P C L T T D M
      - R K N * P R L I E P F G F L V * L P I W
21241 - GGTACGTACGATTGATGTAAAAGACCTCCTTGTGTTTAGGATAGGTCAACAGAAGGATAA - 21300
      - G T Y D * C K R P. C V * D R S T E G *
      - V R T I D V K D L L V F R I G Q Q K D K
      - Y V R L M * K T S L C L G * V N R R I S
21301 - GTGAGAAACTGTACTCGTTTAAAGGAGAATTTAATTCTCCTTGACGACATTACAGAGAAT - 21360
      - V R N C T R L K E N L I L L D D I T E N
      - * E T V L V * R R I * F S L T T L Q R I
      - E K L Y S F K G E F N S P * R H Y R E F
21361 - TCCTCTTAGTTTAGTTACTATACTAAATAAGAGAAGACCTTTTTCCATCCGAATAGTAAT - 21420
      - S S * F S Y Y T K * E K T F F H P N S N
      - P L S L V T I L N K R R P F S I R I V I
      - L L V * L L Y * I R E D L F P S E * * S
21421 - CTCTTTTGTTGTCTCAACACCAAAGTTCACTATAAGAACAATTGTTGATTTGCTTGTACA - 21480
      - L F C C L N T K V H Y K N N C * F A C T
      - S F V V S T P K F T I R T I V D L L V Q
      - L L L S Q H Q S S L * E Q L L I C L Y K
21481 - AATAAAAGAATAATAAAGAATGAGAGTGATCACCATCACTGGAACTGGCCACGTGGTGAA - 21540
      - N K R I I K N E S D H H H W N W P R G E
      - I K E * * R M R V I T I T G T G H V V K
      - * K N N K E * E * S P S L E L A T W * K
21541 - AACTACTACAAGTTCGAGGATTAATGTGAGTTGTATGAAGTAGATACTCCCCCCAAATGA - 21600
      - N Y Y K F E D * C E L Y E V D T P P K *
      - T T T S S R I N V S C M K * I L P P N D
      - L L Q V R G L M * V V * S R Y S P Q M I
```

FIG. 5 Cont'd

```
21601 - TAGGACTACTTTAAAAATCTAGTCTGTGAGAAATAAATTGAGTCCTAAATAAAGAAGGTA - 21660
       -  *  D  Y  F  K  N  L  V  C  E  K  *  I  E  S  *  I  K  K  V
       -  R  T  T  L  K  I  *  S  V  R  N  K  L  S  P  K  *  R  R  *
       -  G  L  L  *  K  S  S  L  *  E  I  N  *  V  L  N  K  E  G  K
21661 - AAATAAGATTACAATGTCCCAAAGTATGATAATTAGTATGCAAACTGTTGGGACAGTATG - 21720
       -  K  *  D  Y  N  V  P  K  Y  D  N  *  Y  A  N  C  W  D  S  M
       -  N  K  I  T  M  S  Q  S  M  I  I  S  M  Q  T  V  G  T  V  W
       -  I  R  L  Q  C  P  K  V  *  *  L  V  C  K  L  L  G  Q  Y  G
21721 - GAAAATTCCTACCATAAATAAAACGACGGTGTCTCTTTAGTTTACAACAGGCACCAACCC - 21780
       -  E  N  S  Y  H  K  *  N  D  G  V  S  L  V  Y  N  R  H  Q  P
       -  K  I  P  T  I  N  K  T  T  V  S  L  *  F  T  T  G  T  N  P
       -  K  F  L  P  *  I  K  R  R  C  L  F  S  L  Q  Q  A  P  T  Q
21781 - AAAAACCAAGATGGTACTTGTTGTTCAGTGTCAGCCACTAATAATAATTGTTAAGATGAT - 21840
       -  K  N  Q  D  G  T  C  C  S  V  S  A  T  N  N  N  C  *  D  D
       -  K  T  K  M  V  L  V  V  Q  C  Q  P  L  I  I  I  V  K  M  I
       -  K  P  R  W  Y  L  L  F  S  V  S  H  *  *  *  L  L  R  *  L
21841 - TACAACAATATGCTCGTACATTGAAACTTAACACACTGTTGGGAAAGAAACGACAAAGAT - 21900
       -  Y  N  N  M  L  V  H  *  N  L  T  H  C  W  E  R  N  D  K  D
       -  T  T  I  C  S  Y  I  E  T  *  H  T  V  G  K  E  T  T  K  I
       -  Q  Q  Y  A  R  T  L  K  L  N  T  L  L  G  K  K  R  Q  R  F
21901 - TTGGGTACCCATGTGTCTGTGTATGATACTATAAGCTATTACGTAAATTAACGTGAAAGC - 21960
       -  L  G  T  H  V  S  V  Y  D  T  I  S  Y  Y  V  N  *  R  E  S
       -  W  V  P  M  C  L  C  M  I  L  *  A  I  T  *  I  N  V  K  A
       -  G  Y  P  C  V  C  V  *  Y  Y  K  L  L  R  K  L  T  *  K  L
21961 - TCATGTATAGACTACGGAAAAGCGAACTACAAAGTCTTTTCAGTCCATTAAAATTTGTGA - 22020
       -  S  C  I  D  Y  G  K  A  N  Y  K  V  F  S  V  H  *  N  L  *
       -  H  V  *  T  T  E  K  R  T  T  K  S  F  Q  S  I  K  I  C  E
       -  M  Y  R  L  R  K  S  E  L  Q  S  L  F  S  P  L  K  F  V  N
22021 - ATGCTCTCAAACACAAATTTTTATTTCTACCCAAAGAGATACAAATATTCCCGATAGTTG - 22080
       -  M  L  S  N  T  N  F  Y  F  Y  P  K  R  Y  K  Y  S  R  *  L
       -  C  S  Q  T  Q  I  F  I  S  T  Q  R  D  T  N  I  P  D  S  W
       -  A  L  K  H  K  F  L  F  L  P  K  E  I  Q  I  F  P  I  V  G
22081 - GATATCTACATCAAGCACTAGATGGAAGACCAAAATTGTGAAACTTTGGATAAAAATTCA - 22140
       -  D  I  Y  I  K  H  *  M  E  D  Q  N  C  E  T  L  D  K  N  S
       -  I  S  T  S  S  T  R  W  K  T  K  I  V  K  L  W  I  K  I  Q
       -  Y  L  H  Q  A  L  D  G  R  P  K  L  *  N  F  G  *  K  F  N
22141 - ACGGAGAACCATAATTGTAATGTTTAAAATCTCGGTAAGAATGTCGGAAAAGTGGACGAG - 22200
       -  T  E  N  H  N  C  N  V  *  N  L  G  K  N  V  G  K  V  D  E
       -  R  R  T  I  I  V  M  F  K  I  S  V  R  M  S  E  K  W  T  S
       -  G  E  P  *  L  *  C  L  K  S  R  *  E  C  R  K  S  G  R  V
22201 - TTCTGTGAACCCCGTGCAGTCGACGTCGGATAAAACAACCGATAAATTTCGGTTGATGTA - 22260
       -  F  C  E  P  R  A  V  D  V  G  *  N  N  R  *  I  S  V  D  V
       -  S  V  N  P  V  Q  S  T  S  D  K  T  T  D  K  F  R  L  M  *
       -  L  *  T  P  C  S  R  R  R  I  K  Q  P  I  N  F  G  *  C  K
22261 - AATACGAGTTCATACTACTTTTACCATGTTAGTGTCTACGACAACTAACAAGAGTTTTAG - 22320
       -  N  T  S  S  Y  Y  F  Y  H  V  S  V  Y  D  N  *  Q  E  F  *
       -  I  R  V  H  T  T  F  T  M  L  V  S  T  T  T  N  K  S  F  R
       -  Y  E  F  I  L  L  L  P  C  *  C  L  R  Q  L  T  R  V  L  G
22321 - GTGAACGACTTGAGTTTACGAGACAATTCTCGAAACTCTAACTGTTTCCTTAAATGGTCT - 22380
       -  V  N  D  L  S  L  R  D  N  S  R  N  S  N  C  F  L  K  W  S
       -  *  T  T  *  V  Y  E  T  I  L  E  T  L  T  V  S  L  N  G  L
       -  E  R  L  E  F  T  R  Q  F  S  K  L  *  L  F  P  *  M  V  W
22381 - GGAGATTAAAGTCCCAACAAGGGAGTCCTCTACAACACTCTAAGGGATTATAATGTTTGA - 22440
       -  G  D  *  S  P  N  K  G  V  L  Y  N  T  L  R  D  Y  N  V  *
       -  E  I  K  V  P  T  R  E  S  S  T  T  L  *  G  I  I  M  F  E
       -  R  L  K  S  Q  Q  G  S  P  L  Q  H  S  K  G  L  *  C  L  N
22441 - ACACAGGAAAACCTCTCCAAAAATTACGATGATTTAAGGGAAGACAGATACGTACCCTCT - 22500
       -  T  Q  E  N  L  S  K  N  Y  D  D  L  R  E  D  R  Y  V  P  S
       -  H  R  K  T  S  P  K  I  T  M  I  *  G  K  T  D  T  Y  P  L
       -  T  G  K  P  L  Q  K  L  R  *  F  K  G  R  Q  I  R  T  L  S
```

FIG. 5 Cont'd

```
22501 - CTTTTTTTTAAAGATTAACACAACGACTAATGAGACACGAGATGTTGAGTTGTAAAAAAA - 22560
      - L  F  F  K  D  *  H  N  D  *  *  D  T  R  C  *  V  V  K  K
      -  F  F  L  K  I  N  T  T  T  N  E  T  R  D  V  E  L  *  K  K
      -   F  F  *  R  L  T  Q  R  L  M  R  H  E  M  L  S  C  K  K  S
22561 - GTTGGAAATTCACGATACCGCAAAGACGGTGATTCAACTTACTAGAAACGAAGAGGTTAC - 22620
      - V  G  N  S  R  Y  R  K  D  G  D  S  T  Y  *  K  R  R  G  Y
      -  L  E  I  H  D  T  A  K  T  V  I  Q  L  T  R  N  E  E  V  T
      -   W  K  F  T  I  P  Q  R  R  *  F  N  L  L  E  T  K  R  L  Q
22621 - AGATACGTCTAAGAAAACATCAGTTCCCTCTACTACATTCTGTTTATCGCGGTCCTGTTT - 22680
      - R  Y  V  *  E  N  I  S  S  L  Y  Y  I  L  F  I  A  V  L  F
      -  D  T  S  K  K  T  S  V  P  S  T  T  F  C  L  S  R  S  C  L
      -   I  R  L  R  K  H  Q  F  P  L  L  H  S  V  Y  R  G  P  V  *
22681 - GACCACAATAACGACTAATATTAATATTTAACGGTCTACTAAAGTACCCAACACAGGAAC - 22740
      - D  H  N  N  *  Y  *  Y  L  T  V  Y  *  S  T  Q  H  R  N
      -  T  T  I  T  T  N  I  N  I  *  R  S  T  K  V  P  N  T  G  T
      -   P  Q  *  R  L  I  L  I  F  N  G  L  L  K  Y  P  T  Q  E  R
22741 - GAACCTTATGATCCTTGTAACTACGATGAAGTTGACCATTAATATTAATATTTATATCCA - 22800
      - E  P  Y  D  P  C  N  Y  D  E  V  D  H  *  Y  *  Y  L  Y  P
      -  N  L  M  I  L  V  T  T  M  K  L  T  I  N  I  N  I  Y  I  H
      -   T  L  *  S  L  *  L  R  *  S  *  P  L  I  L  I  F  I  S  I
22801 - TAGAATCTGTACCGTTCGAATCCGGGAAACTCTCTCTGTATAGATTACACGGAAAGAGGG - 22860
      - *  N  L  Y  R  S  N  P  G  N  S  L  C  I  D  Y  T  E  R  G
      -  R  I  C  T  V  R  I  R  E  T  L  S  V  *  I  T  R  K  E  G
      -   E  S  V  P  F  E  S  G  K  L  S  L  Y  R  L  H  G  K  R  G
22861 - GACTACCGTTTGGAACGTGGGGTGGACGAGAATTAACAATAACCGGTAATTTACTAATAC - 22920
      - D  Y  R  L  E  R  G  V  D  E  N  *  Q  *  P  V  I  Y  *  Y
      -  T  T  V  W  N  V  G  W  T  R  I  N  N  N  R  *  F  T  N  T
      -   L  P  F  G  T  W  G  G  R  E  L  T  I  T  G  N  L  L  I  P
22921 - CAAAAATGTGGTGATGACCGTAACCGATGGTTGGAATGTCTCAACATCATGAAAGAAAAC - 22980
      - Q  K  C  G  D  D  R  N  R  W  L  E  C  L  N  I  M  K  E  N
      -  K  N  V  V  M  T  V  T  D  G  W  N  V  S  T  S  *  K  K  T
      -   K  M  W  *  *  P  *  P  M  V  G  M  S  Q  H  H  E  R  K  L
22981 - TTGAAAATTTACGTGGCCGGTGCCAAACACCTGGTTTTAATAGGTGACTGGAATAATTCT - 23040
      - L  K  I  Y  V  A  G  A  K  H  L  V  L  I  G  D  W  N  N  S
      -  *  K  F  T  W  P  V  P  N  T  W  F  *  *  V  T  G  I  I  L
      -   E  N  L  R  G  R  C  Q  T  P  G  F  N  R  *  L  E  *  F  L
23041 - TGGTCACACAGTTAAAATTAAAATTACCTGAGTGACCATGACCACACAATTGAGGAAGAA - 23100
      - W  S  H  S  *  N  *  N  Y  L  S  D  H  D  H  T  I  E  E  E
      -  G  H  T  V  K  I  K  I  T  *  V  T  M  T  T  Q  L  R  K  K
      -   V  T  Q  L  K  L  K  L  P  E  *  P  *  P  H  N  *  G  R  S
23101 - GTTTCTCTAAAGTTGGTAAAGTTGTTAAACCGGCACTACAAAGACTAAAGTGACTAAGGC - 23160
      - V  S  L  K  L  V  K  L  L  N  R  H  Y  K  D  *  S  D  *  G
      -  F  L  *  S  W  *  S  C  *  T  G  T  T  K  T  K  V  T  K  A
      -   F  S  K  V  G  K  V  V  K  P  A  L  Q  R  L  K  *  L  R  Q
23161 - AAGCTCTAGGATTTTGTAGACTTTATAATCTGTAAAGTGGAACGAGAAAACCCCCACATT - 23220
      - K  L  *  D  F  V  D  F  I  I  C  K  V  E  R  E  N  P  H  I
      -  S  S  R  I  L  *  T  L  *  S  V  K  W  N  E  K  T  P  T  F
      -   A  L  G  F  C  R  L  Y  N  L  *  S  G  T  R  K  P  P  H  S
23221 - CACATTAATGTGGACCTTGTTTACGAAGTAGACTTCAACGACAAGATATAGTTCTACAAT - 23280
      - H  I  N  V  D  L  V  Y  E  V  D  F  N  D  K  I  *  F  Y  N
      -  T  L  M  W  T  L  F  T  K  *  T  S  T  T  R  Y  S  S  T  I
      -   H  *  C  G  P  C  L  R  S  R  L  Q  R  Q  D  I  V  L  Q  L
23281 - TGACGTGACTACAAAGATGTCGTTAAGTACGTCTAGTTGAGTGTGGTCGAACCGCGTATA - 23340
      - *  R  D  Y  K  D  V  V  K  Y  V  *  L  S  V  V  E  P  R  I
      -  D  V  T  T  K  M  S  L  S  T  S  S  *  V  W  S  N  R  V  Y
      -   T  *  L  Q  R  C  R  *  V  R  L  V  E  C  G  R  T  A  Y  I
23341 - TAAGATGACCTTTGTTACATAAGGTCTGAGTTCGTCCGACAGAATATCCTCGACTCGTAC - 23400
      - *  D  D  L  C  Y  I  R  S  E  F  V  R  Q  N  I  L  D  S  Y
      -  K  M  T  F  V  T  *  G  L  S  S  S  D  R  I  S  S  T  R  T
      -   R  *  P  L  L  H  K  V  *  V  R  P  T  E  Y  P  R  L  V  Q
```

FIG. 5 Cont'd

```
23401 - AGCTGTGAAGAATACTCACGCTGTAAGGATAACCTCGACCGTAAACACGATCAATGGTAT - 23460
      -  S  C  E  E  Y  S  R  C  K  D  N  L  D  R  K  H  D  Q  W  Y
      -  A  V  K  N  T  H  A  V  R  I  T  S  T  V  N  T  I  N  G  M
      -  L  *  R  I  L  T  L  *  G  *  P  R  P  *  T  R  S  M  V  C
23461 - GTCAAAGAAATAATGCATCATGATCGGTTTTTAGATAACACCGAATATGATACAGAAATC - 23520
      -  V  K  E  I  M  H  H  D  R  F  L  D  N  T  E  Y  D  T  E  I
      -  S  K  K  *  C  I  M  I  G  F  *  I  T  P  N  M  I  Q  K  S
      -  Q  R  N  N  A  S  *  S  V  F  R  *  H  R  I  *  Y  R  N  P
23521 - CACGACTATCAAGTTAACGAATGAGATTATTGTGGTAACGATATGGATGATTGAAAAGTT - 23580
      -  H  D  Y  Q  V  N  E  *  D  Y  C  G  N  D  M  D  D  *  K  V
      -  T  T  I  K  L  T  N  E  I  I  V  V  T  I  W  M  I  E  K  L
      -  R  L  S  S  *  R  M  R  L  L  W  *  R  Y  G  *  L  K  S  *
23581 - AATCGTAATGATGTCTTCATTACGGACAAAGATACCGATTTTGGAGGCATCTAACATTAT - 23640
      -  N  R  N  D  V  F  I  T  D  K  D  T  D  F  G  G  I  *  H  Y
      -  I  V  M  M  S  S  L  R  T  K  I  P  I  L  E  A  S  N  I  I
      -  S  *  *  C  L  H  Y  G  Q  R  Y  R  F  W  R  H  L  T  L  Y
23641 - ACATGTAGACGCCTCTAAGATGACTTACACGATTAAACGAAGAGGTTATACCATCGAAAA - 23700
      -  T  C  R  R  L  *  D  D  L  H  D  *  T  K  R  L  Y  H  R  K
      -  H  V  D  A  S  K  M  T  Y  T  I  K  R  R  G  Y  T  I  E  N
      -  M  *  T  P  L  R  *  L  T  R  L  N  E  E  V  I  P  S  K  T
23701 - CGTGTGTTGATTTAGCACGTGAGAGTCCATAACGACGACTTGTCCTAGCGTTGTGTGCAC - 23760
      -  R  V  L  I  *  H  V  R  V  H  N  D  D  L  S  *  R  C  V  H
      -  V  C  *  F  S  T  *  E  S  I  T  T  T  C  P  S  V  V  C  T
      -  C  V  D  L  A  R  E  S  P  *  R  R  L  V  L  A  L  C  A  L
23761 - TTCACAAGCGAGTTCAGTTTGTTTACATGTTTTGGGGTTGAAACTTTATAAAACCACCAA - 23820
      -  F  T  S  E  F  S  L  F  T  C  F  G  V  E  T  L  *  N  H  Q
      -  S  Q  A  S  S  V  C  L  H  V  L  G  L  K  L  Y  K  T  T  K
      -  H  K  R  V  Q  F  V  Y  M  F  W  G  *  N  F  I  K  P  P  K
23821 - AATTAAAAAGTGTTTATAATGGACTGGGAGATTTCGGTTGATTCTCCAGAAAATAACTCC - 23880
      -  N  *  K  V  F  I  M  D  W  E  I  S  V  D  S  P  E  N  N  S
      -  I  K  K  C  L  *  W  T  G  R  F  R  L  I  L  Q  K  I  T  P
      -  L  K  S  V  Y  N  G  L  G  D  F  G  *  F  S  R  K  *  L  L
23881 - TGAACGAGAAATTATTCCACTGTGAGCGACTACGACCGAAGTACTTCGTTATACCGCTTA - 23940
      -  *  T  R  N  Y  S  T  V  S  D  Y  D  R  S  T  S  L  Y  R  L
      -  E  R  E  I  I  P  L  *  A  T  T  T  E  V  L  R  Y  T  A  Y
      -  N  E  K  L  F  H  C  E  R  L  R  P  K  Y  F  V  I  P  L  T
23941 - CGGATCCACTATAATTACGATCTCTAGAGTAAACACGCGTCTTCAAGTTACCTGAATGTC - 24000
      -  R  I  H  Y  N  Y  D  L  *  S  K  H  A  S  S  S  Y  L  N  V
      -  G  S  T  I  I  T  I  S  R  V  N  T  R  L  Q  V  T  *  M  S
      -  D  P  L  *  L  R  S  L  E  *  T  R  V  F  K  L  P  E  C  H
24001 - ACAACGGTGGAGACGAGTGACTACTATACTAACGACGGATGTGACGACGAGATCAATCAC - 24060
      -  T  T  V  E  T  S  D  Y  Y  T  N  D  G  C  D  D  E  I  N  H
      -  Q  R  W  R  R  V  T  T  I  L  T  T  D  V  T  T  R  S  I  T
      -  N  G  G  D  E  *  L  L  Y  *  R  R  M  *  R  R  D  Q  S  P
24061 - CATGACGGTGACGACCTACCTGTAAACCACGACCGCGACGAGAAGTTTATGGAAAACGAT - 24120
      -  H  D  G  D  D  L  P  V  N  H  D  R  D  E  K  F  M  E  N  D
      -  M  T  V  T  T  Y  L  *  T  T  T  A  T  R  S  L  W  K  T  I
      -  *  R  *  R  P  T  C  K  P  R  P  R  R  E  V  Y  G  K  R  Y
24121 - ACGTTTACCGTATATCCAAGTTACCGTAACCTCAATGGGTTTTACAAGAGATACTCTTGG - 24180
      -  T  F  T  V  Y  P  S  Y  R  N  L  N  G  F  Y  K  R  Y  S  W
      -  R  L  P  Y  I  Q  V  T  V  T  S  M  G  F  T  R  D  T  L  G
      -  V  Y  R  I  S  K  L  P  *  P  Q  W  V  L  Q  E  I  L  L  V
24181 - TTTTTGTTTAGCGGTTGGTTAAATTGTTCCGCTAATCAGTTTAAGTTCTTAGTGAATGTT - 24240
      -  F  L  F  S  G  W  L  N  C  S  A  N  Q  F  K  F  L  V  N  V
      -  F  C  L  A  V  G  *  I  V  P  L  I  S  L  S  S  *  *  M  L
      -  F  V  *  R  L  V  K  L  F  R  *  S  V  *  V  L  S  E  C  C
24241 - GTTGTAGTTGACGTAACCCGTTCGACGTTCTGCAACAATTGGTCTTACGAGTTCGTAATT - 24300
      -  V  V  V  D  V  T  R  S  T  F  C  N  N  W  S  Y  E  F  V  I
      -  L  *  L  T  *  P  V  R  R  S  A  T  I  G  L  T  S  S  *  F
      -  C  S  *  R  N  P  F  D  V  L  Q  Q  L  V  L  R  V  R  N  L
```

FIG. 5 Cont'd

```
24301 - TGTGTGAACAATTTGTTGAATCGAGATTAAAACCACGTTAAAGTTCACACGATTTACTAT - 24360
      - C  V  N  N  L  L  N  R  D  *  N  H  V  K  V  H  T  I  Y  Y
      -  V  *  T  I  C  *  I  E  I  K  T  T  L  K  F  T  R  F  T  I
      -   C  E  Q  F  V  E  S  R  L  K  P  R  *  S  S  H  D  L  L  *
24361 - AGGAAAGCGCTGAACTATTTCAGCTCCGCCTCCATGTTTAACTGTCCAATTAATGTCCGT - 24420
      - R  K  A  L  N  Y  F  S  S  A  S  M  F  N  C  P  I  N  V  R
      -  G  K  R  *  T  I  S  A  P  P  P  C  L  T  V  Q  L  M  S  V
      -   E  S  A  E  L  F  Q  L  R  L  H  V  *  L  S  N  *  C  P  S
24421 - CTGAAGTTTCGGAAGTTTGGATACATTGTGTTGTTGATTAGTCCCGACGACTTTAGTCCC - 24480
      - L  K  F  R  K  F  G  Y  I  V  L  L  I  S  P  D  D  F  S  P
      -  *  S  F  G  S  L  D  T  L  C  C  *  L  V  P  T  T  L  V  P
      -   E  V  S  E  V  W  I  H  C  V  V  D  *  S  R  R  L  *  S  R
24481 - GAAGACGATTAGAACGACGATGATTTTACAGACTCACACAAGAACCTGTTAGTTTTCTC - 24540
      - E  D  D  *  N  D  D  D  F  T  D  S  H  K  N  L  L  V  F  L
      -  K  T  I  R  T  T  M  I  L  Q  T  H  T  R  T  C  *  F  F  S
      -   R  R  L  E  R  R  *  F  Y  R  L  T  Q  E  P  V  S  F  S  Q
24541 - AACTGAAAACACCTTTCCCGATGGTGGAATACAGGAAGGGTGTTCGTCGGGCGTACCAC - 24600
      - N  *  K  H  L  S  R  W  W  N  T  G  R  V  F  V  G  A  Y  H
      -  T  E  N  T  F  P  D  G  G  I  Q  E  G  C  S  S  G  R  T  T
      -   L  K  T  P  F  P  M  V  E  Y  R  K  G  V  R  R  G  V  P  Q
24601 - AACAGAAGGATGTACAGTGCATACACGGTAGGGTCCTCTCCTTGAAGTGGTGTCGCGGTC - 24660
      - N  R  R  M  Y  S  A  Y  T  V  G  S  S  P  *  S  G  V  A  V
      -  T  E  G  C  T  V  H  T  R  *  G  P  L  L  E  V  V  S  R  S
      -   Q  K  D  V  Q  C  I  H  G  R  V  L  S  L  K  W  C  R  G  R
24661 - GTTAAACAGTACTTCCGTTTCGTATGAAGGGAGCACTTCCACAAAAACACAAATTACCGT - 24720
      - V  K  Q  Y  F  R  F  V  *  R  E  H  F  H  K  N  T  N  Y  R
      -  L  N  S  T  S  V  S  Y  E  G  S  T  S  T  K  T  Q  I  T  V
      -   *  T  V  L  P  F  R  M  K  G  A  L  P  Q  K  H  K  L  P  *
24721 - GAAGAACCAAATAATGTGTCTCCTTGAAGAAAAGAGGTGTTTATTAATGATGTCTGTTAT - 24780
      - E  E  P  N  N  V  S  P  *  R  K  E  V  F  I  N  D  V  C  Y
      -  K  N  Q  I  M  C  L  L  E  E  K  R  C  L  L  M  M  S  V  M
      -   R  T  K  *  C  V  S  L  K  K  R  G  V  Y  *  *  C  L  L  C
24781 - GTAAACAGAGTCCTTTAACACTACAGCAATAACCGTAGTAATTGTTGTGTCAAATACTAG - 24840
      - V  N  R  V  L  *  H  Y  S  N  N  R  S  N  C  C  V  K  Y  *
      -  *  T  E  S  F  N  T  T  A  I  T  V  V  I  V  V  S  N  T  R
      -   K  Q  S  P  L  T  L  Q  Q  *  P  *  *  L  L  C  Q  I  L  G
24841 - GAGACGTTGGACTCGAACTGAGTAAGTTTCTTCTCGACCTGTTCATGAAGTTTTTAGTAT - 24900
      - E  T  L  D  S  N  *  V  S  F  F  S  T  C  S  *  S  F  *  Y
      -  R  R  W  T  R  T  E  *  V  S  S  R  P  V  H  E  V  F  S  M
      -   D  V  G  L  E  L  S  K  F  L  L  D  L  F  M  K  F  L  V  C
24901 - GTAGTGGTCTACAACTAGAACCGCTGTAAAGTCCGTAATTGCGAAGACAGCAGTTGTAAG - 24960
      - V  V  V  Y  N  *  N  R  C  K  V  R  N  C  E  D  S  S  C  K
      -  *  W  S  T  T  R  T  A  V  K  S  V  I  A  K  T  A  V  V  S
      -   S  G  L  Q  L  E  P  L  *  S  P  *  L  R  R  Q  Q  L  *  V
24961 - TTTTTCTTTAACTGGCGGAGTTACTCCAGCGATTTTTAAATTTACTTAGTGAGTAACTGG - 25020
      - F  F  F  N  W  R  S  Y  S  S  D  F  *  I  Y  L  V  S  N  W
      -  F  S  L  T  G  G  V  T  P  A  I  F  K  F  T  *  *  V  T  G
      -   F  L  *  L  A  E  L  L  Q  R  F  L  N  L  L  S  E  *  L  E
25021 - AAGTTCTTAACCCTTTTATACTCGTTATATAATTTACCGGAACCATACAAACCGAGCCGA - 25080
      - K  F  L  T  L  L  Y  S  L  Y  N  L  P  E  P  Y  K  P  S  R
      -  S  S  *  P  F  Y  T  R  Y  I  I  Y  R  N  H  T  N  R  A  E
      -   V  L  N  P  F  I  L  V  I  *  F  T  G  T  I  Q  T  E  P  K
25081 - AGTAACGACCTGATTAACGGTAGCAGTACCAATGTTAGAACGAAACAACGTACTGATCAA - 25140
      - S  N  D  L  I  N  G  S  S  T  N  V  R  T  K  Q  R  T  D  Q
      -  V  T  T  *  L  T  V  A  V  P  M  L  E  R  N  N  V  L  I  N
      -   *  R  P  D  *  R  *  Q  Y  Q  C  *  N  E  T  T  Y  *  S  T
25141 - CAACGTCAACGGAGTTCCCACGTACGAGAACACCAAGAACGACGTTCAAACTACTCCTAC - 25200
      - Q  R  Q  R  S  S  H  V  R  E  H  Q  E  R  R  S  N  Y  S  Y
      -  N  V  N  G  V  P  T  Y  E  N  T  K  N  D  V  Q  T  T  P  T
      -   T  S  T  E  F  P  R  T  R  T  P  R  T  T  F  K  L  L  L  L
```

FIG. 5 Cont'd

```
25201 - TGAGACTCGGTCAAGAGTTCCCACAGTTTAATGTAATGTGTATTTGCTTGAATACCTAAA - 25260
      - *  D  S  V  K  S  S  H  S  L  M  *  C  V  F  A  *  I  P  K
      -  E  T  R  S  R  V  P  T  V  *  C  N  V  Y  L  L  E  Y  L  N
      -   R  L  G  Q  E  F  P  Q  F  N  V  M  C  I  C  L  N  T  *  T
25261 - CAAATACTCTAAAAAATGAGAACCTAGTTAATGACGTGTCGGTCATTTTTAACTGTTACG - 25320
      - Q  I  L  *  K  M  R  T  *  L  M  T  C  R  S  F  L  T  V  T
      -  K  Y  S  K  K  *  E  P  S  *  *  R  V  G  H  F  *  L  L  R
      -   N  T  L  K  N  E  N  L  V  N  D  V  S  V  I  F  N  C  Y  E
25321 - AAGAGGACGTTCATGACAAGTACGATGTCGTTGCTATGGCGATGTTCGGAGTGAGGGAAA - 25380
      - K  R  T  F  M  T  S  T  M  S  L  L  W  R  C  S  E  *  G  K
      -  R  G  R  S  *  Q  V  R  C  R  C  Y  G  D  V  R  S  E  G  K
      -   E  D  V  H  D  K  Y  D  V  V  A  M  A  M  F  G  V  R  E  S
25381 - GCCTACCGAACAATAACCGCAACGTAAAGAACGACAAAAAGTCTCGCGATGGTTTTATTA - 25440
      - A  Y  R  T  I  T  A  T  *  R  T  T  K  S  L  A  M  V  L  L
      -  P  T  E  Q  *  P  Q  R  K  E  R  Q  K  V  S  R  W  F  Y  *
      -   L  P  N  N  N  R  N  V  K  N  D  K  K  S  R  D  G  F  I  N
25441 - ACGCGAGTTATTTTCTACCGTCGATCGGGAAATATTCCCGAAGGTCAAGTAAACGTTAAA - 25500
      - T  R  V  I  F  Y  R  R  S  G  N  I  P  E  G  Q  V  N  V  K
      -  R  E  L  F  S  T  V  D  R  E  I  F  P  K  V  K  *  T  L  N
      -   A  S  Y  F  L  P  S  I  G  K  Y  S  R  R  S  S  K  R  *  M
25501 - TGACGACGATAAACAATGGTAGATAAGTGTAGAAAACGAACAGCGACGTCCATACCTCCG - 25560
      - *  R  R  *  T  M  V  D  K  C  R  K  R  T  A  T  S  I  P  P
      -  D  D  D  K  Q  W  *  I  S  V  E  N  E  Q  R  R  P  Y  L  R
      -   T  T  I  N  N  G  R  *  V  *  K  T  N  S  D  V  H  T  S  A
25561 - CGTTAAAAACATGGAGATACGGAACTATATAAAAGATGTTACGTAGTTGCGTACATCTTA - 25620
      - R  *  K  H  G  D  T  E  L  Y  K  R  C  Y  V  V  A  Y  I  L
      -  V  K  N  M  E  I  R  N  Y  I  K  D  V  T  *  L  R  T  S  *
      -   L  K  T  W  R  Y  G  T  I  *  K  M  L  R  S  C  V  H  L  N
25621 - ATAATACTCTACAACCGAAACAACCTTCACGTTTAGGTTCTTGGGTAATGAAATACTACG - 25680
      - I  I  L  Y  N  R  N  N  L  H  V  *  V  L  G  *  *  N  T  T
      -  *  Y  S  T  T  E  T  T  F  T  F  R  F  L  G  N  E  I  L  R
      -   N  T  L  Q  P  K  Q  P  S  R  L  G  S  W  V  M  K  Y  Y  G
25681 - GTTGATGAAACAAACGACCGTGTGTGTATTGATACTGATGACATATGGTATATTGTCACA - 25740
      - V  D  E  T  N  D  R  V  C  I  D  T  D  D  I  W  Y  I  V  T
      -  L  M  K  Q  T  T  V  C  V  L  I  L  M  T  Y  G  I  L  S  Q
      -   *  *  N  K  R  P  C  V  Y  *  Y  *  *  H  M  V  Y  C  H  S
25741 - GTGTCTATGTTAACAGCAATGACTTCCACTGCCGTAAAGTTGTGGTTTTGAGTTTCTTCT - 25800
      - V  S  M  L  T  A  M  T  S  T  A  V  K  L  W  F  *  V  S  S
      -  C  L  C  *  Q  Q  *  L  P  L  P  *  S  C  G  F  E  F  L  L
      -   V  Y  V  N  S  N  D  F  H  C  R  K  V  V  V  L  S  F  F  *
25801 - GATGGTTTAACCACCAATAAGACTCCTATCCGTGAGTCCACAATTTCTGATACAGCAACA - 25860
      - D  G  L  T  T  N  K  T  P  I  R  E  S  T  I  S  D  T  A  T
      -  M  V  *  P  P  I  R  L  L  S  V  S  P  Q  F  L  I  Q  Q  H
      -   W  F  N  H  Q  *  D  S  Y  P  *  V  H  N  F  *  Y  S  N  M
25861 - TGTACCGATAAAGTGGCTTCAAATGATGGTCGAACTCAGATGTGTTTAATGATGTCTGTG - 25920
      - C  T  D  K  V  A  S  N  D  G  R  T  Q  M  C  L  M  M  S  V
      -  V  P  I  K  W  L  Q  M  M  V  E  L  R  C  V  *  *  C  L  *
      -   Y  R  *  S  G  F  K  *  W  S  N  S  D  V  F  N  D  V  C  D
25921 - ACCATAACTTTTACGATGTAAGAAGTAGAAATTGTTCGAACAATTTCTGGGTGGCTTACA - 25980
      - T  I  T  F  T  M  *  E  V  E  I  V  R  T  I  S  G  W  L  T
      -  P  *  L  L  R  C  K  K  *  K  L  F  E  Q  F  L  G  G  L  H
      -   H  N  F  Y  D  V  R  S  R  N  C  S  N  N  F  W  V  A  Y  T
25981 - CGTTTATGTGTGTTAGCTGCCGAGAAGTCCTCAACGATTAGGTCGTTACCTAGGTTAAAT - 26040
      - R  L  C  V  L  A  A  E  K  S  S  T  I  R  S  L  P  R  L  N
      -  V  Y  V  C  *  L  P  R  S  P  Q  R  L  G  R  Y  L  G  *  I
      -   F  M  C  V  S  C  R  E  V  L  N  D  *  V  V  T  *  V  K  Y
26041 - ACTACTCGGCTGCTGCTGATGATCGCACGGAAACATTCGTGTTCTTTCACTCATGCTTGA - 26100
      - T  T  R  L  L  L  M  I  A  R  K  H  S  C  S  F  T  H  A  *
      -  L  L  G  C  C  *  *  S  H  G  N  I  R  V  L  S  L  M  L  E
      -   Y  S  A  A  A  D  D  R  T  E  T  F  V  F  F  H  S  C  L  N
```

FIG. 5 Cont'd

```
26101 - ATACATGAGTAAGCAAAGCCTTCTTTGTCCATGCAATTATCAATTATCGCATGAAGAAAA - 26160
       - I  H  E  *  A  K  P  S  L  S  M  Q  L  S  I  I  A  *  R  K
       - Y  M  S  K  Q  S  L  L  C  P  C  N  Y  Q  L  S  H  E  E  K
       - T  *  V  S  K  A  F  F  V  H  A  I  I  N  Y  R  M  K  K  K
26161 - AGAACGAAAGCACCATAAGAACGATCAGTGTGATCGGTAGGAATGACGCGAAGCTAACAC - 26220
       - R  T  K  A  P  *  E  R  S  V  *  S  V  G  M  T  R  S  *  H
       - E  R  K  H  H  K  N  D  Q  C  D  R  *  E  *  R  E  A  N  T
       - N  E  S  T  I  R  T  I  S  V  I  G  R  N  D  A  K  L  T  H
26221 - ACGCATGACGACGTTATAACAATTGCACTCAAATCATTTTGGTTGCCAAATGCAGATGAG - 26280
       - T  H  D  D  V  I  T  I  A  L  K  S  F  W  L  P  N  A  D  E
       - R  M  T  T  L  *  Q  L  H  S  N  H  F  G  C  Q  M  Q  M  S
       - A  *  R  R  Y  N  N  C  T  Q  I  I  L  V  A  K  C  R  *  A
26281 - CGCACAATTTTTAGACTTGAGAAGACTTCCTCAAGGACTAGAAGACCAGATTTGCTTGAT - 26340
       - R  T  I  F  R  L  E  K  T  S  S  R  T  R  R  P  D  L  L  D
       - A  Q  F  L  D  L  R  R  L  P  Q  G  L  E  D  Q  I  C  L  I
       - H  N  F  *  T  *  E  D  F  L  K  D  *  K  T  R  F  A  *  L
26341 - TGATAATAATAATAAGACAAACCTTGAAATTGTAACGAATAGTACCGTCTGTTGCCATGA - 26400
       - *  *  *  *  *  D  K  P  *  N  C  N  E  *  Y  R  L  L  P  *
       - D  N  N  N  K  T  N  L  E  I  V  T  N  S  T  V  C  C  H  D
       - I  I  I  I  R  Q  T  L  K  L  *  R  I  V  P  S  V  A  M  I
26401 - TAATGGCAACTCCTCGAATTTGTTGAGGACCTTGTTACCTTGGATCATTATCCAAAGGAT - 26460
       - *  W  Q  L  L  E  F  V  E  D  L  V  T  L  D  H  Y  P  K  D
       - N  G  N  S  S  N  L  L  R  T  L  L  P  W  I  I  I  Q  R  I
       - M  A  T  P  R  I  C  *  G  P  C  Y  L  G  S  L  S  K  G  *
26461 - AAGGATCGGACCTAATACAATGATGTTAAACGGATAAGATTAGCCTTGTCCAAAAACATG - 26520
       - K  D  R  T  *  Y  N  D  V  K  R  I  R  L  A  L  S  K  N  M
       - R  I  G  P  N  T  M  M  L  N  G  *  D  *  P  C  P  K  T  C
       - G  S  D  L  I  Q  *  C  *  T  D  K  I  S  L  V  Q  K  H  V
26521 - TATTATTTCGAACAAAAGGAGACCGAGAACACCGGTCATTGTGAACGAACAAAACACGAA - 26580
       - Y  Y  F  E  Q  K  E  T  E  N  T  G  H  C  E  R  T  K  H  E
       - I  I  S  N  K  R  R  P  R  T  P  V  I  V  N  E  Q  N  T  N
       - L  F  R  T  K  G  D  R  E  H  R  S  L  *  T  N  K  T  R  T
26581 - CGACGACAGATGTCTTAATTAACCCACTGACCGCCCTAACGCTAACGTTACCGAACATAA - 26640
       - R  R  Q  M  S  *  L  T  H  *  P  P  *  R  *  R  Y  R  T  *
       - D  D  R  C  L  N  *  P  T  D  R  P  N  A  N  V  T  E  H  N
       - T  T  D  V  L  I  N  P  L  T  A  L  T  L  T  L  P  N  I  T
26641 - CATCCGAACTACACCGAATCGATGAAGCAACGAAGGAAGTCCGACAAACGAGCATGGGCG - 26700
       - H  P  N  Y  T  E  S  M  K  Q  R  R  K  S  D  K  R  A  W  A
       - I  R  T  T  P  N  R  *  S  N  E  G  S  P  T  N  E  H  G  R
       - S  E  L  H  R  I  D  E  A  T  K  E  V  R  Q  T  S  M  G  E
26701 - AGTTACACCAGTAAGTTGGGTCTTTGTTTGTAAGAAGAGTTACACGGAGAGGCCCCCTGT - 26760
       - S  Y  T  S  K  L  G  L  C  L  *  E  E  L  H  G  E  A  P  C
       - V  T  P  V  S  W  V  F  V  C  K  K  S  Y  T  E  R  P  P  V
       - L  H  Q  *  V  G  S  L  F  V  R  R  V  T  R  R  G  P  L  L
26761 - TAACACTGGTCTGGCGAGTACCTTTCACTTGAACAGTAACCACGACACTAGTAAGCACCA - 26820
       - *  H  W  S  G  E  Y  L  S  L  E  Q  *  P  R  H  *  *  A  P
       - N  T  G  L  A  S  T  F  H  L  N  S  N  H  D  T  S  K  H  Q
       - T  L  V  W  R  V  P  F  T  *  T  V  T  T  T  L  V  S  T  S
26821 - GTGAACGCTTACCGGCCTGTGAGGGATCCCGCGACACTGTAATTCCTGGACGGTTTTCTC - 26880
       - V  N  A  Y  R  P  V  R  D  P  A  T  L  *  F  L  D  G  F  L
       - *  T  L  T  G  L  *  G  I  P  R  H  C  N  S  W  T  V  F  S
       - E  R  L  P  A  C  E  G  S  R  D  T  V  I  P  G  R  F  S  L
26881 - TAGTGACACCGATGTAGTGCTTGCGAAAGAATAATGTTTAATCCTCGCAGCGTCGCACAT - 26940
       - *  *  H  R  C  S  A  C  E  R  I  M  F  N  P  R  S  V  A  H
       - S  D  T  D  V  V  L  A  K  E  *  C  L  I  L  A  A  S  H  I
       - V  T  P  M  *  C  L  R  K  N  N  V  *  S  S  Q  R  R  T  S
26941 - CCGTGACTAAGTCCAAAACGACGTATGTTGGCGATGGCATAACCTTTGATATTTAATTTA - 27000
       - P  *  L  S  P  K  R  R  M  L  A  M  A  *  P  L  I  F  N  L
       - R  D  *  V  Q  N  D  V  C  W  R  W  H  N  L  *  Y  L  I  Y
       - V  T  K  S  K  T  T  Y  V  G  D  G  I  T  F  D  I  *  F  M
```

FIG. 5 Cont'd

```
27001 - TGTCTGGTGCGGCCATCGTTGCTGTTATAACGAAACGATCATGTCATTCACTGTTGTCTA - 27060
      - C  L  V  R  P  S  L  L  L  *  R  N  D  H  V  I  H  C  C  L
      - V  W  C  G  H  R  C  C  Y  N  E  T  I  M  S  F  T  V  V  Y
      - S  G  A  A  I  V  A  V  I  T  K  R  S  C  H  S  L  L  S  T
27061 - CAAAGTAGAACAACTGAAGGTCCAATGTTATCGTCTCTATAACTAATAGTAATACTCCTG - 27120
      - Q  S  R  T  T  E  G  P  M  L  S  S  L  *  L  I  V  I  L  L
      - K  V  E  Q  L  K  V  Q  C  Y  R  L  Y  N  *  *  *  Y  S  *
      - K  *  N  N  *  R  S  N  V  I  V  S  I  T  N  S  N  T  P  E
27121 - AAAGTCCTAACGATAAACCTTAGAACTGCAATATTATTCAAGTTATCACTCTGTTAATAA - 27180
      - K  V  L  T  I  N  L  R  T  A  I  L  F  K  L  S  L  C  *  *
      - K  S  *  R  *  T  L  E  L  Q  Y  Y  S  S  Y  H  S  V  N  K
      - S  P  N  D  K  P  *  N  C  N  I  I  Q  V  I  T  L  L  I  N
27181 - ATTCGGAGATTGATTCTTCTTAATAAGCCTCAATCTACTACTTCTTGGATACCTCAATCT - 27240
      - I  R  R  L  I  L  L  N  K  P  Q  S  T  T  S  W  I  P  Q  S
      - F  G  D  *  F  F  L  I  S  L  N  L  L  L  L  G  Y  L  N  L
      - S  E  I  D  S  S  *  *  A  S  I  Y  Y  F  L  D  T  S  I  *
27241 - AATAGGTATTTTGCTTGTACTTTTAATAAGAGAAGGACTGTAACTAACATAAATGTAGAA - 27300
      - N  R  Y  F  A  C  T  F  N  K  R  R  T  V  T  N  I  N  V  E
      - I  G  I  L  L  V  L  L  I  R  E  G  L  *  L  T  *  M  *  N
      - *  V  F  C  L  Y  F  *  *  E  K  D  C  N  *  H  K  C  R  T
27301 - CGCTCGATATAGTGATAGTCCTCACACAATCTCCATGCTGACATGATGATTTTCTTGGAA - 27360
      - R  S  I  *  *  *  S  S  H  N  L  H  A  D  M  M  I  F  L  E
      - A  R  Y  S  D  S  P  H  T  I  S  M  L  T  *  *  F  S  W  N
      - L  D  I  V  I  V  L  T  Q  S  P  C  *  H  D  D  F  L  G  T
27361 - CGGGTAGTCCTTGTATGCTCCCGTTAAGTGGTAAAGTGGGAGAACGACTGTTATTTAAAC - 27420
      - R  V  V  L  V  C  S  R  *  V  V  K  W  E  N  D  C  Y  L  N
      - G  *  S  L  Y  A  P  V  K  W  *  S  G  R  T  T  V  I  *  T
      - G  S  P  C  M  L  P  L  S  G  K  V  G  E  R  L  L  F  K  R
27421 - GTGATTAACGTGATCGTGTGTGAAACGAAAACGAACACGACTGCCATGAGCTGTATGGA - 27480
      - V  I  E  R  D  R  V  *  N  E  N  E  H  D  C  H  E  L  Y  G
      - *  L  N  V  I  V  C  E  T  K  T  N  T  T  A  M  S  C  M  D
      - D  *  T  *  S  C  V  K  R  K  R  T  R  L  P  *  A  V  W  I
27481 - TAGTCGACGCACGTTCTAGTCAAAGTGGTTTTGAAAAGTAGTCTGTTCTCCTCCAAGTTG - 27540
      - *  S  T  H  V  L  V  K  V  V  L  K  S  S  L  F  S  S  K  L
      - S  R  R  T  F  *  S  K  W  F  *  K  V  V  C  S  P  P  S  C
      - V  D  A  R  S  S  Q  S  G  F  E  K  *  S  V  L  L  Q  V  V
27541 - TTCTCGAGATGAGCGGTGAAAAAGAGTAACAACGACGAGATCATAAAAATTATGAAACGA - 27600
      - F  S  R  *  A  V  K  K  S  N  N  D  E  I  I  K  I  M  K  R
      - S  R  D  E  R  *  K  R  V  T  T  T  R  S  *  K  L  *  N  E
      - L  E  M  S  G  E  K  E  *  Q  R  R  D  H  K  N  Y  E  T  K
27601 - AGTGGTAATTCTCTTTCTGTCTTACTTACTCGAGTGAAATTAACTGAAGATAAACACGAA - 27660
      - S  G  N  S  L  S  V  L  L  T  R  V  K  L  T  E  D  K  H  E
      - V  V  I  L  F  L  S  Y  L  L  E  *  N  *  L  K  I  N  T  K
      - W  *  F  S  F  C  L  T  Y  S  S  E  I  N  *  R  *  T  R  K
27661 - AAATCGGAAAGACGATAAGGAACAAAATTATTACGAATAATATAAAACCAAAAGTGAGCT - 27720
      - K  S  E  R  R  *  G  T  K  L  L  R  I  I  *  N  Q  K  *  A
      - N  R  K  D  D  K  E  Q  N  Y  Y  E  *  Y  K  T  K  S  E  L
      - I  G  K  T  I  R  N  K  I  I  T  N  N  I  K  P  K  V  S  F
27721 - TTAGGTCCTAGATCTTCTTGGAACATGGTTTCAGATTTGCTTGTACTTTGAAGAGTAACA - 27780
      - L  G  P  R  S  S  W  N  M  V  S  D  L  L  V  L  *  R  V  T
      - *  V  L  D  L  L  G  T  W  F  Q  I  C  L  Y  F  E  E  *  Q
      - R  S  *  I  F  L  E  H  G  F  R  F  A  C  T  L  K  S  N  K
27781 - AAACTGAACATAAAGAGATACGTCAACGTATGCGTGACATCATGTCGCGACACGTAGATT - 27840
      - K  L  N  I  K  R  Y  V  N  V  C  V  T  S  C  R  D  T  *  I
      - N  *  T  *  R  D  T  S  T  Y  A  *  H  H  V  A  T  R  R  L
      - T  E  H  K  E  I  R  Q  R  M  R  D  I  M  S  R  H  V  D  Y
27841 - ATTTGGAGTACACGAACTTCTAGGAACATTCCATGTTGTGATCCCCATTATGAATATCGT - 27900
      - I  W  S  T  R  T  S  R  N  I  P  C  C  D  P  H  Y  E  Y  R
      - F  G  V  H  E  L  L  G  T  F  H  V  V  I  P  I  M  N  I  V
      - L  E  Y  T  N  F  *  E  H  S  M  L  *  S  P  L  *  I  S  *
```

FIG. 5 Cont'd

```
27901 - GACGAACCGAAACACGAGATCCTTTCCAAAATGGAAAAGTATCTACCGTGTGATACCAAG - 27960
       - D  E  P  K  H  E  I  L  S  K  M  E  K  Y  L  P  C  D  T  K
        - T  N  R  N  T  R  S  F  P  K  W  K  S  I  Y  R  V  I  P  S
         - R  T  E  T  R  D  P  F  Q  N  G  K  V  S  T  V  *  Y  Q  V
27961 - TTTGTACGTGTGGATTACAATGATAGTTGACAGTTCTAGGTCGACCACCACGCGAATATC - 28020
       - F  V  R  V  D  Y  N  D  S  *  Q  F  *  V  D  H  H  A  N  I
        - L  Y  V  W  I  T  M  I  V  D  S  S  R  S  T  T  T  R  I  S
         - C  T  C  G  L  Q  *  *  L  T  V  L  G  R  P  P  R  E  Y  R
28021 - GATCCACAACCATGGAAGTACTTCCAGTGGTTTGACGACGTAAATCTCTGCATGAACAAC - 28080
       - D  P  Q  P  W  K  Y  F  Q  W  F  D  D  V  N  L  C  M  N  N
        - I  H  N  H  G  S  T  S  S  G  L  T  T  *  I  S  A  *  T  T
         - S  T  T  M  E  V  L  P  V  V  *  R  R  K  S  L  H  E  Q  Q
28081 - AAAATTTATTTGCTTGTTTAATTTTACAGACTATTACCTGGGGTTAGTTTGGTTGCATCA - 28140
       - K  I  Y  L  L  V  *  F  Y  R  L  L  P  G  V  S  L  V  A  S
        - K  F  I  C  L  F  N  F  T  D  Y  Y  L  G  L  V  W  L  H  H
         - N  L  F  A  C  L  I  L  Q  T  I  T  W  G  *  F  G  C  I  T
28141 - CGGGGGGCGTAATGTAAACCACCTGGGTGTCTAAGTTGACTGTTATTGGTCTTACCTCCT - 28200
       - R  G  A  *  C  K  P  P  G  C  L  S  *  L  L  L  V  L  P  P
        - G  G  R  N  V  N  H  L  G  V  *  V  D  C  Y  W  S  Y  L  L
         - G  G  V  M  *  T  T  W  V  S  K  L  T  V  I  G  L  T  S  C
28201 - GCGTTACCCCGTTCCGGTTTTGTCGCGGCTGGGGTTCCAAATGGGTTATTATGACGCAGA - 28260
       - A  L  P  R  S  G  F  V  A  A  G  V  P  N  G  L  L  *  R  R
        - R  Y  P  V  P  V  L  S  R  L  G  F  Q  M  G  Y  Y  D  A  E
         - V  T  P  F  R  F  C  R  G  W  G  S  K  W  V  I  M  T  Q  N
28261 - ACCAAGTGTCGAGAGTGAGTCGTACCGTTCCTCCTTGAATCTAAGGGAGCTCCGGTCCCG - 28320
       - T  K  C  R  E  *  V  V  P  F  L  L  E  S  K  G  A  P  V  P
        - P  S  V  E  S  E  S  Y  R  S  S  L  N  L  R  E  L  R  S  R
         - Q  V  S  R  V  S  R  T  V  P  P  *  I  *  G  S  S  G  P  A
28321 - CAAGGTTAGTTGTGGTTATCACCAGGTCTACTGGTTTAACCGATGATGGCTTCTCGATGG - 28380
       - Q  G  *  L  W  L  S  P  G  L  L  V  *  P  M  M  A  S  R  W
        - K  V  S  C  G  Y  H  Q  V  Y  W  F  N  R  *  W  L  L  D  G
         - R  L  V  V  V  I  T  R  S  T  G  L  T  D  D  G  F  S  M  G
28381 - GCTGCTCAAGCACCACCACTGCCGTTTTACTTTCTCGAGTCGGGGTCTACCATGAAGATA - 28440
       - A  A  Q  A  P  P  L  P  F  Y  F  L  E  S  G  S  T  M  K  I
        - L  L  K  H  H  H  C  R  F  T  F  S  S  R  G  L  P  *  R  *
         - C  S  S  T  T  T  A  V  L  L  S  R  V  G  V  Y  H  E  D  N
28441 - ATGGATCCTTGACCGGGTCTTCGAAGTGAAGGGATGCCGCGATTGTTTCTTCCGTAGCAT - 28500
       - M  D  P  *  P  G  L  R  S  E  G  M  P  R  L  F  L  P  *  H
        - W  I  L  D  R  V  F  E  V  K  G  C  R  D  C  F  F  R  S  I
         - G  S  L  T  G  S  S  K  *  R  D  A  A  I  V  S  S  V  A  Y
28501 - ACCCAACGTTGACTCCCTCGGAACTTATGTGGGTTTCTGGTGTAACCGTGGGCGTTAGGA - 28560
       - T  Q  R  *  L  P  R  N  L  C  G  F  L  V  *  P  W  A  L  G
        - P  N  V  D  S  L  G  T  Y  V  G  F  W  C  N  R  G  R  *  D
         - P  T  L  T  P  S  E  L  M  W  V  S  G  V  T  V  G  V  R  I
28561 - TTATTGTTACGACGGTGGCACGATGTTGAAGGAGTTCCTTGTTGTAACGGTTTTCCGAAG - 28620
       - L  L  L  R  R  W  H  D  V  E  G  V  P  C  C  N  G  F  P  K
        - Y  C  Y  D  G  G  T  M  L  K  E  F  L  V  V  T  V  F  R  R
         - I  V  T  T  V  A  R  C  *  R  S  S  L  L  *  R  F  S  E  D
28621 - ATGCGTCTCCCTTCGTCTCCGCCGTCAGTTCGGAGAAGAGCGAGGAGTAGTGCATCAGCG - 28680
       - M  R  L  P  S  S  P  S  V  R  R  R  A  R  S  S  A  S  A
        - C  V  S  L  R  L  R  R  Q  F  G  E  E  R  G  V  V  H  Q  R
         - A  S  P  F  V  S  A  V  S  S  E  K  S  E  E  *  C  I  S  A
28681 - CCATTAAGTTCTTTAAGTTGAGGACCGTCGTCATCCCCTTTAAGAGGACGAGCTTACCGA - 28740
       - P  L  S  S  L  S  *  G  P  S  S  S  P  L  R  G  R  A  Y  R
        - H  *  V  L  *  V  E  D  R  R  H  P  L  *  E  D  E  L  T  D
         - I  K  F  F  K  L  R  T  V  V  I  P  F  K  R  T  S  L  P  I
28741 - TCGCCTCCACCACTTTGACGGGAGCGCGATAACGACGATCTGTCTAACTTGGTCGAACTC - 28800
       - S  P  P  P  L  *  R  E  R  D  N  D  D  L  S  N  L  V  E  L
        - R  L  H  H  F  D  G  S  A  I  T  T  I  C  L  T  W  S  N  S
         - A  S  T  T  L  T  G  A  R  *  R  R  S  V  *  L  G  R  T  L
```

FIG. 5 Cont'd

```
28801 - TCGTTTCAAAGACCATTTCCGGTTGTTGTTGTTCCGGTTTGACAGTGATTCTTTAGACGA - 28860
       - S F Q R P F P V V V V P V * Q * F F R R
       - R F K D H F R L L L F R F D S D S L D D
       - V S K T I S G C C C S G L T V I L * T T
28861 - CGACTCCGTAGATTTTTCGGAGCGGTTTTTGCATGACGGTGTTTTGTCATGTTGCAGTGA - 28920
       - R L R R F F G A V F A * R C F V M L Q *
       - D S V D F S E R F L H D G V L S C C S E
       - T P * I F R S G F C M T V F C H V A V S
28921 - GTTCGTAAACCCTCTGCACCAGGTCTTGTTTGGGTTCCTTTAAAGCCCCTGGTTCTGGAT - 28980
       - V R K P S A P G L V W V P L K P L V L D
       - F V N P L H Q V L F G F L * S P W F W I
       - S * T L C T R S C L G S F K A P G S G L
28981 - TAGTCTGTTCCTTGACTAATGTTTGTAACCGGCGTTTAACGTGTTAAACGAGGTTCACGG - 29040
       - * S V P * L M F V T G V * R V K R G S R
       - S L F L D * C L * P A F N V L N E V H G
       - V C S L T N V C N R R L T C * T R F T E
29041 - AGACGTAAGAAACCTTACAGTGCGTAACCGTACCTTCAGTGTGGAAGCCCTTGTACCGAC - 29100
       - R R K K P Y S A * P Y L Q C G S P C T D
       - D V R N L T V R N R T F S V E A L V P T
       - T * E T L Q C V T V P S V W K P L Y R L
29101 - TGAATAGTACCTCGGTAATTTAACCTACTGTTTCTAGGTGTTAAGTTTCTGTTGCAGTAT - 29160
       - * I V P R * F N L L F L G V K F L L Q Y
       - E * Y L G N L T Y C F * V L S F C C S M
       - N S T S V I * P T V S R C * V S V A V *
29161 - GACGACTTGTTCGTGTAACTGCGTATGTTTTGTAAGGGTGGTTGTCTCGGATTTTTCCTG - 29220
       - D D L F V * L R M F C K G G C L G F F L
       - T T C S C N C V C F V R V V V S D F S C
       - R L V R V T A Y V L * G W L S R I F P V
29221 - TTTTTCTTTTTCTGACTACTTCGAGTCGGAAACGGCGTCTCTGTTTTCTTCGTCGGGTGA - 29280
       - F F F F * L L R V G N G V S V F F V G *
       - F S F S D Y F E S E T A S L F S S S G D
       - F L F L T T S S R K R R L C F L R R V T
29281 - CACTGAGAAGAAGGACGCCGACTGTACCTACTAAAGAGGTCTGTTGAAGTTTTAAGGTAC - 29340
       - H * E E G R R L Y L L K R S V E V L R Y
       - T E K K D A D C T Y * R G L L K F * G T
       - L R R R T P T V P T K E V C * S F K V L
29341 - TCACCTCGAAGACGACTAAGTTGAGTCCGTATTTGTGAGTACTACTGGTGTGTTCCGTCT - 29400
       - S P R R R L S * V R I C E Y Y W C V P S
       - H L E D D * V E S V F V S T T G V F R L
       - T S K T T K L S P Y L * V L L V C S V Y
29401 - ACCCGATACATTTGCAAAAGCGTTAAGGCAAATGCTATGTATCAGATGAGAACACGTCTT - 29460
       - T R Y I C K S V K A N A M Y Q M R T R L
       - P D T F A K A L R Q M L C I R * E H V L
       - P I H L Q K R * G K C Y V S D E N T S Y
29461 - ACTTAAGAGCATTGATTTGTCGTGTTCATCCAAATCAATTGAAATTAGAGTGTATCGTTA - 29520
       - T * E H * F V V F I Q I N * N * S V S L
       - L K S I D L S C S S K S I E I R V Y R *
       - L R A L I C R V H P N Q L K L E C I V R
29521 - GAAATTAGTTACACATTGTAATCCCTCCTGAACTTTCTCGGTGGTGTAAAAGTAGCTCCG - 29580
       - E I S Y T L * S L L N F L G G V K V A P
       - K L V T H C N P S * T F S V V * K * L R
       - N * L H I V I P P E L S R W C K S S S G
29581 - GTGCGCCTCATGCTAGCTCCCATGTCACTTATTACGATCCCTCTCGACGGATATACCTTC - 29640
       - V R L M L A P M S L I T I P L D G Y T F
       - C A S C * L P C H L L R S L S T D I P S
       - A P H A S S H V T Y Y D P S R R I Y L L
29641 - TCGGGATTACACATTTTAATTAAAATCATCACGATAGGGGTACACTAAAATTATCGAAGA - 29700
       - S G L H I L I K I I T I G V H * N Y R R
       - R D Y T F * L K S S R * G Y T K I I E E
       - G I T H F N * N H H D R G T L K L S K N
```

FIG. 5 Cont'd

```
29701 - ATCCTCTTACTGTTTTTTTTTTTTTTTTTTTTTTTT - 29736
       - I  L  L  L  F  F  F  F  F  F  F  F  X
       - S  S  Y  C  F  F  F  F  F  F  F  X
       -    P  L  T  V  F  F  F  F  F  F  X
```

FIG. 5 Cont'd

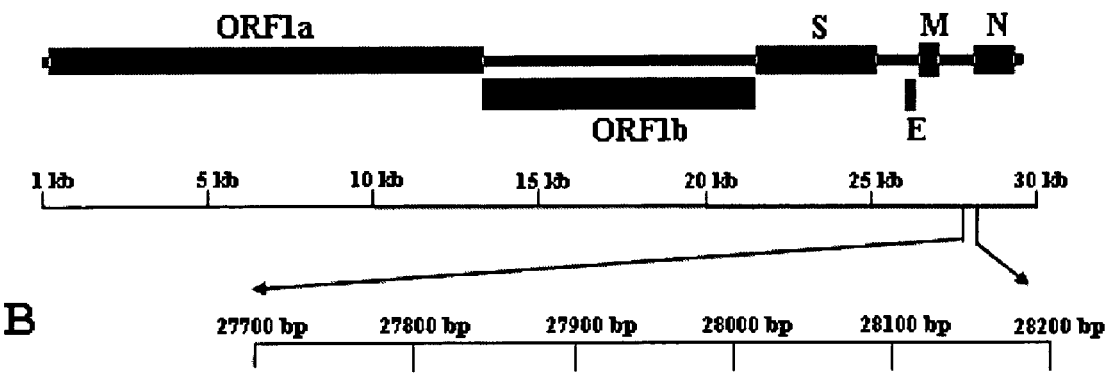
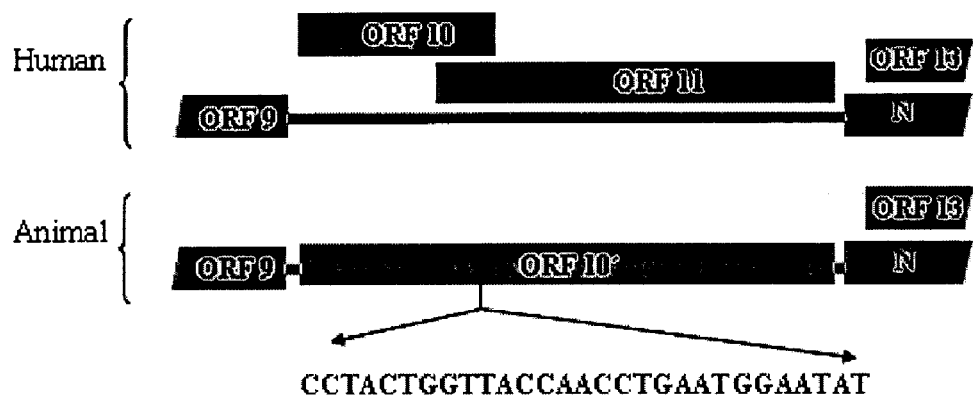

CCTACTGGTTACCAACCTGAATGGAATAT

```
         1                                                      50
ORF10   MKLLIVLTCI SLCSCICTVV QRCASNKPHV LEDPCKVQH~ ~~~~~~~~~~
ORF11   ~~~~~~~~~~ ~~~~~~~~~~ ~~~~~~~~~~ ~~~~~~~~MC LKILVRYNTR
ORF10'  MKLLIVLTCI SLCSCICTVV QRCASNKPHV LEDPCPTGYQ PEWNIRYNTR 51                                                    100
ORF10   ~~~~~~~~~~ ~~~~~~~~~~ ~~~~~~~~~~ ~~~~~~~~~~ ~~~~~~~~~~
ORF11   GNTYSTAWLC ALGKVLPFHR WHTMVQTCTP NVTINCQDPA GGALIARCWY
ORF10'  GNTYSTAWLC ALGKVLPFHR WHTMVQTCTP NVTINCQDPA GGALIARCWY 101        122
ORF10   ~~~~~~~~~~ ~~~~~~~~~~ ~~         SEQ ID NO:8
ORF11   LHEGHQTAAF RDVLVVLNKR TN         SEQ ID NO:9
ORF10'  LHEGHQTAAF RDVLVVLNKR TN         SEQ ID NO:3
```

FIG. 6

| | | | | | | | | | | | | | | | |
|---|---|---|---|---|---|---|---|---|---|---|---|---|---|---|---|
| 1 | ATG | AAA | CTT | CTC | ATT | GTT | TTG | ACT | TGT | ATT | TCT | CTA | TGC | AGT | TGC | 45 |
| 1 | M | K | L | L | I | V | L | T | C | I | S | L | C | S | C | 15 |
| 46 | ATA | CGC | ACT | GTA | GTA | CAG | CGC | TGT | GCA | TCT | AAT | AAA | CCT | CAT | GTG | 90 |
| 16 | I | R | T | V | V | Q | R | C | A | S | N | K | P | H | V | 30 |
| 91 | CTT | GAA | GAT | CCT | TGT | CCT | ACT | GGT | TAC | CAA | CCT | GAA | TGG | AAT | ATA | 135 |
| 31 | L | E | D | P | C | P | T | G | Y | Q | P | E | W | N | I | 45 |
| 136 | AGG | TAC | AAC | ACT | AGG | GGT | AAT | ACT | TAT | AGC | ACT | GCT | TGG | CTT | TGT | 180 |
| 46 | R | Y | N | T | R | G | N | T | Y | S | T | A | W | L | C | 60 |
| 181 | GCT | CTA | GGA | AAG | GTT | TTA | CCT | TTT | CAT | AGA | TGG | CAC | ACT | ATG | GTT | 225 |
| 61 | A | L | G | K | V | L | P | F | H | R | W | H | T | M | V | 75 |
| 226 | CAA | ACA | TGC | ACA | CCT | AAT | GTT | ACT | ATC | AAC | TGT | CAA | GAT | CCA | GCT | 270 |
| 76 | Q | T | C | T | P | N | V | T | I | N | C | Q | D | P | A | 90 |
| 271 | GGT | GGT | GCG | CTT | ATA | GCT | AGG | TGT | TGG | TAC | CTT | CAT | GAA | GGT | CAC | 315 |
| 91 | G | G | A | L | I | A | R | C | W | Y | L | H | E | G | H | 105 |
| 316 | CAA | ACT | GCT | GCA | TTT | AGA | GAC | GTA | CTT | GTT | GTT | TTA | ACT | AAA | CGA | 360 |
| 106 | Q | T | A | A | F | R | D | V | L | V | V | L | T | K | R | 120 |
| 361 | ACA | AAT | TAA | 369 | | | | | | | | | | | | |
| 121 | T | N | * | | | | | | | | | | | | | |

FIG. 7

ISOLATION AND CHARACTERIZATION OF THE PRECURSOR VIRUS OF HUMAN SARS VIRUS: SARS-ASSOCIATED CORONA VIRUS-LIKE VIRUS

This application claims priority benefit to U.S. provisional application No. 60/473,255 filed May 22, 2003, which is incorporated herein by reference in its entirety.

The instant application contains a lengthy Sequence Listing which is being concurrently submitted via triplicate CD-R in lieu of a printed paper copy, and is hereby incorporated by reference in its entirety. Said CD-R, recorded on May 24, 2004, are labeled "CRF", "Copy 1" and "Copy 2", respectively, and each contains only one identical 1.56 Mb file (V9661081.APP).

1. INTRODUCTION

The present invention relates to isolation and characterization of a class of isolated novel viruses which is the precursor of the virus causing Severe Acute Respiratory Syndrome (SARS) in humans ("hSARS virus"). The precursor virus which is a SARS coronavirus-like virus ("SCoV-like virus") is identified to be morphologically and phylogenetically similar to hSARS virus. The present invention relates to a nucleotide sequence comprising the genomic sequence of the SCoV-like virus. The invention further relates to nucleotide sequences comprising a portion of the genomic sequence of the SCoV-like virus. The invention also relates to the deduced amino acid sequences of the SCoV-like virus. The invention further relates to the nucleic acids and peptides encoded by and/or derived from these sequences and their use in diagnostic methods and therapeutic methods. The invention further encompasses chimeric or recombinant viruses encoded by said nucleotide sequences and antibodies directed against polypeptides encoded by the nucleotide sequences. Furthermore, the invention relates to vaccine preparations comprising the SCoV-like virus, including recombinant and chimeric forms of said virus.

2. BACKGROUND OF THE INVENTION

Recently, there has been an outbreak of a typical pneumonia in Guangdong province in mainland China. Between November 2002 and March 2003, there were 792 reported cases with 31 fatalities (WHO. Severe Acute Respiratory Syndrome (SARS) *Weekly Epidemiol Rec.* 2003; 78: 86). In response to this crisis, the Hospital Authority in Hong Kong has increased the surveillance on patients with severe atypical pneumonia. In the course of this investigation, a number of clusters of health care workers with the disease were identified. In addition, there were clusters of pneumonia incidents among persons in close contact with those infected. The disease was unusual in its severity and its progression in spite of the antibiotic treatment typical for the bacterial pathogens that are known to be commonly associated with atypical pneumonia. The disease was given the acronym Severe Acute Respiratory Syndrome ("SARS"). The virus was isolated from the patients suffering from SARS in the recent outbreak of severe atypical pneumonia in China. The isolated virus is an enveloped, single-stranded RNA virus of positive polarity which belongs to the order, Nidovirales, of the family, Coronaviridae. The hSARS virus was deposited with China Center for Type Culture Collection (CCTCC) on Apr. 2, 2003 and accorded an accession number, CCTCC-V200303, which is incorporated by reference in its entirety.

The etiologic agent responsible for this disease is a novel coronavirus known as hSARS virus. The viral genome sequence taken together with the epidemiological evidence suggest that the SARS associated coronavirus (SCoV) crossed the species barrier from animals to humans in the recent past.

3. SUMMARY OF INVENTION

The present invention is based upon the inventors' isolation and identification of a class of novel viruses which is the precursor of the virus causing Severe Acute Respiratory Syndrome in humans ("hSARS virus"). The precursor virus which is a SARS coronavirus-like virus ("SCoV-like virus") is identified to be morphologically and phylogenetically similar to hSARS virus.

An investigation was carried out in a retail live animal market in Guangdong, mainland China, the hypothetical birthplace of SARS, to better understand the animal reservoir of this virus. SCoV-like viruses were isolated from 4 of 6 Himalayan palm civets (*Paguma larvata*, Family Viverridae) and the serum from three of these animals neutralized the virus. Evidence of virus infection was also detected in a raccoon dog (*Nyctereutes procyonoides*) and Chinese ferret badger (*Melogale moschata*). Phylogenetic analysis indicates that these animal viruses have an ancestral relationship with the human SCoV with which they share genetic similarity. Sequence analysis revealed that all the animal virus isolates retain an "additional" 29 nucleotide sequence (SEQ ID NO:1) which is not found in most human virus isolates which results in the nucleotide sequence of SEQ ID NO:2 encoding a new putative protein of 122 amino acids (SEQ ID NO:3). The detection of SCoV-like viruses in small wild mammals found in live retail markets supplying the restaurant trade in Guangdong indicates how this virus may have crossed from its animal reservoir to humans. These findings are important for public health and may provide clues to understanding the inter-species transmission events relevant to the genesis of novel emerging diseases.

Accordingly, the present invention relates to a nucleotide sequence comprising the genomic sequence of the SCoV-like virus. The invention further relates to nucleotide sequences comprising a portion of the genomic sequence of the SCoV-like virus. The invention also relates to the deduced amino acid sequences of the SCoV-like virus. In specific embodiments, the invention provides a virus comprising a nucleic acid sequence of SEQ ID NO:1 or 2. In specific embodiments, the invention provides a virus comprising a nucleic acid sequence that encodes a polypeptide having an amino acid sequence of SEQ ID NO:3. The invention further relates to the nucleic acids and peptides encoded by and/or derived from these sequences. In a specific embodiment, the invention provides the isolated SCoV-like virus that morphologically and phylogenetically relates to hSARS virus and comprises the nucleotide sequence of SEQ ID NO:1 in its genome. In a preferred embodiment, the virus comprises a nucleotide sequence of SEQ ID NO:1, a portion thereof, a complement thereof, or that hybridizes to the complement of SEQ ID NO:1. In another specific embodiment, the virus preferably further comprises a nucleotide sequence of SEQ ID NO: 2, a portion thereof, a complement thereof, or portions that hybridizes to the complement of SEQ ID NO:2, in its genome. In a specific embodiment, the present invention provides isolated nucleic acid molecules comprising or, alternatively, consisting of the nucleotide sequence of SEQ ID NO:1, a complement thereof or a portion thereof, preferably at least 3, 4, 5, 6, 7, 8, 9, 10, 11, 12, 13, 14, 15, 16, 17, 18, 19, 20, 21, 22, 23, 24, 25, 26, 27, or 28 nucleotides of the nucleic acid sequence of SEQ ID NO:1. In another specific embodiment, the invention provides isolated nucleic acid molecules comprising or, alternatively, consisting of the nucleotide sequence of SEQ ID NO:2, a complement there of, or portions thereof, preferably at least, 5, 10, 15, 20, 25, 30, 35, 40, 45, 50, 60, 70, 80, 90, 100, 120, 140, 160, 180, 200, 220, 240, 260, 280, 300, 320, 340, 360, or more contiguous nucleotides of the nucleotide sequence of SEQ ID NO:2. In yet another specific embodiment, the present invention provides isolated nucleic acid molecules further comprising or, alternatively, consisting of the nucleotide sequence of SEQ ID NO:4, a complement thereof or a portion thereof, preferably at least 5, 10, 15, 20, 25, 30, 35, 40, 45, 50, 100, 150, 200, 300, 350, 400, 450, 500, 550, 600, 650, 700, 750, 800, 850, 900, 950, 1,000, 1,050, 1,100, 1,150, 1,200, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, or more contiguous nucleotides of the nucleotide sequence of SEQ ID NO:4, or a complement thereof. Furthermore, in another specific embodiment, the invention provides isolated nucleic acid molecules comprising SEQ ID NO:1 and a sequence which hybridizes under stringent conditions, as defined herein, to a nucleic acid molecule having the sequence of SEQ ID NO:4, or a complement, or a portion thereof. In one embodiment, the invention provides an isolated nucleic acid molecule which is antisense to the coding strand of a nucleic acid of the invention. In another specific embodiment, the invention provides isolated polypeptides or proteins that are encoded by a nucleic acid molecule comprising or, alternatively consisting of a nucleotide sequence that is at least 5, 10, 15, 20, 25, or 28 contiguous nucleotides of the nucleotide sequence of SEQ ID NO:1, or a complement thereof. In yet another specific embodiment, the invention provides isolated polypeptides or proteins that are encoded by a nucleic acid molecule comprising or, alternatively consisting of nucleotide sequence that is at least 5, 10, 15, 20, 25, 30, 35, 40, 45, 50, 60, 70, 80, 90, 100, 120, 140, 160, 180, 200, 220, 240, 260, 280, 300, 320, 340, 360, or more contiguous nucleotides of the nucleotide sequence of SEQ ID NO:2, or a complement thereof. In yet another specific embodiment, the invention provides isolated polypeptides or proteins that are encoded by a nucleic acid molecule comprising or, alternatively consisting of a nucleotide sequence that is at least 5, 10, 15, 20, 25, 30, 35, 40, 45, 50, 100, 150, 200, 300, 350, 400, 450, 500, 550, 600, 650, 700, 750, 800, 850, 900, 950, 1,000, 1,050, 1,100, 1,150, 1,200, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or more contiguous nucleotides of the nucleotide sequence of SEQ ID NO:4, or a complement thereof (SEQ ID NO:1102).

The invention further provides proteins or polypeptides that are isolated from the SCoV-like virus, including viral proteins isolated from cells infected with the virus but not present in comparable uninfected cells. In a specific embodiment, the polypeptide comprises the sequence of SEQ ID NO:3. The invention further provides proteins or polypeptides shown in FIG. 4 (SEQ ID NOS:12-233, 235-729 and 731-1101), 5 (SEQ ID NOS:12-233, 235-729 and 731-1101), and 7 (SEQ ID NO:3). The polypeptides or the proteins of the present invention preferably having a biological activity of the protein (including antigenicity and/or immunogenicity) encoded by the sequence of SEQ ID NO:1, 2, a portion thereof, or their complements. In other embodiments, the polypeptides or the proteins of the present invention have a biological activity of the protein (including antigenicity and/or immunogenicity) encoded by a nucleotide sequence that is at least 5, 10, 15, 20, 25, 30, 35, 40, 45, 100, 150, 200, 300, 350, 400, 450, 500, 550, 600, 650, 700, 750, 800, 850, 900, 950, 1,000, 1,050, 1,100, 1,150, 1,200, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or more contiguous nucleotides of the nucleotide sequence of SEQ ID NO:4, or a complement thereof (SEQ ID NO:1102).

In one aspect, the invention provides a method for propagating the SCoV-like virus in host cells comprising infecting the host cells with the isolated SCoV-like virus, culturing the host cells to allow the virus to multiply, and harvesting the resulting virions. Also provided by the present invention are host cells that are infected with the SCoV-like virus. In specific embodiments, the host cells are from animals for example, but not limited to, feline, canine, palm civet, raccoon-dog, or ferret badger. In another aspect, the invention relates to the use of the isolated SCo-V-like virus for diagnostic and therapeutic methods. In a specific embodiment, the invention provides a method of detecting in a biological sample an antibody immunospecific for the SCoV-like virus using the isolated SCoV-like virus or any proteins or polypeptides thereof. In another specific embodiment, the invention provides a method of screening for an antibody which immunospecifically binds and neutralizes SCoV-like viruses. Such an antibody is useful for a passive immunization or immunotherapy of a subject infected with a SCoV-like virus.

The invention further relates to the use of the sequence information of the isolated virus for diagnostic and therapeutic methods. In a specific embodiment, the invention provides nucleic acid molecules which are suitable for use as primers consisting of or comprising the nucleotide sequence of SEQ ID NO:1, 2, 4, or a complement thereof, or at least a portion of the nucleotide sequence thereof. In another specific embodiment, the invention provides nucleic acid molecules which are suitable for hybridization to SCoV-like viral nucleic acid, including, but not limited to, as PCR primers, Reverse Transcriptase primers, probes for Southern analysis or other nucleic acid hybridization analysis for the detection of SCo-V-like nucleic acids, e.g., consisting of or comprising the nucleotide sequence of SEQ ID NO:1, 2, 4, or a complement thereof, or a portion thereof. The invention further encompasses chimeric or recombinant viruses encoded in whole or in part by said nucleotide sequences.

The invention further provides antibodies that specifically bind a polypeptide of the invention encoded by the nucleotide sequence of SEQ ID NO:1, 2, 4, or a fragment thereof, or encoded by a nucleic acid comprising a nucleotide sequence that hybridizes under stringent conditions to the nucleotide sequence of SEQ ID NO:1, 2, or 4, and/or any SCoV-like viral epitope, having one or more biological activities of a polypeptide of the invention. These polypeptides include those shown in FIG. 4 (SEQ ID NOS:12-233, 235-729 and 731-1101), 5 (SEQ ID NOS:1103-1583, 1585-1958 and 1960-2464), and 7 (SEQ ID NO:3). The invention further provides antibodies that specifically bind polypeptides of the invention encoded by a nucleic acid comprising a nucleotide sequence that hybridizes under stringent conditions to the nucleotide sequence of SEQ ID NO:1, 2, or 4, and/or any SCoV-like viral epitope, having one or more biological activities of a polypeptide of the invention. Such antibodies include, but are not limited to polyclonal, monoclonal, bi-specific, multi-specific, human, humanized, chimeric antibodies, single chain antibodies, Fab fragments, F(ab')$_2$ fragments, disulfide-linked Fvs, intrabodies and fragments containing either a VL or VH domain or even a complementary determining region (CDR) that specifically binds to a polypeptide of the invention.

In one embodiment, the invention provides methods for detecting the presence, activity or expression of the SCoV-like virus of the invention in a biological material, such as cells, blood, sputum, stool, saliva, urine, and so forth. The increased or decreased activity or expression of the SCoV-like virus in a sample relative to a control sample can be determined by contacting the biological material with an agent which can detect directly or indirectly the presence, activity or expression of the SCoV-like virus. In a specific embodiment, the detecting agents are the antibodies or nucleic acid molecules of the present invention.

In another embodiment, the invention provides vaccine preparations, comprising the SCoV-like virus, including recombinant and chimeric forms of said virus, or protein subunits of the virus. In a specific embodiment, the vaccine preparations of the present invention comprise live but attenuated SCoV-like virus with or without adjuvants. In another specific embodiment, the vaccine preparations of the invention comprise an inactivated or killed SCoV-like virus. Such attenuated or inactivated viruses may be prepared by a series of passages of the virus through the host cells or by preparing recombinant or chimeric forms of virus. Accordingly, the present invention further provides methods of preparing recombinant or chimeric forms of SCoV-like virus. In another specific invention, the vaccine preparations of the present invention comprise a nucleic acid or fragment of the SCoV-like virus, e.g., the virus having nucleic acid molecules having the sequence of SEQ ID NO. 1, 2, 4, or a fragment thereof, or a complement thereof. In another embodiment, the invention provides vaccine preparations comprising one or more polypeptides isolated from or produced from nucleic acid of SCoV-like virus. In a specific embodiment, the vaccine preparations comprise a polypeptide of the invention encoded by the nucleotide sequence of SEQ ID NO:1, 2, 4, or a fragment thereof. In a specific embodiment, the vaccine preparations comprise polypeptides of the invention as shown in FIG. 4 (SEQ ID NOS: 12-233, 235-729 and 731-1101), 5 (SEQ ID NOS:1103-1583, 1585-1958 and 1960-2464), or 7 (SEQ ID NO:3).

In another aspect, the present invention provides pharmaceutical compositions comprising anti-viral agents of the present invention and a pharmaceutically acceptable carrier. In a specific embodiment, the anti-viral agent of the invention is an antibody that immunospecifically binds SCoV-like virus or any SCoV-like viral epitope. In another specific embodiment, the anti-viral agent is a polypeptide or protein of the present invention or nucleic acid molecule of the invention. The invention also provides kits containing a pharmaceutical composition of the present invention.

3.1 Definitions

The term "an antibody or an antibody fragment that immunospecifically binds a polypeptide of the invention" as used herein refers to an antibody or a fragment thereof that immunospecifically binds to the polypeptide encoded by the nucleotide sequence of the invention, or a fragment thereof, and does not non-specifically bind to other polypeptides. An antibody or a fragment thereof that immunospecifically binds to the polypeptide of the invention may cross-react with other antigens. Preferably, an antibody or a fragment thereof that immunospecifically binds to a polypeptide of the invention does not cross-react with other antigens. An antibody or a fragment thereof that immunospecifically binds to the polypeptide of the invention, can be identified by, for example, immunoassays or other techniques known to those skilled in the art.

An "isolated" or "purified" or "cloned" peptide or protein is substantially free of cellular material or other contaminating proteins from the cell or tissue source from which the protein is derived, or substantially free of chemical precursors or other chemicals when chemically synthesized. The language "substantially free of cellular material" includes preparations of a polypeptide/protein in which the polypeptide/protein is separated from cellular components of the cells from which it is isolated or recombinantly produced. Thus, a polypeptide/protein that is substantially free of cellular material includes preparations of the polypeptide/protein having less than about 30%, 20%, 10%, 5%, 2.5%, or 1%, (by dry weight) of contaminating protein. When the polypeptide/protein is recombinantly produced, it is also preferably substantially free of culture medium, i.e., culture medium represents less than about 20%, 10%, or 5% of the volume of the protein preparation. When polypeptide/protein is produced by chemical synthesis, it is preferably substantially free of chemical precursors or other chemicals, i.e., it is separated from chemical precursors or other chemicals which are involved in the synthesis of the protein. Accordingly, such preparations of the polypeptide/protein have less than about 30%, 20%, 10%, 5% (by dry weight) of chemical precursors or compounds other than polypeptide/protein fragment of interest. In a preferred embodiment of the present invention, polypeptides/proteins are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a preferred embodiment of the invention, nucleic acid molecules encoding polypeptides/proteins of the invention are isolated or purified. The term "isolated" nucleic acid molecule does not include a nucleic acid that is a member of a library that has not been purified away from other library clones containing other nucleic acid molecules.

The term "portion" or "fragment" as used herein refers to a fragment of a nucleic acid molecule containing at least about 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 100, 150, 200, 250, 300, 350, 400, 450, 500, 550, 600, 650, 700, 750, 800, 850, 900, 950, 1000, 1050, 1100, 1150, 1200, 1250, 1300, 1350, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, or more contiguous nucleic acids in length of the relevant nucleic acid molecule and having at least one functional feature of the nucleic acid molecule (or the encoded protein has one functional feature of the protein encoded by the nucleic acid molecule); or a fragment of a protein or a polypeptide containing at least 5, 10, 15, 20, 25, 30, 35, 40, 45, 50, 55, 60, 65, 70, 75, 80, 90, 100, 120, 140, 160, 180, 200, 220, 240, 260, 280, 300, 320, 340, 360, 400, 500, 600, 700, 800, 900, 1,000, 1,500, 2,000, 2,500, 3,000, 3,500, 4,000, 4,100, 4,200, 4,300, 4,350, 4,360, 4,370, 4,380 amino acid residues in length of the relevant protein or polypeptide and having at least one functional feature of the protein or polypeptide.

The term "having a biological activity of the protein" or "having biological activities of the polypeptides of the invention" refers to the characteristics of the polypeptides or proteins having a common biological activity similar or identical structural domain and/or having sufficient amino acid identity to the polypeptide encoded by the nucleic acid of the present invention. Such common biological activities of the polypeptides of the invention include antigenicity and immunogenicity.

The term "under stringent condition" refers to hybridization and washing conditions under which nucleotide sequences having at least 70%, at least 75%, at least 80%, at least 85%, at least 90%, or at least 95% identity to each other remain hybridized to each other. Such hybridization conditions are described in, for example but not limited to, Current Protocols in Molecular Biology, John Wiley & Sons, N.Y. (1989), 6.3.1-6.3.6.; Basic Methods in Molecular Biology, Elsevier Science Publishing Co., Inc., N.Y. (1986), pp. 75-78, and 84-87; and Molecular Cloning, Cold Spring Harbor Laboratory, N.Y. (1982), pp. 387-389, and are well known to those skilled in the art. A preferred, non-limiting example of stringent hybridization conditions is hybridization in 6× sodium chloride/sodium citrate (SSC), 0.5% SDS at about 68° C. followed by one or more washes (e.g., about 5 to 30 min each) in 2×SSC, 0.5% SDS at room temperature. Another preferred, non-limiting example of stringent hybridization conditions is hybridization in 6×SSC at about 45° C. followed by one or more washes (e.g., about 5 to 30 min each) in 0.2×SSC, 0.1% SDS at about 50-65° C.

The term "variant" as used herein refers either to a naturally occurring genetic mutant of SCoV-like virus or a recombinantly prepared variation of SCoV-like virus each of which contain one or more mutations in its genome compared to the hSARS virus. The term "variant" may also refers either to a naturally occurring variation of a given peptide or a recombinantly prepared variation of a given peptide or protein in which one or more amino acid residues have been modified by amino acid substitution, addition, or deletion.

4. BRIEF DESCRIPTION OF FIGURES

FIGS. 1A and B show the characteristics of animal SARS-CoV-like virus grown in FRhK-4 cells. (A) shows a negatively stained (potassium phosphotungstate, 2%) preparations of an animal virus isolate showing particles with club-shaped spikes surrounding the periphery of the particles. (B) shows a thin-section electron microscope view of the viral particles growing inside a cell (FRhK-4) and released through cell membrane.

FIG. 2 shows the additional 29 nucleotides (SEQ ID NO:1) found in animal SCoV-like virus.

FIG. 3 shows the entire genomic DNA sequence (SEQ ID NO:4) of the SARS virus deposited in GenBank with accession number AY278554.

FIG. 4 shows the deduced amino acid sequences (SEQ ID NOS:12-233, 235-729 and 731-1101) obtained from SEQ ID NO:4 in three frames. An asterisk (*) indicates a stop codon which marks the end of a peptide.

FIG. 5 shows the deduced amino acid sequences obtained from the complement (SEQ ID NO:1102) of SEQ ID NO:4 in three frames. An asterisk (*) indicates a stop codon which marks the end of a peptide.

FIG. 6 shows the genomic organization of human and animal SCoV-like viruses. (A) Genetic organization of SCoV-like viruses found in humans and animals. ORFs 1a and 1b, encoding the nonstructural polyproteins, and those encoding the S, E, M, and N structural proteins are indicated. (B) Expanded view of the SCoV genomic sequence (27700 nt to 28200 nt, based on AY278554 numbering). ORFs for putative proteins (9-11 and 13) and for N in human isolates are indicated (Peiris et al., 2003, *Lancet* 361:1319; Zhong et al., 2003, *Lancet* 362:1353). An extra 29 nucleotide sequence is present down-stream of the nucleotide of 27868 (based on AY278554 numbering) of the animal SCoV. The presence of this 29 nt sequence in animal isolates results in fusing the ORFs 10 (SEQ ID NO:8) and 11 (SEQ ID NO:9) (upper panel) into a new ORF (lower panel; ORF10'; SEQ ID NO:3). (C) Protein sequence alignment of ORF10 and 11 from human isolates and ORF 10' from animal isolates (SCoV-like virus strain SZ3, AY304486).

FIG. 7 shows the nucleotide sequence (SEQ ID NO:2) and its deduced amino acid sequence (SEQ ID NO:3) of a portion of the genome of SCoV-like virus (strain SZ3, AY304486) comprising SEQ ID NO:1, which is the additional 29 nucleotide residues not found in hSARS virus, resulting in encoding a new putative protein of 122 amino acids (SEQ ID NO:3).

Figure 8:
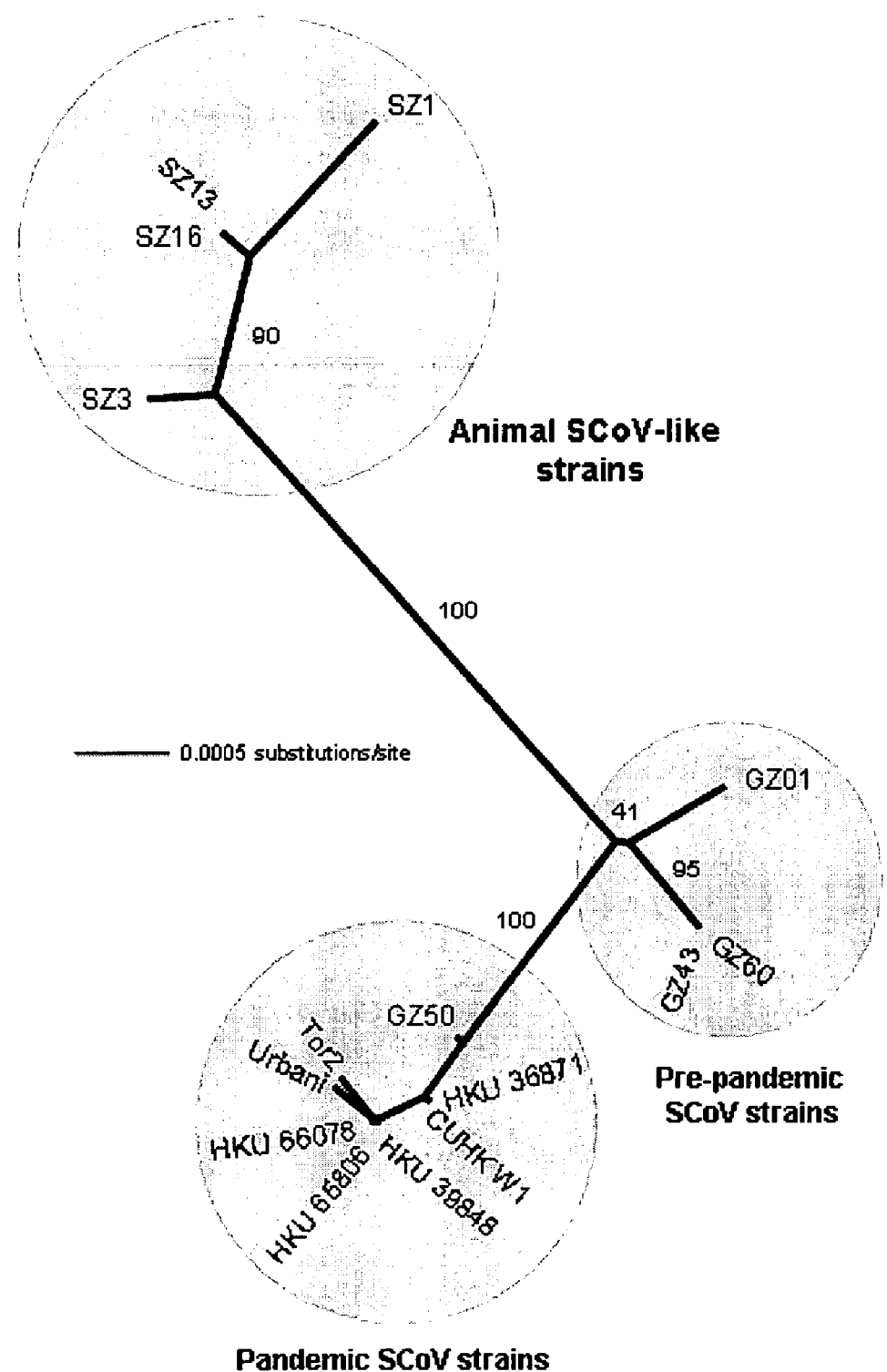

FIG. 8 shows a phylogenetic analysis of a partial nucleotide acid sequence of spike gene of SCoV-like viruses. An unrooted phylogram derived from the partial nucleotide sequence of representative SCoV S genes (S coding region residue 344 to 3765, 3422 bp). Multiple sequence alignments were done using Clustal X 1.81 and trees generated using Neighbor-Joining algorithms within PAUP 4.0b10. Bootstrap scores are percentages out of 1000 replicates. Similar tree topologies were seen with Maximum Parsimony analysis (data not shown). Except for the viruses sequenced in current study, the other sequences used in the analysis could be found in GenBank with accession number: AY278741, AY278554, AY278491, AY274119, and AY278489, all of which are incorporated by reference in their entirety.

5. DETAILED DESCRIPTION OF THE INVENTION

Severe acute respiratory syndrome (SARS) is a recently emerged human disease associated with pneumonia. This disease was first recognized in Guangdong Province, China in November 2002. Subsequent to its introduction to Hong Kong in mid February 2003, the virus spread to more than 28 countries causing disease in over 7,900 patients across 5 continents. The disease is unusual in its predilection to affect health care workers. A novel coronavirus (SCoV) was identified as the etiological agent of SARS (Peiris et al., 2003, *Lancet* 361:1319; Ksiazek et al., 2003, *N. Engl. J. Med.* 348:1953) and the virus causes a similar disease in cynomolgous macaques. Fouchier et al., 2003, *Nature* 423:240. While the majority of patients with SARS seroconvert to SCoV, patients with other respiratory disease and healthy blood donors had no detectable antibody. Peiris et al., 2003, *Lancet* 361:1319; Zhong et al., 2003, *Lancet* 362:1353). These results suggest that the human SCoV is an animal virus that crossed to humans relatively recently. Thus, identifying the animal reservoir is of major scientific interest as well as public health importance. A range of domestic and wild mammals in Guangdong Province were examined.

The present invention is based upon the inventor's isolation and identification of a class of novel viruses which is the precursor of the virus causing Severe Acute Respiratory Syndrome in humans ("hSARS virus"). The precursor virus which is a SARS coronavirus-like virus ("SCoV-like virus") is identified to be morphologically and phylogenetically similar to hSARS virus.

An investigation was carried out in a retail live animal market in Guangdong, mainland China, the hypothetical birthplace of SARS, to better understand the animal reservoir of this virus. SCoV-like coronaviruses were isolated from 4 of 6 Himalayan palm civets (*Paguma larvata*, Family Viverridae) and the serum from one of these animals neutralized the virus. Phylogenetic analysis indicates that these animal viruses have an ancestral relationship with the human SCoV with which they share genetic similarity. Sequence analysis revealed that all the animal virus isolates retain an "additional" 29 nucleotide residues which are not found in most human virus isolates which results in encoding a new putative protein of 122 amino acids. These 29 nucleotide residues are inserted at the nucleotide position corresponding to 27859 of GenBank accession no: AY278554 or 27874 of AY274119. The detection of SCoV-like viruses in small wild mammals found in live retail markets supplying the restaurant trade in Guangdong indicates how this virus may have crossed from its animal reservoir to humans. These findings are important for public health and may provide clues to understanding the inter-species transmission events relevant to the genesis of novel emerging diseases.

Accordingly, the present invention relates to a nucleotide sequence comprising the genomic sequence of the SCoV-like virus. The invention further relates to nucleotide sequences comprising a portion of the genomic sequence of the SCoV-like virus. The invention also relates to the deduced amino acid sequences of the SCoV-like virus. The invention further relates to the nucleic acids and peptides encoded by and/or derived from these sequences. In a specific embodiment, the invention provides the isolated SCoV-like virus that morphologically and phylogenetically relates to hSARS virus and comprises the nucleotide sequence of SEQ ID NO:1 in its genome. In another embodiment, the virus comprises a nucleotide sequence of SEQ ID NO:2. In another embodiment, the virus comprises a nucleotide sequence that encodes an amino acid sequence of SEQ ID NO:3. In a preferred embodiment, the virus comprises a nucleotide sequence of SEQ ID NO:1. In another specific embodiment, the virus preferably further comprises a nucleotide sequence of SEQ ID NO:2, portions thereof, or portions that hybridizes to the complement of SEQ ID NO:2, in its genome. In a specific embodiment, the present invention provides isolated nucleic acid molecules comprising or, alternatively, consisting of the nucleotide sequence of SEQ ID NO:1, a complement thereof or a portion thereof, preferably at least 3, 4, 5, 6, 7, 8, 9, 10, 11, 12, 13, 14, 15, 16, 17, 18, 19, 20, 21, 22, 23, 24, 25, 26, 27, or 28 nucleotides of the nucleic acid sequence of SEQ ID NO:1. In another specific embodiment, the present invention provides isolated nucleic acid molecules comprising or, alternatively, consisting of the nucleotide sequence of SEQ ID NO:2, a complement thereof or a portion thereof, preferably at least 5, 10, 15, 20, 25, 30, 35, 40, 45, 50, 60, 70, 80, 90, 100, 120, 140, 160, 180, 200, 220, 240, 260, 280, 300, 320, 340, 360, or more contiguous nucleotides of the nucleotide sequence of SEQ ID NO:2, or a complement thereof. In yet another specific embodiment, the present invention provides isolated nucleic acid molecules further comprising or, alternatively, consisting of the nucleotide sequence of SEQ ID NO:4, a complement thereof or a portion thereof, preferably at least 5, 10, 15, 20, 25, 30, 35, 40, 45, 100, 150, 200, 300, 350, 400, 450, 500, 550, 600, 650, 700, 750, 800, 850, 900, 950, 1,000, 1,050, 1,100, 1,150, 1,200, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, or more contiguous nucleotides of the nucleotide sequence of SEQ ID NO:4, or a complement thereof. Furthermore, in another specific embodiment, the invention provides isolated nucleic acid molecules which hybridize under stringent conditions, as defined herein, to a nucleic acid molecule having the sequence of SEQ ID NO:1, 2, 4, or a complement, or a portion thereof. In one embodiment, the invention provides an isolated nucleic acid molecule which is antisense to the coding strand of a nucleic acid of the invention. In another specific embodiment, the invention provides isolated polypeptides or proteins that are encoded by a nucleic acid molecule comprising or, alternatively consisting of a nucleotide sequence that is at least 5, 10, 15, 20, 25, or 28 contiguous nucleotides of the nucleotide sequence of SEQ ID NO:1, or a complement thereof. In another specific embodiment, the invention provides isolated polypeptides or proteins that are encoded by a nucleic acid molecule comprising or, alternatively consisting of a nucleotide sequence that is at least 5, 10, 15, 20, 25, 30, 35, 40, 45, 50, 60, 70, 80, 90, 100, 120, 140, 160, 180, 200, 220, 240, 260, 280, 300, 320, 340, 360, or more contiguous nucleotides of the nucleotide sequence of SEQ ID NO:2, or a complement thereof. In yet another specific embodiment, the invention provides isolated polypeptides or proteins that are encoded by a nucleic acid molecule comprising or, alternatively consisting of a nucleotide sequence that is at least 5, 10, 15, 20, 25, 30, 35, 40, 45, 100, 150, 200, 300, 350, 400, 450, 500, 550, 600, 650, 700, 750, 800, 850, 900, 950, 1,000, 1,050, 1,100, 1,150, 1,200, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or more contiguous nucleotides of the nucleotide sequence of SEQ ID NO:4, or a complement thereof.

The invention further provides proteins or polypeptides that are isolated from the SCoV-like virus, including viral proteins isolated from cells infected with the virus but not present in comparable uninfected cells. Specifically, the protein comprises the amino acid sequence of SEQ ID NO:3 or encoded by the nucleic acid of SEQ ID NO:2. The invention further provides proteins or polypeptides shown in FIG. 4 (SEQ ID NOS:12-233, 235-729 and 731-1101) and 5 (SEQ ID NOS:1103-1583, 1585-1958 and 1960-2464). The polypeptides or the proteins of the present invention preferably have a biological activity of the protein (including antigenicity and/or immunogenicity) encoded by the sequence of SEQ ID NO:1, 2, or a portion thereof, or their complements. In other embodiments, the polypeptides or the proteins of the present invention have a biological activity of the protein (including antigenicity and/or immunogenicity) encoded by a nucleotide sequence that is at least 5, 10, 15, 20, 25, 30, 35, 40, 45, 100, 150, 200, 300, 350, 400, 450, 500, 550, 600, 650, 700, 750, 800, 850, 900, 950, 1,000, 1,050, 1,100, 1,150, 1,200, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or more contiguous nucleotides of the nucleotide sequence of SEQ ID NO:4, or a complement thereof.

In one aspect, the invention provides a method for propagating the SCoV-like virus in host cells comprising infecting the host cells with the isolated SCoV-like virus, culturing the host cells to allow the virus to multiply, and harvesting the resulting virions. Also provide by the present invention are host cells that are infected with the SCoV-like virus. In another aspect, the invention relates to the use of the isolated SCoV-like virus for diagnostic and therapeutic methods. In a specific embodiment, the invention provides a method of detecting in a biological sample an antibody immunospecific for the SCoV-like virus using the isolated SCoV-like virus or any proteins or polypeptides thereof. In another specific embodiment, the invention provides a method of screening for an antibody which immunospecifically binds and neutralizes SCoV-like virus. Such an antibody is useful for a passive immunization or immunotherapy of a subject infected with SCoV-like virus.

The invention further relates to the use of the sequence information of the isolated virus for diagnostic and therapeutic methods. In a specific embodiment, the invention provides nucleic acid molecules which are suitable for use as primers consisting of or comprising the nucleotide sequence of SEQ ID NO:1, 2, 4, or a complement thereof, or at least a portion of the nucleotide sequence thereof. In another specific embodiment, the invention provides nucleic acid molecules which are suitable for hybridization to SCoV-like nucleic acid, including, but not limited to, as PCR primers, Reverse Transcriptase primers, probes for Southern analysis or other nucleic acid hybridization analysis for the detection of SCo-V-like nucleic acids, e.g., consisting of or comprising the nucleotide sequence of SEQ ID NO:1, 2, 4, or a complement thereof, or a portion thereof. The invention further encompasses chimeric or recombinant viruses encoded in whole or in part by said nucleotide sequences.

The invention further provides antibodies that specifically bind a polypeptide of the invention encoded by the nucleotide sequence of SEQ ID NO:1, 2, or 4, or a fragment thereof, or encoded by a nucleic acid comprising a nucleotide sequence that hybridizes under stringent conditions to the nucleotide sequence of SEQ ID NO:1, 2, or 4, and/or any SCoV-like viral epitope, having one or more biological activities of a polypeptide of the invention. The invention further provides antibodies that specifically bind polypeptides of the invention encoded by the nucleotide sequence of SEQ ID NO:1, 2, or 4, or a fragment thereof. These polypeptides include those shown in FIGS. 4, 5 and 7. The invention further provides antibodies that specifically bind polypeptides of the invention encoded by a nucleic acid comprising a nucleotide sequence that hybridizes under stringent conditions to the nucleotide sequence of SEQ ID NO:1, 2, 4, and/or any SCo-V viral epitope, having one or more biological activities of a polypeptide of the invention. Such antibodies include, but are not limited to polyclonal, monoclonal, bi-specific, multi-specific, human, humanized, chimeric antibodies, single chain antibodies, Fab fragments, $F(ab')_2$ fragments, disulfide-linked Fvs, intrabodies and fragments containing either a VL or VH domain or even a complementary determining region (CDR) that specifically binds to a polypeptide of the invention.

In one embodiment, the invention provides methods for detecting the presence, activity or expression of the SCoV-like virus of the invention in a biological material, such as cells, blood, sputum, stool, saliva, urine, and so forth. The increased or decreased activity or expression of the SCoV-like virus in a sample relative to a control sample can be determined by contacting the biological material with an agent which can detect directly or indirectly the presence, activity or expression of the SCoV-like virus. In a specific embodiment, the detecting agents are the antibodies or nucleic acid molecules of the present invention.

In another embodiment, the invention provides vaccine preparations, comprising the SCoV-like virus, including recombinant and chimeric forms of said virus, or protein subunits of the virus. In a specific embodiment, the vaccine preparations of the present invention comprise live but attenuated SCoV-like virus with or without adjuvants. In another specific embodiment, the vaccine preparations of the invention comprise an inactivated or killed SCoV-like virus. Such attenuated or inactivated viruses may be prepared by a series of passages of the virus through the host cells or by preparing recombinant or chimeric forms of virus. Accordingly, the present invention further provides methods of preparing recombinant or chimeric forms of SCoV-like virus. In another specific invention, the vaccine preparations of the present invention comprise a nucleic acid or fragment of the SCoV-like virus, e.g., the virus having nucleic acid molecules having the sequence of SEQ ID NO. 1, 2, 4, or a fragment thereof. In another embodiment, the invention provides vaccine preparations comprising one or more polypeptides isolated from or produced from nucleic acid of SCoV-like virus. In a specific embodiment, the vaccine preparations comprise a polypeptide of the invention encoded by the nucleotide sequence of SEQ ID NO:1, 2, 4, or a fragment thereof. In a specific embodiment, the vaccine preparations comprise polypeptides of the invention as shown in FIG. 4, 5, or 7.

In another aspect, the present invention provides pharmaceutical compositions comprising anti-viral agents of the present invention and a pharmaceutically acceptable carrier. In a specific embodiment, the anti-viral agent of the invention is an antibody that immunospecifically binds SCoV-like virus or any SCoV-like viral epitope. In another specific embodiment, the anti-viral agent is a polypeptide or protein of the present invention or nucleic acid molecule of the invention. The invention also provides kits containing a pharmaceutical composition of the present invention.

Since the early cases of SARS in Guangdong reportedly occurred in restaurant workers handling wild mammals as exotic food (Zhong et al., 2003, *Lancet* 362:1353). A live animal retail market in Shenzhen was investigated. Animals were held, one per cage, in small wire cages. The animals sampled included seven wild, and one domestic animal species (Table 1). They originated from different regions of southern China and had been kept in separate storehouses before arrival to the market. The animals remain in the markets for a variable period of time and each stall holder has only a few animals of a given species. Animals from a different stalls within the market were sampled. Nasal and fecal swabs were collected and stored in viral transport medium. Where possible, blood samples were collected for serology. Prior to sampling, all animals were examined by a veterinary surgeon and confirmed to be free of overt disease.

Figures 1A, 1B:
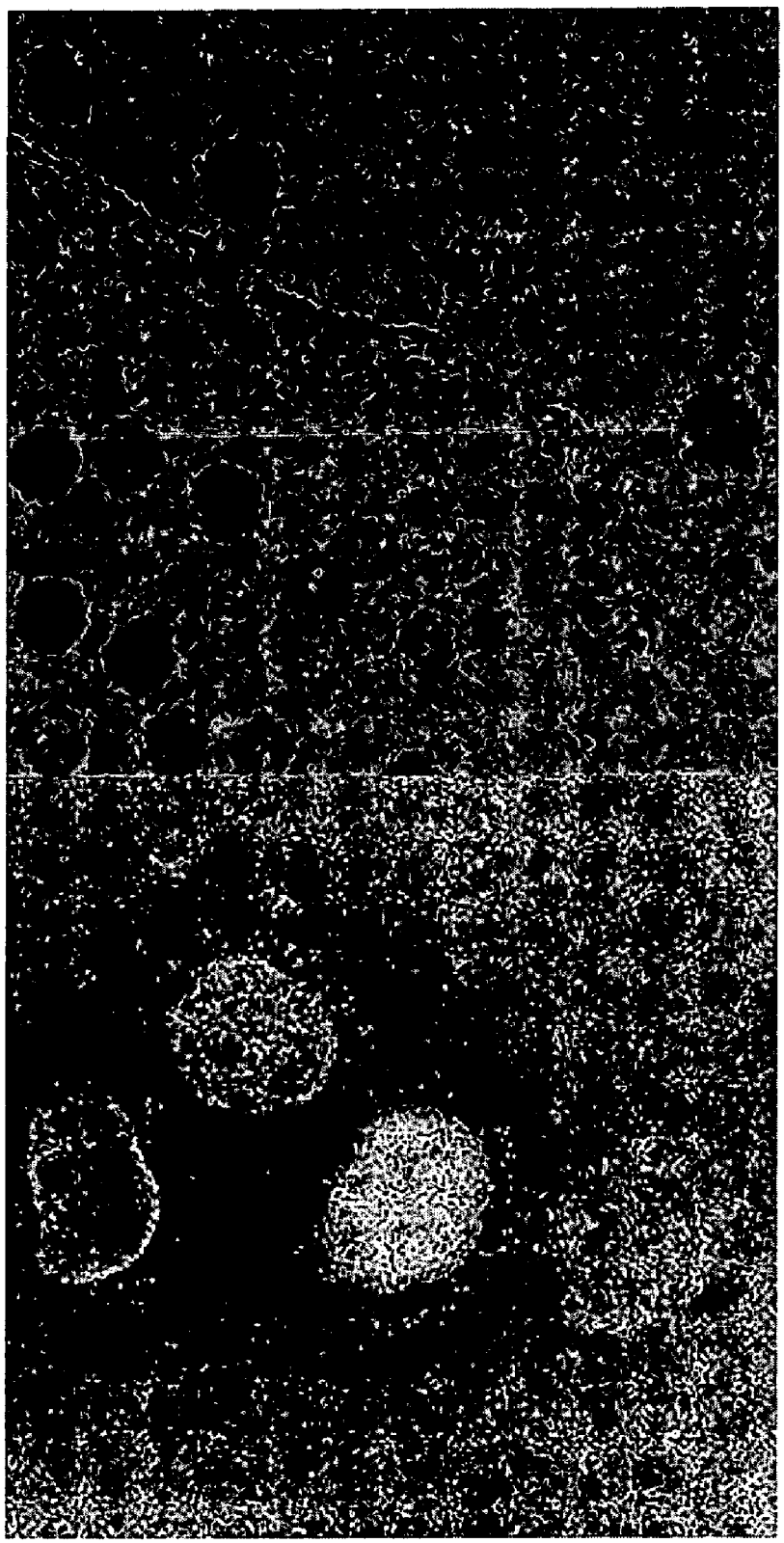

Nasal and fecal swabs were obtained from 25 animals and tested for SCoV viral nucleic acid using RT-PCR for the N gene of the hSARS. Swabs from 4 of 6 Himalayan palm civets were positive in the RT-PCR assay (Table 1). All specimens were inoculated on to FRhk-4 cells as previously described for virus isolation (Peiris et al., 2003, Lancet 361:1319). Cytopathic effect was observed in infected cells after 2-3 days post-infection specimens from 4 Himalayan palm civets (*Paguma larvata*), two of whom were also RT-PCR positive. Thus there was either RT-PCR or culture evidence of a virus in all 6 civets tested (Table 1). A virus was also detected by virus isolation and direct RT-PCR from the fecal swab of a Racoon-dog (*Nyctereutes procyonoides*). No virus was detectable in 6 other species sampled. Electron microscopy of one infected cell supernatant (SZ16N) showed viral particles with a morphology comparable to a coronavirus (FIG. 1) and all the virus isolates were confirmed to be SCoV-like viruses by RT-PCR and direct sequencing of the PCR product. Sera from three animals had neutralizing antibody to the animal coronavirus; these were from a palm civet, Racoon-dog and a Chinese ferret badger, respectively.

TABLE 1

Animal types tested and coronavirus detection

| Sample number | Animal type (Species) | Virus detection RT-PCR detection Nasal | Virus detection RT-PCR detection Fecal | Virus detection Isolation Nasal | Virus detection Isolation Fecal | Neutralizing antibody titer to SZ16 |
|---|---|---|---|---|---|---|
| SZ1 | HPC | + | + | | | <20 |
| SZ2 | HPC | + | + | | | <20 |
| SZ3 | HPC | + | + | + | | <20 |
| SZ4 | HB | | | | | <20 |
| SZ5 | B | | | | | <20 |
| SZ6 | DC | | | | | <20 |
| SZ7 | DC | | | | | <20 |
| SZ8 | CH | | | | | <20 |
| SZ9 | CH | | | | | <20 |
| SZ10 | CM | | | | | <20 |
| SZ11 | CFB | | | | | 160 |
| SZ12 | CFB | | | | | <20 |
| SZ13 | RD | | + | | + | ≧640 |
| SZ14 | CM | | | | | <20 |
| SZ15 | B | | | | | <20 |
| SZ16 | HPC | + | + | + | + | <20 |
| SZ17 | HPC | | + | | | ≧640 |
| SZ18 | B | | | | | <20 |
| SZ19 | CH | | | | | <20 |
| SZ20 | CH | | | | | <20 |
| SZ21 | DC | | | | | <20 |
| SZ22 | DC | | | | | <20 |
| SZ23 | HB | | | | | <20 |
| SZ24 | HB | | | | | <20 |
| SZ25 | HPC | | | | + | <20 |

Abbreviation of animal species: HPC, Himalayan palm civet (*Paguma larvata*); HB, Hog-badger (*Arctonyx collaris*); RD, Racoon-dog (*Nyctereutes procyonoides*); B, Beaver (Castor fiber); CM, Chinese muntjac (*Muntiacus reevesi*); DC, Domestic cat (*Felis catus*); CH, Chinese Hare (*Lepus sinensis*); CFB, Chinese Ferret-Badger (*Melogale moschata*) [China species information system provided at the web site of Wildlife Conservation Society (WCS) and Institute of Zoology].

+ positive by RT-PCR or virus isolation, * the PCR product or virus isolates being sequenced.

Two of the virus isolates (SZ3N and SZ16N) isolated from the nasal swabs of palm civets were completely sequenced and the amino acid sequence deduced. Two other viruses were partially sequenced, from the S gene onward to the 3' end of the virus. The full-length genome sequences had 99.8% homology to the human SCoV indicating the human and animal SCoV-like viruses were closely related. Phylogenetic analysis of the S gene of both human and animal SCoV-like viruses indicated that the animal viruses are separate from the human virus cluster (FIG. 8). However, the viruses SZ1, SZ3 and SZ16 from palm civets were not clonally related (FIG. 8). The viruses SZ3 and SZ16 had 18 nucleotide differences between them over the 29,709 base pair genome while the human SCoV cluster of 5 geographically separated human viruses (GZ50, CUHK-W1, Tor-2, HKU-39848 and Urbani, FIG. 7) differed by only 14 nucleotides. On the other hand, animal viruses SZ13 (Racoon-dog) and SZ16 (palm civet) were genetically almost identical.

When viruses in the human and animal groups are compared, 72 to 86 nucleotide differences were observed over the whole virus genome, many of them scattered across the whole genome. However, there were 19 consistent nucleotide differences between animal and human viruses localized in the S (Table 2) and M genes, 15 of them being non-synonymous mutations. Interestingly, some of the human virus isolates (e.g. GZ43 and GZ60) share some of the amino acid residues (positions 22192, 23470 and 23808, based on AY278554 numbering) with animal viruses (Table 2) suggesting that the human viruses isolated during the early phase of the SARS outbreak retained some of the "signatures" of the animal precursor.

TABLE 2

Nucleotide and amino acid substitutions of the SCoV-like viruses and SCoV

| Gene | S | | | | | | | |
|---|---|---|---|---|---|---|---|---|
| Site* | 22157 | 22192 | 22258 | 22555 | 22913 | 23148 | 23295 | 23470 |
| SZ3 | A (K) | T (L) | A (K) | C (S) | A (K) | T (F) | C (P) | C (S) |
| SZ16 | A (K) | T (L) | A (K) | C (S) | A (K) | A (I) | C (P) | C (S) |
| SZ1 | A (K) | T (L) | A (K) | C (S) | A (K) | A (I) | C (P) | C (S) |
| SZ13 | A (K) | T (L) | A (K) | C (S) | A (K) | A (I) | C (P) | C (S) |
| GZ43 | C (N) | T (L) | C (T) | T (F) | T (N) | T (F) | T (S) | C (S) |
| GZ60 | C (N) | T (L) | C (T) | T (F) | T (N) | T (F) | T (S) | C (S) |
| GZ50 | C (N) | C (S) | C (T) | T (F) | T (N) | T (F) | T (S) | T (L) |
| CUHK-W1 | C (N) | C (S) | C (T) | T (F) | T (N) | T (F) | T (S) | T (L) |
| HKU-36871 | C (N) | C (S) | C (T) | T (F) | T (N) | T (F) | T (S) | T (L) |
| HKU-39848 | C (N) | C (S) | C (T) | T (F) | T (N) | T (F) | T (S) | T (L) |
| HKU-66078 | C (N) | C (S) | C (T) | T (F) | T (N) | T (F) | T (S) | T (L) |
| HKU-65806 | C (N) | C (S) | C (T) | T (F) | T (N) | T (F) | T (S) | T (L) |
| Urbani | C (N) | C (S) | C (T) | T (F) | T (N) | T (F) | T (S) | T (L) |
| Tor2 | C (N) | C (S) | C (T) | T (F) | T (N) | T (F) | T (S) | T (L) |

TABLE 2-continued

Nucleotide and amino acid substitutions of the SCoV-like viruses and SCoV

| Gene | S | | | | | | M |
|---|---|---|---|---|---|---|---|
| Site* | 23578 | 23703 | 23737 | 23808 | 24156 | 24963 | 26395 |
| SZ3 | T (L) | G (A) | T (V) | G (D) | G (A) | G (E) | A (S) |
| SZ16 | T (L) | G (A) | T (V) | G (D) | G (A) | G (E) | A (S) |
| SZ1 | T (L) | G (A) | T (V) | G (D) | G (A) | G (E) | A (S) |
| SZ13 | T (L) | G (A) | T (V) | G (D) | G (A) | G (E) | A (S) |
| GZ43 | C (S) | A (T) | C (A) | G (D) | A (T) | A (K) | G (G) |
| GZ60 | C (S) | A (T) | C (A) | G (D) | A (T) | A (K) | G (G) |
| GZ50 | C (S) | A (T) | C (A) | G (D) | A (T) | A (K) | G (G) |
| CUHK-W1 | C (S) | A (T) | C (A) | T (Y) | A (T) | A (K) | G (G) |
| HKU-36871 | C (S) | A (T) | C (A) | T (Y) | A (T) | A (K) | G (G) |
| HKU-39848 | C (S) | A (T) | C (A) | T (Y) | A (T) | A (K) | G (G) |
| HKU-66078 | C (S) | A (T) | C (A) | T (Y) | A (T) | A (K) | G (G) |
| HKU-65806 | C (S) | A (T) | C (A) | T (Y) | A (T) | A (K) | G (G) |
| Urbani | C (S) | A (T) | C (A) | T (Y) | A (T) | A (K) | G (G) |
| Tor2 | C (S) | A (T) | C (A) | T (Y) | A (T) | A (K) | G (G) |

Numbering based on AY278554.

The most striking genetic difference between the animal and human virus groups was that the human viruses (with the exception of GZ01) all share a 29 nucleotide acid (nt) deletion [5'-CCTACTGGTTACCAACCTGAATGGAATAT-3' (SEQ ID NO:1), residue 27869 to 27897] at 246 nucleotide upstream of the start codon of the N gene. Sequence analysis of the animal isolates revealed that all of them retain this "additional" 29 nucleotide sequence. This 29 base pair deletion might have occurred during adaptation to humans and for to human to human transmission. Interestingly, the existence of this additional sequence in the animal viruses results in demolishing the open reading frames (ORFs) 10 and 11 (Marra et al., Science May 1 2003:1085953, electronically published at the web site of American Association for the Advancement of Science) and merging these two ORFs into a new ORF encoding a putative protein of 122 amino acid. This 122 amino acids putative peptide has a high homology to the putative proteins encoded by ORF10 and ORF12. Since the ORF11 does not have a typical transcription regulatory sequence for SCoV the putative ORF11 may be the direct result of the deletion of the 29 nt sequence. The loss of this peptide may help the virus in its adaptation to transmit efficiently from human to human.

Phylogenetic analysis of the S gene of both human and animal viruses indicated that the animal viruses are separated from the human virus cluster (FIG. 8). Taken together with the fact that most human SCoV have a deletion in the non-coding region of the genome, it is highly unlikely that the isolation of SCoV-like viruses in these wild animals is due to the reverse transmission of SCoV from human to animal. A more plausible hypothesis for these observations is that these animal viruses are the precursor of the human SCoV or that both the human and these animal viruses have been infected from the same source.

Of the eight animal species investigated in the market, two species, viz. palm civet and Racoon-dog had virus isolated from them and a third, (Chinese ferret badger) had serological evidence of infection. It is clear that a number of these species can amplify the virus within the retail market setting and are probably important from the point of view of public health. These animals may be the natural reservoir infection in the wild or that both humans and civets, Racoon-dog and ferret badgers were all infected from another animal source, which is in fact the true reservoir in nature. Alternatively, these market animals may be an intermediate host that, because of the culinary practices of southern China, brings the virus into close proximity with humans. However, the virus infected civets and Racoon-dogs were apparently healthy suggesting that virus is well adapted to this species and may be in ecological equilibrium with each other. This shows that the civet (or Racoon-dog) being a natural reservoir rather than a short-term incidental host.

5.1 Recombinant and Chimeric SCoV-Like Viruses

The present invention encompasses recombinant or chimeric viruses encoded by viral vectors derived from the genome of SCoV-like virus or natural variants thereof. In another specific embodiment, a recombinant virus is one derived from a natural variant of SCoV-like virus. A natural variant of SCoV-like virus has a sequence that is different from the genomic sequence (SEQ ID NO:4) of the hSARS virus, due to one or more naturally occurred mutations, including, but not limited to, point mutations, rearrangements, insertions, deletions etc., to the genomic sequence that may or may not result in a phenotypic change. In accordance with the present invention, a viral vector which is derived from the genome of the SCoV-like virus, is one that contains a nucleic acid sequence that encodes at least a part of one ORF of the virus. In a specific embodiment, the ORF comprises or consists of a nucleotide sequence of SEQ ID NO:1, 2, or 4, or a fragment thereof. In a specific embodiment, there are more than one ORF within the nucleotide sequence of SCoV-like virus, as shown in FIG. 4, 5 or 7, or a fragment thereof. In another embodiment, the polypeptide encoded by the ORF comprises or consists of an amino acid sequence of SEQ ID NO:3, or a fragment thereof, or shown in FIG. 4, 5, or 7, or a fragment thereof. In accordance with the present invention these viral vectors may or may not include nucleic acids that are non-native to the viral genome.

In another specific embodiment, a chimeric virus of the invention is a recombinant SCoV-like virus which further comprises a heterologous nucleotide sequence. In accordance with the invention, a chimeric virus may be encoded by a nucleotide sequence in which heterologous nucleotide sequences have been added to the genome or in which endogenous or native nucleotide sequences have been replaced with heterologous nucleotide sequences.

According to the present invention, the chimeric viruses are encoded by the viral vectors of the invention which further comprise a heterologous nucleotide sequence. In accordance with the present invention a chimeric virus is encoded by a viral vector that may or may not include nucleic acids that are non-native to the viral genome. In accordance with the invention a chimeric virus is encoded by a viral vector to which heterologous nucleotide sequences have been added, inserted or substituted for native or non-native sequences. In accordance with the present invention, the chimeric virus may be encoded by nucleotide sequences derived from different strains or variants of SCoV-like virus. In particular, the chimeric virus is encoded by nucleotide sequences that encode antigenic polypeptides derived from different strains or variants of SCoV-like virus.

A chimeric virus may be of particular use for the generation of recombinant vaccines protecting against two or more viruses (Tao et al., J. Virol. 72, 2955-2961; Durbin et al., 2000, J. Virol. 74, 6821-6831; Skiadopoulos et al., 1998, J. Virol. 72, 1762-1768 (1998); Teng et al., 2000, J. Virol. 74, 9317-9321). For example, it can be envisaged that a virus vector derived from the SCoV-like virus expressing one or more proteins of variants of SCoV-like virus, or vice versa, will protect a subject vaccinated with such vector against infections by both the native SCoV-like virus and the variant. Attenuated and replication-defective viruses may be of use for vaccination purposes with live vaccines as has been suggested for other viruses. (See, PCT WO 02/057302, at pp. 6 and 23, incorporated by reference herein).

In accordance with the present invention the heterologous sequence to be incorporated into the viral vectors encoding the recombinant or chimeric viruses of the invention include sequences obtained or derived from different strains or variants of SCoV-like virus.

In certain embodiments, the chimeric or recombinant viruses of the invention are encoded by viral vectors derived from viral genomes wherein one or more sequences, intergenic regions, termini sequences, or portions or entire ORF have been substituted with a heterologous or non-native sequence. In certain embodiments of the invention, the chimeric viruses of the invention are encoded by viral vectors derived from viral genomes wherein one or more heterologous sequences have been inserted or added to the vector.

The selection of the viral vector may depend on the species of the subject that is to be treated or protected from a viral infection. If the subject is human, then an attenuated SCoV-like virus can be used to provide the antigenic sequences.

In accordance with the present invention, the viral vectors can be engineered to provide antigenic sequences which confer protection against infection by the SCoV-like virus and natural variants thereof. The viral vectors may be engineered to provide one, two, three or more antigenic sequences. In accordance with the present invention the antigenic sequences may be derived from the same virus, from different strains or variants of the same type of virus, or from different viruses.

The expression products and/or recombinant or chimeric virions obtained in accordance with the invention may advantageously be utilized in vaccine formulations. The expression products and chimeric virions of the present invention may be engineered to create vaccines against a broad range of pathogens, including viral and bacterial antigens, tumor antigens, allergen antigens, and auto antigens involved in autoimmune disorders. In particular, the chimeric virions of the present invention may be engineered to create vaccines for the protection of a subject from infections with SCoV-like virus and variants thereof.

In certain embodiments, the expression products and recombinant or chimeric virions of the present invention may be engineered to create vaccines against a broad range of pathogens, including viral antigens, tumor antigens and autoantigens involved in autoimmune disorders. One way to achieve this goal involves modifying existing SCoV-like viral genes to contain foreign sequences in their respective external domains. Where the heterologous sequences are epitopes or antigens of pathogens, these chimeric viruses may be used to induce a protective immune response against the disease agent from which these determinants are derived.

Thus, the present invention relates to the use of viral vectors and recombinant or chimeric viruses to formulate vaccines against a broad range of viruses and/or antigens. The present invention also encompasses recombinant viruses comprising a viral vector derived from the SCoV-like virus or variants thereof which contains sequences which result in a virus having a phenotype more suitable for use in vaccine formulations, e.g., attenuated phenotype or enhanced antigenicity. The mutations and modifications can be in coding regions, in intergenic regions and in the leader and trailer sequences of the virus.

The invention provides a host cell comprising a nucleic acid or a vector according to the invention. Plasmid or viral vectors containing the polymerase components of SCoV-like virus are generated in prokaryotic cells for the expression of the components in relevant cell types (bacteria, insect cells, eukaryotic cells). Plasmid or viral vectors containing full-length or partial copies of the SCoV-like viral genome will be generated in prokaryotic cells for the expression of viral nucleic acids in-vitro or in-vivo. The latter vectors may contain other viral sequences for the generation of chimeric viruses or chimeric virus proteins, may lack parts of the viral genome for the generation of replication defective virus, and may contain mutations, deletions or insertions for the generation of attenuated viruses. In addition, the present invention provides a host cell infected with SCoV-like virus.

Infectious copies of SCoV-like virus (being wild type, attenuated, replication-defective or chimeric) can be produced upon co-expression of the polymerase components according to the state-of-the-art technologies described above.

In addition, eukaryotic cells, transiently or stably expressing one or more full-length or partial proteins can be used. Such cells can be made by transfection (proteins or nucleic acid vectors), infection (viral vectors) or transduction (viral vectors) and may be useful for complementation of mentioned wild type, attenuated, replication-defective or chimeric viruses.

The viral vectors and chimeric viruses of the present invention may be used to modulate a subject's immune system by stimulating a humoral immune response, a cellular immune response or by stimulating tolerance to an antigen. As used herein, a subject means: humans, primates, horses, cows, sheep, pigs, goats, dogs, cats, avian species, rodents, raccoon-dog, civet, and ferret.

5.2 Formulation of Vaccines and Antivirals

In a preferred embodiment, the invention provides a proteinaceous molecule or SCoV-like virus specific viral protein or functional fragment thereof encoded by a nucleic acid according to the invention. Useful proteinaceous molecules are for example derived from any of the genes or genomic fragments derivable from the virus according to the invention, including envelop protein (E protein), integral membrane protein (M protein), spike protein (S protein), nucleocapsid protein (N protein), hemaglutinin esterase (HE protein), and RNA-dependent RNA polymerase. Such molecules, or antigenic fragments thereof, as provided herein, are for example useful in diagnostic methods or kits and in pharmaceutical compositions such as subunit vaccines. Particularly useful are polypeptides encoded by the nucleotide sequence of SEQ ID NO:1, 2, or 4, or as shown in FIGS. 4, 5, 7, or antigenic fragments thereof for inclusion as antigen or subunit immunogen, but inactivated whole virus can also be used. Particularly useful are also those proteinaceous substances that are encoded by recombinant nucleic acid fragments of the SCoV-like viral genome, of course preferred are those that are within the preferred bounds and metes of ORFs, in particular, for eliciting SCoV-like virus specific antibody or T cell responses, whether in vivo (e.g. for protective or therapeutic purposes or for providing diagnostic antibodies) or in vitro (e.g. by phage display technology or another technique useful for generating synthetic antibodies).

The invention provides vaccine formulations for the prevention and treatment of infections with SCoV-like virus. In certain embodiments, the vaccine of the invention comprises recombinant and chimeric viruses of the SCoV-like virus. In certain embodiments, the virus is attenuated.

In another embodiment of this aspect of the invention, inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled. The resulting vaccine is usually inoculated intramuscularly.

Inactivated viruses may be formulated with a suitable adjuvant in order to enhance the immunological response. Such adjuvants may include but are not limited to mineral gels, e.g., aluminum hydroxide; surface active substances such as lysolecithin, pluronic polyols, polyanions; peptides; oil emulsions; and potentially useful human adjuvants such as BCG and *Corynebacterium parvum*.

In another aspect, the present invention also provides DNA vaccine formulations comprising a nucleic acid or fragment of the SCoV-like virus, or nucleic acid molecules having the sequence of SEQ ID NO:1, 2, or 4, or a fragment thereof. In another specific embodiment, the DNA vaccine formulations of the present invention comprises a nucleic acid or fragment thereof encoding the antibodies which immunospecifically binds SCoV-like viruses. In DNA vaccine formulations, a vaccine DNA comprises a viral vector, such as that derived from the SCoV-like virus, bacterial plasmid, or other expression vector, bearing an insert comprising a nucleic acid molecule of the present invention operably linked to one or more control elements, thereby allowing expression of the vaccinating proteins encoded by said nucleic acid molecule in a vaccinated subject. Such vectors can be prepared by recombinant DNA technology as recombinant or chimeric viral vectors carrying a nucleic acid molecule of the present invention (see also Section 5.1, supra).

Various heterologous vectors are described for DNA vaccinations against viral infections. For example, the vectors described in the following references may be used to express SCoV-like viral sequences instead of the sequences of the viruses or other pathogens described; in particular, vectors described for hepatitis B virus (Michel, M. L. et al., 1995, DNA-mediated immunization to the hepatitis B surface antigen in mice: Aspects of the humoral response mimic hepatitis B viral infection in humans, *Proc. Natl. Aca. Sci. USA* 92:5307-5311; Davis, H. L. et al., 1993, DNA-based immunization induces continuous seretion of hepatitis B surface antigen and high levels of circulating antibody, *Human Molec. Genetics* 2:1847-1851), HIV virus (Wang, B. et al., 1993, Gene inoculation generates immune responses against human immunodeficiency virus type 1, *Proc. Natl. Acad. Sci. USA* 90:4156-4160; Lu, S. et al., 1996, Simian immunodeficiency virus DNA vaccine trial in macques, *J. Virol.* 70:3978-3991; Letvin, N. L. et al., 1997, Potent, protective anti-HIV immune responses generated by bimodal HIV envelope DNA plus protein vaccination, *Proc Natl Acad Sci USA*. 94(17):9378-83), and influenza viruses (Robinson, H L et al., 1993, Protection against a lethal influenza virus challenge by immunization with a haemagglutinin-expressing plasmid DNA, *Vaccine* 11:957-960; Ulmer, J. B. et al., Heterologous protection against influenza by injection of DNA encoding a viral protein, *Science* 259:1745-1749), as well as bacterial infections, such as tuberculosis (Tascon, R. E. et al., 1996, Vaccination against tuberculosis by DNA injection, *Nature Med.* 2:888-892; Huygen, K. et al., 1996, Immunogenicity and protective efficacy of a tuberculosis DNA vaccine, *Nature Med.,* 2:893-898), and parasitic infection, such as malaria (Sedegah, M., 1994, Protection against malaria by immunization with plasmid DNA encoding circumsporozoite protein, *Proc. Natl. Acad. Sci. USA* 91:9866-9870; Doolan, D. L. et al., 1996, Circumventing genetic restriction of protection against malaria with multigene DNA immunization: CD8+ T cell-interferon δ, and nitric oxide-dependent immunity, *J. Exper. Med.,* 1183:1739-1746).

Many methods may be used to introduce the vaccine formulations described above. These include, but are not limited to, oral, intradermal, intramuscular, intraperitoneal, intravenous, subcutaneous, and intranasal routes. Alternatively, it may be preferable to introduce the chimeric virus vaccine formulation via the natural route of infection of the pathogen for which the vaccine is designed. The DNA vaccines of the present invention may be administered in saline solutions by injections into muscle or skin using a syringe and needle (Wolff J. A. et al., 1990, Direct gene transfer into mouse muscle in vivo, *Science* 247:1465-1468; Raz, E., 1994, Intradermal gene immunization: The possible role of DNA uptake in the induction of cellular immunity to viruses, *Proc. Natl. Acd. Sci. USA* 91:9519-9523). Another way to administer DNA vaccines is called "gene gun" method, whereby microscopic gold beads coated with the DNA molecules of interest is fired into the cells (Tang, D. et al., 1992, Genetic immunization is a simple method for eliciting an immune response, *Nature* 356:152-154). For general reviews of the methods for DNA vaccines, see Robinson, H. L., 1999, DNA vaccines: basic mechanism and immune responses (Review), *Int. J. Mol. Med.* 4(5):549-555; Barber, B., 1997, Introduction: Emerging vaccine strategies, *Seminars in Immunology* 9(5):269-270; and Robinson, H. L. et al., 1997, DNA vaccines, *Seminars in Immunology* 9(5):271-283.

5.3 Attenuation of SCoV-Like Virus or Variants Thereof

The SCoV-like virus or variants thereof of the invention can be genetically engineered to exhibit an attenuated phenotype. In particular, the viruses of the invention exhibit an attenuated phenotype in a subject to which the virus is administered as a vaccine. Attenuation can be achieved by any method known to a skilled artisan. Without being bound by theory, the attenuated phenotype of the viruses of the invention can be caused, e.g., by using a virus that naturally does not replicate well in an intended host species, for example, by reduced replication of the viral genome, by reduced ability of the virus to infect a host cell, or by reduced ability of the viral proteins to assemble to an infectious viral particle relative to the wild type strain of the virus.

The attenuated phenotypes of SCoV-like virus or variants thereof can be tested by any method known to the artisan. A candidate virus can, for example, be tested for its ability to infect a host or for the rate of replication in a cell culture system. In certain embodiments, growth curves at different temperatures are used to test the attenuated phenotype of the virus. For example, an attenuated virus is able to grow at 35° C., but not at 39° C. or 40° C. In certain embodiments, different cell lines can be used to evaluate the attenuated phenotype of the virus. For example, an attenuated virus may only be able to grow in monkey cell lines but not the human cell lines, or the achievable virus titers in different cell lines are different for the attenuated virus. In certain embodiments, viral replication in the respiratory tract of a small animal model, including but not limited to, hamsters, cotton rats, mice and guinea pigs, is used to evaluate the attenuated phenotypes of the virus. In other embodiments, the immune response induced by the virus, including but not limited to, the antibody titers (e.g., assayed by plaque reduction neutralization assay or ELISA) is used to evaluate the attenuated phenotypes of the virus. In a specific embodiment, the plaque reduction neutralization assay or ELISA is carried out at a low dose. In certain embodiments, the ability of the SCoV-like virus to elicit pathological symptoms in an animal model can be tested. A reduced ability of the virus to elicit pathological symptoms in an animal model system is indicative of its attenuated phenotype. In a specific embodiment, the candidate viruses are tested in a monkey model for nasal infection, indicated by mucous production.

The viruses of the invention can be attenuated such that one or more of the functional characteristics of the virus are impaired. In certain embodiments, attenuation is measured in comparison to the wild type strain of the virus from which the attenuated virus is derived. In other embodiments, attenuation is determined by comparing the growth of an attenuated virus in different host systems. Thus, for a non-limiting example, SCoV-like virus or a variant thereof is said to be attenuated when grown in a human host if the growth of the SCoV-like virus or variant thereof in the human host is reduced compared to the non-attenuated SCoV-like virus or variant thereof.

In certain embodiments, the attenuated virus of the invention is capable of infecting a host, is capable of replicating in a host such that infectious viral particles are produced. In comparison to the wild type strain, however, the attenuated strain grows to lower titers or grows more slowly. Any technique known to the skilled artisan can be used to determine the growth curve of the attenuated virus and compare it to the growth curve of the wild type virus.

In certain embodiments, the attenuated virus of the invention (e.g., a recombinant or chimeric SCoV-like virus) cannot replicate in human cells as well as the wild type virus (e.g., wild type SCoV-like virus) does. However, the attenuated virus can replicate well in a cell line that lack interferon functions, such as Vero cells.

In other embodiments, the attenuated virus of the invention is capable of infecting a host, of replicating in the host, and of causing proteins of the virus of the invention to be inserted into the cytoplasmic membrane, but the attenuated virus does not cause the host to produce new infectious viral particles. In certain embodiments, the attenuated virus infects the host, replicates in the host, and causes viral proteins to be inserted in the cytoplasmic membrane of the host with the same efficiency as the wild type SCoV-like virus. In other embodiments, the ability of the attenuated virus to cause viral proteins to be inserted into the cytoplasmic membrane into the host cell is reduced compared to the wild type virus. In certain embodiments, the ability of the attenuated SCoV-like virus to replicate in the host is reduced compared to the wild type virus. Any technique known to the skilled artisan can be used to determine whether a virus is capable of infecting a mammalian cell, of replicating within the host, and of causing viral proteins to be inserted into the cytoplasmic membrane of the host.

In certain embodiments, the attenuated virus of the invention is capable of infecting a host. In contrast to the wild type SCoV-like virus, however, the attenuated SCoV-like virus cannot be replicated in the host. In a specific embodiment, the attenuated SCoV-like virus can infect a host and can cause the host to insert viral proteins in its cytoplasmic membranes, but the attenuated virus is incapable of being replicated in the host. Any method known to the skilled artisan can be used to test whether the attenuated SCoV-like virus has infected the host and has caused the host to insert viral proteins in its cytoplasmic membranes.

In certain embodiments, the ability of the attenuated virus to infect a host is reduced compared to the ability of the wild type virus to infect the same host. Any technique known to the skilled artisan can be used to determine whether a virus is capable of infecting a host.

In certain embodiments, mutations (e.g., missense mutations) are introduced into the genome of the virus, for example, into the sequence of SEQ ID NO:1, 2, 4, or to generate a virus with an attenuated phenotype. Mutations (e.g., missense mutations) can be introduced into the structural genes and/or regulatory genes of the SCoV-like virus. Mutations can be additions, substitutions, deletions, or combinations thereof. Such variant of SCoV-like virus can be screened for a predicted functionality, such as infectivity, replication ability, protein synthesis ability, assembling ability, as well as cytopathic effect in cell cultures. In a specific embodiment, the missense mutation is a cold-sensitive mutation. In another embodiment, the missense mutation is a heat-sensitive mutation. In another embodiment, the missense mutation prevents a normal processing or cleavage of the viral proteins.

In other embodiments, deletions are introduced into the genome of the SCoV-like virus, which result in the attenuation of the virus.

In certain embodiments, attenuation of the virus is achieved by replacing a gene of the wild type virus with a gene of a virus of a different species, of a different subgroup, or of a different variant. In another aspect, attenuation of the virus is achieved by replacing one or more specific domains of a protein of the wild type virus with domains derived from the corresponding protein of a virus of a different species. In certain other embodiments, attenuation of the virus is achieved by deleting one or more specific domains of a protein of the wild type virus.

When a live attenuated vaccine is used, its safety must also be considered. The vaccine must not cause disease. Any techniques known in the art that can make a vaccine safe may be used in the present invention. In addition to attenuation techniques, other techniques may be used. One non-limiting example is to use a soluble heterologous gene that cannot be incorporated into the virion membrane. For example, a single copy of the soluble version of a viral transmembrane protein lacking the transmembrane and cytosolic domains thereof, can be used.

Various assays can be used to test the safety of a vaccine. For example, sucrose gradients and neutralization assays can be used to test the safety. A sucrose gradient assay can be used to determine whether a heterologous protein is inserted in a virion. If the heterologous protein is inserted in the virion, the virion should be tested for its ability to cause symptoms in an appropriate animal model since the virus may have acquired new, possibly pathological, properties.

5.4 Adjuvants and Carrier Molecules

SCoV-like-viral-associated antigens are administered with one or more adjuvants.

In one embodiment, the SCoV-like-viral-associated antigen is administered together with a mineral salt adjuvants or mineral salt gel adjuvant. Such mineral salt and mineral salt gel adjuvants include, but are not limited to, aluminum hydroxide (ALHYDROGEL, REHYDRAGEL), aluminum phosphate gel, aluminum hydroxyphosphate (ADJU-PHOS), and calcium phosphate.

In another embodiment, SCoV-like-viral-associated antigen is administered with an immunostimulatory adjuvant. Such class of adjuvants, include, but are not limited to, cytokines (e.g., interleukin-2, interleukin-7, interleukin-12, granulocyte-macrophage colony stimulating factor (GM-CSF), interfereon-γ interleukin-1β (IL-1β), and IL-1β peptide or Sclavo Peptide), cytokine-containing liposomes, triterpenoid glycosides or saponins (e.g., QuilA and QS-21, also sold under the trademark STIMULON, ISCOPREP), Muramyl Dipeptide (MDP) derivatives, such as N-acetyl-muramyl-L-threonyl-D-isoglutamine (Threonyl-MDP, sold under the trademark TERMURTIDE), GMDP, N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxy phosphoryloxy)-ethylamine, muramyl tripeptide phosphatidylethanolamine (MTP-PE), unmethylated CpG dinucleotides and oligonucleotides, such as bacterial DNA and fragments thereof, LPS, monophosphoryl Lipid A (3D-MLA sold under the trademark MPL), and polyphosphazenes.

In another embodiment, the adjuvant used is a particular adjuvant, including, but not limited to, emulsions, e.g., Freund's Complete Adjuvant, Freund's Incomplete Adjuvant, squalene or squalane oil-in-water adjuvant formulations, such as SAF and MF59, e.g., prepared with block-copolymers, such as L-121 (polyoxypropylene/polyoxyetheylene) sold under the trademark PLURONIC L-121, Liposomes, Virosomes, cochleates, and immune stimulating complex, which is sold under the trademark ISCOM.

In another embodiment, a microparticular adjuvant is used. Microparticular adjuvants include, but are not limited to biodegradable and biocompatible polyesters, homo- and copolymers of lactic acid (PLA) and glycolic acid (PGA), poly(lactide-co-glycolides) (PLGA) microparticles, polymers that self-associate into particulates (poloxamer particles), soluble polymers (polyphosphazenes), and virus-like particles (VLPs) such as recombinant protein particulates, e.g., hepatitis B surface antigen (HbsAg).

Yet another class of adjuvants that may be used include mucosal adjuvants, including, but not limited to heat-labile enterotoxin from *Escherichia coli* (LT), cholera holotoxin (CT) and cholera Toxin B Subunit (CTB) from *Vibrio cholerae*, mutant toxins (e.g., LTK63 and LTR72), microparticles, and polymerized liposomes.

In other embodiments, any of the above classes of adjuvants may be used in combination with each other or with other adjuvants. For example, non-limiting examples of combination adjuvant preparations that can be used to administer the SCoV-like-viral-associated antigens of the invention include liposomes containing immunostimulatory protein, cytokines, or T-cell and/or B-cell peptides, or microbes with or without entrapped IL-2 or microparticles containing enterotoxin. Other adjuvants known in the art are also included within the scope of the invention (see *Vaccine Design: The Subunit and Adjuvant Approach*, Chap. 7, Michael F. Powell and Mark J. Newman (eds.), Plenum Press, New York, 1995, which is incorporated herein in its entirety).

The effectiveness of an adjuvant may be determined by measuring the induction of antibodies directed against an immunogenic polypeptide containing a SCoV-like viral polypeptide epitope, the antibodies resulting from administration of this polypeptide in vaccines which are also comprised of the various adjuvants.

The polypeptides may be formulated into the vaccine as neutral or salt forms. Pharmaceutically acceptable salts include the acid additional salts (formed with free amino groups of the peptide) and which are formed with inorganic acids, such as, for example, hydrochloric or phosphoric acids, or organic acids such as acetic, oxalic, tartaric, maleic, and the like. Salts formed with free carboxyl groups may also be derived from inorganic bases, such as, for example, sodium potassium, ammonium, calcium, or ferric hydroxides, and such organic bases as isopropylamine, trimethylamine, 2-ethylamino ethanol, histidine, procaine and the like.

The vaccines of the invention may be multivalent or univalent. Multivalent vaccines are made from recombinant viruses that direct the expression of more than one antigen.

Many methods may be used to introduce the vaccine formulations of the invention; these include but are not limited to oral, intradermal, intramuscular, intraperitoneal, intravenous, subcutaneous, intranasal routes, and via scarification (scratching through the top layers of skin, e.g., using a bifurcated needle).

The patient to which the vaccine is administered is preferably a mammal, most preferably a human, but can also be a non-human animal including but not limited to cows, horses, sheep, pigs, fowl (e.g., chickens), goats, cats, dogs, hamsters, mice and rats.

5.5 Preparation of Antibodies

Antibodies which specifically recognize a polypeptide of the invention, such as, but not limited to, polypeptides comprising the sequence of SEQ ID NO:3, and polypeptides as shown in FIGS. 4, 5, and 7, or SCoV-like viral epitope or antigen-binding fragments thereof can be used for detecting, screening, and isolating the polypeptide of the invention or fragments thereof, or similar sequences that might encode similar enzymes from the other organisms. For example, in one specific embodiment, an antibody which immunospecifically binds SCoV-like viral epitope, or a fragment thereof, can be used for various in vitro detection assays, including enzyme-linked immunosorbent assays (ELISA), radioimmunoassays, Western blot, etc., for the detection of a polypeptide of the invention or, preferably, SCoV-like virus, in samples, for example, a biological material, including cells, cell culture media (e.g., bacterial cell culture media, mammalian cell culture media, insect cell culture media, yeast cell culture media, etc.), blood, plasma, serum, tissues, sputum, naseopharyngeal aspirates, etc.

Antibodies specific for a polypeptide of the invention or any epitope of SCoV-like virus may be generated by any suitable method known in the art. Polyclonal antibodies to an antigen-of-interest, for example, the SCoV-like virus or comprises a nucleic acid sequence of SEQ ID NO:1, 2, or 4 can be produced by various procedures well known in the art. For example, an antigen can be administered to various host animals including, but not limited to, rabbits, mice, rats, etc., to induce the production of antisera containing polyclonal antibodies specific for the antigen. Various adjuvants may be used to increase the immunological response, depending on the host species, and include but are not limited to, Freund's (complete and incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful adjuvants for humans such as BCG (Bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Antibody fragments which recognize specific epitopes may be generated by known techniques. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the complete light chain, and the variable region, the CH1 region and the hinge region of the heavy chain.

The antibodies of the invention or fragments thereof can be also produced by any method known in the art for the synthesis of antibodies, in particular, by chemical synthesis or preferably, by recombinant expression techniques.

The nucleotide sequence encoding an antibody may be obtained from any information available to those skilled in the art (i.e., from Genbank, the literature, or by routine cloning and sequence analysis). If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., supra; and Ausubel et al., eds., 1998, Current Protocols in Molecular Biology, John Wiley & Sons, NY, which are both incorporated by reference herein in their entireties), to generate antibodies having a different amino acid sequence by, for example, introducing amino acid substitutions, deletions, and/or insertions into the epitope-binding domain regions of the antibodies or any portion of antibodies which may enhance or reduce biological activities of the antibodies.

Recombinant expression of an antibody requires construction of an expression vector containing a nucleotide sequence that encodes the antibody. Once a nucleotide sequence encoding an antibody molecule or a heavy or light chain of an antibody, or portion thereof has been obtained, the vector for the production of the antibody molecule may be produced by recombinant DNA technology using techniques well known in the art as discussed in the previous sections. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The nucleotide sequence encoding the heavy-chain variable region, light-chain variable region, both the heavy-chain and light-chain variable regions, an epitope-binding fragment of the heavy- and/or light-chain variable region, or one or more complementarity determining regions (CDRs) of an antibody may be cloned into such a vector for expression. Thus-prepared expression vector can be then introduced into appropriate host cells for the expression of the antibody. Accordingly, the invention includes host cells containing a polynucleotide encoding an antibody specific for the polypeptides of the invention or fragments thereof.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides or different selectable markers to ensure maintenance of both plasmids. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature, 322:52, 1986; and Kohler, Proc. Natl. Acad. Sci. USA, 77:2 197, 1980). The coding sequences for the heavy and light chains may comprise cDNA or genomic DNA.

In another embodiment, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman et al., J. Immunol. Methods, 182:41-50, 1995; Ames et al., J. Immunol. Methods, 184: 177-186, 1995; Kettleborough et al., Eur. J. Immunol., 24:952-958, 1994; Persic et al., Gene, 187:9-18, 1997; Burton et al., Advances in Immunology, 57:191-280, 1994; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques, 12(6):864-869, 1992; and Sawai et al., AJRI, 34:26-34, 1995; and Better et al., Science, 240:1041-1043, 1988 (each of which is incorporated by reference in its entirety). Examples of techniques which can be used to produce single-chain Fvs and antibodies include those described in U.S. Pat. Nos. 4,946,778 and 5,258,498; Huston et al., Methods in Enzymology, 203:46-88, 1991; Shu et al., PNAS, 90:7995-7999, 1993; and Skerra et al., Science, 240:1038-1040, 1988.

Once an antibody molecule of the invention has been produced by any methods described above, it may then be purified by any method known in the art for purification of an immunoglobulin molecule, for example, by chromatography (e.g., ion exchange, affinity, particularly by affinity for the specific antigen after Protein A or Protein G purification, and sizing column chromatography), centrifugation, differential solubility, or by any other standard techniques for the purification of proteins. Further, the antibodies of the present invention or fragments thereof may be fused to heterologous polypeptide sequences described herein or otherwise known in the art to facilitate purification.

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a constant region derived from a human immunoglobulin. Methods for producing chimeric antibodies are known in the art. See e.g., Morrison, Science, 229:1202, 1985; Oi et al., BioTechniques, 4:214 1986; Gillies et al., J. Immunol. Methods, 125:191-202, 1989; U.S. Pat. Nos. 5,807,715; 4,816,567; and 4,816,397, which are incorporated herein by reference in their entireties. Humanized antibodies are antibody molecules from non-human species that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. No. 5,585,089; Riechmann et al., Nature, 332:323, 1988, which are incorporated herein by reference in their entireties. Antibodies can be humanized using a variety of techniques known in the art including, for example, CDR-grafting (EP 239,400; PCT publication WO 91/09967; U.S. Pat. Nos. 5,225,539; 5,530,101 and 5,585, 089), veneering or resurfacing (EP 592,106; EP 519,596; Padlan, Molecular Immunology, 28(4/5):489-498, 1991; Studnicka et al., Protein Engineering, 7(6):805-814, 1994; Roguska et al., Proc Natl. Acad. Sci. USA, 91:969-973, 1994), and chain shuffling (U.S. Pat. No. 5,565,332), all of which are hereby incorporated by reference in their entireties.

Completely human antibodies are particularly desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety.

Human antibodies can also be produced using transgenic mice which are incapable of expressing functional endogenous immunoglobulins, but which can express human immunoglobulin genes. For an overview of this technology for producing human antibodies, see Lonberg and Huszar, Int. Rev. Immunol., 13:65-93, 1995. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318;

5,885,793; 5,916,771; and 5,939,598, which are incorporated by reference herein in their entireties. In addition, companies such as Abgenix, Inc. (Fremont, Calif.), Medarex (NJ) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology, 12:899-903, 1988).

Antibodies fused or conjugated to heterologous polypeptides may be used in in vitro immunoassays and in purification methods (e.g., affinity chromatography) well known in the art. See e.g., PCT publication Number WO 93/21232; EP 439,095; Naramura et al., Immunol. Lett., 39:91-99, 1994; U.S. Pat. No. 5,474,981; Gillies et al., PNAS, 89:1428-1432, 1992; and Fell et al., J. Immunol., 146:2446-2452, 1991, which are incorporated herein by reference in their entireties.

Antibodies may also be attached to solid supports, which are particularly useful for immunoassays or purification of the polypeptides of the invention or fragments, derivatives, analogs, or variants thereof, or similar molecules having the similar enzymatic activities as the polypeptide of the invention. Such solid supports include, but are not limited to, glass, cellulose, polyacrylamide, nylon, polystyrene, polyvinyl chloride or polypropylene.

5.6 Pharmaceutical Compositions and Kits

The present invention encompasses pharmaceutical compositions comprising anti-viral agents of the present invention. In a specific embodiment, the anti-viral agent is an antibody which immunospecifically binds and neutralize the SCoV-like virus or variants thereof, or any proteins derived therefrom. In another specific embodiment, the anti-viral agent is a polypeptide or nucleic acid molecule of the invention. The pharmaceutical compositions have utility as an anti-viral prophylactic agent and may be administered to a subject where the subject has been exposed or is expected to be exposed to a virus.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu and Wu, 1987, J. Biol. Chem. 262:4429 4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In a preferred embodiment, it may be desirable to introduce the pharmaceutical compositions of the invention into the lungs by any suitable route. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non porous, or gelatinous material, including membranes, such as sialastic membranes, or fibers. In one embodiment, administration can be by direct injection at the site (or former site) infected tissues.

In another embodiment, the pharmaceutical composition can be delivered in a vesicle, in particular a liposome (see Langer, 1990, Science 249:1527-1533; Treat et al., in Liposomes in the Therapy of Infectious Disease and Cancer, Lopez Berestein and Fidler (eds.), Liss, New York, pp. 353-365 (1989); Lopez-Berestein, ibid., pp. 317-327; see generally ibid.).

In yet another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; and Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the composition's target, i.e., the lung, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

The pharmaceutical compositions of the present invention comprise a therapeutically effective amount of an live attenuated, inactivated or killed SCoV-like virus, or recombinant or chimeric SCoV-like virus, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the pharmaceutical composition is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2 ethylamino ethanol, histidine, procaine, etc.

The amount of the pharmaceutical composition of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20 500 micrograms of active compound per kilogram body weight. Suitable dosage ranges for intranasal administration are generally about 0.01 pg/kg body weight to 1 mg/kg body weight. Effective doses may be extrapolated from dose response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a preferred embodiment, the kit contains an antiviral agent of the invention, e.g., an antibody specific for the polypeptides encoded by a nucleotide sequence of SEQ ID NO:1, 2 or 4, or as shown in FIGS. 4, 5 and 7, or any SCoV-like viral epitope, or a polypeptide or protein of the present invention, or a nucleic acid molecule of the invention, alone or in combination with adjuvants, antivirals, antibiotics, analgesic, bronchodialaters, or other pharmaceutically acceptable excipients.

The present invention further encompasses kits comprising a container containing a pharmaceutical composition of the present invention and instructions to for use.

5.7 Detection Assays

An exemplary method for detecting the presence or absence of a polypeptide or nucleic acid of the invention in a biological sample involves obtaining a biological sample from various sources and contacting the sample with a compound or an agent capable of detecting an epitope or nucleic acid (e.g., mRNA, genomic DNA) of the SCoV-like virus such that the presence of the SCoV-like virus is detected in the sample. A preferred agent for detecting SCoV-like viral mRNA or genomic RNA of the invention is a labeled nucleic acid probe capable of hybridizing to mRNA or genomic RNA encoding a polypeptide of the invention. The nucleic acid probe can be, for example, a nucleic acid molecule comprising or consisting of the nucleotide sequence or SEQ ID NO:1, 2, 4, or a portion thereof, such as an oligonucleotide of at least 15, 20, 25, 30, 50, 100, 250, 500, 750, 1,000 or more contiguous nucleotides in length and sufficient to specifically hybridize under stringent conditions to a SCoV-like viral mRNA or genomic RNA.

In another preferred specific embodiment, the presence of SCoV-like virus is detected in the sample by an reverse transcription polymerase chain reaction (RT-PCR) using the primers that are constructed based on a partial nucleotide sequence of the genome of SCoV-like virus. In a non-limiting specific embodiment, preferred primers to be used in a RT-PCR method comprises SEQ ID NO:5 and/or 6 in the presence of 2.5 mM $MgCl_2$ and the thermal cycles are, for example, but not limited to, 94° C. for 8 min followed by 40 cycles of 94° C. for 1 min, 50° C. for 1 min, 72° C. for 1 min. In more preferred specific embodiment, the present invention provides a real-time quantitative PCR assay to detect the presence of SCoV-like virus in a biological sample by subjecting the cDNA obtained by reverse transcription of the extracted total RNA from the sample to PCR reactions using the specific primers, such as those having nucleotide sequences of SEQ ID NOS:5 and/or 6, and a fluorescence dye, such as SYBR® Green I, which fluoresces when bound non-specifically to double-stranded DNA. The fluorescence signals from these reactions are captured at the end of extension steps as PCR product is generated over a range of the thermal cycles, thereby allowing the quantitative determination of the viral load in the sample based on an amplification plot.

A preferred agent for detecting SCoV-like virus is an antibody that specifically binds a polypeptide of the invention or any SCoV-like viral epitope, preferably an antibody with a detectable label. Antibodies can be polyclonal, or more preferably, monoclonal. An intact antibody, or a fragment thereof (e.g., Fab or F(ab')2) can be used.

The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The detection method of the invention can be used to detect mRNA, protein (or any epitope), or genomic RNA in a sample in vitro as well as in vivo. For example, in vitro techniques for detection of mRNA include northern hybridizations, in situ hybridizations, RT-PCR, and RNase protection. In vitro techniques for detection of an epitope of SCoV-like virus include enzyme linked immunosorbent assays (ELISAs), Western blots, immunoprecipitations and immunofluorescence. In vitro techniques for detection of genomic RNA include nothern hybridizations, RT-PCT, and RNase protection. Furthermore, in vivo techniques for detection of SCoV-like virus include introducing into a subject organism a labeled antibody directed against the polypeptide. For example, the antibody can be labeled with a radioactive marker whose presence and location in the subject organism can be detected by standard imaging techniques, including autoradiography.

In a specific embodiment, the methods further involve obtaining a control sample from a control subject, contacting the control sample with a compound or agent capable of detecting SCoV-like virus, e.g., a polypeptide of the invention or mRNA or genomic RNA encoding a polypeptide of the invention, such that the presence of SCoV-like virus or the polypeptide or mRNA or genomic RNA encoding the polypeptide is detected in the sample, and comparing the presence of SCoV-like virus or the polypeptide or mRNA or genomic RNA encoding the polypeptide in the control sample with the presence of SCoV-like virus, or the polypeptide or mRNA or genomic DNA encoding the polypeptide in the test sample.

The invention also encompasses kits for detecting the presence of SCoV-like virus or a polypeptide or nucleic acid of the invention in a test sample. The kit, for example, can comprise a labeled compound or agent capable of detecting SCoV-like virus or the polypeptide or a nucleic acid molecule encoding the polypeptide in a test sample and, in certain embodiments, a means for determining the amount of the polypeptide or mRNA in the sample (e.g., an antibody which binds the polypeptide or an oligonucleotide probe which binds to DNA or mRNA encoding the polypeptide). Kits can also include instructions for use.

For antibody-based kits, the kit can comprise, for example: (1) a first antibody (e.g., attached to a solid support) which binds to a polypeptide of the invention or SCoV-like viral epitope; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence encoding a polypeptide of the invention or to a sequence within the SCoV-like viral genome or (2) a pair of primers useful for amplifying a nucleic acid molecule containing an SCoV-like viral sequence. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for use.

5.8 Screening Assays to Identify Anti-Viral Agents

The invention provides methods for the identification of a compound that inhibits the ability of SCoV-like virus to infect a host or a host cell. In certain embodiments, the invention provides methods for the identification of a compound that reduces the ability of SCoV-like virus to replicate in a host or a host cell. Any technique well-known to the skilled artisan can be used to screen for a compound that would abolish or reduce the ability of SCoV-like virus to infect a host and/or to replicate in a host or a host cell.

In certain embodiments, the invention provides methods for the identification of a compound that inhibits the ability of SCoV-like virus to replicate in a mammal or a mammalian cell. More specifically, the invention provides methods for the identification of a compound that inhibits the ability of SCoV-like virus to infect a mammal or a mammalian cell. In certain embodiments, the invention provides methods for the identification of a compound that inhibits the ability of SCoV-like virus to replicate in a mammalian cell. In a specific embodiment, the mammalian cell is a human cell.

In another embodiment, a cell is contacted with a test compound and infected with the SCoV-like virus. In certain embodiments, a control culture is infected with the SCoV-like virus in the absence of a test compound. The cell can be contacted with a test compound before, concurrently with, or subsequent to the infection with the SCoV-like virus. In a specific embodiment, the cell is a mammalian cell. In an even more specific embodiment, the cell is a human cell. In certain embodiments, the cell is incubated with the test compound for at least 1 minute, at least 5 minutes at least 15 minutes, at least 30 minutes, at least 1 hour, at least 2 hours, at least 5 hours, at least 12 hours, or at least 1 day. The titer of the virus can be measured at any time during the assay. In certain embodiments, a time course of viral growth in the culture is determined. If the viral growth is inhibited or reduced in the presence of the test compound, the test compound is identified as being effective in inhibiting or reducing the growth or infection of the SCoV-like virus. In a specific embodiment, the compound that inhibits or reduces the growth of the SCoV-like virus is tested for its ability to inhibit or reduce the growth rate of other viruses to test its specificity for the SCoV-like virus.

In one embodiment, a test compound is administered to a model animal and the model animal is infected with the SCoV-like virus. In certain embodiments, a control model animal is infected with the SCoV-like virus without the administration of a test compound. The test compound can be administered before, concurrently with, or subsequent to the infection with the SCoV-like virus. In a specific embodiment, the model animal is a mammal. In an even more specific embodiment, the model animal can be, but is not limited to, a cotton rat, a mouse, or a monkey. The titer of the virus in the model animal can be measured at any time during the assay. In certain embodiments, a time course of viral growth in the culture is determined. If the viral growth is inhibited or reduced in the presence of the test compound, the test compound is identified as being effective in inhibiting or reducing the growth or infection of the SCoV-like virus. In a specific embodiment, the compound that inhibits or reduces the growth of the SCoV-like virus in the model animal is tested for its ability to inhibit or reduce the growth rate of other viruses to test its specificity for the SCoV-like virus.

6. EXAMPLES

The following examples illustrate the isolation and identification of the novel hSARS virus. These examples should not be construed as limiting.

6.1 Materials and Methods

6.1.1 Sampling

Specimens were collected at a main food retail market, Dongmen Market, in Shenzhen, Guangdong Province. Nasal and faecal swabs were taken for each examined animal and blood was taken wherever possible. After collection, all swabs were kept in virus transport medium (Medium199) with antibiotics.

6.1.2 Virus Isolation and RT-PCR Diagnostic Test

Nasal and faecal swabs were screened by RT-PCR using a pair primers designed to amplify the N gene of SCoV Forward primer 5'-CAGCCCCAGATGGTACTTC-3' (SEQ ID NO:5)

Reverse primer 5'-TCTGCTTCCCTCTGCGTAC-3' (SEQ ID NO:6)

Nasal and faecal samples were cultured on faecal rhesus kidney (FRhK-4) cells for virus isolation as described. Peiris et al., 2003, Lancet 361:1319. Virus isolates were identified by RT-PCR followed by sequencing.

6.1.3 Neutralisation Assay

Animal sera were heat inactivated (56° C. for 30 minutes) and serially diluted from 1:20 to 1:640 and then mixed with 100 $TCID_{50}$ of the animal SCoV-like virus isolate SZ16. After incubation for 1 hour at 37° C., the mixture was inoculated in triplicate on to 96-well plates of FRhK-4 cell cultures. The results were read after 3 days incubation at 37° C.

6.1.4 Genetic Analysis

Viral RNA was extracted from the filtered supernatant of virus-infected FRhK-4 cells with the RNesay Mini Kit (Qiagen, Chatsworth, Calif.). A primer (5'-TTT TTT TTT TTT TTT GTG ATT-3') (SEQ ID NO:7) was designed for reverse transcription of viral RNA. Subsequently, polymerase chain reactions (PCR) were carried out using a series of primers prepared in our laboratory.

After purification of PCR products, cycling sequencing reactions were carried out to determine nucleotide sequence as reported. Guan et al., 2002, Proc. Natl. Acad. Sci. U.S.A. 99:8950. All sequence data were translated and analysed by Wisconsin Software Package, Version 10.1 (GCG). Phylogenetic relationship was determined using Clustal X 1.81 (Thompson et al., 1994, Nucleic Acids Res. 22:4673) and trees generated using Neighboring-Joining algorithms within PAUP, Version 4.0 (Genetics Computer Group, Madison, Wis.). Bootstrap scores are percentages out of 1000 replicates. Similar tree topologies were seen with Maximum Parsimony analysis.

6.2 Discussion

The isolation and identification of SCoV like viruses from animals has now confirmed the hypothesis that SCoV is of animal origin. Both phylogenetic and sequence analysis of SCoV-like viruses suggest that these animal viruses are closely related to human SCoV isolated in the early stage of SARS outbreak. These animal species are either the natural reservoir of SCoV, or an intermediate host that is important in its transmission of the virus to humans. There is a role of the Racoon-dog in the ecology of these viruses and that the Racoon-dog may be the reservoir or they themselves may have acquired it from other sources such as a palm civets.

The factors associated with the emergence of novel infectious diseases are diverse and include human population growth and mobility, global transportation, urban crowding, agriculture practice changes and rapid virus evolution. Holland et al., 1991, J. Viol. 65:1960; Domingo et al., 1997, Med Viol 7:87. The emergence of human H5N1 influenza viruses in 1997 (Jong et al., 1997, Nature 389:544; Subbarao et al., 1998, Science 279:393) and early 2003 (author unpublished data) were good examples to highlight some of these factors. The emergence of SARS in humans is another, even more dramatic example of this. Exotic animals wild caught or farmed meeting culinary demand may be a continued source of introduction of this SCoV to humans. The present invention will help to better understand the inter-species transmission events that lead to the SARS outbreak.

Both H5N1 influenza and SARS emerged in the hypothetical pandemic influenza epicenter of southern China. Shortridge et al., 1982, Lancet ii:812; Guan et al., 2002, Proc. Natl. Acad. Sci. U.S.A. 99:8950. In the case of H5N1, chickens were the immediate source of virus for humans (Shortridge et al., 1998, Virology 252:331) and the depopulation of chicken in the live poultry markets and farms in Hong Kong resulted in the interruption of the outbreak and possibly averted an influenza pandemic in humans. However, nearly half year since the emergence of SARS, the precursor SCoV-like viruses are still simmering in food markets of southern China. Thus the recognition of SCoV-like viruses in animals is of pivotal significance in the control of SARS. An immediate ban of wild-animal trading for food or other use is of the highest priority in the global fight against SARS.

7. EQUIVALENTS

Those skilled in the art will recognize, or be able to ascertain many equivalents to the specific embodiments of the invention described herein using no more than routine experimentation. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07361747B2). An electronic copy of the "Sequence Listing" will also be available from the USPTO upon request and payment of the fee set forth in 37 CFR 1.19(b)(3).

What is claimed is:

1. An isolated nucleic acid molecule consisting of at least 12 contiguous nucleotides of the nucleotide sequence of SEQ ID NO:1, or the full-length complement thereof.

2. The nucleic acid molecule of claim 1, wherein the molecule is RNA.

3. The nucleic acid molecule of claim 1, wherein the molecule is DNA.

4. A vector consisting of at least 12 contiguous nucleotides of the nucleotide sequence of SEQ ID NO:1 operably linked to one or more control elements.

5. An isolated host cell comprising the vector of claim 4.

\* \* \* \* \*